(12) United States Patent
Romine et al.

(10) Patent No.: US 8,809,548 B2
(45) Date of Patent: *Aug. 19, 2014

(54) HEPATITIS C VIRUS INHIBITORS

(75) Inventors: Jeffrey Lee Romine, Meriden, CT (US);
Denis R. St. Laurent, Newington, CT (US); Makonen Belema, North Haven, CT (US); Lawrence B. Snyder, Killingworth, CT (US); Lawrence G. Hamann, North Grafton, MA (US); John F. Kadow, Wallingford, CT (US); Jayne Kapur, Houston, TX (US); Andrew C. Good, Wallingford, CT (US); Omar D. Lopez, Wallingford, CT (US); Rico Lavoie, Candiac (CA); John A. Bender, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 325 days.

This patent is subject to a terminal disclaimer.

(21) Appl. No.: 12/701,919

(22) Filed: Feb. 8, 2010

(65) Prior Publication Data

US 2010/0215616 A1 Aug. 26, 2010

Related U.S. Application Data

(60) Provisional application No. 61/153,186, filed on Feb. 17, 2009.

(51) Int. Cl.
*A61K 31/422* (2006.01)
*A61K 31/4184* (2006.01)
*C07D 403/14* (2006.01)
*C07D 413/14* (2006.01)

(52) U.S. Cl.
USPC ............. 548/306.1; 548/235; 548/302.1; 548/305.1; 514/374; 514/394

(58) Field of Classification Search
USPC ........................................ 548/306.1
See application file for complete search history.

(56) References Cited

U.S. PATENT DOCUMENTS

| | | | |
|---|---|---|---|
| 5,654,451 A | 8/1997 | Kari | |
| 6,277,830 B1 * | 8/2001 | Ganguly et al. | 514/43 |
| 8,101,643 B2 * | 1/2012 | Qiu et al. | 514/394 |
| 8,394,968 B2 * | 3/2013 | Romine | 548/302.1 |
| 2008/0193411 A1 | 8/2008 | Leivers et al. | |
| 2010/0158862 A1 | 6/2010 | Kim et al. | |
| 2010/0249190 A1 | 9/2010 | Lopez et al. | |
| 2010/0260708 A1 | 10/2010 | Belema et al. | |
| 2011/0195044 A1 * | 8/2011 | Romine | 424/85.2 |

FOREIGN PATENT DOCUMENTS

| | | |
|---|---|---|
| WO | WO 94/15909 | 7/1994 |
| WO | WO 2004/005264 | 1/2004 |
| WO | WO 2006/022442 | 3/2006 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/076034 | 7/2007 |
| WO | WO 2007/077186 | 7/2007 |
| WO | WO 2007/081517 | 7/2007 |
| WO | WO 2007/138242 | 12/2007 |
| WO | WO 2008/014430 | 1/2008 |
| WO | WO 2008/021927 | 2/2008 |
| WO | WO 2008/021928 | 2/2008 |
| WO | WO 2008/021936 | 2/2008 |
| WO | WO 2008/070447 | 6/2008 |
| WO | WO 2008/133753 | 11/2008 |
| WO | WO 2009/020825 | 2/2009 |
| WO | WO 2009/020828 | 2/2009 |
| WO | WO 2009/102318 | 8/2009 |
| WO | WO 2009/102325 | 8/2009 |
| WO | WO 2009/102568 | 8/2009 |
| WO | WO 2009/102633 | 8/2009 |
| WO | WO 2009/102694 | 8/2009 |
| WO | WO 2010/017401 | 2/2010 |
| WO | WO 2010/039793 | 4/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO-2010/138791 A1 * | 12/2010 |
| WO | WO-2011/031934 A1 * | 3/2011 |

OTHER PUBLICATIONS

Moyer et al., American Family Physician, (Jan. 15, 1999), 59(2), pp. 349-354.*
U.S. Appl. No. 12/729,940, filed Mar. 23, 2010, Bender et al.
U.S. Appl. No. 12/755,631, filed Apr. 7, 2010, Lavoie et al.
U.S. Appl. No. 12/780,415, filed May 14, 2010, Lopez et al.

* cited by examiner

*Primary Examiner* — Laura L. Stockton
(74) *Attorney, Agent, or Firm* — Pamela A. Mingo

(57) ABSTRACT

The present disclosure relates to compounds, compositions and methods for the treatment of hepatitis C virus (HCV) infection. Also disclosed are pharmaceutical compositions containing such compounds and methods for using these compounds in the treatment of HCV infection.

22 Claims, No Drawings

HEPATITIS C VIRUS INHIBITORS

CROSS-REFERENCE TO RELATED APPLICATIONS

This application claims the benefit of U.S. Provisional Application Ser. No. 61/153,186 filed Feb. 17, 2009.

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

HCV is a major human pathogen, infecting an estimated 170 million persons worldwide—roughly five times the number infected by human immunodeficiency virus type 1, A substantial fraction of these HCV infected individuals develop serious progressive liver disease, including cirrhosis and hepatocellular carcinoma.

The current standard of care for HCV, which employs a combination of pegylated-interferon and ribavirin, has a non-optimal success rate in achieving sustained viral response and causes numerous side effects. Thus, there is a clear and long-felt need to develop effective therapies to address this unmet medical need.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Viral*, 83, 4395 (2009); N. Appel, et al., *J. Biol. Chem.*, 281, 9833 (2006); L. Huang, *J. Biol. Chem.*, 280, 36417 (2005); C. Rice, et al., WO2006093867.

In a first aspect the present disclosure provides a compound of Formula (I)

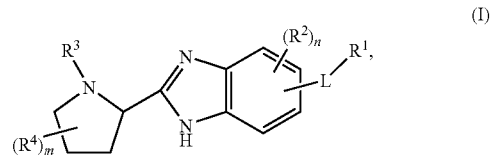

or a pharmaceutically acceptable salt thereof, wherein
each m is independently 0 or 1;
each n is independently 0 or 1;
L is a bond or is selected from

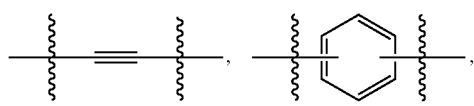

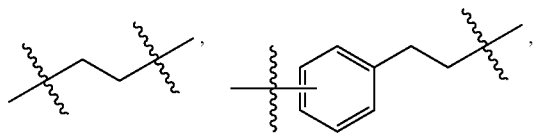

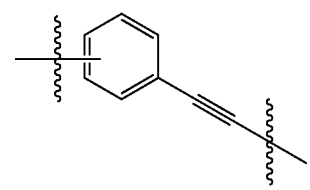, and 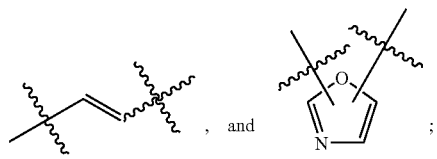;

wherein each group is drawn with its left end attached to the benzimidazole and its right end attached to $R^1$;

$R^1$ is selected from

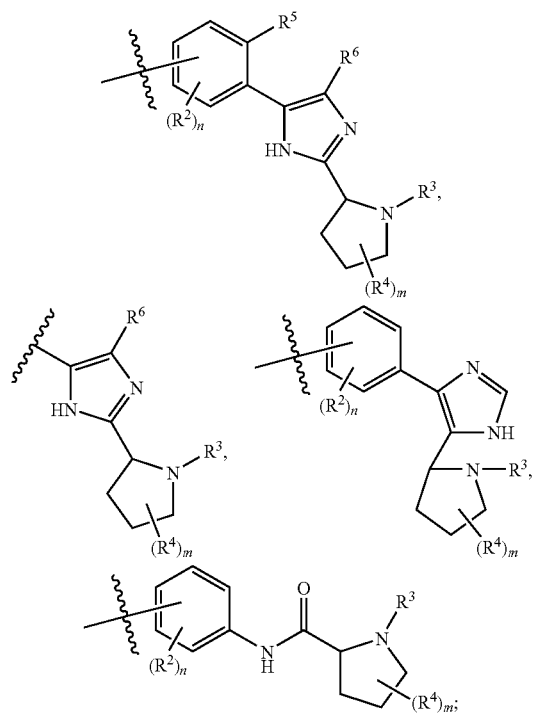

each $R^2$ is independently selected from alkyl and halo;
each $R^3$ is independently selected from hydrogen and —C(O)$R^7$;
$R^4$ is alkyl;
$R^5$ and $R^6$ are independently selected from hydrogen, alkyl, cyanoalkyl, and halo, or
$R^5$ and $R^6$, together with the carbon atoms to which they are attached, form a six- or seven-membered ring optionally containing one heteroatom selected from nitrogen and oxygen and optionally containing an additional double bond; and
each $R^7$ is independently selected from alkoxy, alkyl, arylalkoxy, arylalkyl, cycloalkyl, (cycloalkyl)alkyl, heterocyclyl, heterocyclylalkyl, (NR$^c$R$^d$)alkenyl, and (NR$^c$R$^d$)alkyl.

In a first embodiment of the first aspect the present disclosure provides a compound of Formula (I), or a pharmaceutically acceptable salt thereof, wherein L is a bond.

In a second embodiment of the first aspect $R^1$ is

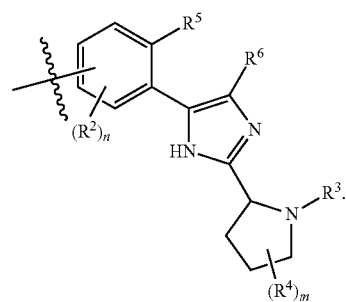

In a third embodiment of the first aspect the present disclosure provides a compound of Formula (I), or a pharmaceutically acceptable salt thereof, wherein L is

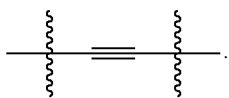

In a fourth embodiment of the first aspect the present disclosure provides a compound of Formula (I), or a pharmaceutically acceptable salt thereof, wherein L is

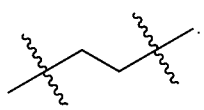

In a fifth embodiment $R^1$ is selected from

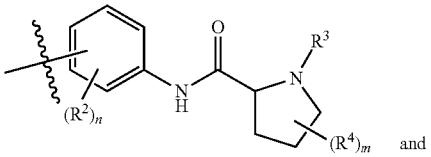

and

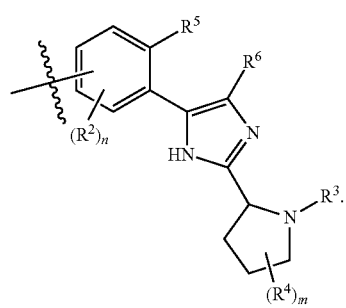

In a sixth embodiment of the first aspect the present disclosure provides a compound of Formula (I), or a pharmaceutically acceptable salt thereof, wherein L is

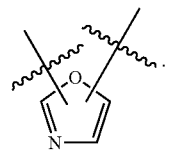

In a seventh embodiment L is selected from

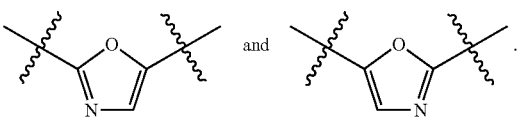 [SMILES: *c1cnc(*)o1 ; "and" ; *c1cnc(*)o1 ; "."]

In an eighth embodiment R¹ is

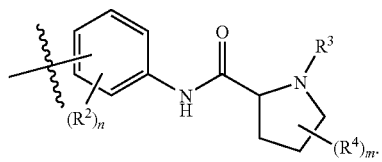

In a ninth embodiment of the first aspect the present disclosure provides a compound of Formula (I), or a pharmaceutically acceptable salt thereof, wherein L is

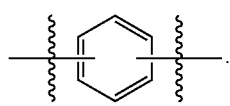

In a tenth embodiment R¹ is

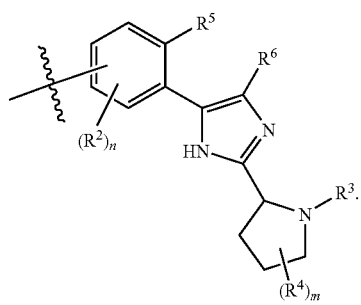

In an eleventh embodiment of the first aspect the present disclosure provides a compound of Formula (I), or a pharmaceutically acceptable salt thereof, wherein L is wherein L is selected from

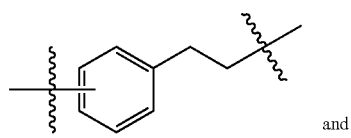

and

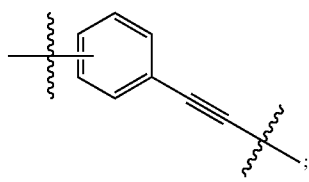

;

wherein each group is drawn with its left end attached to the benzimidazole and its right end attached to R¹.

In a twelfth embodiment R¹ is

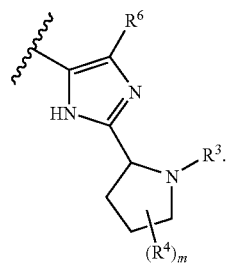

In a second aspect the present disclosure provides a compound of Formula

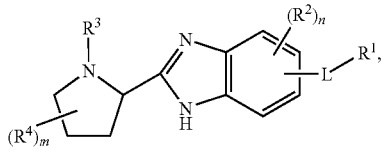

(II)

or a pharmaceutically acceptable salt thereof, wherein
each m is independently 0 or 1;
each n is independently 0 or 1;
L is a bond or is selected from

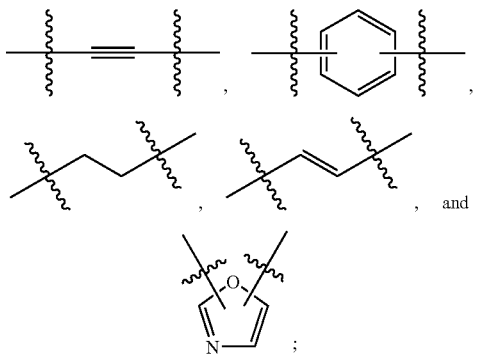

, and

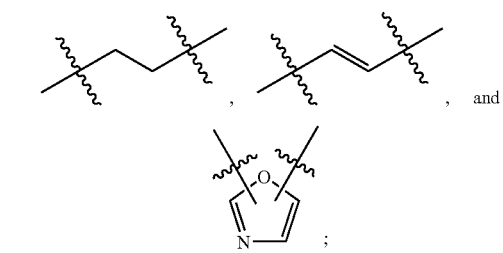

;

R¹ is selected from

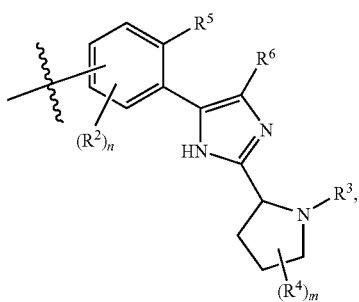

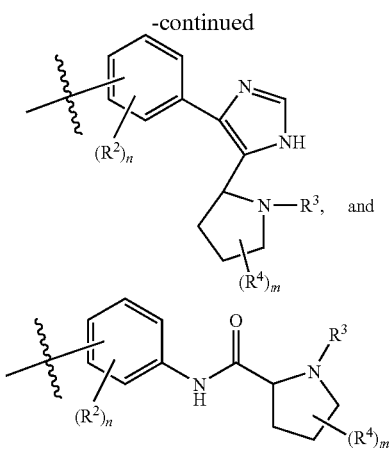

each R² is independently selected from alkyl and halo;
each R³ is independently selected from hydrogen and —C(O)R⁷;
R⁴ is alkyl;
R⁵ and R⁶ are independently hydrogen or halo, or
R⁵ and R⁶, together with the carbon atoms to which they are attached, form a six- or seven-membered ring optionally containing one heteroatom selected from nitrogen and oxygen and optionally containing an additional double bond; and
each R⁷ is independently selected from alkoxy, alkyl, arylalkyl, cycloalkyl, heterocyclyl, heterocyclylalkyl, (NR$^c$R$^d$)alkenyl, and (NR$^c$R$^d$)alkyl.

In a third aspect the present disclosure provides a composition comprising a compound of Formula (I), or a pharmaceutically acceptable salt thereof, and a pharmaceutically acceptable carrier. In a first embodiment of the third aspect the composition further comprises one or two additional compounds having anti-HCV activity. In a second embodiment of the third aspect at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau.

In a fourth embodiment of the third aspect the present disclosure provides a composition comprising a compound of Formula (I), or a pharmaceutically acceptable salt thereof, a pharmaceutically acceptable carrier, and one or two additional compounds having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the third aspect the present disclosure provides a composition comprising a compound of Formula (I), or a pharmaceutically acceptable salt thereof, a pharmaceutically acceptable carrier, and one or two additional compounds having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of Formula (I), or a pharmaceutically acceptable salt thereof. In a first embodiment of the fourth aspect the method further comprises administering one or two additional compounds having anti-HCV activity prior to, after or simultaneously with the compound of Formula (I), or a pharmaceutically acceptable salt thereof. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, and lymphoblastiod interferon tau.

In a fourth embodiment of the fourth aspect the present disclosure provides a method of treating an HCV infection in a patient, comprising administering to the patient a therapeutically effective amount of a compound of Formula (I), or a pharmaceutically acceptable salt thereof, and one or two additional compounds having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the fourth aspect the present disclosure provides a method of treating an HCV infection in a patient, comprising administering to the patient a therapeutically effective amount of a compound of Formula (I), or a pharmaceutically acceptable salt thereof, and one or two additional compounds having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other embodiments of the present disclosure may comprise suitable combinations of two or more of embodiments and/or aspects disclosed herein.

Yet other embodiments and aspects of the disclosure will be apparent according to the description provided below.

The compounds of the present disclosure also exist as tautomers; therefore the present disclosure also encompasses all tautomeric forms.

The description of the present disclosure herein should be construed in congruity with the laws and principals of chemical bonding.

It should be understood that the compounds encompassed by the present disclosure are those that are suitably stable for use as pharmaceutical agent.

It is intended that the definition of any substituent or variable (e.g., R² and R⁴) at a particular location in a molecule be independent of its definitions elsewhere in that molecule. For example, when n is 2, each of the two R² groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term 'aryl'.

The term "alkoxy," as used herein, refers to an alkyl group attached to the parent molecular moiety through an oxygen atom.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to six carbon atoms. In the compounds of the present disclosure, when m is 1 and $R^4$ is alkyl, the alkyl can optionally form a fused three- or four-membered ring with an adjacent carbon atom to provide one of the structures shown below:

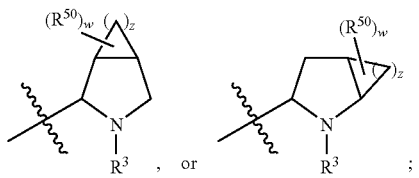

where z is 1 or 2, w is 0, 1, or 2, and $R^{50}$ is alkyl. When w is 2, the two $R^{50}$ alkyl groups may be the same or different.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^xR^y$, ($NR^xR^y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkoxy," as used herein, refers to an arylalkyl group attached to the parent molecular moiety through an oxygen atom.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —$NR^cR^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, $NR^xR^y$, and oxo.

The term "carbonyl," as used herein, refers to —C(O)—.

The term "cyanoalkyl," as used herein, refers to an alkyl group substituted with one, two, or three cyano groups.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclobutyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —$NR^xR^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The terms "halo" and "halogen," as used herein, refer to F, Br, Cl, or I.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oct-2-yl, and 2-azabicyclo[2.2.2]oct-3-yl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isoquinolinyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, quinolinyl, thiazolyl, thienyl, and thiomorpholinyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^xR^y$, ($NR^xR^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "—NR$^c$R$^d$," as used herein, refers to two groups, R$^c$ and R$^d$, which are attached to the parent molecular moiety through a nitrogen atom. R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkyloxycarbonyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylearbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "(NR$^e$R$^d$)alkenyl," as used herein, refers to

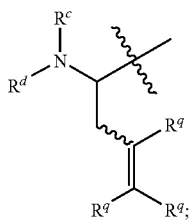

wherein R$^c$ and R$^d$ are as defined herein and each R$^q$ is independently hydrogen or C$_{1-3}$ alkyl.

The term "(NR$^c$R$^d$)alkyl," as used herein, refers to an alkyl group substituted with one, two, or three —NR$^c$R$^d$ groups. The alkyl part of the (NR$^c$R$^d$)alkyl is further optionally substituted with one or two additional groups selected from alkoxy, alkoxyalkylcarbonyl, alkoxycarbonyl, alkylsulfanyl, arylalkoxycarbonyl, carboxy, cycloalkyl, heterocyclyl, heterocyclylcarbonyl, hydroxy, and (NR$^e$R$^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "—NR$^e$R$^f$," as used herein, refers to two groups, R$^e$ and R$^f$, which are attached to the parent molecular moiety through a nitrogen atom. R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^x$R$^y$)alkyl, and (NR$^x$R$^y$)carbonyl.

The term "—NR$^x$R$^y$," as used herein, refers to two groups, R$^x$ and R$^y$, which are attached to the parent molecular moiety through a nitrogen atom, R$^x$ and R$^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{x'}$R$^{y'}$)carbonyl, wherein R$^{x'}$ and R$^{y'}$ are independently selected from hydrogen and alkyl.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and routes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin inhibitors | Novartis Debiopharm |
| Debio-025 | | | |
| Zadaxin | | Immunomodulator | SciClone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/ Elan Pharmaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO 2005/047288 May 26, 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co., Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novartis |
| 2'C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering-Plough |
| Zadazim | Immune modulator | Immune modulator | SciClone Pharmaceuticals Inc., San Mateo, CA |

TABLE 1-continued

| Brand Name | Physiological Class | Type of Inhibitor or Target | Source Company |
|---|---|---|---|
| Ceplene | Immunomodulator | Immune modulator | Maxim Pharmaceuticals Inc., San Diego, CA |
| CELLCEPT ® | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| REBIF ® | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering-Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |

TABLE 1-continued

| Brand Name | Physiological Class | Type of Inhibitor or Target | Source Company |
|---|---|---|---|
| MK-7009 | Antiviral | Serine protease inhibitor | Merck |
| PF-00868554 | Antiviral | Replicase inhibitor | Pfizer |
| ANA598 | Antiviral | Non-Nucleoside NS5B polymerase inhibitor | Anadys Pharmaceuticals, Inc., San Diego, CA, USA |
| IDX375 | Antiviral | Non-Nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | ViroChem Pharma |
| VCH-916 | Antiviral | NS5B polymerase inhibitor | ViroChem Pharma |
| GS-9190 | Antiviral | NS5B polymerase inhibitor | Gilead |
| Peg-interferon lamda | Antiviral | Interferon | ZymoGenetics/ Bristol-Myers Squibb |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: RT for room temperature or retention time (context will dictate); $R_t$ for retention time; min for minutes; TFA for trifluoroacetic acid; DMSO for dimethylsulfoxide; Ph for phenyl; THF for tetrahydrofuran; $Et_2O$ for diethyl ether; Boc or BOC for tert-butoxycarbonyl; MeOH for methanol; Et for ethyl; DMF for dimethylformamide; h or hr for hours; TBDPS for tert-butyl-diphenylsilyl; DMAP for N,N-dimethylaminopyridine; TBAF for tetrabutylammonium fluoride; $Et_3N$ or TEA for triethylamine; HATU for O-(7-azabenzotriazol-1-yl)-N,N,N',N'-tetramethyluronium hexafluorophosphate; Ac for acetate or acetyl; SEM for 2-trimethylsilylethoxymethoxy; EDC or EDCI for 1-ethyl-3-(3-dimethylaminopropyl)carbodiimide; EEDQ for N-ethoxycarbonyl-2-ethoxy-1,2-dihydroquinoline; MeOH for methanol; i-Bu for isobutyl; Bn for benzyl; and Me for methyl.

The compounds and processes of the present disclosure will be better understood in connection with the following synthetic schemes which illustrate the methods by which the compounds of the present disclosure may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

Scheme 1

Substituted Phenylglycine Derivatives

Substituted phenylglycine derivatives can be prepared by a number of methods shown below. Phenylglycine t-butyl ester can be reductively alkylated (pathway A) with an appropriate aldehyde and a reductant such as sodium cyanoborohydride in acidic medium. Hydrolysis of the t-butyl ester can be accomplished with strong acid such as HCl or trifluoroacetic acid. Alternatively, phenylglycine can be alkylated with an alkyl halide such as ethyl iodide and a base such as sodium bicarbonate or potassium carbonate (pathway B). Pathway C illustrates reductive alkylation of phenylglycine as in pathway A followed by a second reductive alkylation with an alternate aldehyde such as formaldehyde in the presence of a reducing agent and acid. Pathway D illustrates the synthesis of substituted phenylglycines via the corresponding mandelic acid analogs. Conversion of the secondary alcohol to a competent leaving group can be accomplished with p-toluensulfonyl chloride. Displacement of the tosylate group with an appropriate amine followed by reductive removal of the benzyl ester can provide substituted phenylglycine derivatives. In pathway E a racemic substituted phenylglycine derivative is resolved by esterification with an enantiomerically pure chiral auxiliary such as but not limited to (+)-1-phenylethanol, (−)-1-phenylethanol, an Evan's oxazolidinone, or enantiomerically pure pantolactone. Separation of the diastereomers is accomplished via chromatography (silica gel, HPLC, crystallization, etc) followed by removal of the chiral auxiliary providing enantiomerically pure phenylglycine derivatives. Pathway H illustrates a synthetic sequence which intersects with pathway E wherein the aforementioned chiral auxiliary is installed prior to amine addition. Alternatively, an ester of an arylacetic acid can be brominated with a source of bromonium ion such as bromine, N-bromosuccinimide, or $CBr_4$. The resultant benzylic bromide can be displaced with a variety of mono- or disubstituted amines in the presence of a tertiary amine base such as triethylamine or Hunig's base. Hydrolysis of the methyl ester via treatment with lithium hydroxide at low temperature or 6N HCl at elevated temperature provides the substituted phenylglycine derivatives. Another method is shown in pathway G. Glycine analogs can be derivatized with a variety of aryl halides in the presence of a source of palladium (0) such as palladium bis(tributylphosphine) and base such as potassium phosphate. The resultant ester can then be hydrolyzed by treatment with base or acid. It should be understood that other well known methods to prepare phenylglycine derivatives exist in the art and can be amended to provide the desired compounds in this description. It should also be understood that the final phenylglycine derivatives can be purified to enantiomeric purity greater than 98% ee via preparative HPLC.

Scheme 2: Acylated Amino Acid Derivatives

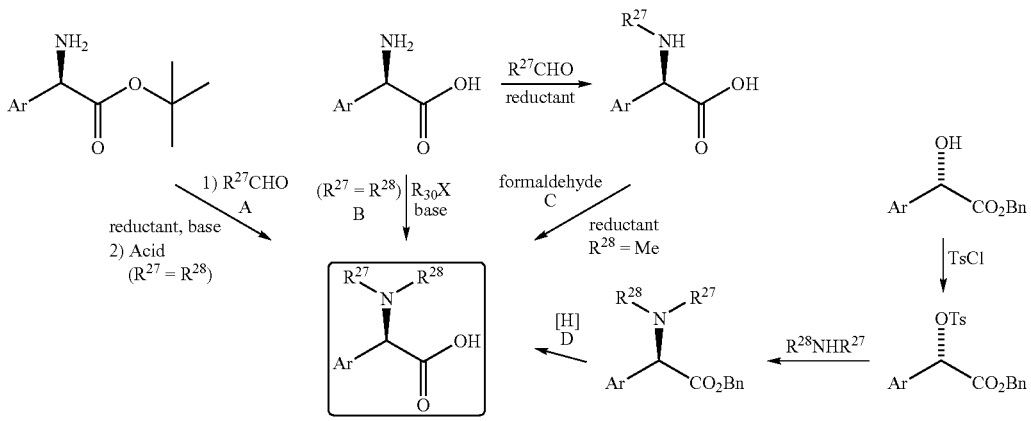

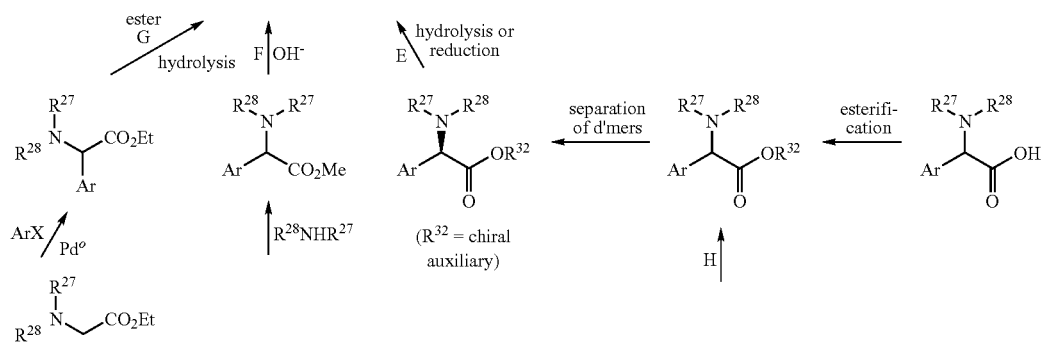

In another embodiment of the present disclosure, acylated phenylglycine derivatives may be prepared as illustrated below. Phenylglycine derivatives wherein the carboxylic acid is protected as an easily removed ester, may be acylated with an acid chloride in the presence of a base such as triethylamine to provide the corresponding amides (pathway A). Pathway B illustrates the acylation of the starting phenylglycine derivative with an appropriate chloroformate while pathway C shows reaction with an appropriate isocyanate or carbamoyl chloride. Each of the three intermediates shown in pathways A-C may be deprotected by methods known by those skilled in the art (i.e.; treatment of the t-butyl ester with strong base such as HCl or trifluoroacetic acid).

Micromass ZQ MS system. It should be noted that retention times may vary slightly between machines. Additional LC conditions applicable to the current section, unless noted otherwise.

| Cond.-MS-W1 | |
| --- | --- |
| Column = | XTERRA 3.0 × 50 mm S7 |
| Start % B = | 0 |
| Final % B = | 100 |
| Gradient time = | 2 min |
| Stop time = | 3 min |

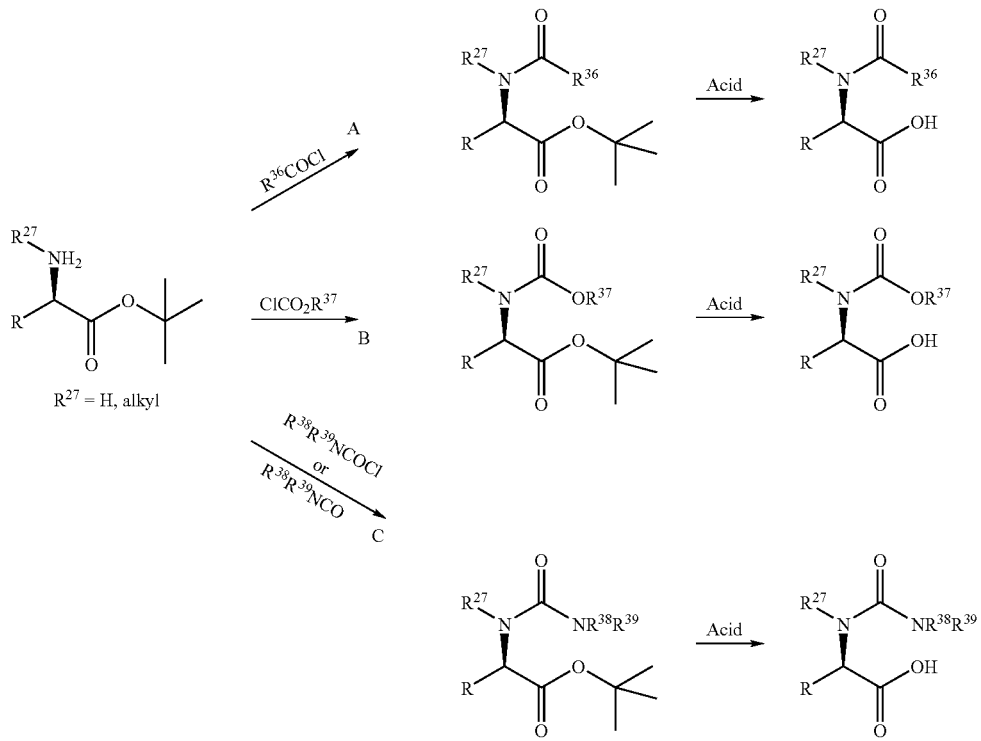

Scheme 3

Amino-substituted phenylacetic acids may be prepared by treatment of a chloromethylphenylacetic acid with an excess of an amine.

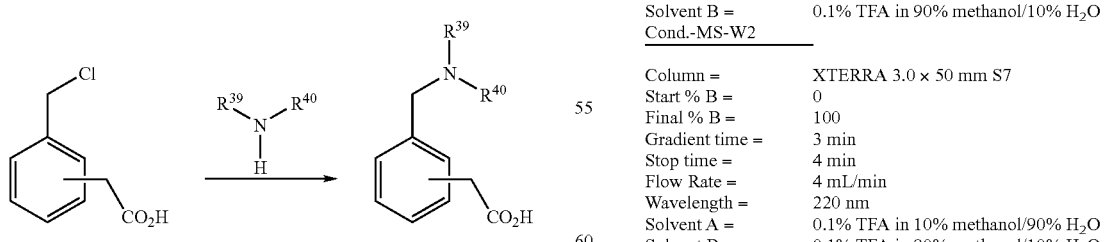

Synthesis of Common Caps

Compound Analysis Conditions:

Purity assessment and low resolution mass analysis were conducted on a Shimadzu LC system coupled with Waters

| -continued | |
| --- | --- |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Cond.-MS-W2 | |
| Column = | XTERRA 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |
| Cond.-MS-W5 | |
| Column = | XTERRA 3.0 × 50 mm S7 |
| Start % B = | 0 |
| Final % B = | 30 |
| Gradient time = | 2 min |
| Stop time = | 3 min |

| | |
|---|---|
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Cond.-D1 | |
| Column = | XTERRA C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Cond.-D2 | |
| Column = | Phenomenex-Luna 4.6 × 50 mm S10 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Cond.-MD1 | |
| Column = | XTERRA 4.6 × 50 mm S5 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Cond.-M3 | |
| Column = | XTERRA C18 3.0 × 50 mm S7 |
| Start % B = | 0 |
| Final % B = | 40 |
| Gradient time = | 2 min |
| Stop time = | 3 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Condition OL1 | |
| Column = | Phenomenex-Luna 3.0 × 50 mm S10 |
| Start % B = | 0 |
| Final % B = | 100 |
| Gradient time = | 4 min |
| Stop time = | 5 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Condition OL2 | |
| Column = | Phenomenex-Luna 50 × 2 mm 3 u |
| Start % B = | 0 |
| Final % B = | 100 |
| Gradient time = | 4 min |
| Stop time = | 5 min |
| Flow Rate = | 0.8 mL/min |
| Oven Temp = | 40° C. |
| Wavelength = | 220 nm |
| Solvent A = | 0.1% TFA in 10% Acetonitrile/90% H$_2$O |
| Solvent B = | 0.1% TFA in 90% Acetonitrile/10% H$_2$O |
| Condition I = | |
| Column = | Phenomenex-Luna 3.0 × 50 mm S10 |
| Start % B = | 0 |
| Final % B = | 100 |
| Gradient time = | 2 min |
| Stop time = | 3 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Condition II | |
| Column = | Phenomenex-Luna 4.6 × 50 mm S10 |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Condition III | |
| Column = | XTERRA C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

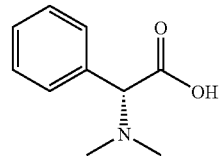

Cap-1

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to H$_2$ (60 psi) for 3 hours. The reaction mixture was filtered through diatomaceous earth (Celite®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in H$_2$O; λ=589 nm]. $^1$H NMR (DMSO-d$_6$, δ=2.5 ppm, 500 MHz): δ 7.43-7.34 (m, 5H), 4.14 (s, 1H), 2.43 (s, 6H); LC (Cond. I): RT=0.25; LC/MS: Anal. Calcd. for [M+H]$^+$ C$_{10}$H$_{14}$NO$_2$ 180.10; found 180.17; HRMS: Anal. Calcd. for [M+H]$^+$ C$_{10}$H$_{14}$NO$_2$ 180.1025; found 180.1017.

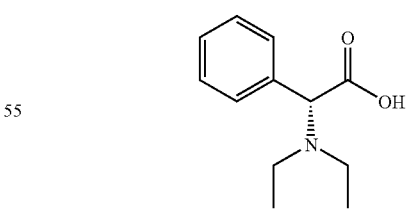

Cap-2

NaBH$_3$CN (6.22 g, 94 mmol) was added in portions over a few minutes to a cooled (ice/water) mixture of (R)-2-Phenylglycine (6.02 g, 39.8 mmol) and methanol (100 mL), and stirred for 5 minutes, Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). $^1$H NMR (DMSO-$d_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: $[α]^{25}$ −102.21° (c=0.357, $H_2O$); crop-2: $[α]^{25}$ −99.7° (c=0.357, $H_2O$). LC (Cond. I): RT=0.43 min; LC/MS: Anal. Calcd. for $[M+H]^+$ $C_{12}H_{18}NO_2$: 208.13; found 208.26.

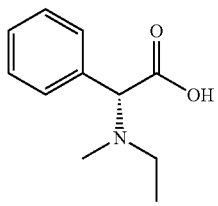

Cap-3

Acetaldehyde (5.0 mL, 89.1 mmol) and a suspension of 10% Pd/C (720 mg) in methanol/$H_2O$ (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of $H_2$ for 17 hours. An additional acetaldehyde (10 mL, 178.2 mmol) was added and stirring continued under $H_2$ atmosphere for 24 hours [Note: the supply of $H_2$ was replenished as needed throughout the reaction]. The reaction mixture was filtered through diatomaceous earth (Celite®), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-$d_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. I): RT=0.39 min; >95% homogeneity index; LC/MS: Anal. Calcd. for $[M+H]^+$ $C_{10}H_{14}NO_2$: 180.10; found 180.18.

A suspension of 10% Pd/C (536 mg) in methanol/$H_2O$ (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL) The reaction mixture was stirred under a balloon of $H_2$ for ~72 hours, where the $H_2$ supply was replenished as needed. The reaction mixture was filtered through diatomaceous earth (Celite®) and the filtrate was concentrated in vacuo. The resulting crude material was recrystallized from isopropanol (50 mL) to provide the HCl salt of Cap-3 as a white solid (985 mg). $^1$H NMR (DMSO-$d_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Cond. I): RT=0.39 min; >95% homogeneity index; LC/MS: Anal. Calcd. for $[M+H]^+$ $C_{11}H_{16}NO_2$: 194.12; found 194.18; HRMS: Anal. Calcd. for $[M+H]^+$ $C_{11}H_{16}NO_2$: 194.1180; found 194.1181.

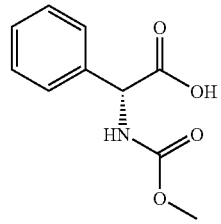

Cap-4

$ClCO_2Me$ (3.2 mL, 41.4 mmol) was added dropwise to a cooled (ice/water) THF (410 mL) semi-solution of (R)-tent-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated $NaHCO_3$ solution (30 mL), dried ($MgSO_4$), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1$H NMR (DMSO-$d_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. I): RT=1.53 min; ~90% homogeneity index; LC/MS: Anal. Calcd. for $[M+Na]^+$ $C_{14}H_{19}NNaO_4$: 288.12; found 288.15.

TFA (16 mL) was added dropwise to a cooled (ice/water) $CH_2Cl_2$ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in $H_2O$; λ=589 nm]. $^1$H NMR (DMSO-$d_6$, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Cond. I): RT=1.01 min; >95% homogeneity index; LC/MS: Anal. Calcd. for $[M+H]^+$ $C_{10}H_{12}NO_4$ 210.08; found 210.17; HRMS: Anal. Calcd. for $[M+H]^+$ $C_{10}H_{12}NO_4$ 210.0766; found 210.0756.

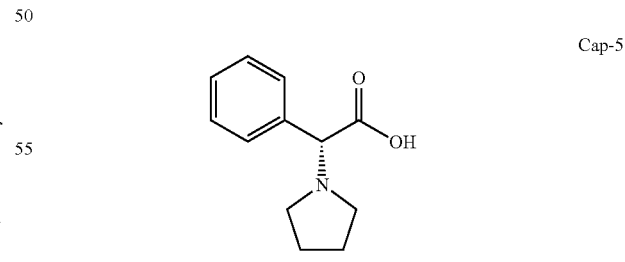

Cap-5

A mixture of (R)-2-phenylglycine (1.0 g, 6.62 mmol), 1,4-dibromobutane (1.57 g, 7.27 mmol) and $Na_2CO_3$ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-d$_5$, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 minutes (Cond. I); >98% homogeneity index; LC/MS: Anal. Calcd. for [M+H]$^+$ C$_{12}$H$_{16}$NO$_2$: 206.12; found 206.25.

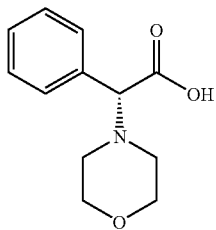

Cap-6

The TFA salt of Cap-6 was synthesized from (R)-2-phenylglycine and 1-bromo-2-(2-bromoethoxy)ethane by using the method of preparation of Cap-5. $^1$H NMR (DMSO-d$_6$, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 minutes (Cond. I); >98%; LC/MS: Anal. Calcd. for [M+H]$^+$ C$_{12}$H$_{16}$NO$_3$: 222.11; found 222.20; HRMS: Anal. Calcd. for [M+H]$^+$ C$_{12}$H$_{16}$NO$_3$: 222.1130; found 222.1121.

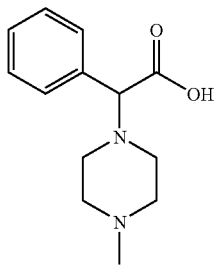

Cap-7

Cap-7a: enantiomer-1
Cap-7b: enantiomer-2

A CH$_2$Cl$_2$ (200 mL) solution of p-toluenesulfonyl chloride (8.65 g, 45.4 mmol) was added dropwise to a cooled (~5° C.) CH$_2$Cl$_2$ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO$_4$), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-d$_6$, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. III); >90% homogeneity index; LC/MS: Anal. Calcd. for [M+H]$^+$ C$_{22}$H$_{20}$NaO$_5$S: 419.09; found 419.04.

A THF (75 mL) solution of benzyl 2-phenyl-2-(tosyloxy)acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO$_4$), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (Chiralcel OD-H) indicated that the sample is a mixture of enantiomers in a 38.2 to 58.7 ratio. The separation of the enantiomers were effected as follow: the product was dissolved in 120 mL of ethanol/heptane (1:1) and injected (5 mL/injection) on chiral HPLC column (Chiracel OJ, 5 cm ID×50 cm L, 20 μm) eluting with 85:15 Heptane/ethanol at 75 mL/min, and monitored at 220 nm. Enantiomer-1 (1.474 g) and enantiomer-2 (2.2149 g) were retrieved as viscous oil. $^1$H NMR (CDCl$_3$, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. III); >98% homogeneity index; LC/MS: Anal. Calcd. for [M+H]$^+$ C$_{20}$H$_{25}$N$_2$O$_2$: 325.19; found 325.20.

A methanol (10 mL) solution of either enantiomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (Celite®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-d$_6$, δ=2.5, 500 MHz) δ 7.44-7.37 (m, 2H), 7.37-7.24 (m, 3H), 3.92 (s, 1H) 2.63-2.48 (app. br s, 2H), 2.48-2.32 (m, 6H), 2.19 (s, 3H); RT=0.31 (Cond. II); >90% homogeneity index; LC/MS: Anal. Calcd. for [M+H]$^+$ C$_{13}$H$_{19}$N$_2$O$_2$: 235.14; found 235.15; HRMS: Anal. Calcd. for [M+H]$^+$ C$_{13}$H$_{19}$N$_2$O$_2$: 235.1447; found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermediates, as described below.

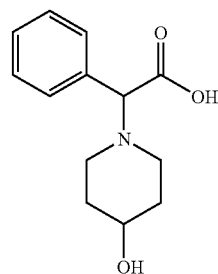

Cap-8

8a: enantiomer-1
8b: enantiomer-2

The enantiomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 μm) eluting with 80:20 heptane/ethanol at 10 mL/min, monitored at 220 nm, to provide 186.3 mg of enantiomer-1 and 209.1 mg of enantiomer-2 as light-yellow viscous oils. These benzyl ester was hydrogenolysed according to the preparation of Cap-7 to provide Cap-8: $^1$H NMR (DMSO-$d_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Cond, II); >98% homogeneity index; LC/MS: Anal. Calcd. for [M+H]$^+$ $C_{13}H_{18}NO_3$: 236.13; found 236.07; HRMS: Calcd. for [M+H]$^+$ $C_{13}H_{18}NO_3$: 236.1287; found 236.1283.

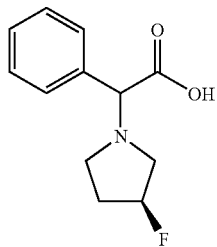

Cap-9

9a: diastereomer-1
9b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% $CO_2$/5% methanol with 0.1% TFA, at 10 bar pressure, 70 mL/min flow rate, and a temperature of 35° C. The HPLC elute for the respective stereoisomers was concentrated, and the residue was dissolved in $CH_2Cl_2$ (20 mL) and washed with an aqueous medium (10 mL water+1 mL saturated NaHCO$_3$ solution). The organic phase was dried (MgSO$_4$), filtered, and concentrated in vacuo to provide 92.5 mg of fraction-1 and 59.6 mg of fraction-2. These benzyl esters were hydrogenolysed according to the preparation of Cap-7 to prepare Caps 9a and 9b. Cap-9a (diastereomer-1; the sample is a TFA salt as a result of purification on a reverse phase HPLC using $H_2O$/methanol/TFA solvent): $^1$H NMR (DMSO-$d_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT-0.42 (Cond. I); >95% homogeneity index; LC/MS: Anal. Calcd. for [M+H]$^+$ $C_{12}H_{15}FNO_2$: 224.11; found 224.14; Cap-9b (diastereomer-2): $^1$H NMR (DMSO-$d_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. I); LC/MS: Anal. Calcd. for [M+H]$^+$ $C_{12}H_{15}FNO_2$: 224.11; found 224.14.

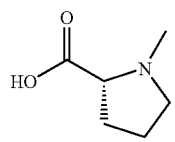

Cap-10

To a solution of D-proline (2.0 g, 17 mmol) and formaldehyde (2.0 mL of 37% wt. in $H_2O$) in methanol (15 mL) was added a suspension of 10% Pd/C (500 mg) in methanol (5 mL). The mixture was stirred under a balloon of hydrogen for 23 hours. The reaction mixture was filtered through diatomaceous earth (Celite®) and concentrated in vacuo to provide Cap-10 as an off-white solid (2.15 g). $^1$H NMR (DMSO-$d_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. II); >98% homogeneity index; LC/MS: Anal. Calcd. for [M+H]$^+$ $C_6H_{12}NO_2$: 130.09; found 129.96.

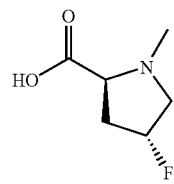

Cap-11

A mixture of (2S,4R)-4-fluoropyrrolidine-2-carboxylic acid (0.50 g, 3.8 mmol), formaldehyde (0.5 mL of 37% wt. in $H_2O$), 12N HCl (0.25 mL) and 10% Pd/C (50 mg) in methanol (20 mL) was stirred under a balloon of hydrogen for 19 hours. The reaction mixture was filtered through diatomaceous earth (Celite®) and the filtrate was concentrated in vacuo. The residue was recrystallized from isopropanol to provide the HCl salt of Cap-11 as a white solid (337.7 mg). $^1$H NMR (DMSO-$d_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Cond. II); >98% homogeneity index; LC/MS: Anal. Calcd. for [M+H]$^+$ $C_6H_{11}FNO_2$: 148.08; found 148.06.

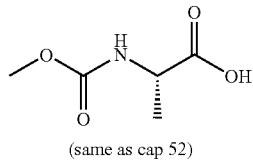

Cap-12

(same as cap 52)

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH ~2-3. The resulting solutions was extracted with ethyl acetate (3×100 mL), and the combined organic phase was dried (Na$_2$SO$_4$), filtered, and concentrated in vacuo to provide a colorless oil (2.58 g). 500 mg of this material was purified by a reverse phase HPLC ($H_2O$/methanol/TFA) to provide 150 mg of Cap-12 as a colorless oil. $^1$H NMR (DMSO-$d_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

Cap-13

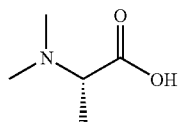

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (Celite®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-d$_6$, δ=2.5, 500 MHz) δ 12.1 (br s, 1H), 4.06 (q, J=7.4, 1H), 2.76 (s, 6H), 1.46 (d, J=7.3, 3H).

Step 2: To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; CH$_3$CN—H$_2$O-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-d$_6$) δ 7.50 (s, 5H), 5.13 (s, 1H), 3.09 (br s, 2H), 2.92-2.89 (m, 2H), 1.74 (m, 4H), 1.48 (br s, 2H). LC/MS: Anal. Calcd. for C$_{13}$H$_{17}$NO$_2$: 219; found: 220 (M+H)$^+$.

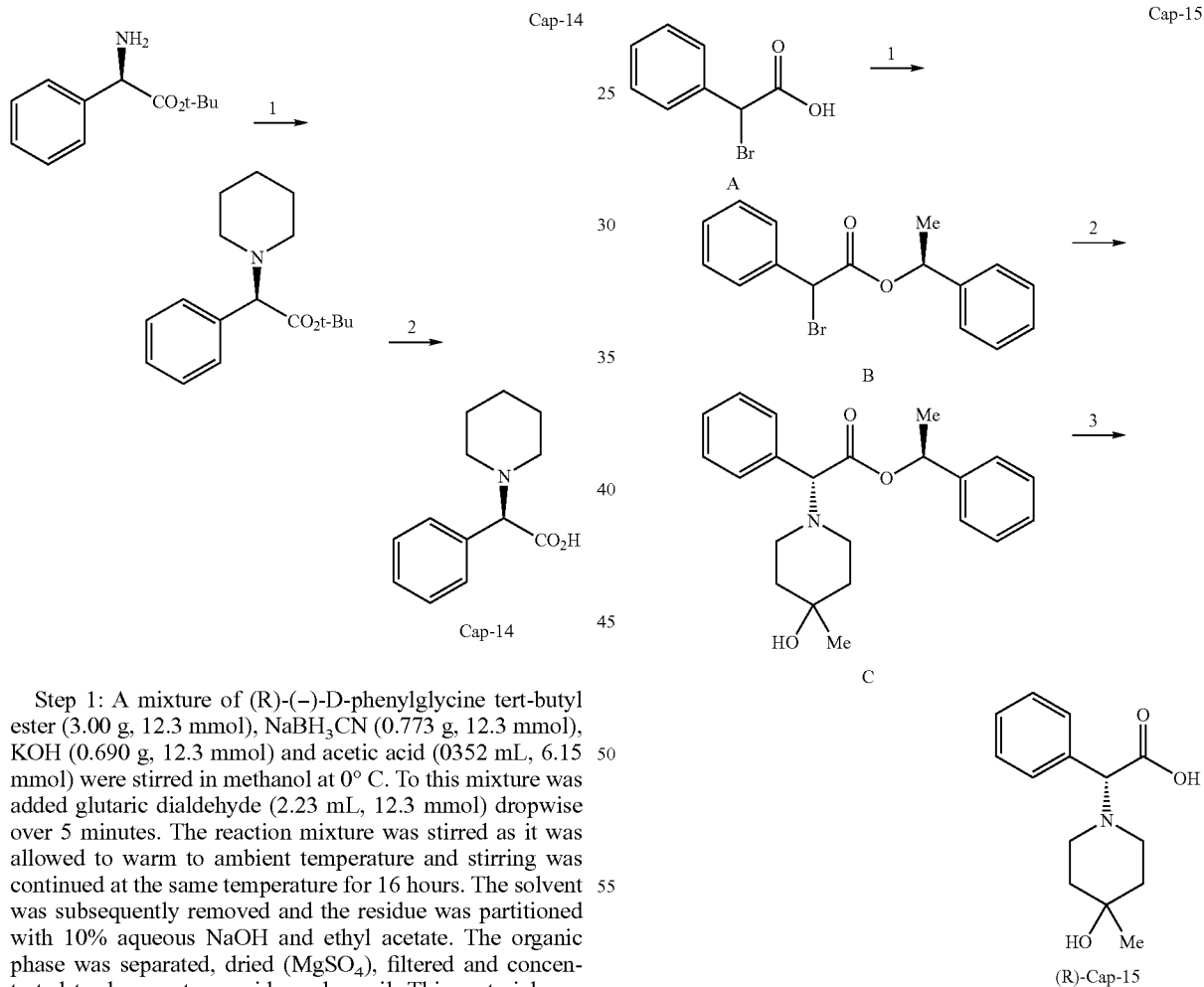

Step 1: A mixture of (R)-(−)-D-phenylglycine tert-butyl ester (3.00 g, 12.3 mmol), NaBH$_3$CN (0.773 g, 12.3 mmol), KOH (0.690 g, 12.3 mmol) and acetic acid (0352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O-0.1% TFA) to give the intermediate ester (2.70 g, 56%) as a clear oil. $^1$H NMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for C$_{17}$H$_{25}$NO$_2$: 275; found: 276 (M+H)$^+$.

Step 1: (S)-1-Phenylethyl 2-bromo-2-phenylacetate: To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed ($H_2O\times2$, brine), dried ($Na_2SO_4$), filtered, and concentrated to give a pale yellow oil. Flash chromatography ($SiO_2$/hexane-ethyl acetate, 4:1) of this oil provided the title compound (11.64 g, 73%) as a white solid. $^1H$ NMR (400 MHz, $CDCl_3$) δ 7.53-7.17 (m, 10H), 5.95 (q, J=6.6 Hz, 0.5H), 5.94 (q, J=6.6 Hz, 0.5), 5.41 (s, 0.5H), 5.39 (s, 0.5H), 1.58 (d, J=6.6 Hz, 1.5H), 1.51 (d, J=6.6 Hz, 1.5H).

Step 2: (S)-1-Phenylethyl(R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed ($H_2O\times2$, brine), dried ($MgSO_4$), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid, (S,R)-isomer: $^1H$ NMR ($CD_3OD$) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LCMS: Anal. Calcd. for $C_{22}H_{27}NO_3$: 353; found: 354 $(M+H)^+$. (S,S)-isomer: $^1H$ NMR ($CD_3OD$) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for $C_{22}H_{27}NO_3$: 353; found: 354 $(M+H)^+$.

Step 3: (R)-2-(4-Hydroxy-4-methylpiperidin-1-yl)-2-phenylacetic acid: To a solution of (S)-1-phenylethyl (R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a pale bluish solid (0.128 g, 98%). LCMS: Anal. Calcd. for $C_{14}H_{19}NO_3$: 249; found: 250 $(M+H)^+$.

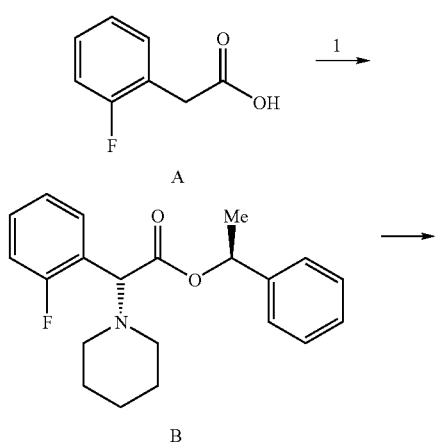

Cap-16

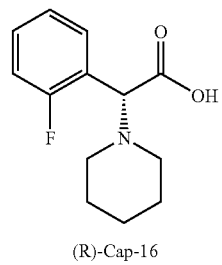

(R)-Cap-16

Step 1: (S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in $CH_2Cl_2$ (100 mL) was stirred at room temperature for 12 hours. The solvent was then concentrated and the residue partitioned with $H_2O$-ethyl acetate. The phases were separated and the aqueous layer back-extracted with ethyl acetate (2×). The combined organic phases were washed ($H_2O$, brine), dried ($Na_2SO_4$), filtered, and concentrated in vacuo. The residue was purified by silica gel chromatography (Biotage/0-20% ethyl acetate-hexane) to provide the title compound as a colorless oil (8.38 g, 92%). $^1H$ NMR (400 MHz, $CD_3OD$) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2: (R)-((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of $CBr_4$ (13.5 g, 40.7 mmol) in THF (100 mL) was added and the mixture was allowed to warm to −10° C. and stirred at this temperature for 2 hours. The reaction mixture was quenched with saturated aq. $NH_4Cl$ and the layers were separated. The aqueous layer was back-extracted with ethyl acetate (2×) and the combined organic phases were washed ($H_2O$, brine), dried ($Na_2SO_4$), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (Biotage/0-30% diethyl ether-hexane) to provide a pure mixture of diastereomers (2:1 ratio by $^1H$ NMR) as a yellow oil (2.07 g, 31%), along with unreacted starting material (2.53 g, 51%). Further chromatography of the diastereomeric mixture (Biotage/0-10% diethyl ether-toluene) provided the title compound as a colorless oil (0.737 g, 11%). $^1H$ NMR (400 MHz, $CD_3OD$) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for $C_{21}H_{24}FNO_2$: 341; found: 342 $(M+H)^+$.

Step 3: (R)-2-(2-fluorophenyl)-2-(piperidin-1-yl)acetic acid: A mixture of (R)-((S)-1-phenylethyl) 2-(2-fluorophenyl)-2-(piperidin-1-yl)acetate (0.737 g, 2.16 mmol) and 20% $Pd(OH)_2/C$ (0.070 g) in ethanol (30 mL) was hydrogenated at room temperature and atmospheric pressure ($H_2$ balloon) for 2 hours. The solution was then purged with Ar, filtered through diatomaceous earth (Celite®), and concentrated in vacuo. This provided the title compound as a colorless solid (0.503 g, 98%). $^1H$ NMR (400 MHz, $CD_3OD$) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for $C_{13}H_{16}FNO_2$: 237; found: 238 (M+H)$^+$.

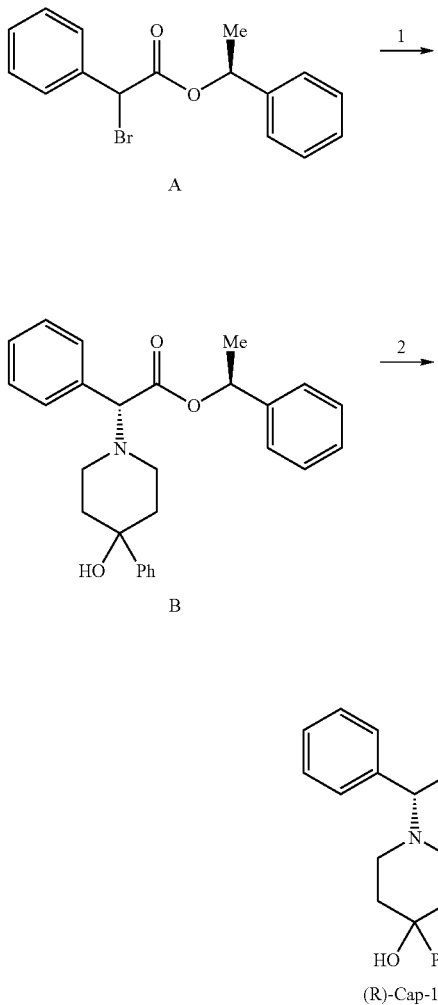

Step 1: (S)-1-Phenylethyl(R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed (H$_2$O×2, brine), dried (MgSO$_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (Chiralcel OJ-H, 30×250 mm; 20% ethanol in CO$_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, CD$_3$OD) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for $C_{27}H_{29}NO_3$: 415; found: 416 (M+H)$^+$; (S,S)-isomer: H$^1$NMR (400 MHz, CD$_3$OD) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for $C_{27}H_{29}NO_3$: 415; found: 416 (M+H)$^+$.

The following esters were prepared in similar fashion:

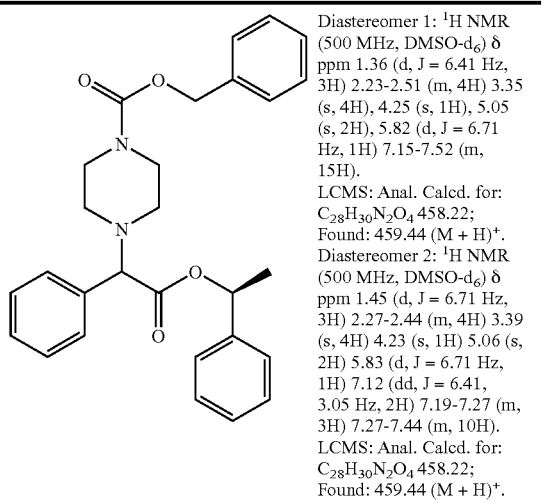

Intermediate-17a

Diastereomer 1: $^1$H NMR (500 MHz, DMSO-d$_6$) δ ppm 1.36 (d, J = 6.41 Hz, 3H) 2.23-2.51 (m, 4H) 3.35 (s, 4H), 4.25 (s, 1H), 5.05 (s, 2H), 5.82 (d, J = 6.71 Hz, 1H) 7.15-7.52 (m, 15H).
LCMS: Anal. Calcd. for: $C_{28}H_{30}N_2O_4$ 458.22; Found: 459.44 (M + H)$^+$.
Diastereomer 2: $^1$H NMR (500 MHz, DMSO-d$_6$) δ ppm 1.45 (d, J = 6.71 Hz, 3H) 2.27-2.44 (m, 4H) 3.39 (s, 4H) 4.23 (s, 1H) 5.06 (s, 2H) 5.83 (d, J = 6.71 Hz, 1H) 7.12 (dd, J = 6.41, 3.05 Hz, 2H) 7.19-7.27 (m, 3H) 7.27-7.44 (m, 10H).
LCMS: Anal. Calcd. for: $C_{28}H_{30}N_2O_4$ 458.22; Found: 459.44 (M + H)$^+$.

-continued

| | | |
|---|---|---|
| Intermediate-17b | 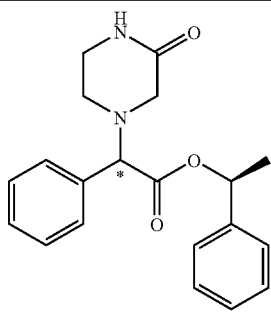 | Diastereomer 1: RT = 11.76 minutes (Cond'n II); LCMS: Anal. Calcd. for: $C_{20}H_{22}N_2O_3$ 338.16 Found: 339.39 $(M + H)^+$; Diastereomer 2: RT = 10.05 minutes (Cond'n II); LCMS: Anal. Calcd. for: $C_{20}H_{22}N_2O_3$ 338.16; Found: 339.39 $(M + H)^+$. |
| Intermediate-17c | 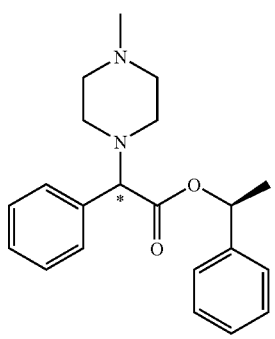 [SMILES: C[C@H](OC(=O)C(c1ccccc1)N1CCN(C)CC1)c1ccccc1] | Diastereomer 1: $T_R$ = 4.55 minutes (Cond'n I); LCMS: Anal. Calcd. for: $C_{21}H_{26}N_2O_2$ 338.20 Found: 339.45 $(M + H)^+$; Diastereomer 2: $T_R$ = 6.00 minutes (Cond'n I); LCMS: Anal. Calcd. for: $C_{21}H_{26}H_2O_2$ 338.20 Found: 339.45 $(M + H)^+$. |
| Intermediate-17d | 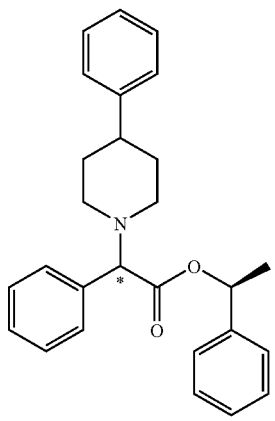 [SMILES: C[C@H](OC(=O)C(c1ccccc1)N1CCC(c2ccccc2)CC1)c1ccccc1] | Diastereomer 1: RT = 7.19 minutes (Cond'n I); LCMS: Anal. Calcd. for: $C_{27}H_{29}NO_2$ 399.22 Found: 400.48 $(M + H)^+$; Diastereomer 2: RT = 9.76 minutes (Cond'n I); LCMS: Anal. Calcd. for: $C_{27}H_{29}NO_2$ 399.22 Found: 400.48 $(M + H)^+$. |

Chiral SEC Conditions for Determining Retention Time
Condition I
Column: Chiralpak AD-H Column, 4.62×50 mm, 5 μm
Solvents: 90% CO2-10% methanol with 0.1% DEA
Temp: 35° C.
Pressure: 150 bar
Flow rate: 2.0 mL/min.
UV monitored @ 220 nm
Injection: 1.0 mg/3 mL methanol
Condition II
Column: Chiralcel OD-H Column, 4.62×50 mm, 5 μm
Solvents: 90% CO2-10% methanol with 0.1% DEA
Temp: 35° C.
Pressure: 150 bar
Flow rate: 2.0 mL/min.
UV monitored @ 220 nm
Injection: 1.0 mg/mL methanol Cap 17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LCMS: Anal. Calcd. for $C_{19}H_{21}NO_3$: 311.15; found: 312 $(M+H)^+$.

The following carboxylic acids were prepared in optically pure form in a similar fashion:

| | | |
|---|---|---|
| Cap-17a | 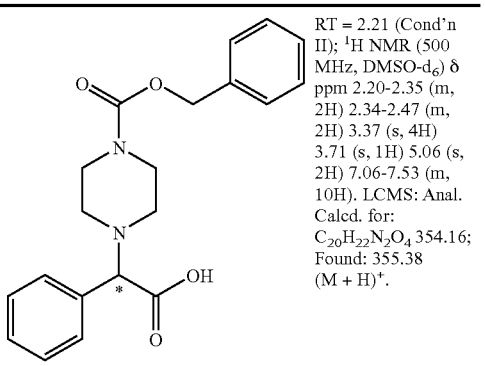 | RT = 2.21 (Cond'n II); $^1$H NMR (500 MHz, DMSO-$d_6$) δ ppm 2.20-2.35 (m, 2H) 2.34-2.47 (m, 2H) 3.37 (s, 4H) 3.71 (s, 1H) 5.06 (s, 2H) 7.06-7.53 (m, 10H). LCMS: Anal. Calcd. for: $C_{20}H_{22}N_2O_4$ 354.16; Found: 355.38 $(M + H)^+$. |
| Cap-17b | 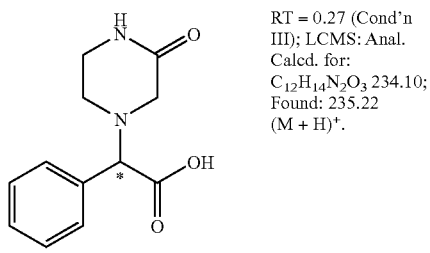 | RT = 0.27 (Cond'n III); LCMS: Anal. Calcd. for: $C_{12}H_{14}N_2O_3$ 234.10; Found: 235.22 $(M + H)^+$. |
| Cap-17c | 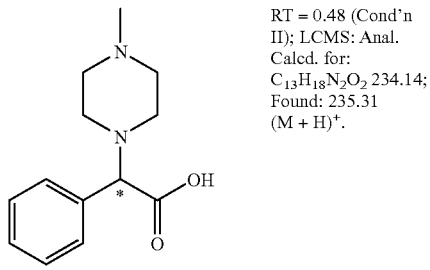 | RT = 0.48 (Cond'n II); LCMS: Anal. Calcd. for: $C_{13}H_{18}N_2O_2$ 234.14; Found: 235.31 $(M + H)^+$. |
| Cap-17d | 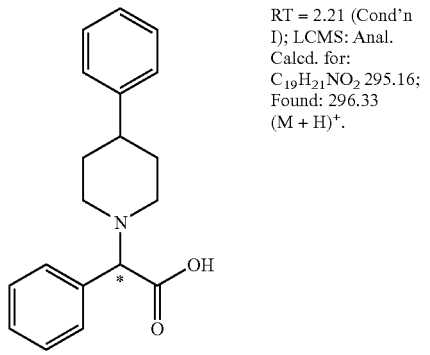 | RT = 2.21 (Cond'n I); LCMS: Anal. Calcd. for: $C_{19}H_{21}NO_2$ 295.16; Found: 296.33 $(M + H)^+$. |

LCMS Conditions for Determining Retention Time
Condition I
Column: Phenomenex-Luna 4.6×50 mm S10
Start % B=0
Final % B=100
Gradient Time=4 min
Flow Rate=4 mL/min
Wavelength=220
Solvent A=10% methanol-90% $H_2O$-0.1% TFA
Solvent B=90% methanol-10% $H_2O$-0.1% TFA
Condition II
Column: Waters-Sunfire 4.6×50 mm S5
Start % B=0
Final % B=100
Gradient Time=2 min
Flow Rate=4 mL/min
Wavelength=220
Solvent A=10% methanol-90% $H_2O$-0.1% TFA
Solvent B=90% methanol-10% $H_2O$-0.1% TFA
Condition III
Column: Phenomenex 10μ 3.0×50 mm
Start % B=0
Final % B=100
Gradient Time=2 min
Flow Rate=4 mL/min
Wavelength=220
Solvent A=10% methanol-90% $H_2O$-0.1% TFA
Solvent B=90% methanol-10% $H_2O$-0.1% TFA

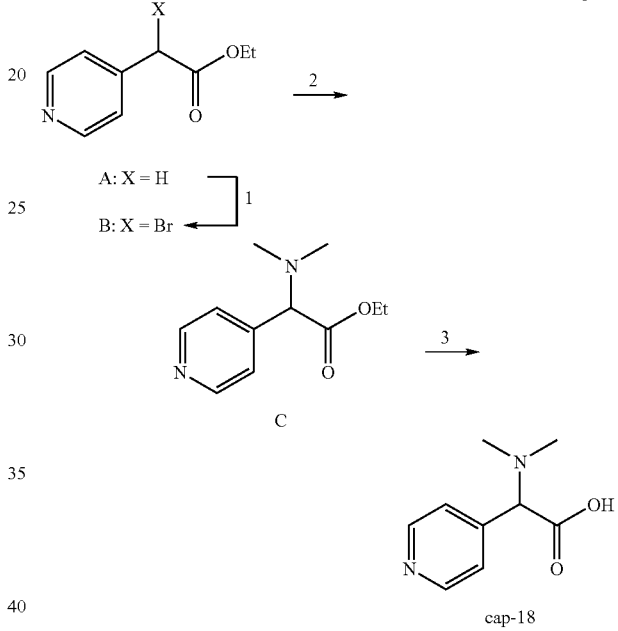

Cap-18

Step 1; (R,S)-Ethyl 2-(4-pyridyl)-2-bromoacetate: To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added $CBr_4$ (2.21 g, 6.66 mmol) and stirring was continued at −78° C. for 2 hours. The reaction mixture was then quenched with sat. aq. $NH_4Cl$ and the phases were separated. The organic phase was washed (brine), dried ($Na_2SO_4$), filtered, and concentrated in vacuo. The resulting yellow oil was immediately purified by flash chromatography ($SiO_2$/hexane-ethyl acetate, 1:1) to provide the title compound (1.40 g, 95%) as a somewhat unstable yellow oil. $^1$H NMR (400 MHz, $CDCl_3$) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for $C_9H_{10}BrNO_2$: 242, 244; found: 243, 245 $(M+H)^+$.

Step 2; (R,S)-Ethyl 2-(4-pyridyl)-2-(N,N-dimethylamino) acetate: To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (Biotage, 40+M $SiO_2$ column; 50%-100% ethyl acetate-hexane) to provide the title compound (0.539 g, 31%) as a light yellow oil. $^1$H NMR (400 MHz, CDCl$_3$) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LCMS: Anal. Calcd. for C$_{11}$H$_{16}$N$_2$O$_2$: 208; found; 209 (M+H)$^+$.

Step 3; (R,S)-2-(4-Pyridyl)-2-(N,N-dimethylamino)acetic acid: To a solution of (R,S)-ethyl 2-(4-pyridyl)-2-(N,N-dimethylamino)acetate (0.200 g, 0.960 mmol) in a mixture of THF-methanol-H$_2$O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. $^1$H NMR (400 MHz, DMSO-d$_6$) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above;

| | | |
|---|---|---|
| Cap-19 | 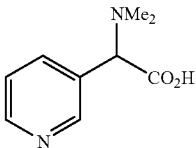 [SMILES: CN(C)C(C(=O)O)c1cccnc1] | LCMS: Anal. Calcd. for C$_9$H$_{12}$N$_2$O$_2$: 180; found: 181 (M + H)$^+$. |
| Cap-20 | 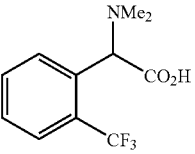 | LCMS: no ionization. $^1$H NMR (400 MHz, CD$_3$OD) δ 8.55 (d, J = 4.3 Hz, 1H), 7.84 (app t, J = 5.3 Hz, 1H), 7.61 (d, J = 7.8 Hz, 1H), 7.37 (app t, J = 5.3 Hz, 1H), 4.35 (s, 1H), 2.60 (s, 6H). |
| Cap-21 | 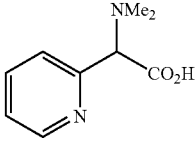 [SMILES: CN(C)C(C(=O)O)c1ccccn1] | LCMS: Anal. Calcd. for C$_9$H$_{11}$ClN$_2$O$_2$: 214, 216; found: 215, 217 (M + H)$^+$. |
| Cap-22 | 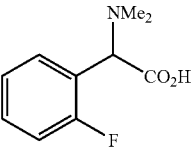 | LCMS: Anal. Calcd. for C$_{10}$H$_{12}$N$_2$O$_4$: 224; found: 225 (M + H)$^+$. |
| Cap-23 | 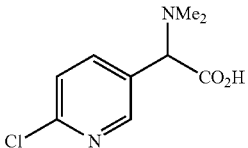 | LCMS: Anal. Calcd. for C$_{14}$H$_{15}$NO$_2$: 229; found: 230 (M + H)$^+$. |
| Cap-24 | 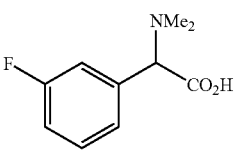 | LCMS: Anal. Calcd. for C$_{11}$H$_{12}$F$_3$NO$_2$: 247; found: 248 (M + H)$^+$. |
| Cap-25 | 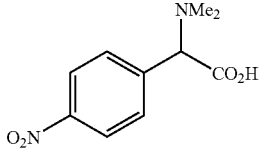 [SMILES: CN(C)C(C(=O)O)c1ccc([N+](=O)[O-])cc1] | LCMS: Anal. Calcd. for C$_{11}$H$_{12}$F$_3$NO$_2$: 247; found: 248 (M + H)$^+$. |
| Cap-26 | 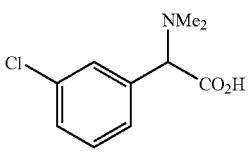 | LCMS: Anal. Calcd. for C$_{10}$H$_{12}$FNO$_2$: 197; found: 198 (M + H)$^+$. |
| Cap-27 | 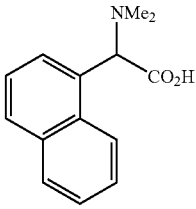 [SMILES: CN(C)C(C(=O)O)c1cccc2ccccc12] | LCMS: Anal. Calcd. for C$_{10}$H$_{12}$FNO$_2$: 247; found: 248 (M + H)$^+$. |
| Cap-28 | 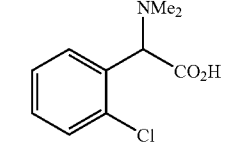 [SMILES: CN(C)C(C(=O)O)c1ccccc1Cl] | LCMS: Anal. Calcd. for C$_{10}$H$_{12}$ClNO$_2$: 213; found: 214 (M + H)$^+$. |
| Cap-29 | 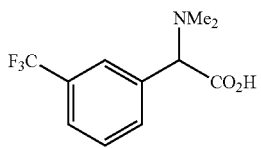 | LCMS: Anal. Calcd. for C$_{10}$H$_{12}$ClNO$_2$: 213; found: 214 (M + H)$^+$. |
| Cap-30 | 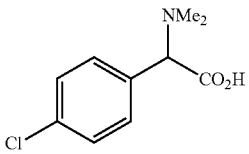 [SMILES: CN(C)C(C(=O)O)c1ccc(Cl)cc1] | LCMS: Anal. Calcd. for C$_{10}$H$_{12}$ClNO$_2$: 213; found: 214 (M + H)$^+$. |
| Cap-31 | 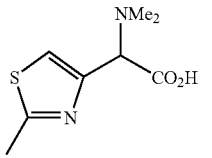 | LCMS: Anal. Calcd. for C$_8$H$_{12}$N$_2$O$_2$S: 200; found: 201 (M + H)$^+$. |
| Cap-32 | 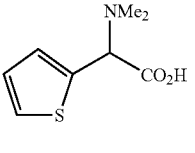 [SMILES: CN(C)C(C(=O)O)c1cccs1] | LCMS: Anal. Calcd. for C$_8$H$_{11}$NO$_2$S: 185; found: 186 (M + H)$^+$. |
| Cap-33 | 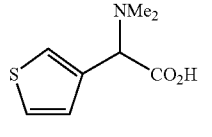 | LCMS: Anal. Calcd. for C$_8$H$_{11}$NO$_2$S: 185; found: 186 (M + H)$^+$. |
| Cap-34 | 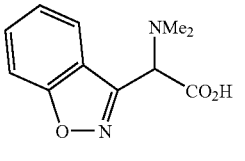 [SMILES: CN(C)C(C(=O)O)c1noc2ccccc12] | LCMS: Anal. Calcd. for C$_{11}$H$_{12}$N$_2$O$_3$: 220; found: 221 (M + H)$^+$. |

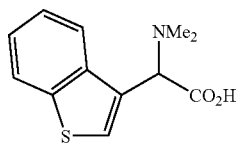 [SMILES: CN(C)C(C(=O)O)c1csc2ccccc12]

| Cap-35 | | LCMS: Anal. Calcd. for $C_{12}H_{13}NO_2S$: 235; found: 236 $(M + H)^+$. |
|---|---|---|
| Cap-36 | | LCMS: Anal. Calcd. for $C_{12}H_{14}N_2O_2S$: 250; found: 251 $(M + H)^+$. |

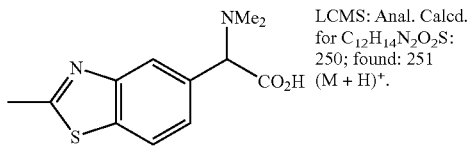

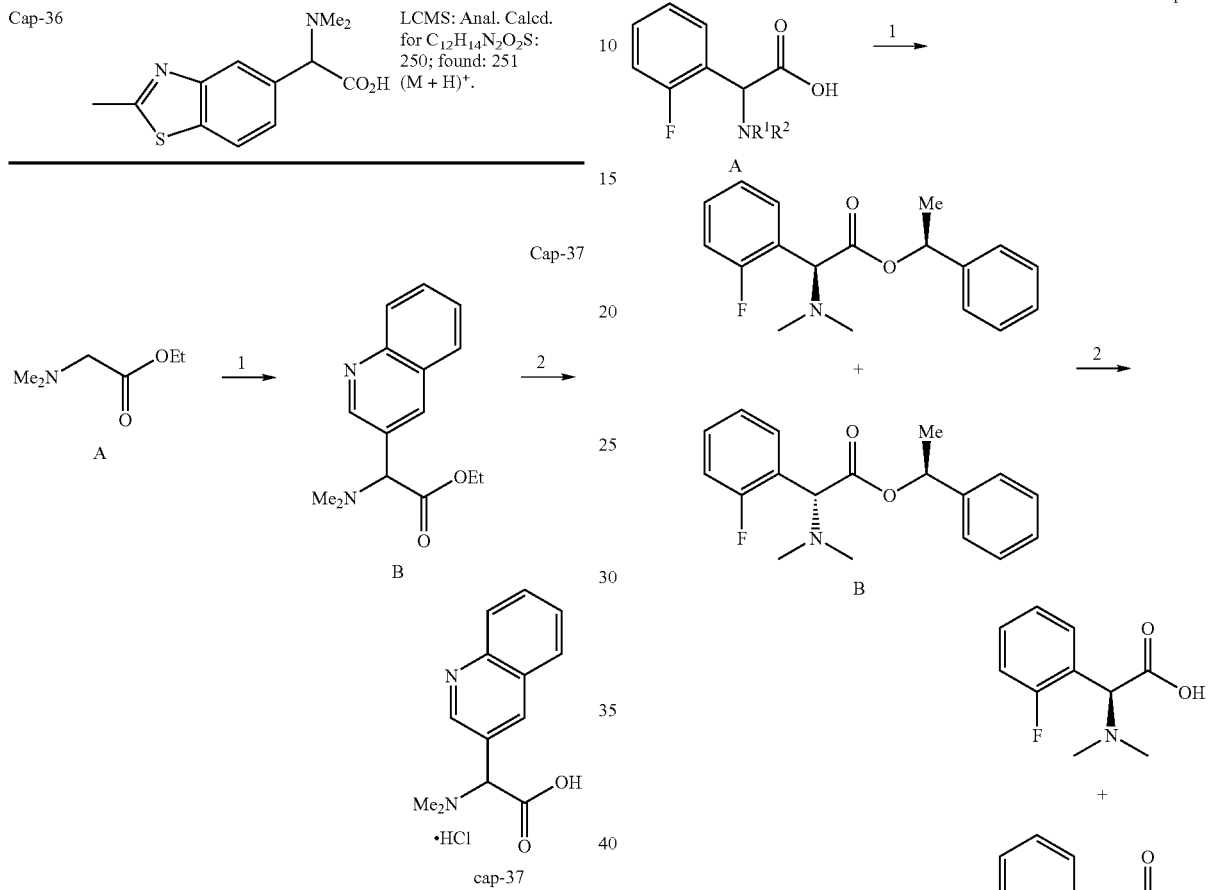

Step 1; (R,S)-Ethyl 2-(quinolin-3-yl)-2-(N,N-dimethylamino)-acetate: A mixture of ethyl N,N-dimethylaminoacetate (0.462 g, 3.54 mmol), $K_3PO_4$ (1.90 g, 8.95 mmol), $Pd(t-Bu_3P)_2$ (0.090 g, 0.176 mmol) and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1H$ NMR (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for $C_{15}H_{18}N_2O_2$: 258; found: 259 $(M+H)^+$.

Step 2; (R,S) 2-(Quinolin-3-yl)-2-(N,N-dimethylamino) acetic acid: A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LCMS: Anal. Calcd. for $C_{13}H_{14}N_2O_2$: 230; found: 231 $(M+H)^+$.

Step 1; (R)—((S)-1-phenylethyl) 2-(dimethylamino)-2-(2-fluorophenyl)acetate and (S)—((S)-1-phenylethyl) 2-(dimethylamino)-2-(2-fluorophenyl)acetate: To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried ($Na_2SO_4$), filtered, and concentrated in vacuo. The residue was purified by silica gel chromatography (Biotage/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl (R)-2-(dimethylamino)-2-(2-fluorophenyl)acetate (0.501 g, 13%) and then (S)-1-phenethyl(S)-2-(dimethylamino)-2-(2-fluorophenyl)-acetate (0.727 g, 18%), both as their TFA salts. (S,R)-isomer: ¹H NMR (400 MHz, CD₃OD) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H), LCMS: Anal. Calcd. for C₁₈H₂₀FNO₂: 301; found: 302 (M+H)⁺; (S,S)-isomer: ¹H NMR (400 MHz, CD₃OD) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for C₁₈H₂₀FNO₂: 301; found: 302 (M+H)⁺.

Step 2; (R)-2-(dimethylamino)-2-(2-fluorophenyl)acetic acid: A mixture of (R)—(S)-1-phenylethyl) 2-(dimethylamino)-2-(2-fluorophenyl)acetate TFA salt (1.25 g, 3.01 mmol) and 20% Pd(OH)₂/C (0.125 g) in ethanol (30 mL) was hydrogenated at room temperature and atmospheric pressure (H₂ balloon) for 4 hours. The solution was then purged with Ar, filtered through diatomaceous earth (Celite®), and concentrated in vacuo. This gave the title compound as a colorless solid (0.503 g, 98%). ¹H NMR (400 MHz, CD₃OD) δ 7.53-7.63 (m, 2H), 7.33-7.38 (m, 2H), 5.36 (s, 1H), 2.86 (s, 6H). LCMS: Anal. Calcd. for C₁₀H₁₂FNO₂: 197; found: 198 (M+H)⁺.

The S-isomer could be obtained from (S)—((S)-1-phenylethyl) 2-(dimethylamino)-2-(2-fluorophenyl)acetate TFA salt in similar fashion.

Cap-39

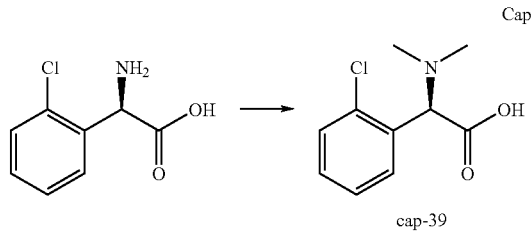

cap-39

A mixture of (R)-(2-chlorophenyl)glycine (0.300 g, 1.62 mmol), formaldehyde (35% aqueous solution, 0.80 mL, 3.23 mmol) and 20% Pd(OH)₂/C (0.050 g) was hydrogenated at room temperature and atmospheric pressure (H₂ balloon) for 4 hours. The solution was then purged with Ar, filtered through diatomaceous earth (Celite®) and concentrated in vacuo. The residue was purified by reverse-phase preparative HPLC (Primesphere C-18, 30×100 mm; CH₃CN—H₂O-0.1% TFA) to give the TFA salt of the title compound (R)-2-(dimethylamino)-2-(2-chlorophenyl)acetic acid as a colorless oil (0.290 g, 55%). NMR (400 MHz, CD₃OD) δ 7.59-7.65 (m, 2H), 7.45-7.53 (m, 2H), 5.40 (s, 1H), 2.87 (s, 6H). LCMS: Anal. Calcd. for C₁₀H₁₂ClNO₂: 213; found: 214 (M+H)⁺.

Cap-40

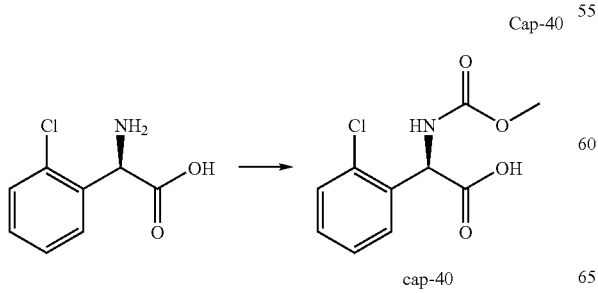

cap-40

To an ice-cold solution of (R)-(2-chlorophenyl)glycine (1.00 g, 5.38 mmol) and NaOH (0.862 g, 21.6 mmol) in H₂O (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed (H₂O, brine), dried (Na₂SO₄), filtered, and concentrated in vacuo to give the title compound (R)-2-(methoxycarbonylamino)-2-(2-chlorophenyl)acetic acid as a yellow-orange foam (1.31 g, 96%). ¹H NMR (400 MHz, CD₃OD) δ 7.39-7.43 (m, 2H), 7.29-7.31 (m, 2H), 5.69 (s, 1H), 3.65 (s, 3H). LCMS: Anal. Calcd. for C₁₀H₁₀ClNO₄: 243; found: 244 (M+H)⁺.

Cap-41

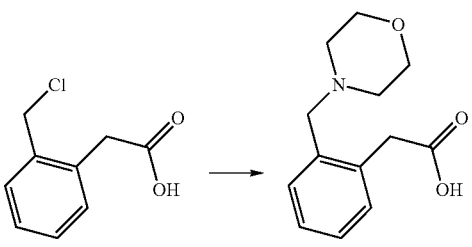

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with H₂O (2×). The aqueous phase was lyophilized and the residue was purified by silica gel chromatography (Biotage/0-10% methanol-CH₂Cl₂) to give the title compound 2-(2-(Morpholinomethyl)phenyl)acetic acid as a colorless solid (2.22 g, 87%). ¹H NMR (400 MHz, CD₃OD) δ 7.37-7.44 (m, 3H), 7.29-7.33 (m, 1H), 4.24 (s, 2H), 3.83 (br s, 4H), 3.68 (s, 2H), 3.14 (br s, 4H). LCMS: Anal. Calcd. for C₁₃H₁₇NO₃: 235; found: 236 (M+H)⁺.

The following examples were similarly prepared using the method described for Cap-41:

| Cap-42 |  | LCMS: Anal. Calcd. for C₁₄H₁₉NO₂: 233; found: 234 (M + H)⁺. |
|---|---|---|
| Cap-43 |  | LCMS: Anal. Calcd. for C₁₃H₁₇NO₂: 219; found: 220 (M + H)⁺. |

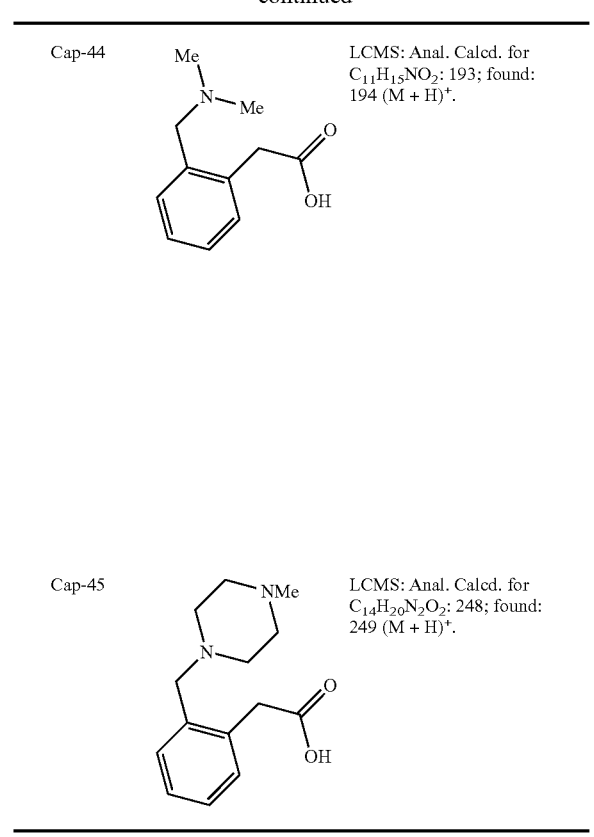

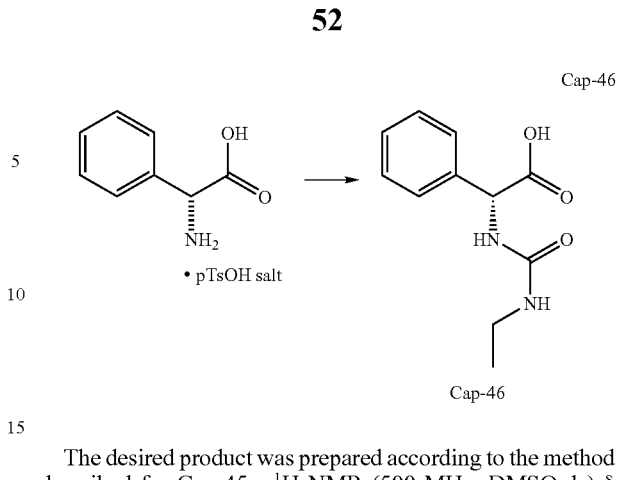

The desired product was prepared according to the method described for Cap-45a. $^1$H NMR (500 MHz, DMSO-d$_6$) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for C$_{11}$H$_{14}$N$_2$O$_3$ 222.10 found 223.15 (M+H)$^+$. HPLC XTERRA C-18 3.0×506 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=0.87 min, 90% homogeneity index.

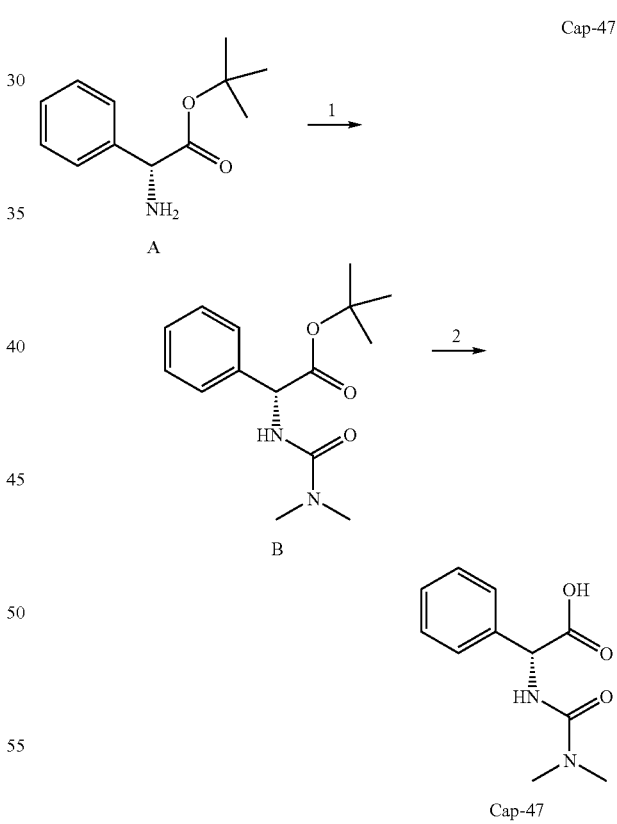

HMDS (1.85 mL, 8.77 mmol) was added to a suspension of (R)-2-amino-2-phenylacetic acid p-toluenesulfonate (2.83 g, 8.77 mmol) in CH$_2$Cl$_2$ (10 mL) and the mixture was stirred at room temperature for 30 minutes. Methyl isocyanate (0.5 g, 8.77 mmol) was added in one portion stirring continued for 30 minutes. The reaction was quenched by addition of H$_2$O (5 mL) and the resulting precipitate was filtered, washed with H$_2$O and n-hexanes, and dried under vacuum. (R)-2-(3-methylureido)-2-phenylacetic acid (1.5 g; 82%). was recovered as a white solid and it was used without further purification. $^1$H NMR (500 MHz, DMSO-d$_5$) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for C$_{10}$H$_{12}$N$_2$O$_3$ 208.08 found 209.121 (M+H)$^+$; HPLC Phenomenex C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

Step 1; (R)-tert-butyl 2-(3,3-dimethylureido)-2-phenylacetate: To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with H₂O, 1N aq. HCl and brine, dried (MgSO₄), filtered and concentrated under reduced pressure. (R)-tort-butyl 2-(3,3-dimethylureido)-2-phenylacetate was obtained as a white solid (0.86 g; 75%) and used without further purification. ¹H NMR (500 MHz, DMSO-d₆) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for $C_{15}H_{22}N_2O_3$ 278.16 found 279.23 (M+H)⁺; HPLC Phenomenex LUNA C-18 4.6×50 mm, 0 to 100% B over 4 minutes, 1 minute hold time, A=90% water, 10% methanol, 0.1% TFA, B-10% water, 90% methanol, 0.1% TFA, RT=2.26 min, 97% homogeneity index.

Step 2; (R)-2-(3,3-dimethylureido)-2-phenylacetic acid: To a stirred solution of ((R)-tert-butyl 2-(3,3-dimethylureido)-2-phenylacetate (0.86 g, 3.10 mmol) in CH₂Cl₂ (250 mL) was added TFA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. ¹H NMR (500 MHz, DMSO-d₆) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LCMS: Anal. Calcd. for $C_{11}H_{14}N_2O_3$: 222.24; found: 223.21 (M+H)⁺. HPLC XTERRA C-18 3.0×50 mm, 0 to 100% B over 2 minutes, 1 minute hold time, A=90% water, 10% methanol, 0.2% H₃PO₄, B=10% water, 90% methanol, 0.2% H₃PO₄, RT=0.75 min, 93% homogeneity index.

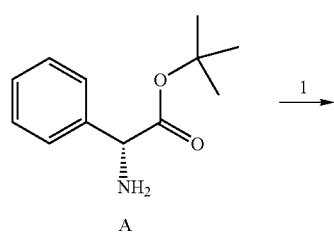

Cap-48

A

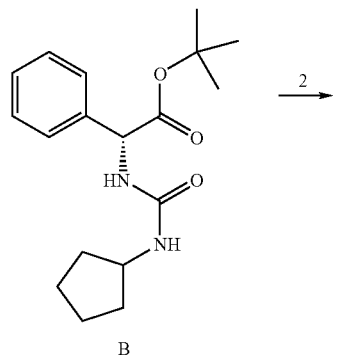

B

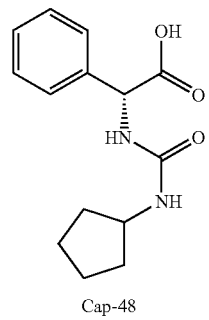

Cap-48

Step 1; (R)-tert-butyl 2-(3-cyclopentylureido)-2-phenylacetate: To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with H₂O and brine, dried (MgSO₄), filtered, and concentrated under reduced pressure. (R)-tert-butyl 2-(3-cyclopentylureido)-2-phenylacetate was obtained as an opaque oil (1.32 g; 100%) and used without further purification. ¹H NMR (500 MHz, CD₃Cl-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LCMS: Anal. Calcd. for $C_{18}H_{26}N_2O_3$ 318.19 found 319.21 (M+H)⁺; HPLC XTERRA C-18 3.0×50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2; (R)-2-(3-cyclopentylureido)-2-phenylacetic acid: To a stirred solution of (R)-tert-butyl 2-(3-cyclopentylureido)-2-phenylacetate (1.31 g, 4.10 mmol) in CH₂Cl₂ (25 mL) was added TFA (4 mL) and trietheylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). ¹H NMR (500 MHz, DMSO-d₆) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for $C_{14}H_{18}N_2O_3$: 262.31; found: 263.15 (M+H)⁺. HPLC XTERRA C-18 3.0×50 mm, 0 to 100% B over 2 minutes, 1 minute hold time, A=90% water, 10% methanol, 0.2% H₃PO₄, B=10% water, 90% methanol, 0.2% H₃PO₄, RT=1.24 min, 100% homogeneity index.

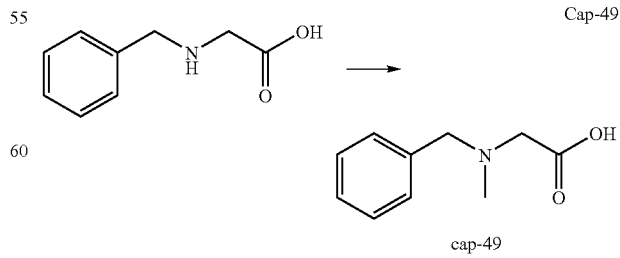

Cap-49 cap-49

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (Xterra 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl (methyl)-amino)acetic acid as its TFA salt (723 mg, 33%) as a colorless wax. $^1$H NMR (300 MHz, DMSO-$d_6$) δ ppm 2.75 (s, 3H) 4.04 (s, 2H) 4.34 (s, 2H) 7.29-7.68 (m, 5H). LCMS: Anal. Calcd. for: $C_{10}H_{13}NO_2$ 179.09; Found: 180.20 $(M+H)^+$.

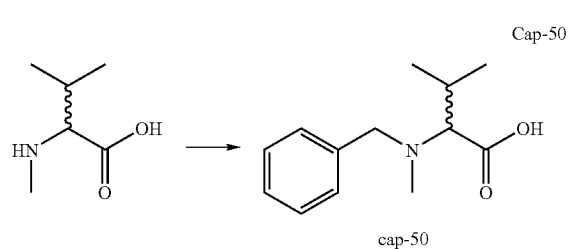

cap-50

To a stirred solution of 3-methyl-2-(methylamino)butanoic acid (0.50 g, 3.81 mmol) in water (30 mL) was added $K_2CO_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (Xterra 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1$H NMR (500 MHz, DMSO-$d_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LCMS: Anal. Calcd. for: $C_{13}H_{19}NO_2$ 221.14; Found: 222.28 $(M+H)^+$.

Cap-51

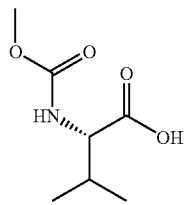

$Na_2CO_3$ (1.83 g, 17.2 mmol) was added to NaOH (33 mL of 1M/$H_2O$, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with $CH_2Cl_2$ (50 mL, 3×). The organic phase was dried (MgSO$_4$) and evaporated in vacuo to afford Cap-51 as a white solid (6 g). $^1$H NMR for the dominant rotamer (DMSO-$d_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for $[M+H]^+$ $C_7H_{14}NO_4$: 176.0923; found 176.0922.

Cap 51 (alternate route)

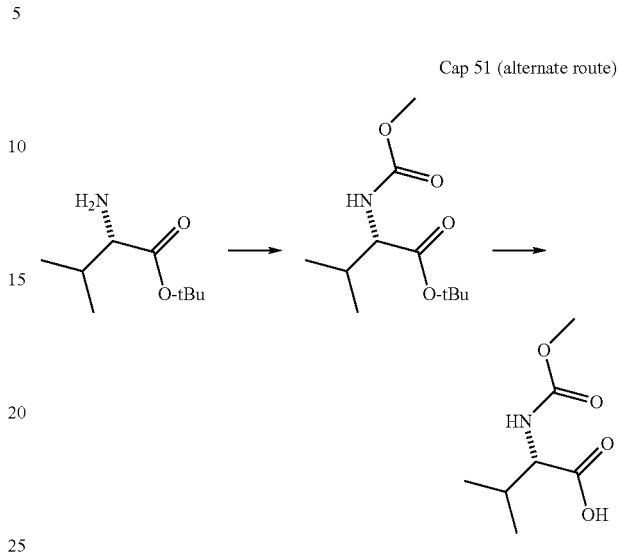

DIEA (137.5 mL, 0.766 mol) was added to a suspension of (S)-tert-butyl 2-amino-3-methylbutanoate hydrochloride (75.0 g, 0.357 mol) in THF (900 mL), and the mixture was cooled to 0° C. (ice/water bath). Methyl chloroformate (29.0 mL, 0.375 mol) was added dropwise over 45 min, the cooling bath was removed and the heterogeneous mixture was stirred at ambient temperature for 3 h. The solvent was removed under diminished pressure and the residue partitioned between EtOAc and water (1 L each). The organic layer was washed with $H_2O$ (1 L) and brine (1 L), dried (MgSO$_4$), filtered and concentrated under diminished pressure. The crude material was passed through a plug of silica gel (1 kg), eluting with hexanes (4 L) and 15:85 EtOAc/hexanes (4 L) to afford (S)-tert-butyl 2-(methoxycarbonylamino)-3-methylbutanoate as a clear oil (82.0 g, 99% yield). $^1$H-NMR (500 MHz, DMSO-$d_6$, δ=2.5 ppm) 7.34 (d, J=8.6, 1H), 3.77 (dd, J=8.6, 6.1, 1H), 3.53 (s, 3H), 1.94-2.05 (m, 1H), 1.39 (s, 9H), 0.83-0.92 (m, 6H). $^{13}$C-NMR (126 MHz, DMSO-$d_6$, δ=39.2 ppm) 170.92, 156.84, 80.38, 60.00, 51.34, 29.76, 27.62, 18.92, 17.95. LC/MS: $[M+Na]^+$ 254.17.

Trifluoroacetic acid (343 mL, 4.62 mol) and Et$_3$SiH (142 mL, 0.887 mol) were added sequentially to a solution of (S)-tort-butyl 2-(methoxycarbonylamino)-3-methylbutanoate (82.0 g, 0.355 mol) in $CH_2Cl_2$ (675 mL), and the mixture was stirred at ambient temperature for 4 h. The volatile component was removed under diminished pressure and the resultant oil triturated with petroleum ether (600 mL) to afford a white solid, which was filtered and washed with hexanes (500 mL) and petroleum ether (500 mL). Recrystallization from EtOAc/petroleum ether afforded Cap-51 as white flaky crystals (54.8 g, 88% yield). MP=108.5-109.5° C. $^1$H NMR (500 MHz, DMSO-$d_6$, δ=2.5 ppm) 12.52 (s, 1H), 7.31 (d, J=8.6, 1H), 3.83 (dd, J=8.6, 6.1, 1H), 3.53 (s, 3H), 1.94-2.07 (m, 1H), 0.86 (dd, J=8.9, 7.0, 6H). $^{13}$C NMR (126 MHz, DMSO-$d_6$, δ=39.2 ppm) 173.30, 156.94, 59.48, 51.37, 29.52, 19.15, 17.98. LC/MS: $[M+H]^+$=176.11. Anal. Calcd. for $C_7H_{13}NO_4$: C, 47.99; H, 7.48; N, 7.99. Found: C, 48.17; H, 7.55; N, 7.99. Optical Rotation: $[α]_D$=−4.16 (12.02 mg/mL; MeOH). Optical purity: >99.5% ee. Note: the optical purity assessment was made on the methyl ester derivative of Cap-51, which was prepared under a standard TMSCHN$_2$ (benzene/MeOH) esterification protocol. HPLC analytical conditions: column, ChiralPak AD-H (4.6×250 mm, 5 µm); solvent, 95% heptane/5% IPA (isocratic); flow rate, 1 mL/min; temperature, 35° C.; UV monitored at 205 nm.

[Note: Cap 51 could also be purchased from Flamm.]

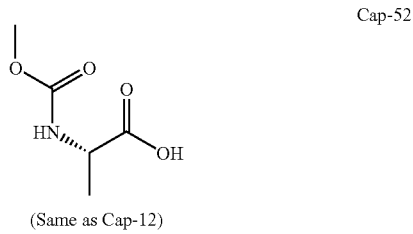

Cap-52

(Same as Cap-12)

Cap-52 was synthesized from L-alanine according to the procedure described for the synthesis of Cap-51. For characterization purposes, a portion of the crude material was purified by a reverse phase HPLC (H$_2$O/methanol/TFA) to afford Cap-52 as a colorless viscous oil. $^1$H NMR (DMSO-d$_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to -64 were prepared from appropriate starting materials according to the procedure described for the synthesis of Cap-51, with noted modifications if any.

| | | |
|---|---|---|
| Cap-53a: (R) Cap-53b: (S) | 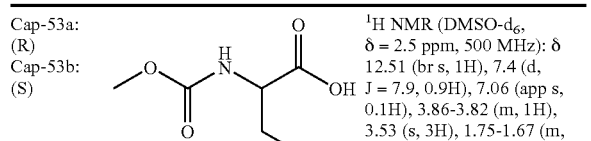 | $^1$H NMR (DMSO-d$_6$, δ = 2.5 ppm, 500 MHz): δ 12.51 (br s, 1H), 7.4 (d, J = 7.9, 0.9H), 7.06 (app s, 0.1H), 3.86-3.82 (m, 1H), 3.53 (s, 3H), 1.75-1.67 (m, 1H), 1.62-1.54 (m, 1H), 0.88 (d, J = 7.3, 3H). RT = 0.77 minutes (Cond. 2); LC/MS: Anal. Calcd. for [M + Na]$^+$ C$_6$H$_{11}$NNaO$_4$: 184.06; found 184.07. HRMS Calcd. for [M + Na]$^+$ C$_6$H$_{11}$NNaO$_4$: 184.0586; found 184.0592. |
| Cap-54a: (R) Cap-54b: (S) | 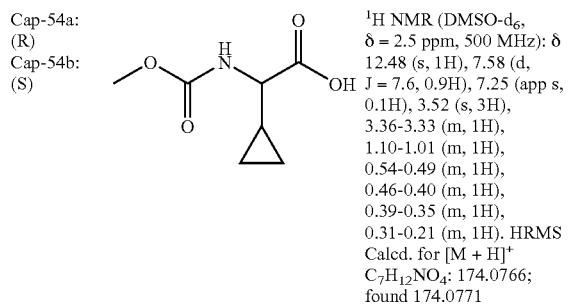 | $^1$H NMR (DMSO-d$_6$, δ = 2.5 ppm, 500 MHz): δ 12.48 (s, 1H), 7.58 (d, J = 7.6, 0.9H), 7.25 (app s, 0.1H), 3.52 (s, 3H), 3.36-3.33 (m, 1H), 1.10-1.01 (m, 1H), 0.54-0.49 (m, 1H), 0.46-0.40 (m, 1H), 0.39-0.35 (m, 1H), 0.31-0.21 (m, 1H). HRMS Calcd. for [M + H]$^+$ C$_7$H$_{12}$NO$_4$: 174.0766; found 174.0771 |
| Cap-55 | 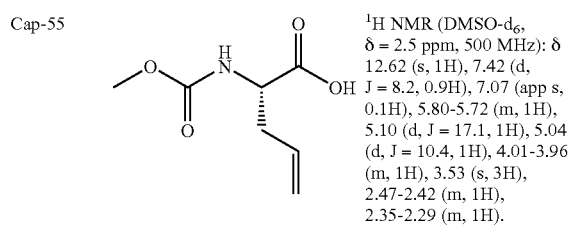 | $^1$H NMR (DMSO-d$_6$, δ = 2.5 ppm, 500 MHz): δ 12.62 (s, 1H), 7.42 (d, J = 8.2, 0.9H), 7.07 (app s, 0.1H), 5.80-5.72 (m, 1H), 5.10 (d, J = 17.1, 1H), 5.04 (d, J = 10.4, 1H), 4.01-3.96 (m, 1H), 3.53 (s, 3H), 2.47-2.42 (m, 1H), 2.35-2.29 (m, 1H). |

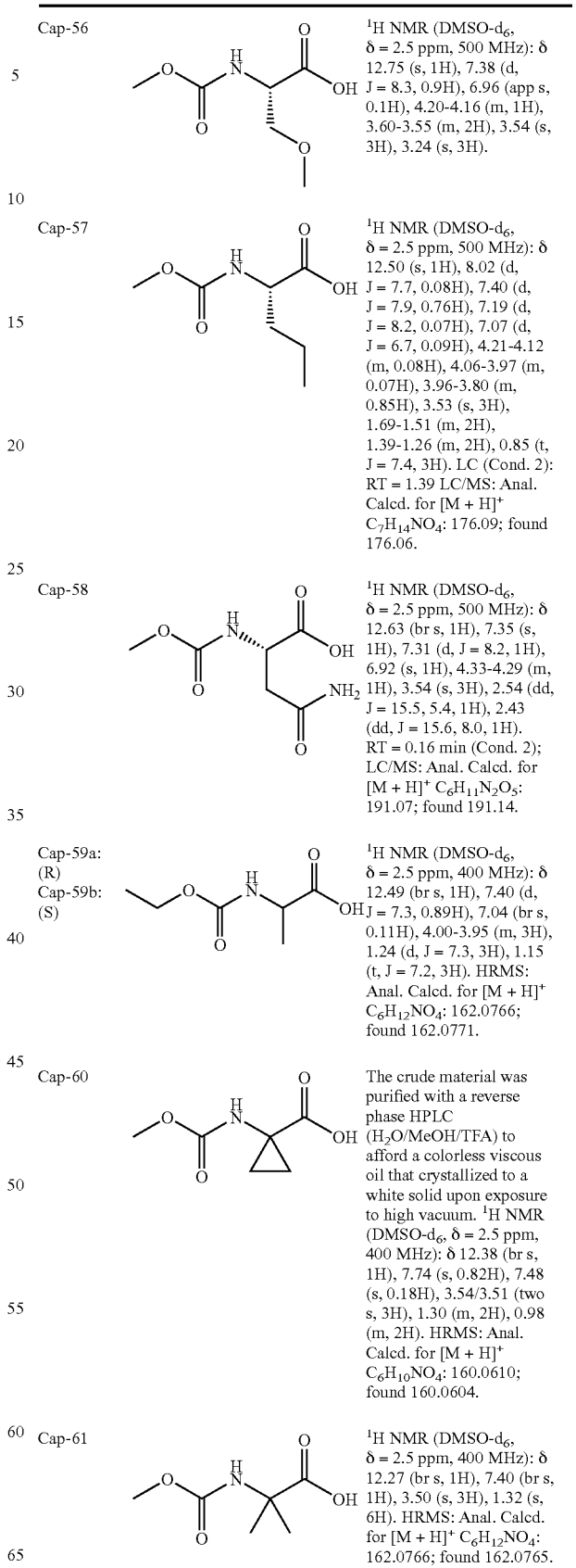

| | | |
|---|---|---|
| Cap-56 | | $^1$H NMR (DMSO-d$_6$, δ = 2.5 ppm, 500 MHz): δ 12.75 (s, 1H), 7.38 (d, J = 8.3, 0.9H), 6.96 (app s, 0.1H), 4.20-4.16 (m, 1H), 3.60-3.55 (m, 2H), 3.54 (s, 3H), 3.24 (s, 3H). |
| Cap-57 | | $^1$H NMR (DMSO-d$_6$, δ = 2.5 ppm, 500 MHz): δ 12.50 (s, 1H), 8.02 (d, J = 7.7, 0.08H), 7.40 (d, J = 7.9, 0.76H), 7.19 (d, J = 8.2, 0.07H), 7.07 (d, J = 6.7, 0.09H), 4.21-4.12 (m, 0.08H), 4.06-3.97 (m, 0.07H), 3.96-3.80 (m, 0.85H), 3.53 (s, 3H), 1.69-1.51 (m, 2H), 1.39-1.26 (m, 2H), 0.85 (t, J = 7.4, 3H). LC (Cond. 2): RT = 1.39 LC/MS: Anal. Calcd. for [M + H]$^+$ C$_7$H$_{14}$NO$_4$: 176.09; found 176.06. |
| Cap-58 | | $^1$H NMR (DMSO-d$_6$, δ = 2.5 ppm, 500 MHz): δ 12.63 (br s, 1H), 7.35 (s, 1H), 7.31 (d, J = 8.2, 1H), 6.92 (s, 1H), 4.33-4.29 (m, 1H), 3.54 (s, 3H), 2.54 (dd, J = 15.5, 5.4, 1H), 2.43 (dd, J = 15.6, 8.0, 1H). RT = 0.16 min (Cond. 2); LC/MS: Anal. Calcd. for [M + H]$^+$ C$_6$H$_{11}$N$_2$O$_5$: 191.07; found 191.14. |
| Cap-59a: (R) Cap-59b: (S) | | $^1$H NMR (DMSO-d$_6$, δ = 2.5 ppm, 400 MHz): δ 12.49 (br s, 1H), 7.40 (d, J = 7.3, 0.89H), 7.04 (br s, 0.11H), 4.00-3.95 (m, 3H), 1.24 (d, J = 7.3, 3H), 1.15 (t, J = 7.2, 3H). HRMS: Anal. Calcd. for [M + H]$^+$ C$_6$H$_{12}$NO$_4$: 162.0766; found 162.0771. |
| Cap-60 | | The crude material was purified with a reverse phase HPLC (H$_2$O/MeOH/TFA) to afford a colorless viscous oil that crystallized to a white solid upon exposure to high vacuum. $^1$H NMR (DMSO-d$_6$, δ = 2.5 ppm, 400 MHz): δ 12.38 (br s, 1H), 7.74 (s, 0.82H), 7.48 (s, 0.18H), 3.54/3.51 (two s, 3H), 1.30 (m, 2H), 0.98 (m, 2H). HRMS: Anal. Calcd. for [M + H]$^+$ C$_6$H$_{10}$NO$_4$: 160.0610; found 160.0604. |
| Cap-61 | | $^1$H NMR (DMSO-d$_6$, δ = 2.5 ppm, 400 MHz): δ 12.27 (br s, 1H), 7.40 (br s, 1H), 3.50 (s, 3H), 1.32 (s, 6H). HRMS: Anal. Calcd. for [M + H]$^+$ C$_6$H$_{12}$NO$_4$: 162.0766; found 162.0765. |

| Cap | Structure | Notes |
|---|---|---|
| Cap-62 | 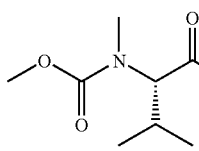 | ¹H NMR (DMSO-d₆, δ = 2.5 ppm, 400 MHz): δ 12.74 (br s, 1H), 4.21 (d, $J$ = 10.3, 0.6H), 4.05 (d, $J$ = 10.0, 0.4H), 3.62/3.60 (two singlets, 3H), 3.0 (s, 3H), 2.14-2.05 (m, 1H), 0.95 (d, $J$ = 6.3, 3H), 0.81 (d, $J$ = 6.6, 3H). LC/MS: Anal. Calcd. for [M − H]⁻ $C_8H_{14}NO_4$: 188.09; found 188.05. |
| Cap-63 | 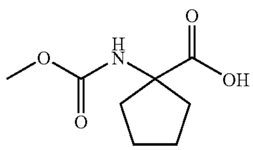 | [Note: the reaction was allowed to run for longer than what was noted for the general procedure.] ¹H NMR (DMSO-d₆, δ = 2.5 ppm, 400 MHz): 12.21 (br s, 1H), 7.42 (br s, 1H), 3.50 (s, 3H), 2.02-1.85 (m, 4H), 1.66-1.58 (m, 4H). LC/MS: Anal. Calcd. for [M + H]⁺ $C_8H_{14}NO_4$: 188.90; found 188.19. |
| Cap-64 | 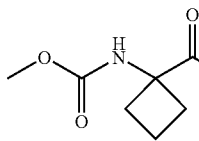 | [Note: the reaction was allowed to run for longer than what was noted for the general procedure.] ¹H NMR (DMSO-d₆, δ = 2.5 ppm, 400 MHz): 12.35 (br s, 1H), 7.77 (s, 0.82H), 7.56/7.52 (overlapping br s, 0.18H), 3.50 (s, 3H), 2.47-2.40 (m, 2H), 2.14-2.07 (m, 2H), 1.93-1.82 (m, 2H). |

Cap-65

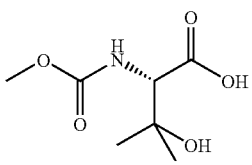

Methyl chloroformate (0.65 mL, 8.39 mmol) was added dropwise over 5 min to a cooled (ice-water) mixture of $Na_2CO_3$ (0.449 g, 4.23 mmol), NaOH (8.2 mL of 1M/$H_2O$, 8.2 mmol) and (S)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with $CH_2Cl_2$, and the aqueous phase was cooled with ice-water bath and acidified with concentrated HCl to a pH region of 1-2. The volatile component was removed in vacuo and the residue was taken up in a 2:1 mixture of $MeOH/CH_2Cl_2$ (15 mL) and filtered, and the filterate was rotervaped to afford Cap-65 as a white semi-viscous foam (1.236 g). ¹H NMR (DMSO-d₆, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and -67 were prepared from appropriate commercially available starting materials by employing the procedure described for the synthesis of Cap-65.

Cap-66

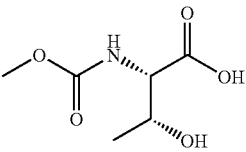

¹H NMR (DMSO-d₆, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

Cap-67

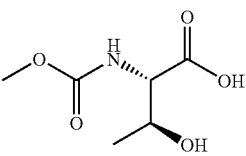

¹H NMR (DMSO-d₆, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted].

Cap-68

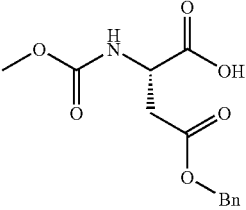

Methyl chloroformate (0.38 ml, 4.9 mmol) was added drop-wise to a mixture of 1N NaOH (aq) (9.0 ml, 9.0 mmol), 1M $NaHCO_3$ (aq) (9.0 ml, 9.0 mol), L-aspartic acid β-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH ~1-2, and extracted with ethyl acetate (3×50 ml). The combined organic layers were washed with brine, dried ($Na_2SO_4$), filtered, and concentrated in vacuo to afford Cap-68 as a light yellow oil (1.37 g; mass is above theoretical yield, and the product was used without further purification). ¹H NMR (DMSO-d₆, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC/MS: Anal. Calcd. For [M+H]⁺ $C_{13}H_{16}NO_6$: 282.10; found 282.12.

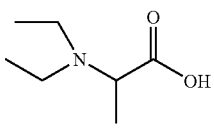

Cap-69a and -69b

Cap-69a: (R)-enantiomer
Cap-69b: (S)-enantiomer

NaCNBH$_3$ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a Dowex® 50WX8-100 ion-exchange resin (column was washed with water, and the compound was eluted with dilute NH$_4$OH, prepared by mixing 18 ml of NH$_4$OH and 282 ml of water) to afford Cap-69 (2.0 g) as an off-white soft hygroscopic solid. $^1$H NMR (DMSO-d$_6$, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to -74x were prepared according to the procedure described for the synthesis of Cap-69 by employing appropriate starting materials.

| | | |
|---|---|---|
| Cap-70a: (R) Cap-70b: (S) | ![structure] | $^1$H NMR (DMSO-d$_6$, δ = 2.5 ppm, 400 MHz): δ 3.42 (q, J = 7.1, 1H), 2.68-2.60 (m, 4H), 1.53-1.44 (m, 4H), 1.19 (d, J = 7.3, 3H), 0.85 (t, J = 7.5, 6H). LC/MS: Anal. Calcd. for [M + H]$^+$ C$_9$H$_{20}$NO$_2$: 174.15; found 174.13. |
| Cap-71a: (R) Cap-71b: (S) | ![structure] | $^1$H NMR (DMSO-d$_6$, δ = 2.5 ppm, 500 MHz): δ 3.18-3.14 (m, 1H), 2.84-2.77 (m, 2H), 2.76-2.68 (m, 2H), 1.69-1.54 (m, 2H), 1.05 (t, J = 7.2, 6H), 0.91 (t, J = 7.3, 3H). LC/MS: Anal. Calcd. for [M + H]$^+$ C$_8$H$_{18}$NO$_2$: 160.13; found 160.06. |
| Cap-72 | ![structure] | $^1$H NMR (DMSO-d$_6$, δ = 2.5 ppm, 400 MHz): δ 2.77-2.66 (m, 3H), 2.39-2.31 (m, 2H), 1.94-1.85 (m, 1H), 0.98 (t, J = 7.1, 6H), 0.91 (d, J = 6.5, 3H), 0.85 (d, J = 6.5, 3H). LC/MS: Anal. Calcd. for [M + H]$^+$ C$_9$H$_{20}$NO$_2$: 174.15; found 174.15. |
| Cap-73 | ![structure] | $^1$NMR (DMSO-d$_6$, δ = 2.5 ppm, 500 MHz): δ 9.5 (br s, 1H), 3.77 (dd, J = 10.8, 4.1, 1H), 3.69-3.61 (m, 2H), 3.26 (s, 3H), 2.99-2.88 (m, 4H), 1.13 (t, J = 7.2, 6H). |
| Cap-74 | ![structure] | $^1$NMR (DMSO-d$_6$, δ = 2.5 ppm, 500 MHz): δ 7.54 (s, 1H), 6.89 (s, 1H), 3.81 (t, J = 6.6, k, 1H), 2.82-2.71 (m, 4H), 2.63 (dd, J = 15.6, 7.0 1H), 2.36 (dd, J = 15.4, 6.3, 1H), 1.09 (t, J = 7.2, 6H). RT = 0.125 minutes (Cond. 2); LC/MS: Anal. Calcd. for [M + H]$^+$ C$_8$H$_{17}$N$_2$O$_3$: 189.12; found 189.13. |
| Cap-74x | ![structure] | LC/MS: Anal. Calcd. for [M + H]$^+$ C$_{10}$H$_{22}$NO$_2$: 188.17; found 188.21 |

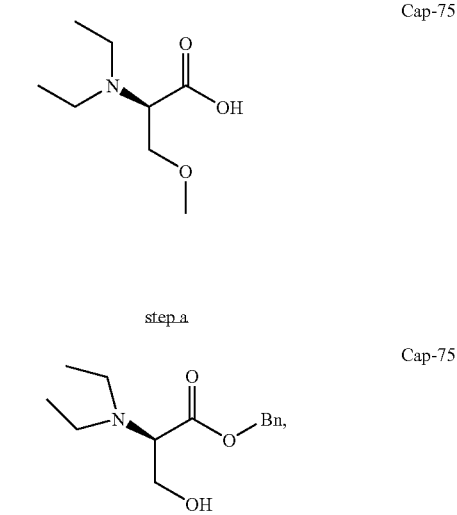

Cap-75 step a

Cap-75

NaBH$_3$CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H$_2$O/TFA) to afford the TFA salt of (R)-benzyl 2-(diethylamino)-3-hydroxypropanoate as a colorless viscous oil (1.9 g). $^1$H NMR (DMSO-d$_6$, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21

(m, 4H), 1.23 (t, J=7.2, 6H). LC/MS (Cond. 2): RT=1.38 min; LC/MS: Anal. Calcd. for [M+H]$^+$ C$_{14}$H$_{22}$NO$_3$: 252.16; found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 μL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH$_3$/Methanol. Removal of the volatile component in vacuo afforded Cap-75, contaminated with (R)-2-(diethylamino)-3-hydroxypropanoic acid, as a yellow semisolid (100 mg). The product was used as is without further purification.

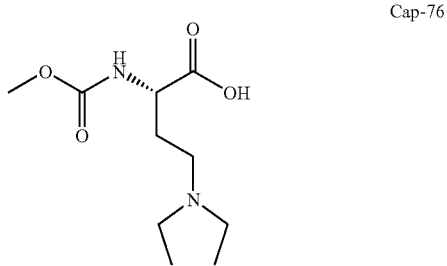 [SMILES: CCN(CC)CC[C@H](NC(=O)OC)C(=O)O]

Cap-76

NaCNBH$_3$ (1.60 g, 24.2 mmol) was added in batches to a chilled (~15° C.) water/MeOH (12 mL each) solution of (S)-4-amino-2-(tert-butoxycarbonylamino)butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with Dowex® 50WX8-100 ion-exchange resin (column was washed with water and the compound was eluted with dilute NH$_4$OH, prepared from 18 ml of NH$_4$OH and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na$_2$CO$_3$ (0.243 g, 2.29 mmol), NaOH (4.6 mL of 1M/H$_2$O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH$_2$Cl$_2$ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M NH$_3$/MeOH) to afford impure Cap-76 as an off-white solid (704 mg). $^1$H NMR (MeOH-d$_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]$^+$ C$_{10}$H$_{21}$N$_2$O$_4$: 233.15; found 233.24.

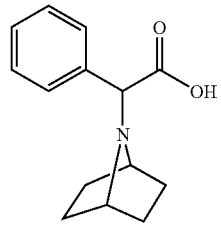

Cap-77a and -77b

Cap-77a: enantiomer-1
Cap-77b: enantiomer-2

The synthesis of Cap-77 was conducted according to the procedure described for Cap-7 by using 7-azabicyclo[2.2.1] heptane for the SN$_2$ displacement step, and by effecting the enantiomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% CO$_2$-10% EtOH at 70 mL/min, and a temperature of 35° C. to provide 124.5 mg of enantiomer-1 and 133.8 mg of enantiomer-2. These benzyl esters were hydrogenolysed according to the preparation of Cap-7 to provide Cap-77: $^1$H NMR (DMSO-d$_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC/MS: Anal. Calcd. for [M+H]$^+$ C$_{14}$H$_{18}$NO$_2$: 232.13; found 232.18. HRMS: Anal. Calcd. for [M+H]$^+$ C$_{14}$H$_{18}$NO$_2$: 232.1338; found 232.1340.

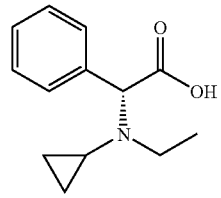

Cap-78

NaCNBH$_3$ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH$_3$ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC (H$_2$O/MeOH/TFA) to afford the TFA salt of Cap-78 as a colorless viscous oil (353 mg). $^1$H NMR (DMSO-d$_6$, δ=2.5 ppm, 400 MHz; after D$_2$O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC/MS: Anal. Calcd. for [M+H]$^+$ C$_{13}$H$_{18}$NO$_2$: 220.13; found 220.21. HRMS: Anal. Calcd. for [M+H]$^+$ C$_{13}$H$_{18}$NO$_2$: 220.1338; found 220.1343.

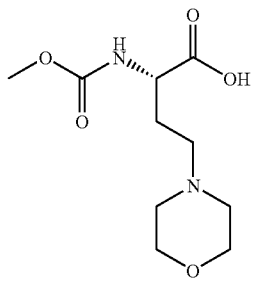

Cap-79

Ozone was bubbled through a cooled (−78° C.) CH$_2$Cl$_2$ (5.0 mL) solution Cap-55 (369 mg, 2.13 mmol) for about 50 min until the reaction mixture attained a tint of blue color. Me$_2$S (10 pipet drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH$_3$CN (149 mg, 2.25 mmol) was added to a MeOH (5.0 mL) solution of the above crude material and morpholine (500 μL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH$_3$/MeOH elution) and a reverse phase HPLC (H$_2$O/MeOH/TFA) to afford Cap-79 containing unknown amount of morpholine.

In order to consume the morpholine contaminant, the above material was dissolved in CH$_2$Cl$_2$ (1.5 mL) and treated with Et$_3$N (0.27 mL, 1.94 mmol) followed by acetic anhydride (0.10 mL, 1.06 mmol) and stirred at ambient condition for 18 hr. THF (1.0 mL) and H$_2$O (0.5 mL) were added and stirring continued for 1.5 hr. The volatile component was removed in vacuo, and the resultant residue was passed through MCX resin (MeOH wash; 2.0 N NH$_3$/MeOH elution) to afford impure Cap-79 as a brown viscous oil, which was used for the next step without further purification.

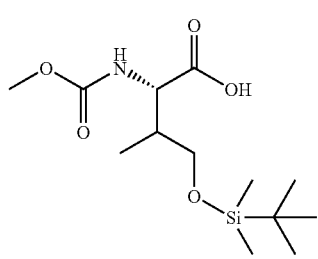

Cap-80a and -80b

Cap-80a: S/S-diastereomer
Cap-80b: S/R-diastereomer

SOCl$_2$ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO$_3$ solution. The aqueous phase was extracted with EtOAc (150 mL, 2×), and the combined organic phase was dried (MgSO$_4$), filtered, and concentrated in vacuo to afford (S)-1-benzyl 4-methyl 2-aminosuccinate as a colorless oil (9.706 g). $^1$H NMR (DMSO-d$_6$, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]$^+$ C$_{12}$H$_{16}$NO$_4$: 238.11; found 238.22.

Pb(NO$_3$)$_2$ (6.06 g, 18.3 mmol) was added over 1 min to a CH$_2$Cl$_2$ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et$_3$N (3.0 mL, 21.5 mmol), and the heterogeneous mixture was stirred at ambient condition for 48 hr. The mixture was filtered and the filtrate was treated with MgSO$_4$ and filtered again, and the final filtrate was concentrated. The resulting crude material was submitted to a Biotage purification (350 g silica gel, CH$_2$Cl$_2$ elution) to afford (S)-1-benzyl 4-methyl 2-(9-phenyl-9H-fluoren-9-ylamino)succinate as highly viscous colorless oil (7.93 g). $^1$H NMR (DMSO-d$_6$, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]$^+$ C$_{31}$H$_{28}$NO$_4$: 478.20; found 478.19.

LiHMDS (9.2 mL of 10 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for ~1 hr. MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a Biotage (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ 4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ 4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC/MS: Anal. Calcd. for [M+H]$^+$ C$_{32}$H$_{30}$NO$_4$: 492.22; found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-d$_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]$^+$ C$_{31}$H$_{30}$NO$_3$: 464.45; found 464.22. (2S,3R) isomer: $^1$H NMR (DMSO-d$_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H), LC (Cond. 1): RT=1.92 min; LC/MS: Anal. Calcd. for [M+H]$^+$ C$_{31}$H$_{30}$NO$_3$: 464.45; found 464.52.

The relative stereochemical assignments of the DIBAL-reduction products were made based on NOE studies conducted on lactone derivatives prepared from each isomer by employing the following protocol: LiHMDS (50 μM, of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a Biotage purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz): 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for [M+Na]$^+$ C$_{24}$H$_{21}$NNaO$_2$: 378.15; found 378.42. (3S,4R)-lactone isomer: $^1$H NMR (DMSO-d$_6$, δ=2.5 ppm, 400 MHz): 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for [M+Na]$^+$ C$_{24}$H$_{21}$NNaO$_2$: 378.15; found 378.49.

TBDMS-Cl (48 mg, 0.312 mmol) followed by imidazole (28.8 mg, 0.423 mmol) were added to a CH$_2$Cl$_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH$_2$Cl$_2$ (30 mL) and washed with water (15 mL), and the organic layer was dried (MgSO$_4$), filtered, and concentrated in vacuo. The resultant crude material was purified with a Biotage (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-d$_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for [M+H]$^+$ C$_{37}$H$_{44}$NO$_3$Si: 578.31; found 578.40. (2S,3R)-silyl ether isomer: $^1$H NMR (DMSO-d$_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S,3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H$_2$ as necessary. The reaction mixture was diluted with CH$_2$Cl$_2$ and filtered through a pad of diatomaceous earth (Celite-545®), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/H$_2$O) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S,3R)-2-amino-4-(tert-butyldimethylsilyloxy)-3-methylbutanoic acid. (2S,3S)-amino acid isomer: $^1$H NMR (Methanol-d$_4$, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC/MS: Anal. Calcd. for [M+H]$^+$ C$_{11}$H$_{26}$NO$_3$Si: 248.17; found 248.44. (2S,3R)-amino acid isomer: $^1$H NMR (Methanol-d$_4$, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]$^+$ C$_{11}$H$_{26}$NO$_3$Si: 248.17; found 248.44.

Water (1 mL) and NaOH (0.18 mL of 1.0 M/H$_2$O, 0.18 mmol) were added to a mixture of (2S,3S)-2-amino-4-(tert-butyldimethylsilyloxy)-3-methylbutanoic acid (41.9 mg, 0.169 mmol) and Na$_2$CO$_3$ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH$_2$Cl$_2$ (15 mL, 2×). The combined organic phase was dried (MgSO$_4$), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: $^1$H NMR (DMSO-d$_6$, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for [M+Na]⁺ $C_{13}H_{27}NNaO_5Si$: 328.16; found 328.46. Cap-80b: ¹H NMR (CDCl₃, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for [M+Na]⁺ $C_{13}H_{27}NNaO_5Si$: 328.16; found 328.53. The crude products were utilized without further purification.

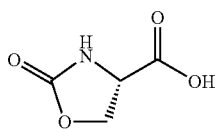

Cap-81

Prepared according to the protocol described by Falb et al. *Synthetic Communications* 1993, 23, 2839.

Cap-82 to Cap-85

Cap-82 to Cap-85 were synthesized from appropriate starting materials according to the procedure described for Cap-51 or Cap-13. The samples exhibited similar spectral profiles as that of their enantiomers (i.e., Cap-4, Cap-13, Cap-51 and Cap-52, respectively).

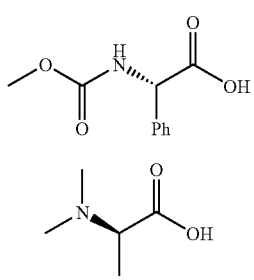

Cap-82

Cap-83

Cap-84

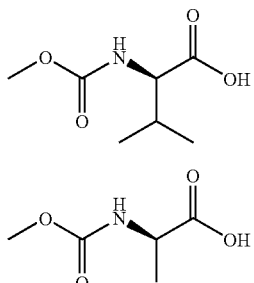

Cap-85

Cap-86

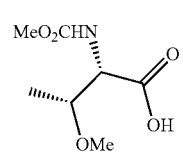

To a mixture of O-methyl-L-threonine (3.0 g, 22.55 mmol), NaOH (0.902 g, 22.55 mmol) in H₂O (15 mL) was added ClCO₂Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH₂Cl₂ (250 mL) and the combined organic phases were concentrated under in vacuo to afford a colorless oil (4.18 g, 97%) which was of sufficient purity for use in subsequent steps. ¹HNMR (400 MHz, CDCl₃) δ 4.19 (s, 1H), 3.92-3.97 (m, 1H), 3.66 (s, 3H), 1.17 (d, J=7.7 Hz, 3H). LCMS: Anal. Calcd. for $C_7H_{13}NO_5$: 191; found: 190 (M-H)⁻.

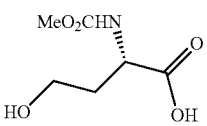

Cap-87

To a mixture of L-homoserine (2.0 g, 9.79 mmol), Na₂CO₃ (2.08 g, 19.59 mmol) in H₂O (15 mL) was added ClCO₂Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated in vacuo to afford a colorless solid (0.719 g, 28%) which was of sufficient purity for use in subsequent steps. ¹HNMR (400 MHz, CDCl₃) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for $C_7H_{13}NO_5$: 191; found: 192 (M+H)⁺.

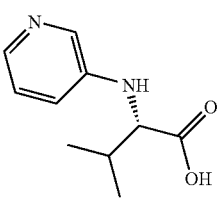

Cap-88

A mixture of L-valine (1.0 g, 8.54 mmol), 3-bromopyridine (1.8 mL, 18.7 mmol), K₂CO₃ (2.45 g, 17.7 mmol) and CuI (169 mg, 0.887 mmol) in DMSO (10 mL) was heated at 100° C. for 12 h. The reaction mixture was cooled to rt, poured into H₂O (ca. 150 mL) and washed with EtOAc (×2). The organic layers were extracted with a small amount of H₂O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H₂O (200 mL), MeOH (200 mL), and then NH₃ (3M in MeOH, 2×200 mL). The appropriate fractions was concentrated in vacuo and the residue (ca. 1.1 g) was dissolved in H₂O, frozen and lyophyllized. The title compound was obtained as a foam (1.02 g, 62%). ¹HNMR (400 MHz, DMSO-d₆) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for $C_{10}H_{14}N_2O_2$: 194; found: 195 (M+H)⁺.

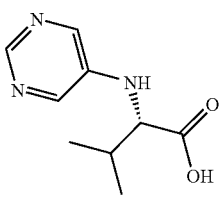

Cap-89

A mixture of L-valine (1.0 g, 8.54 mmol), 5-bromopyrimidine (4.03 g, 17.0 mmol), $K_2CO_3$ (2.40 g, 17.4 mmol) and CuI (179 mg, 0.94 mmol) in DMSO (10 mL) was heated at 100° C. for 12 h. The reaction mixture was cooled to RT, poured into $H_2O$ (ca. 150 mL) and washed with EtOAc (×2). The organic layers were extracted with a small amount of $H_2O$ and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with $H_2O$ (200 mL), MeOH (200 mL), and then $NH_3$ (3M in MeOH, 2×200 mL). The appropriate fractions was concentrated in vacuo and the residue (ca. 1.1 g) was dissolved in $H_2O$, frozen and lyophyllized. The title compound was obtained as a foam (1.02 g, 62%). $^1$HNMR (400 MHz, $CD_3OD$) showed the mixture to contain valine and the purity could not be estimated. The material was used as is in subsequent reactions. LCMS: Anal. Calcd. for $C_9H_{13}N_3O_2$: 195; found: 196 $(M+H)^+$.

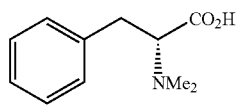

Cap-90

Cap-90 was prepared according to the method described for the preparation of Cap-1. The crude material was used as is in subsequent steps. LCMS: Anal. Calcd. for $C_{11}H_{15}NO_2$: 193; found: 192 $(M-H)^-$.

The following caps were prepared according to the method used for preparation of cap 51 unless noted otherwise:

| Cap | Structure | LCMS |
|---|---|---|
| Cap-91 | ![structure] | LCMS: Anal. Calcd. for $C_{11}H_{13}NO_4$: 223; found: 222 $(M-H)^-$. |
| Cap-92 | ![structure] | LCMS: Anal. Calcd. for $C_{11}H_{13}NO_4$: 223; found: 222 $(M-H)^-$. |
| Cap-93 | ![structure] | LCMS: Anal. Calcd. for $C_{10}H_{12}N_2O_4$: 224; found: 225 $(M+H)^+$. |
| Cap-94 | ![structure] | LCMS: Anal. Calcd. for $C_8H_{11}N_3O_4$: 213; found: 214 $(M+H)^+$. |
| Cap-95 | ![structure] | LCMS: Anal. Calcd. for $C_{13}H_{17}NO_4$: 251; found: 250 $(M-H)^-$. |

| Cap | Structure | LCMS |
|---|---|---|
| Cap-96 | 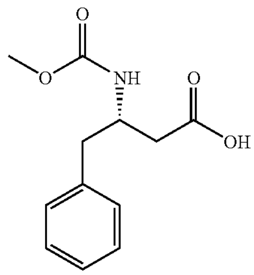 [SMILES: COC(=O)N[C@H](CC(=O)O)Cc1ccccc1] | LCMS: Anal. Calcd. for C$_{12}$H$_{15}$NO$_4$: 237; found: 236 (M – H)$^-$. |
| Cap-97 | 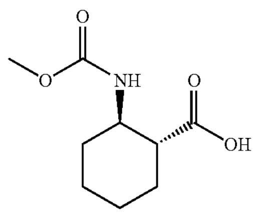 | LCMS: Anal. Calcd. for C$_9$H$_{15}$NO$_4$: 201; found: 200 (M – H)$^-$. |
| Cap-98 | 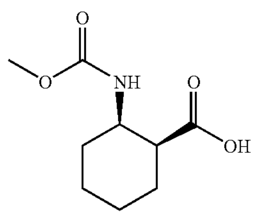 | LCMS: Anal. Calcd. for C$_9$H$_{15}$NO$_4$: 201; found: 202 (M + H)$^+$. |
| Cap-99 | 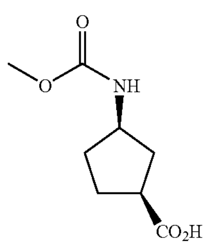 | $^1$HNMR (400 MHz, CD$_3$OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-99a | 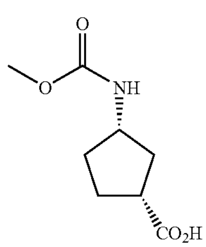 | $^1$HNMR (400 MHz, CD$_3$OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-100 | 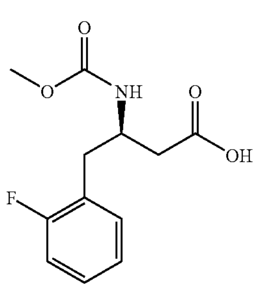 [SMILES: COC(=O)N[C@@H](CC(=O)O)Cc1ccccc1F] | LCMS: Anal. Calcd. for C$_{12}$H$_{14}$NO$_4$F: 255; found: 256 (M + H)$^+$. |

| Cap | Structure | LCMS |
|---|---|---|
| Cap-101 | 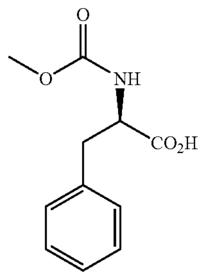 [SMILES: COC(=O)N[C@H](Cc1ccccc1)C(=O)O] | LCMS: Anal. Calcd. for $C_{11}H_{13}NO_4$: 223; found: 222 $(M - H)^-$. |
| Cap-102 | 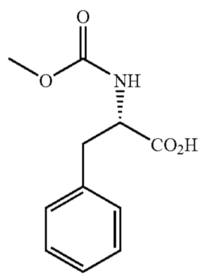 [SMILES: COC(=O)N[C@@H](Cc1ccccc1)C(=O)O] | LCMS: Anal. Calcd. for $C_{11}H_{13}NO_4$: 223; found: 222 $(M - H)^-$. |
| Cap-103 | 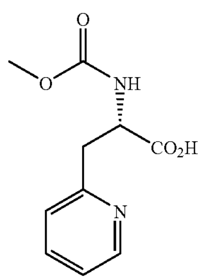 [SMILES: COC(=O)N[C@@H](Cc1ccccn1)C(=O)O] | LCMS: Anal. Calcd. for $C_{10}H_{12}N_2O_4$: 224; found: 225 $(M + H)^+$. |
| Cap-104 | 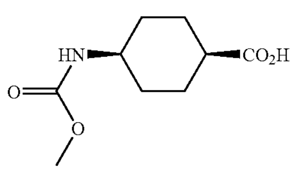 | $^1$HNMR (400 MHz, $CD_3OD$) δ 3.60 (s, 3H), 3.50-3.53 (m, 1H), 2.66-2.69 and 2.44-2.49 (m, 1H), 1.91-2.01 (m, 2H), 1.62-1.74 (m, 4H), 1.51-1.62 (m, 2H). |
| Cap-105 | 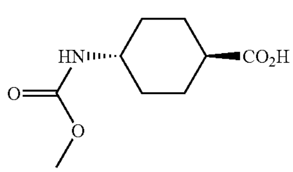 | $^1$HNMR (400 MHz, $CD_3OD$) δ 3.60 (s, 3H), 3.33-3.35 (m, 1H, partially obscured by solvent), 2.37-2.41 and 2.16-2.23 (m, 1H), 1.94-2.01 (m, 4H), 1.43-1.53 (m, 2H), 1.17-1.29 (m, 2H). |
| Cap-106 | Prepared from cis-4-aminocyclohexane carboxylic acid and acetaldehyde by employing a similar procedure described for the synthesis of Cap-2. The crude HCl salt was passed through MCX (MeOH/$H_2O$/$CH_2Cl_2$ wash; 2 N $NH_3$/MeOH elution) to afford an oil, which was dissolved in $CH_3CN$/$H_2O$ and lyophilized to afford a tan solid. | $^1$HNMR (400 MHz, $CD_3OD$) δ 3.16 (q, J = 7.3 Hz, 4H), 2.38-2.4 (m, 1H), 2.28-2.31 (m, 2H), 1.79-1.89 (m, 2H), 1.74 (app, ddd J = 3.5, 12.5, 15.9 Hz, 2H), 1.46 (app dt J = 4.0, 12.9 Hz, 2H), 1.26 (t, J = 7.3 Hz, 6H) |

| Cap | Structure | LCMS |
|---|---|---|
| Cap-107 | 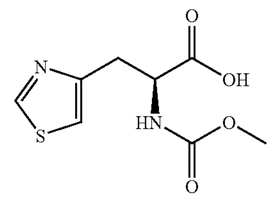 | LCMS: Anal. Calcd. for $C_8H_{10}N_2O_4S$: 230; found: 231 $(M + H)^+$. |
| Cap-108 | 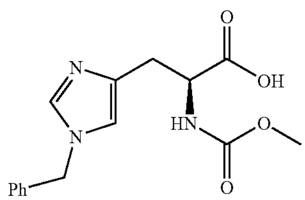 [SMILES: COC(=O)N[C@@H](Cc1cn(Cc2ccccc2)cn1)C(=O)O] | LCMS: Anal. Calcd. for $C_{15}H_{17}N_3O_4$: 303; found: 304 $(M + H)^+$. |
| Cap-109 | 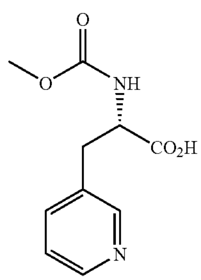 [SMILES: COC(=O)N[C@@H](Cc1cccnc1)C(=O)O] | LCMS: Anal. Calcd. for $C_{10}H_{12}N_2O_4$: 224; found: 225 $(M + H)^+$. |
| Cap-110 | 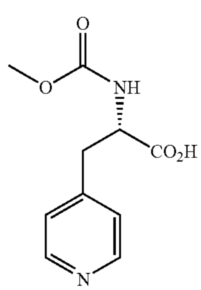 [SMILES: COC(=O)N[C@@H](Cc1ccncc1)C(=O)O] | LCMS: Anal. Calcd. for $C_{10}H_{12}N_2O_4$: 224; found: 225 $(M + H)^+$. |
| Cap-111 | 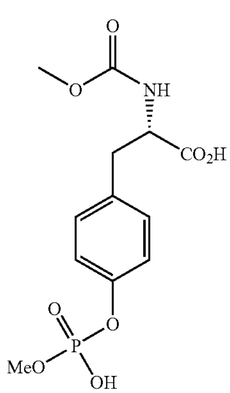 [SMILES: COC(=O)N[C@@H](Cc1ccc(OP(=O)(O)OC)cc1)C(=O)O] | LCMS: Anal. Calcd. for $C_{12}H_{16}NO_8P$: 333; found: 334 $(M + H)^+$. |

| Cap | Structure | LCMS |
|---|---|---|
| Cap-112 | (structure: methyl carbamate-protected tryptophan) | LCMS: Anal. Calcd. for $C_{13}H_{14}N_2O_4$: 262; found: 263 $(M + H)^+$. |
| Cap-113 | (structure: methyl carbamate-protected O-benzyl tyrosine) | LCMS: Anal. Calcd. for $C_{18}H_{19}NO_5$: 329; found: 330 $(M + H)^+$. |
| Cap-114 | (structure: N-CO2Me azetidine-2-carboxylic acid) | $^1$HNMR (400 MHz, CDCl$_3$) δ 4.82-4.84 (m, 1H), 4.00-4.05 (m, 2H), 3.77 (s, 3H), 2.56 (s, br, 2H) |
| Cap-115 | (structure: N-methoxycarbonyl β-methyl-β-amino acid) | $^1$HNMR (400 MHz, CDCl$_3$) δ 5.13 (s, br, 1H), 4.13 (s, br, 1H), 3.69 (s, 3H), 2.61 (d, J = 5.0 Hz, 2H), 1.28 (d, J = 9.1 Hz, 3H). |
| Cap-116 | (structure: N-methoxycarbonyl β-isopropyl-β-amino acid) | $^1$HNMR (400 MHz, CDCl$_3$) δ 5.10 (d, J = 8.6 Hz, 1H), 3.74-3.83 (m, 1H), 3.69 (s, 3H), 2.54-2.61 (m, 2H), 1.88 (sept, J = 7.0 Hz, 1H), 0.95 (d, J = 7.0 Hz, 6H). |

Cap-117 to Cap-123

For the preparation of Cap-117 to Cap-123 the Boc amino acids were obtained from commercially sources and were deprotected by treatment with 25% TFA in CH$_2$Cl$_2$. After complete reaction as judged by LCMS the solvents were removed in vacuo and the corresponding TFA salt of the amino acid was carbamoylated with methyl chloroformate according to the procedure described for Cap-51.

| Cap | Structure | LCMS |
|---|---|---|
| Cap-117 | (structure: N-methoxycarbonyl β-benzyl-β-amino acid) | LCMS: Anal. Calcd. for $C_{12}H_{15}NO_4$: 237; found: 238 $(M + H)^+$. |

-continued

| Cap | Structure | LCMS |
|---|---|---|
| Cap-118 | 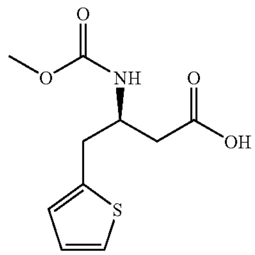 [SMILES: COC(=O)N[C@@H](CC(=O)O)Cc1cccs1] | LCMS: Anal. Calcd. for $C_{10}H_{13}NO_4S$: 243; found: 244 $(M + H)^+$. |
| Cap-119 | 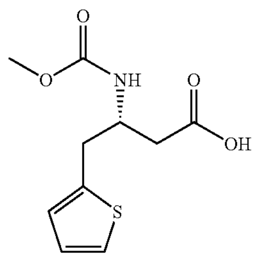 [SMILES: COC(=O)N[C@H](CC(=O)O)Cc1cccs1] | LCMS: Anal. Calcd. for $C_{10}H_{13}NO_4S$: 243; found: 244 $(M + H)^+$. |
| Cap-120 | 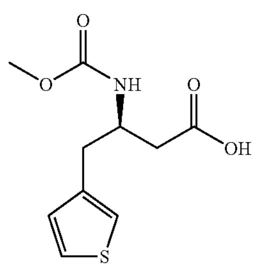 [SMILES: COC(=O)N[C@@H](CC(=O)O)Cc1ccsc1] | LCMS: Anal. Calcd. for $C_{10}H_{13}NO_4S$: 243; found: 244 $(M + H)^+$. |
| Cap-121 | 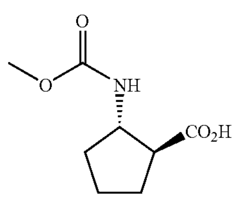 | $^1$HNMR (400 MHz, CDCl$_3$) δ 4.06-4.16 (m, 1H), 3.63 (s, 3H), 3.43 (s, 1H), 2,82 and 2.66 (s, br, 1H), 1.86-2.10 (m, 3H), 1.64-1.76 (m, 2H), 1.44-1.53 (m, 1H). |
| Cap-122 | 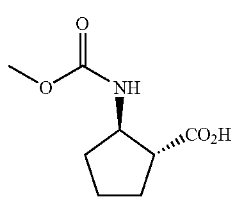 | $^1$HNMR profile is similar to that of its enantiomer, Cap-121. |
| Cap-123 | 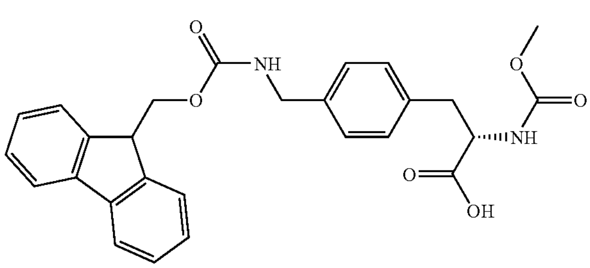 [SMILES: COC(=O)N[C@@H](Cc1ccc(CNC(=O)OCC2c3ccccc3-c3ccccc32)cc1)C(=O)O] | LCMS: Anal. Calcd. for $C_{27}H_{26}N_2O_6$: 474; found: 475 $(M + H)^+$. |

Cap-124

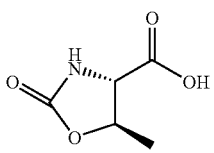

The hydrochloride salt of L-threonine tert-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc-CH$_2$Cl$_2$-MeOH (1:1:0.1) and then the organic phase concentrated in vacuo to give a colorless oil which was shown by LCMS to be the desired product. Both crops were combined to give 0.52 g of a solid. $^1$HNMR (400 MHz, CD$_3$OD) δ 4.60 (m, 1H), 4.04 (d, J=5.0 Hz, 1H), 1.49 (d, J=6.3 Hz, 3H). LCMS: Anal. Calcd. for C$_5$H$_7$NO$_4$: 145; found: 146 (M−H)$^+$.

Cap-125

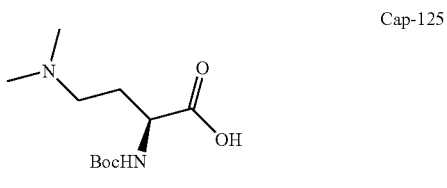 [SMILES: CN(C)CC[C@H](NC(=O)OC(C)(C)C)C(=O)O]

To a suspension of Pd(OH)$_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temp. The reaction mixture was filtered through a pad of diatomaceous earth (Celite®), and the volatile component was removed in vacuo. The resulting crude material was used as is for the next step. LC/MS: Anal. Calcd. for C$_{11}$H$_{22}$N$_2$O$_4$: 246; found: 247 (M+H)$^+$.

Cap-126

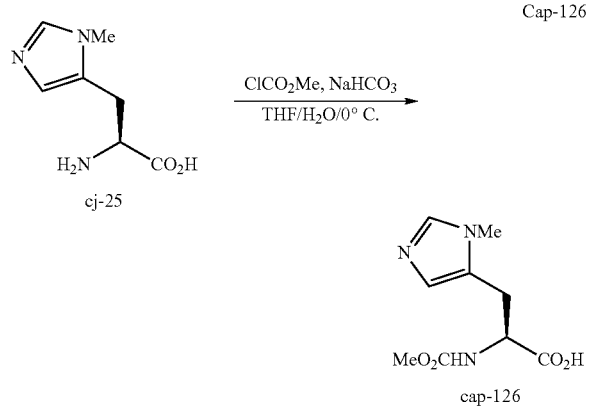

This procedure is a modification of that used to prepare Cap-51. To a suspension of 3-methyl-L-histidine (0.80 g, 4.70 mmol) in THF (10 mL) and H$_2$O (10 mL) at 0° C. was added NaHCO$_3$ (0.88 g, 10.5 mmol). The resulting mixture was treated with ClCO$_2$Me (0.40 mL, 5.20 mmol) and the mixture allowed to stir at 0° C. After stirring for ca. 2 h LCMS showed no starting material remaining. The reaction was acidified to pH 2 with 6 N HCl.

The solvents were removed in vacuo and the residue was suspended in 20 mL of 20% MeOH in CH$_2$Cl$_2$. The mixture was filtered and concentrated to give a light yellow foam (1.21 g). LCMS and $^1$H NMR showed the material to be a 9:1 mixture of the methyl ester and the desired product. This material was taken up in THF (10 mL) and H$_2$O (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and $^1$H NMR confirm the absence of the ester. The title compound was obtained as its HCl salt contaminated with inorganic salts (1.91 g, >100%). The compound was used as is in subsequent steps without further purification. $^1$HNMR (400 MHz, CD$_3$OD) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H). LCMS: Anal. Calcd. for C$_9$H$_{13}$N$_3$O$_4$: 227.09; found: 228.09 (M+H)$^+$.

Cap-127

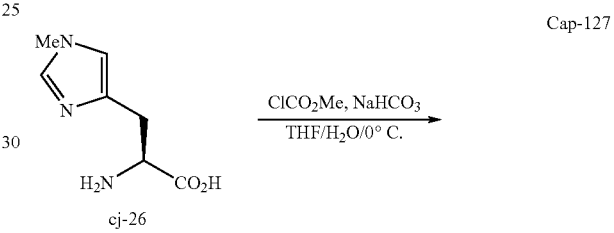

Cap-127 was prepared according to the method for Cap-126 above starting from (S)-2-amino-3-(1-methyl-1H-imidazol-4-yl)propanoic acid (1.11 g, 6.56 mmol), NaHCO$_3$ (1.21 g, 14.4 mmol) and ClCO$_2$Me (0.56 mL, 7.28 mmol). The title compound was obtained as its HCl salt (1.79 g, >100%) contaminated with inorganic salts. LCMS and $^1$H NMR showed the presence of ca. 5% of the methyl ester. The crude mixture was used as is without further purification. $^1$HNMR (400 MHz, CD$_3$OD) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H); LCMS: Anal. Calcd. for C$_9$H$_{13}$N$_3$O$_4$: 227.09; found: 228 (M+H)$^+$.

Preparation of Cap-128

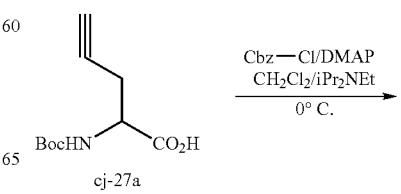

-continued

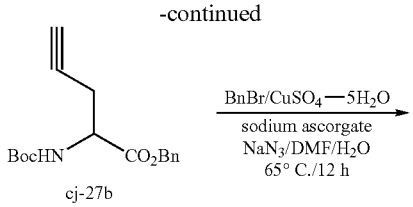

2H), 2.00 (t, J=2.5 Hz, 1H), 1.44 (s, 9H). LCMS: Anal. Calcd. for $C_{17}H_{21}NO_4$: 303; found: 304 $(M+H)^+$.

Step 2. Preparation of (S)-benzyl 3-(1-benzyl-1H-1, 2,3-triazol-4-yl)-2-(tert-butoxycarbonylamino)propanoate (cj-28)

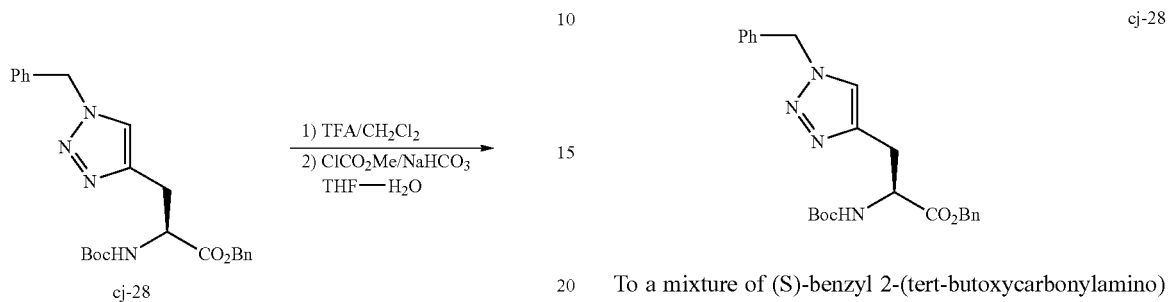

To a mixture of (S)-benzyl 2-(tert-butoxycarbonylamino)pent-4-ynoate (0.50 g, 1.65 mmol), sodium ascorbate (0.036 g, 0.18 mmol), $CuSO_4 \cdot 5H_2O$ (0.022 g, 0.09 mmol) and $NaN_3$ (0.13 g, 2.1 mmol) in DMF-$H_2O$ (5 mL, 4:1) at rt was added BnBr (0.24 mL, 2.02 mmol) and the mixture was warmed to 65° C. After 5 h LCMS indicated low conversion. A further portion of $NaN_3$ (100 mg) was added and heating was continued for 12 h. The reaction was poured into EtOAc and $H_2O$ and shaken. The layers were separated and the aqueous layer extracted 3× with EtOAc and the combined organic phases washed ($H_2O\times 3$, brine), dried ($Na_2SO_4$), filtered, and concentrated. The residue was purified by flash (Biotage, 40+M 0-5% MeOH in $CH_2Cl_2$; TLC 3% MeOH in $CH_2Cl_2$) to afford a light yellow oil which solidified on standing (748.3 mg, 104%). The NMR was consistent with the desired product but suggests the presence of DMF. The material was used as is without further purification. $^1$HNMR (400 MHz, DMSO-$d_6$) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz, 1H), 2.96 (dd, J=9.1, 14.7 Hz, 1H), 1.31 (s, 9H).

LCMS: Anal. Calcd. for $C_{24}H_{28}N_4O_4$: 436; found: 437 $(M+H)^+$.

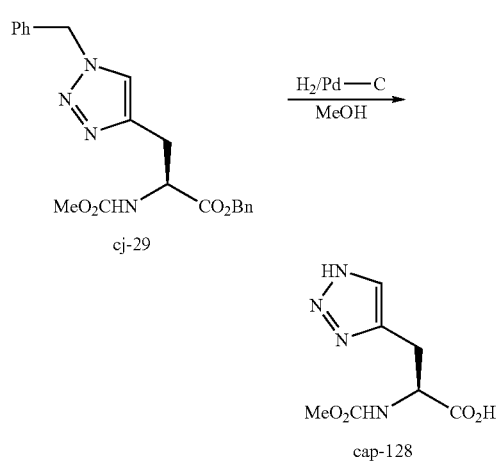

Step 1. Preparation of (S)-benzyl 2-(tert-butoxycarbonylamino)pent-4-ynoate (cj-27b)

Step 3. Preparation of (S)-benzyl 3-(1-benzyl-1H-1,2,3-triazol-4-yl)-2-(methoxycarbonylamino)propanoate (cj-29)

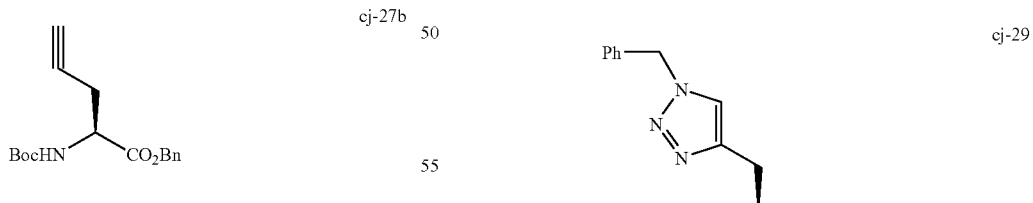

To a solution of cj-27a (1.01 g, 4.74 mmol), DMAP (58 mg, 0.475 mmol) and $iPr_2NEt$ (1.7 mL, 9.8 mmol) in $CH_2Cl_2$ (100 mL) at 0° C. was added Cbz-Cl (0.68 mL, 4.83 mmol). The solution was allowed to stir for 4 h at 0° C., washed (1N $KHSO_4$, brine), dried ($Na_2SO_4$), filtered, and concentrated in vacuo. The residue was purified by flash column chromatography (TLC 6:1 hex:EtOAc) to give the title compound (1.30 g, 91%) as a colorless oil. $^1$HNMR (400 MHz, $CDCl_3$) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, A solution of (S)-benzyl 3-(1-benzyl-1H-1,2,3-triazol-4-yl)-2-(tert-butoxycarbonylamino)propanoate (0.52 g, 1.15 mmol) in $CH_2Cl_2$ was added TFA (4 mL). The mixture was allowed to stir at room temperature for 2 h. The mixture was concentrated in vacuo to give a colorless oil which solidified on standing. This material was dissolved in THF-$H_2O$ and cooled to 0° C. Solid $NaHCO_3$ (0.25 g, 3.00 mmol) was added followed by $ClCO_2Me$ (0.25 mL, 3.25 mmol). After stirring for 1.5 h the mixture was acidified to pH~2 with 6N HCl and then poured into H$_2$O-EtOAc. The layers were separated and the aq phase extracted 2× with EtOAc. The combined org layers were washed (H$_2$O, brine), dried (Na$_2$SO$_4$), filtered, and concentrated in vacuo to give a colorless oil (505.8 mg, 111%, NMR suggested the presence of an unidentified impurity) which solidified while standing on the pump. The material was used as is without further purification. $^1$HNMR (400 MHz, DMSO-d$_6$) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LCMS: Anal. Calcd. for C$_{21}$H$_{22}$N$_4$O$_4$: 394; found: 395 (M+H)$^+$.

Step 4. Preparation of (S)-2-(methoxycarbonylamino)-3-(1H-1,2,3-triazol-4-yl)propanoic acid (Cap-128)

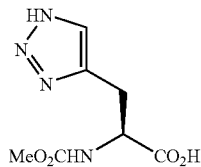

Cap-128

(S)-benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (Celite®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification. $^1$HNMR (400 MHz, DMSO-d$_6$) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LCMS: Anal. Calcd. for C$_7$H$_{10}$N$_4$O$_4$: 214; found: 215 (M+H)$^+$.

Preparation of Cap-129

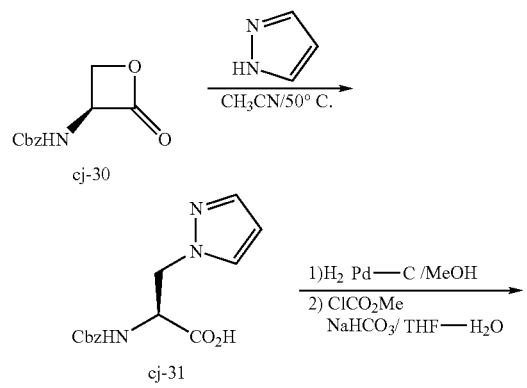

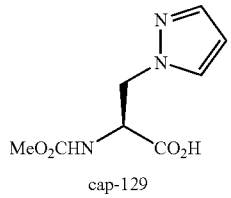

cap-129

Step 1. Preparation of (S)-2-(benzyloxycarbonylamino)-3-(1H-pyrazol-1-yl)propanoic acid (cj-31)

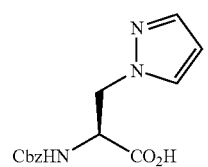

cj-31

A suspension of (S)-benzyl 2-oxooxetan-3-ylcarbamate (0.67 g, 3.03 mmol), and pyrazole (0.22 g, 3.29 mmol) in CH$_3$CN (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of CH$_3$CN (ca. 4 mL) to afford a second crop (43.5 mg). Total yield 370.4 mg (44%). m.p. 165.5-168° C. lit m.p. 168.5-169.5 [Vederas et al. J. Am. Chem. Soc. 1985, 107, 7105]. $^1$HNMR (400 MHz, CD$_3$OD) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for C$_{14}$H$_{15}$N$_3$O$_4$: 289; found: 290 (M+H)$^+$.

Step 2. Preparation of (S)-2-(methoxycarbonylamino)-3-(1H-pyrazol-1-yl)propanoic acid (Cap-129)

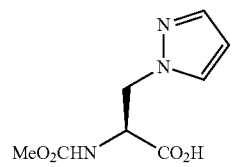

cap-129

(S)-2-(benzyloxycarbonylamino)-3-(1H-pyrazol-1-yl) propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL H$_2$O and a few drops of 6N HCl. The homogeneous solution was filtered through diatomaceous earth (Celite®), and the MeOH removed in vacuo. The remaining solution was frozen and lyophyllized to give a yellow foam (188.9 mg). This material was suspended in THF-H$_2$O (1:1, 10 mL) and then cooled to 0° C. To the cold mixture was added NaHCO$_3$ (146.0 mg, 1.74 mmol) carefully (evolution of CO$_2$). After gas evolution had ceased (ca. 15 min) ClCO$_2$Me (0.06 mL, 0.78 mmol) was added dropwise. The mixture was allowed to stir for 2 h and was acidified to pH~2 with 6N HCl and poured into EtOAc. The layers were separated and the aqueous phase extracted with EtOAC (×5). The combined organic layers were washed (brine), dried (Na$_2$SO$_4$), filtered, and concentrated to give the title compound as a colorless solid (117.8 mg, 79%). $^1$HNMR (400 MHz, DMSO-d$_6$) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for C$_8$H$_{11}$N$_3$O$_4$: 213; found: 214 (M+H)$^+$.

200 mg) and the resulting black suspension was flushed with N$_2$ (3×) and placed under 1 atm of H$_2$. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. $^1$H NMR (500 MHz, DMSO-d$_6$) δ ppm 0.87 (d, J=4.27 Hz, 3H), 0.88 (d, J=3.97 Hz, 3H), 1.93-2.11 (m, 1H), 2.80 (s, 6H), 3.90 (dd, J=8.39, 6.87 Hz, 1H), 5.93 (d, J=8.54 Hz, 1H), 12.36 (s, 1H). LC (Cond. 1): RT=0.33 min; MS: Anal. Calcd. for [M+H]$^+$ C$_8$H$_{17}$N$_2$O$_3$: 189.12; found 189.04.

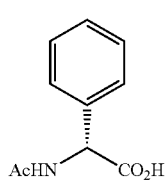

Cap-130

Cap-130 was prepared by acylation of commercially available (R)-phenylglycine analgous to the procedure given in: Calmes, M.; Daunis, J.; Jacquier, R.; Verducci, J. *Tetrahedron,* 1987, 43(10), 2285.

Cap-131

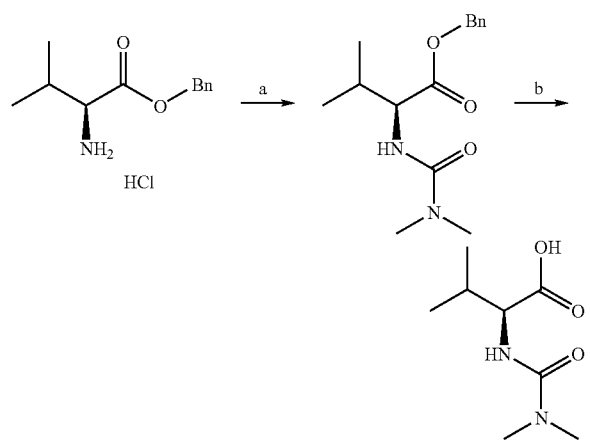

Step a: Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried (MgSO$_4$), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. $^1$H NMR (300 MHz, DMSO-d$_6$) δ ppm 0.84 (d, J=6.95 Hz, 3H), 0.89 (d, J=6.59 Hz, 3H), 1.98-2.15 (m, 1H), 2.80 (s, 6H), 5.01-5.09 (m, J=12.44 Hz, 1H), 5.13 (d, J=12.44 Hz, 1H), 6.22 (d, J=8.05 Hz, 1H), 7.26-7.42 (m, 5H). LC (Cond. 1): RT=1.76 min; MS: Anal. Calcd. for [M+H]$^+$ C$_{16}$H$_{22}$N$_2$O$_3$: 279.17; found 279.03.

Step b: To a MeOH (50 mL) solution of the intermediate prepared above (2.35 g; 8.45 mmol) was added Pd/C (10%;

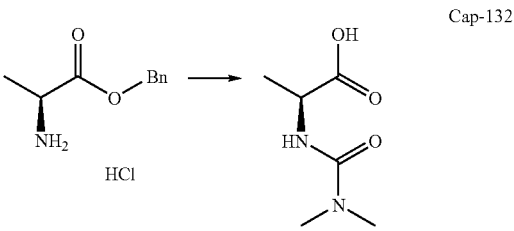

Cap-132

Cap-132 was prepared from (S)-benzyl 2-aminopropanoate hydrochloride according to the method described for Cap-131. $^1$H NMR (500 MHz, DMSO-d$_6$) δ ppm 1.27 (d, J=7.32 Hz, 3H), 2.80 (s, 6H), 4.06 (qt, 1H), 6.36 (d, J=7.32 Hz, 1H), 12.27 (s, 1H). LC (Cond. 1): RT=0.15 min; MS: Anal. Calcd. for [M+H]$^+$ C$_6$H$_{13}$N$_2$O$_3$: 161.09; found 161.00.

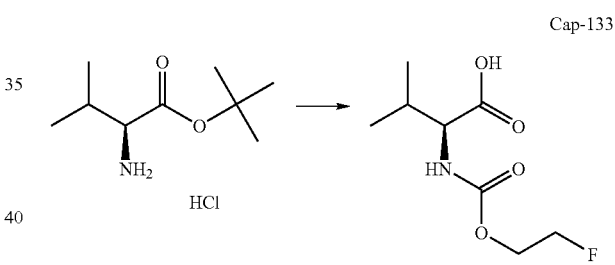

Cap-133

Cap-133 was prepared from (S)-tert-butyl 2-amino-3-methylbutanoate hydrochloride and 2-fluoroethyl chloroformate according to the method described for Cap-47. $^1$H NMR (500 MHz, DMSO-d$_6$) δ ppm 0.87 (t, J=6.71 Hz, 6H), 1.97-2.10 (m, 1H), 3.83 (dd, J=8.39, 5.95 Hz, 1H), 4.14-4.18 (m, 1H), 4.20-4.25 (m, 1H), 4.50-4.54 (m, 1H), 4.59-4.65 (m, 1H), 7.51 (d, J=8.54 Hz, 1H), 12.54 (s, 1H).

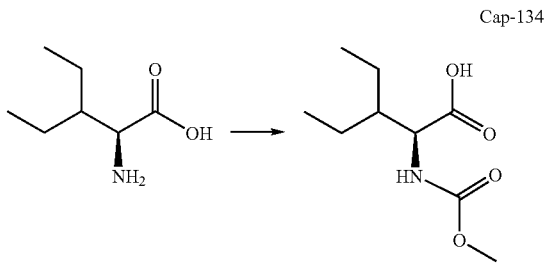

Cap-134

Cap-134 was prepared from (S)-diethyl alanine and methyl chloroformate according to the method described for Cap-51. $^1$H NMR (500 MHz, DMSO-d$_6$) δ ppm 0.72-0.89 (m, 6H), 1.15-1.38 (m, 4H), 1.54-1.66 (m, 1H), 3.46-3.63 (m, 3H), 4.09 (dd, J=8.85, 5.19 Hz, 1H), 7.24 (d, J=8.85 Hz, 1H), 12.55 (s, 1H). LC (Cond. 2): RT=0.66 min; LC/MS: Anal. Calcd. for [M+H]$^+$ C$_9$H$_{18}$NO$_4$: 204.12; found 204.02.

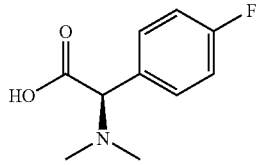

Cap-135

A solution of D-2-amino-(4-fluorophenyl)acetic acid (338 mg, 2.00 mmol), 1N HCl in diethylether (2.0 mL, 2.0 mmol) and formalin (37%, 1 mL) in methanol (5 mL) was subjected to balloon hydrogenation over 10% palladium on carbon (60 mg) for 16 h at 25° C. The mixture was then filtered through Celite to afford the HCl salt of Cap-135 as a white foam (316 mg, 80%). $^1$H NMR (300 MHz, MeOH-d$_4$) δ 7.59 (dd, J=8.80, 5.10 Hz, 2H), 7.29 (t, J=8.6 Hz, 2H), 5.17 (s, 1H), 3.05 (v br s, 3H), 2.63 (v br s, 3H); R$_f$=0.19 min (Cond.-MS-W5); 95% homogenity index; LRMS: Anal. Calcd. for [M+H]$^+$ C$_{10}$H$_{13}$FNO$_2$: 198.09; found: 198.10.

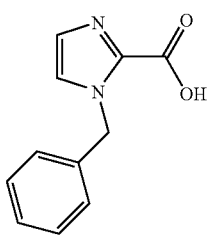

Cap-136

To a cooled (−50° C.) suspension of 1-benzyl-1H-imidazole (1.58 g, 10.0 mmol) in anhydrous diethyl ether (50 mL) under nitrogen was added n-butyl lithium (2.5 M in hexanes, 4.0 mL, 10.0 mmol) dropwise. After being stirred for 20 min at −50° C., dry carbon dioxide (passed through Drierite) was bubbled into the reaction mixture for 10 min before it was allowed to warm up to 25° C. The heavy precipitate which formed on addition of carbon dioxide to the reaction mixture was filtered to yield a hygroscopic, white solid which was taken up in water (7 mL), acidified to pH=3, cooled, and induced to crystallize with scratching. Filtration of this precipitate gave a white solid which was suspended in methanol, treated with 1N HCl/diethyl ether (4 mL) and concentrated in vacuo. Lyophilization of the residue from water (5 mL) afforded the HCl salt of Cap-136 as a white solid (817 mg, 40%). $^1$H NMR (300 MHz, DMSO-d$_6$) δ 7.94 (d, J=1.5 Hz, 1H), 7.71 (d, J=1.5 Hz, 1H), 7.50-7.31 (m, 5H), 5.77 (s, 2H); R$_f$=0.51 min (Cond.-MS-W5); 95% homogenity index; LRMS: Anal. Calc. for [M+H]$^+$ C$_{11}$H$_{12}$N$_2$O$_2$: 203.08; found: 203.11.

Cap-137

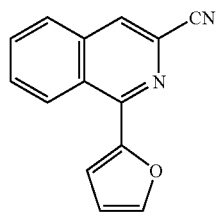

Cap-137, step a

A suspension of 1-chloro-3-cyanoisoquinoline (188 mg, 1.00 mmol; prepared according to the procedure in WO 2003/099274) (188 mg, 1.00 mmol), cesium fluoride (303.8 mg, 2.00 mmol), bis(tri-tert-butylphosphine)palladium dichloride (10 mg, 0.02 mmol) and 2-(tributylstannyl)furan (378 µL, 1.20 mmol) in anhydrous dioxane (10 mL) under nitrogen was heated at 80° C. for 16 h before it was cooled to 25° C. and treated with saturated, aqueous potassium fluoride solution with vigorous stirring for 1 h. The mixture was partitioned between ethyl acetate and water and the organic phase was separated, washed with brine, dried over Na$_2$SO$_4$, filtered and concentrated. Purification of the residue on silica gel (elution with 0% to 30% ethyl acetate/hexanes) afforded Cap-137, step a (230 mg, 105%) as a white solid which was carried forward directly. R$_f$=1.95 min (Cond.-MS-W2); 90% homogeneity index; LRMS: Anal. Calc. for [M+H]$^+$ C$_{14}$H$_8$N$_2$O: 221.07; found: 221.12.

Cap-137

To a suspension of Cap 137, step a, (110 mg, 0.50 mmol) and sodium periodate (438 mg, 2.05 mmol) in carbon tetrachloride (1 mL), acetonitrile (1 mL) and water (1.5 mL) was added ruthenium trichloride hydrate (2 mg, 0.011 mmol). The mixture was stirred at 25° C. for 2 h and then partitioned between dichloromethane and water. The aqueous layer was separated, extracted twice more with dichloromethane and the combined dichloromethane extracts were dried over Na$_2$SO$_4$, filtered and concentrated. Trituration of the residue with hexanes afforded Cap-137 (55 mg, 55%) as a grayish-colored solid. R$_f$=1.10 min (Cond.-MS-W2); 90% homogeneity index; LCMS: Anal. Calc. for [M+H]$^+$ C$_{11}$H$_8$N$_2$O$_2$: 200.08; found: 200.08.

Caps 138 to 158

Synthetic Strategy. Method A.

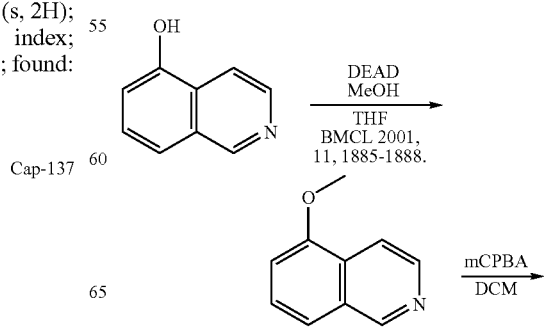

-continued

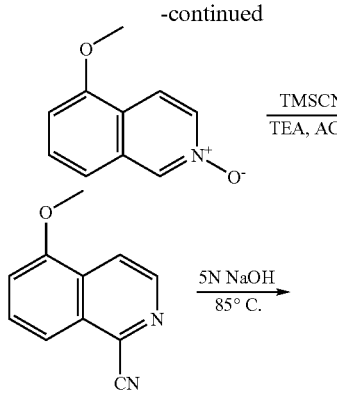

To a stirred suspension of 5-hydroxyisoquinoline (prepared according to the procedure in WO 2003/099274) (2.0 g, 13.8 mmol) and triphenylphosphine (4.3 g, 16.5 mmol) in dry tetrahydrofuran (20 mL) was added dry methanol (0.8 mL) and diethyl azodicarboxylate (3.0 mL, 16.5 mmol) portionwise. The mixture was stirred at room temperature for 20 h before it was diluted with ethyl acetate and washed with brine, dried over $Na_2SO_4$, filtered and concentrated. The residue was preabsorbed onto silica gel and chromatographed (elution with 40% ethyl acetate/hexanes) to afford Cap-138, step a (1.00 g, 45%) as a light yellow solid. $^1$H NMR (CDCl$_3$, 500 MHz) δ 9.19 (s, 1H), 8.51 (d, J=6.0 Hz, 1H), 7.99 (d, J=6.0 Hz, 1H), 7.52-7.50 (m, 2H), 7.00-6.99 (m, 1H), 4.01 (s, 3H); $R_t$=0.66 min (Cond.-D2); 95% homogeneity index; LCMS: Anal. Calc. for [M+H]$^+$ C$_{10}$H$_{10}$NO: 160.08; found 160.1.

Cap-138, step b

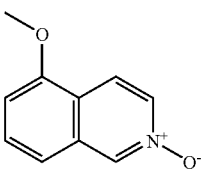

To a stirred solution of Cap 138, step a (2.34 g, 14.7 mmol) in anhydrous dichloromethane (50 mL) at room temperature was added meta-chloroperbenzoic acid (77%, 3.42 g, 19.8 mmol) in one portion. After being stirred for 20 h, powdered potassium carbonate (2.0 g) was added and the mixture was stirred for 1 h at room temperature before it was filtered and concentrated in vacuo to afford Cap-138, step b (2.15 g, 83%) as a pale, yellow solid which was sufficiently pure to carry forward directly. $^1$H NMR (CDCl$_3$, 400 MHz) δ 8.73 (d, J=1.5 Hz, 1H), 8.11 (dd, J=7.3, 1.7 Hz, 1H), 8.04 (d, J=7.1 Hz, 1H), 7.52 (t, J=8.1 Hz, 1H), 7.28 (d, J=8.3 Hz, 1H), 6.91 (d, J=7.8 Hz, 1H), 4.00 (s, 3H); $R_t$=0.92 min, (Cond.-D1); 90% homogenity index; LCMS: Anal. Calc. for [M+H]$^+$ C$_{10}$H$_{10}$NO$_2$: 176.07; found: 176.0.

Cap-138, step c

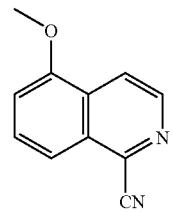

To a stirred solution of Cap 138, step b (0.70 g, 4.00 mmol) and triethylamine (1.1 mL, 8.00 mmol) in dry acetonitrile (20 mL) at room temperature under nitrogen was added trimethylsilylcyanide (1.60 mL, 12.00 mmol). The mixture was heated at 75° C. for 20 h before it was cooled to room temperature, diluted with ethyl acetate and washed with saturated sodium bicarbonate solution and brine prior to drying over $Na_2SO_4$ and solvent concentration. The residue was flash chromatographed on silica gel (gradient elution with 5% ethyl acetate in hexanes to 25% ethyl acetate in hexanes) to afford Cap-138, step c (498.7 mg, 68%) as a white, crystalline solid along with 223 mg (30%) of additional Cap-138, step c recovered from the filtrate. $^1$H NMR (CDCl$_3$, 500 MHz) δ 8.63 (d, J=5.5 Hz, 1H), 8.26 (d, J=5.5 Hz, 1H), 7.88 (d, J=8.5 Hz, 1H), 7.69 (t, J=8.0 Hz, 1H), 7.08 (d, J=7.5 Hz, 1H), 4.04 (s, 3H); $R_t$=1.75 min, (Cond.-D1); 90% homogeneity index; LCMS: Anal. Calc. for [M+H]$^+$ C$_{11}$H$_9$N$_2$O: 185.07; found: 185.10.

Cap-138

Cap-138, step c (0.45 g, 2.44 mmol) was treated with 5N sodium hydroxide solution (10 mL) and the resulting suspension was heated at 85° C. for 4 h, cooled to 25° C., diluted with dichloromethane and acidified with 1N hydrochloric acid. The organic phase was separated, washed with brine, dried over Na$_2$SO$_4$, concentrated to ¼ volume and filtered to afford Cap-138 (0.44 g, 88.9%) as a yellow solid. $^1$H NMR (DMSO-d$_6$, 400 MHz) δ 13.6 (br s, 1H), 8.56 (d, J=6.0 Hz, 1H), 8.16 (d, J=6.0 Hz, 1H), 8.06 (d, J=8.8 Hz, 1H), 7.71-7.67 (m, 1H), 7.30 (d, J=8.0 Hz, 1H), 4.02 (s, 3H); $R_t$=0.70 min (Cond.-D1); 95% homogenity index; LCMS: Anal. Calc. for [M+H]$^+$ C$_{11}$H$_{10}$NO$_3$: 204.07; found: 204.05.

Synthetic Strategy. Method B (derived from *Tetrahedron Letters*, 2001, 42, 6707).

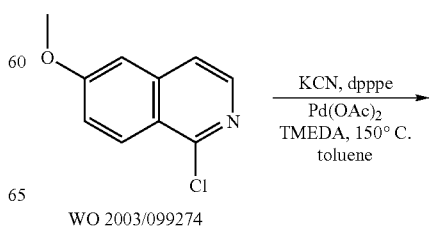

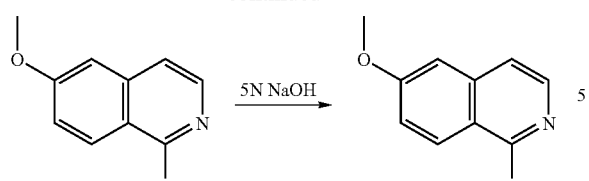

Cap-140

Cap-139

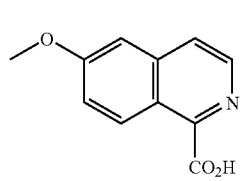

Cap-139, step a

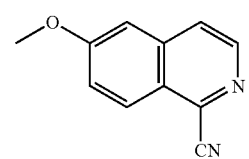

To a thick-walled, screw-top vial containing an argon-degassed suspension of 1-chloro-6-methoxyisoquinoline (1.2 g, 6.2 mmol; prepared according to the procedure in WO 2003/099274), potassium cyanide (0.40 g, 6.2 mmol), 1,5-bis (diphenylphosphino)pentane (0.27 g, 0.62 mmol) and palladium (II) acetate (70 mg, 0.31 mmol) in anhydrous toluene (6 mL) was added N,N,N',N'-tetramethylethylenediamine (0.29 mL, 2.48 mmol). The vial was sealed, heated at 150° C. for 22 h and then allowed to cool to 25° C. The reaction mixture was diluted with ethyl acetate, washed with water and brine, dried over $Na_2SO_4$, filtered and concentrated. The residue was purified on silica gel (gradient elution with 5% ethyl acetate/hexanes to 25% ethyl acetate/hexanes) to afford Cap-139, step a (669.7 mg, 59%) as a white solid. $^1$H NMR (CDCl$_3$, 500 MHz) δ 8.54 (d, J=6.0 Hz, 1H), 8.22 (d, J=9.0 Hz, 1H), 7.76 (d, J=5.5 Hz, 1H), 7.41-7.39 (m, 1H), 7.13 (d, J=2.0 Hz, 1H), 3.98 (s, 3H); $R_f$=1.66 min (Cond.-D1); 90% homogenity index; LCMS: Anal. Calc. for [M+H]$^+$ C$_{11}$H$_9$N$_2$O: 185.07; found: 185.2.

Cap-139

Cap-139 was prepared from the basic hydrolysis of Cap-139, step a with 5N NaOH according to the procedure described for Cap 138. $^1$H NMR (400 MHz, DMSO-d$_6$) δ 13.63 (v br s, 1H), 8.60 (d, J=9.3 Hz, 1H), 8.45 (d, J=5.6 Hz, 1H), 7.95 (d, J=5.9 Hz, 1H), 7.49 (d, J=2.2 Hz, 1H), 7.44 (dd, J=9.3, 2.5 Hz, 1H), 3.95 (s, 3H); $R_f$=0.64 min (Cond.-D1); 90% homogenity index; LCMS: Anal. Calc. for [M+H]$^+$ C$_{11}$H$_{10}$NO$_3$: 204.07; found: 204.05.

Cap-140, step a

To a vigorously-stirred mixture of 1,3-dichloro-5-ethoxy-isoquinoline (482 mg, 2.00 mmol; prepared according to the procedure in WO 2005/051410), palladium (II) acetate (9 mg, 0.04 mmol), sodium carbonate (223 mg, 2.10 mmol) and 1,5-bis(diphenylphosphino)pentane (35 mg, 0.08 mmol) in dry dimethylacetamide (2 mL) at 25° C. under nitrogen was added N,N,N',N'-tetramethylethylenediamine (60 mL, 0.40 mmol). After 10 min, the mixture was heated to 150° C., and then a stock solution of acetone cyanohydrin (prepared from 457 μL of acetone cyanohydrin in 4.34 mL DMA) was added in 1 mL portions over 18 h using a syringe pump. The mixture was then partitioned between ethyl acetate and water and the organic layer was separated, washed with brine, dried over Na$_2$SO$_4$, filtered and concentrated. The residue was purified on silica gel (gradient elution with 10% ethyl acetate in hexanes to 40% ethyl acetate in hexanes) to afford Cap-140, step a (160 mg, 34%) as a yellow solid. $R_f$=2.46 min (Cond.-MS-W2); 90% homogenity index; LCMS: Anal. Calc. for [M+H]$^+$ C$_{12}$H$_9$ClN$_2$O: 233.05; found: 233.08.

Cap-140

Cap-140 was prepared by the acid hydrolysis of Cap-140, step a with 12N HCl as described in the procedure for the preparation of Cap 141, described below. $R_f$=2.24 min (Cond.-MS-W2); 90% homogenity index; LCMS: Anal. Calc. for [M+H]$^+$ C$_{12}$H$_{11}$ClNO$_3$: 252.04; found: 252.02.

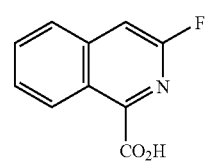

Cap-141

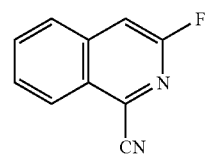

Cap-141, step a

Cap-141, step a was prepared from 1-bromo-3-fluoroiso-quinoline (prepared from 3-amino-1-bromoisoquinoline using the procedure outlined in J. Med. Chem. 1970, 13, 613) as described in the procedure for the preparation of Cap-140, step a (vide supra). $^1$H NMR (500 MHz, CDCl$_3$) δ 8.35 (d, J=8.5 Hz, 1H), 7.93 (d, J=8.5 Hz, 1H), 7.83 (t, J=7.63 Hz, 1H), 7.77-7.73 (m, 1H), 7.55 (s, 1H); R$_t$=1.60 min (Cond.-D1); 90% homogenity index; LCMS: Anal. Calc. for [M+H]$^+$ C$_{10}$H$_6$FN$_2$: 173.05; found: 172.99.

Cap-141

Cap-141, step a (83 mg, 0.48 mmol) was treated with 12N HCl (3 mL) and the resulting slurry was heated at 80° C. for 16 h before it was cooled to room temperature and diluted with water (3 mL). The mixture was stirred for 10 min and then filtered to afford Cap-141 (44.1 mg, 48%) as an off-white solid. The filtrate was diluted with dichloromethane and washed with brine, dried over Na$_2$SO$_4$, and concentrated to afford additional Cap-141 (29.30 mg, 32%) which was sufficiently pure to be carried forward directly. $^1$H NMR (DMSO-d$_6$, 500 MHz) δ 14.0 (br s, 1H), 8.59-8.57 (m, 1H), 8.10 (d, J=8.5 Hz, 1H), 7.88-7.85 (m, 2H), 7.74-7.71 (m, 1H); R$_t$=1.33 min (Cond.-D1); 90% homogenity index; LCMS: Anal. Calc. for [M+H]$^+$ C$_{10}$H$_7$FNO$_2$: 192.05; found: 191.97.

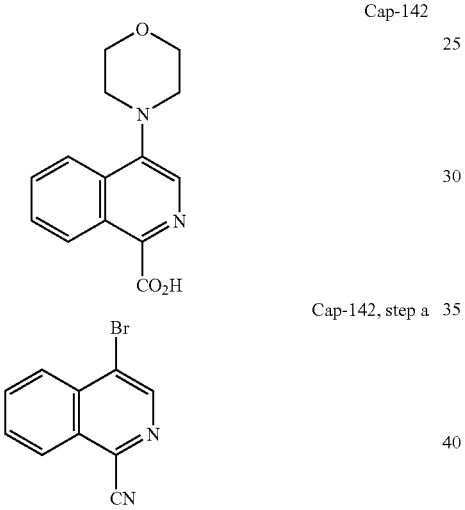

Cap-142

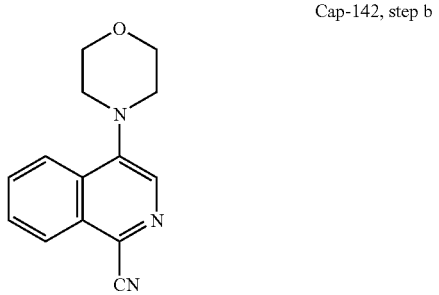 [SMILES: N#Cc1ncc(N2CCOCC2)c2ccccc12]

Cap-142, step a

Cap-142, step a was prepared from 4-bromoisoquinoline N-oxide as described in the two-step procedure for the preparation of Cap-138, steps b and c. R$_t$=1.45 min (Cond.-MS-W1); 90% homogenity index; LCMS: Anal. Calc. for [M+H]$^+$ C$_{10}$H$_6$BrN$_2$: 232.97; found: 233.00.

Cap-142, step b

To an argon-degassed suspension of Cap-142, step a (116 mg, 0.50 mmol), potassium phosphate tribasic (170 mg, 0.80 mmol), palladium (II) acetate (3.4 mg, 0.015 mmol) and 2-(dicyclohexylphosphino)biphenyl (11 mg, 0.03 mmol) in anhydrous toluene (1 mL) was added morpholine (61 μL, 0.70 mmol). The mixture was heated at 100° C. for 16 h, cooled to 25° C., filtered through diatomaceous earth (Celite®) and concentrated. Purification of the residue on silica gel (gradient elution with 10% to 70% ethyl acetate in hexanes) afforded Cap-142, step b (38 mg, 32%) as a yellow solid which was carried forward directly. R$_t$=1.26 min (Cond.-MS-W1); 90% homogenity index; LCMS: Anal. Calc. for [M+H]$^+$ C$_{14}$H$_{14}$N$_3$O: 240.11; found: 240.13.

Cap-142

Cap-142 was prepared from Cap-142, step b with 5N sodium hydroxide as described in the procedure for Cap 138. R$_t$=0.72 min (Cond.-MS-W1); 90% homogenity index; LCMS: Anal. Calc. for [M+H]$^+$ C$_{14}$H$_{15}$N$_2$O$_3$: 259.11; found: 259.08.

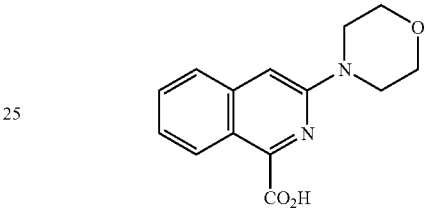

Cap-143

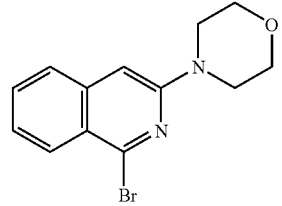

Cap-143, step a

To a stirred solution of 3-amino-1-bromoisoquinoline (444 mg, 2.00 mmol) in anhydrous dimethylformamide (10 mL) was added sodium hydride (60%, unwashed, 96 mg, 2.4 mmol) in one portion. The mixture was stirred at 25° C. for 5 min before 2-bromoethyl ether (90%, 250 μL, 2.00 mmol) was added. This mixture was stirred further at 25° C. for 5 h and at 75° C. for 72 h before it was cooled to 25° C., quenched with saturated ammonium chloride solution and diluted with ethyl acetate. The organic layer was separated, washed with water and brine, dried over Na$_2$SO$_4$, filtered and concentrated. Purification of the residue on silica gel (gradient elution with 0% to 70% ethyl acetate in hexanes) afforded Cap-143, step a (180 mg, 31%) as a yellow solid. R$_t$=1.75 min (Cond.-MS-W1); 90% homogenity index; LCMS: Anal. Calc. for [M+H]$^+$ C$_{13}$H$_{14}$BrN$_2$O: 293.03; found: 293.04.

Cap-143

To a cold (−60° C.) solution of Cap-143, step a (154 mg, 0.527 mmol) in anhydrous tetrahydrofuran (5 mL) was added a solution of n-butyllithium in hexanes (2.5 M, 0.25 mL, 0.633 mmol). After 10 min, dry carbon dioxide was bubbled into the reaction mixture for 10 min before it was quenched with 1N HCl and allowed to warm to 25° C. The mixture was then extracted with dichloromethane (3×30 mL) and the combined organic extracts were concentrated in vacuo. Purification of the residue by reverse phase HPLC (MeOH/water/TFA) afforded Cap-143 (16 mg, 12%). R$_t$=1.10 min (Cond.-

MS-W1); 90% homogenity index; LCMS: Anal. Calc. for [M+H]+ C14H15N2O3: 259.11; found: 259.08.

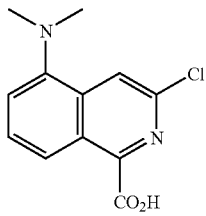

Cap-144

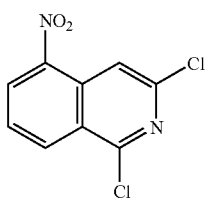

Cap-144, step a 1,3-Dichloroisoquinoline (2.75 g, 13.89 mmol) was added in small portions to a cold (0° C.) solution of fuming nitric acid (10 mL) and concentrated sulfuric acid (10 mL). The mixture was stirred at 0° C. for 0.5 h before it was gradually warmed to 25° C. where it stirred for 16 h. The mixture was then poured into a beaker containing chopped ice and water and the resulting suspension was stirred for 1 h at 0° C. before it was filtered to afford Cap-144, step a (2.73 g, 81%) as a yellow solid which was used directly. $R_f$=2.01 min (Cond.-D1); 95% homogenity index; LCMS: Anal. Calc. for [M+H]+ C9H5Cl2N2O2: 242.97; found: 242.92.

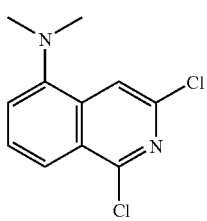

Cap-144, step b

Cap-144, step a (0.30 g, 1.23 mmol) was taken up in methanol (60 mL) and treated with platinum oxide (30 mg), and the suspension was subjected to Parr hydrogenation at 7 psi H2 for 1.5 h before formalin (5 mL) and additional platinum oxide (30 mg) were added. The suspension was resubjected to Parr hydrogenation at 45 psi H2 for 13 h before it was suction-filtered through diatomaceous earth (Celite®) and concentrated down to ¼ volume. Suction-filtration of the ensuing precipitate afforded the title compound as a yellow solid which was flash chromatographed on silica gel (gradient elution with 5% ethyl acetate in hexanes to 25% ethyl acetate in hexanes) to afford Cap-144, step b (231 mg, 78%) as a pale, yellow solid. $R_f$=2.36 min (Cond.-D1); 95% homogenity index; 1H NMR (400 MHz, CDCl3) δ 8.02 (s, 1H), 7.95 (d, J=8.6 Hz, 1H), 7.57-7.53 (m, 1H), 7.30 (d, J=7.3 Hz, 1H), 2.88 (s, 6H); LCMS: Anal. Calc. for [M+H]+ C11H11Cl2N2: 241.03; found: 241.02. HRMS: Anal. Calc. for [M+H]+ C11H11Cl2N2: 241.0299; found: 241.0296.

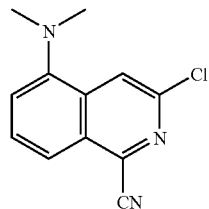

Cap-144, step c

Cap-144, step c was prepared from Cap-144, step b according to the procedure described for the preparation of Cap-139, step a. $R_f$=2.19 min (Cond.-D1); 95% homogenity index; LCMS: Anal. Calc. for [M+H]+ C12H11ClN3: 232.06; found: 232.03. HRMS: Anal. Calc. for [M+H]+ C12H11ClN3: 232.0642; found: 232.0631.

Cap-144

Cap-144 was prepared according to the procedure described for Cap-141. $R_f$=2.36 min (Cond.-D1); 90%; LCMS: Anal. Calc. for [M+H]+ C12H12ClN2O2: 238.01; found: 238.09.

Caps-145 to -162

Caps-145 to 162 were prepared from the appropriate 1-chloroisoquinolines according to the procedure described for the preparation of Cap-138 (Method A) or Cap-139 (Method B) unless noted otherwise as outlined below.

| Cap # | Cap | Method | Hydrolysis | $R_f$ (LC-Cond.); % homogeneity index; MS data |
|---|---|---|---|---|
| Cap-145 | Prepared from commercially available 1,3-dichloroisoquinoline | B | 12N HCl | 1.14 min (Cond.-MS-W1); 90%; LCMS: Anal. Calc. for [M + H]+ C10H7ClNO2: 208.02; found: 208.00. |

-continued

| Cap # | Cap | Method | Hydrolysis | R$_t$ (LC-Cond.); % homogeneity index; MS data |
|---|---|---|---|---|
| Cap-146 | Prepared from commercially available 3-hydroxyisoquinoline | A | 5N NaOH | 1.40 min (Cond.-D1); 95%; LCMS: Anal. Calc. for [M + H]$^+$ C$_{11}$H$_{10}$NO$_3$: 204.07; found: 204.06. |
| Cap-147 | Prepared from commercially available 1-chloro-4-hydroxyisoquinoline | B | 5N NaOH | 0.87 min (Cond.-D1); 95%; LCMS: Anal. Calc. for [M + H]$^+$ C$_{11}$H$_{10}$NO$_3$: 204.07; found: 204.05. |
| Cap-148 | Prepared from commercially available 7-hydroxyisoquinoline | A | 5N NaOH | 0.70 min (Cond.-D1); 95%; LCMS: Anal. Calc. for [M + H]$^+$ C$_{11}$H$_{10}$NO$_3$: 204.07; found: 204.05. |
| Cap-149 | Prepared from commercially available 5-hydroxyisoquinoline | A | 5N NaOH | 0.70 min (Cond.-D1); 95%; LCMS: Anal. Calc. for [M + H]$^+$ C$_{11}$H$_{10}$NO$_3$: 204.07; found: 204.05. |
| Cap-150 | Prepared from 8-methoxy-1-chloroisoquinoline, which can be synthesized following the procedure in WO 2003/099274 | A | 12N HCl | 0.26 min (Cond.-D1); 95%; LCMS: Anal. Calc. for [M + H]$^+$ C$_{11}$H$_{10}$NO$_3$: 204.07; found: 204.04. |
| Cap-151 | Prepared from 5-methoxy-1,3-dichloroisoquinoline, which can be synthesized following the procedure in WO 2005/051410. | B | 12N HCl | 1.78 min (Cond.-D1); 90%; LCMS: Anal. Calc. for [M + H]$^+$ C$_{11}$H$_9$ClNO$_3$: 238.03; found: 238.09. |

-continued

| Cap # | Cap | Method | Hydrolysis | $R_t$ (LC-Cond.); % homogeneity index; MS data |
|---|---|---|---|---|
| Cap-152 | 6-methoxy-3-chloroisoquinoline-1-carboxylic acid structure<br>Prepared from commercially available 6-methoxy-1,3-dichloroisoquinoline | B | 12N HCl | 1.65 min (Cond.-D1): 95%; LCMS: Anal. Calc. for [M + H]$^+$ $C_{11}H_9ClNO_3$: 238.00; found: 238.09. |
| Cap-153 | 4-bromoisoquinoline-1-carboxylic acid structure<br>Prepared from 4-bromoisoquinoline, which can be synthesized following the procedure in WO 2003/062241 | A | 6N HCl | 1.18 min (Cond.-MS-W1); 95%; LCMS: Anal. Calc. for [M + H]$^+$ $C_{10}H_7BrNO_2$: 251.97; found: 251.95. |
| Cap-154 | 7-fluoroisoquinoline-1-carboxylic acid structure<br>Prepared from 7-fluoro-1-chloroisoquinoline, which can be synthesized following the procedure in WO 2003/099274 | B | 5N NaOH | 0.28 min (Cond.-MS-W1); 90%; LCMS: Anal. Calc. for [M + H]$^+$ $C_{10}H_7FNO_2$: 192.05; found: 192.03. |
| Cap-155 | 7-chloroisoquinoline-1-carboxylic acid structure<br>Prepared from 1,7-dichloroisoquinoline, which can be synthesized following the procedure in WO 2003/099274 | B | 5N NaOH | 0.59 min (Cond.-MS-W1); 90%; LCMS: Anal. Calc. for [M + H]$^+$ $C_{10}H_7ClNO_2$: 208.02; found: 208.00. |
| Cap-156 | 6-chloroisoquinoline-1-carboxylic acid structure<br>Prepared from 1,6-dichloroisoquinoline, which can be synthesized following the procedure in WO 2003/099274 | B | 5N NaOH | 0.60 min (Cond.-MS-W1); 90%; LCMS: Anal. Calc. for [M + H]$^+$ $C_{10}H_7ClNO_2$: 208.02; found: 208.03. |
| Cap-157 | 4-chloroisoquinoline-1-carboxylic acid structure<br>Prepared from 1,4-dichloroisoquinoline, which can be synthesized following the procedure in WO 2003/062241 | B | 12N HCl | 1.49 min (Cond.-D1); 95%; LCMS: Anal. Calc. for [M + H]$^+$ $C_{10}H_{17}ClNO$: 208.02; found: 208.00. |

-continued

| Cap # | Cap | Method | Hydrolysis | $R_t$ (LC-Cond.); % homogeneity index; MS data |
|---|---|---|---|---|
| Cap-158 | 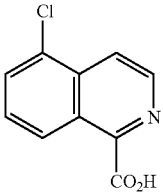<br>Prepared from 1,5-dichloroisoquinoline, which can be synthesized following the procedure in WO 2003/099274 | B | 5N NaOH | 0.69 min (Cond.-MS-W1); 90%; LCMS: Anal. Calc. for $[M + H]^+$ $C_{10}H_7ClNO_2$: 208.02; found: 208.01. |
| Cap-159 | 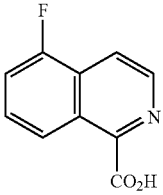<br>Prepared from 5-fluoro-1-chloroisoquinoline, which can be synthesized following the procedure in WO 2003/099274 | B | 5N NaOH | 0.41 min (Cond.-MS-W1); 90%; LCMS: Anal. Calc. for $[M + H]^+$ $C_{10}H_7FNO_2$: 192.05; found: 192.03. |
| Cap-160 | 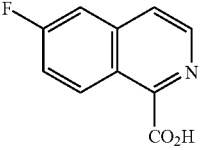<br>Prepared from 6-fluoro-1-chloroisoquinoline, which can be synthesized following the procedure in WO 2003/099274 | B | 5N NaOH | 0.30 min (Cond.-MS-W1); 90%; LCMS: Anal. Calc. for $[M + H]^+$ $C_{10}H_7FNO_2$: 192.05; found: 192.03. |
| Cap-161 | 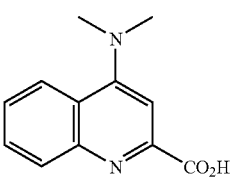<br>Prepared from 4-bromoquinoline-2-carboxylic acid and dimethylamine (DMSO, 100° C.) | — | — | 0.70 min (Cond.-D1); 95%; LCMS: Anal. Calc. for $[M + H]^+$ $C_{12}H_{13}N_2O_2$: 217.10; found: 217.06. |
| Cap-162 | 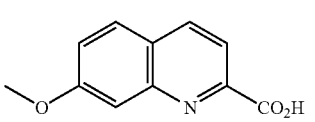<br>Prepared from m-anisidine following the procedure described in *J. Hetero. Chem.* 1993, 17 and *Heterocycles*, 2003, 60, 953. | — | — | 0.65 min (Cond.-M3); 95%; LCMS: Anal. Calc. for $[M + H]^+$ $C_{11}H_{10}NO_3$: 204.07; found: 203.94. |

Cap-163

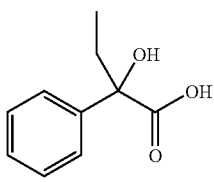

To a solution of 2-ketobutyric acid (1.0 g, 9.8 mmol) in diethylether (25 ml) was added phenylmagnesium bromide (22 ml, 1M in THF) dropwise. The reaction was stirred at ~25° C. under nitrogen for 17.5 h. The reaction was acidified with 1N HCl and the product was extracted with ethyl acetate (3×100 ml). The combined organic layer was washed with water followed by brine and dried over $MgSO_4$. After concentration in vacuo, a white solid was obtained. The solid was recrystallized from hexanes/ethyl acetate to afford Cap-163 as white needles (883.5 mg). $^1$H NMR (DMSO-$d_6$, δ=2.5 ppm, 500 MHz): 12.71 (br s, 1H), 7.54-7.52 (m, 2H), 7.34-7.31 (m, 2H), 7.26-7.23 (m, 1H), 5.52-5.39 (br s, 1H), 2.11 (m, 1H), 1.88 (m, 1H), 0.79 (app t, J=7.4 Hz, 3H).

Cap-164

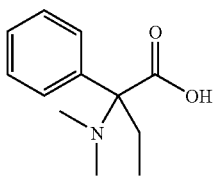

A mixture of 2-amino-2-phenylbutyric acid (1.5 g, 8.4 mmol), formaldehyde (14 mL, 37% in water), 1N HCl (10 mL) and 10% Pd/C (0.5 mg) in MeOH (40 mL) was exposed to $H_2$ at 50 psi in a Parr bottle for 42 h. The reaction was filtered over Celite and concentrated in vacuo, the residue was taken up in MeOH (36 mL) and the product was purified with a reverse phase HPLC (MeOH/$H_2$O/TFA) to afford the TFA salt of Cap-164 as a white solid (1.7 g). $^1$H NMR (DMSO-$d_6$, δ=2.5 ppm, 500 MHz) 7.54-7.47 (m, 5H), 2.63 (m, 1H), 2.55 (s, 6H), 2.31 (m, 1H), 0.95 (app t, J=7.3 Hz, 3H).

Cap-165

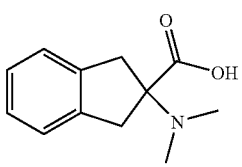

To a mixture of 2-amino-2-indanecarboxylic acid (258.6 mg, 1.46 mmol) and formic acid (0.6 ml, 15.9 mmol) in 1,2-dichloroethane (7 ml) was added formaldehyde (0.6 ml, 37% in water). The mixture was stirred at ~25° C. for 15 min then heated at 70° C. for 8 h. The volatile component was removed in vacuo, and the residue was dissolved in DMF (14 mL) and purified by a reverse phase HPLC (MeOH/$H_2$O/TFA) to afford the TFA salt of Cap-165 as a viscous oil (120.2 mg). $^1$H NMR (DMSO-$d_6$, δ=2.5 ppm, 500 MHz): 7.29-7.21 (m, 4H), 3.61 (d, J=17.4 Hz, 2H), 3.50 (d, J=17.4 Hz, 2H), 2.75 (s, 6H). LC/MS: Anal. Calcd. for [M+H]$^+$ $C_{12}H_{16}NO_2$: 206.12; found: 206.07.

Cap-166a and -166b

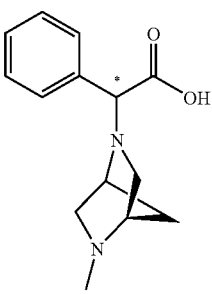

Cap-166a: Diastereomer-1
Cap-166b: Diastereomer-2

Caps-166a and -166b were prepared from (1S,4S)-(+)-2-methyl-2,5-diazabicyclo[2.2.1]heptane (2HBr) according to the method described for the synthesis of Cap-7a and Cap-7b, with the exception that the benzyl ester intermediate was separated using a semi-prep Chrialcel OJ column, 20×250 mm, 10 μm eluting with 85:15 heptane/ethanol mixture at 10 mL/min elution rate for 25 min. Cap-166b: $^1$H NMR (DMSO-$d_6$, δ=2.5 ppm, 500 MHz): 7.45 (d, J=7.3 Hz, 2H), 7.27-7.19 (m, 3H), 4.09 (s, 1H), 3.34 (app br s, 1H), 3.16 (app br s, 1H), 2.83 (d, J=10.1 Hz, 1H), 2.71 (m, 2H), 2.46 (m, 1H), 2.27 (s, 3H), 1.77 (d, J=9.8 Hz, 1H), 1.63 (d, J=9.8 Hz, 1H). LC/MS: Anal. Calcd. for [M+H]$^+$ $C_{14}H_{19}N_2O_2$: 247.14; found: 247.11.

Cap-167

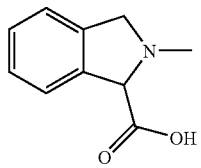

A solution of racemic Boc-1,3-dihydro-2H-isoindole carboxylic acid (1.0 g, 3.8 mmol) in 20% TFA/$CH_2Cl_2$ was stirred at ~25° C. for 4 h. All the volatile component was removed in vacuo. A mixture of the resultant crude material, formaldehyde (15 mL, 37% in water), 1N HCl (10 mL) and 10% Pd/C (10 mg) in MeOH was exposed to $H_2$ (40 PSI) in a Parr bottle for 23 h. The reaction mixture was filtered over Celite and concentrated in vacuo to afford Cap-167 as a yellow foam (873.5 mg). $^1$H NMR (DMSO-$d_6$, δ=2.5 ppm, 500 MHz) 7.59-7.38 (in, 4H), 5.59 (s, 1H), 4.84 (d, J=14 Hz, 1H), 4.50 (d, J=14.1 Hz, 1H), 3.07 (s, 3H). LC/MS: Anal. Calcd. for [M+H]$^+$ $C_{10}H_{12}NO_2$: 178.09; found: 178.65.

Cap-168

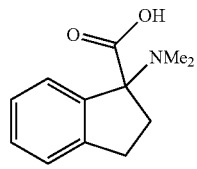

Racemic Cap-168 was prepared from racemic Boc-aminoindane-1-carboxylic acid according to the procedure described for the preparation of Cap-167. The crude material was employed as such.

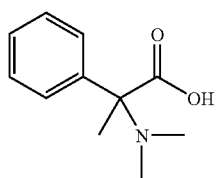

Cap-169

A mixture of 2-amino-2-phenylpropanoic acid hydrochloride (5.0 g, 2.5 mmol), formaldehyde (15 ml, 37% in water), 1N HCl (15 ml), and 10% Pd/C (1.32 g) in MeOH (60 mL) was placed in a Parr bottle and shaken under hydrogen (55 PSI) for 4 days. The reaction mixture was filtered over Celite and concentrated in vacuo. The residue was taken up in MeOH and purified by reverse phase prep-HPLC (MeOH/water/TFA) to afford the TFA salt of Cap-169 as a viscous semi-solid (2.1 g). $^1$H NMR (CDCl$_3$, δ=7.26 ppm, 500 MHz): 7.58-7.52 (m, 2H), 7.39-7.33 (m, 3H), 2.86 (br s, 3H), 2.47 (br s, 3H), 1.93 (s, 3H). LC/MS: Anal. Calcd. for [M+H]$^+$ C$_{11}$H$_{16}$NO$_2$: 194.12; found: 194.12.

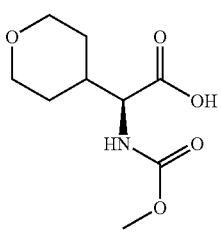

Cap-170

To (S)-2-amino-2-(tetrahydro-2H-pyran-4-yl)acetic acid (505 mg; 3.18 mmol; obtained from Astatech) in water (15 ml) was added sodium carbonate (673 mg; 6.35 mmol), and the resultant mixture was cooled to 0° C. and then methyl chloroformate (0.26 ml; 3.33 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford Cap-170 a colorless residue. $^1$H NMR (500 MHz, DMSO-d$_6$) δ ppm 12.65 (1H, br s), 7.44 (1H, d, J=8.24 Hz), 3.77-3.95 (3H, m), 3.54 (3H, s), 3.11-3.26 (2H, m), 1.82-1.95 (1H, m), 1.41-1.55 (2H, m), 1.21-1.39 (2H, m); LC/MS: Anal. Calcd. for [M+H]$^+$ C$_9$H$_{16}$NO$_5$: 218.1; found 218.1.

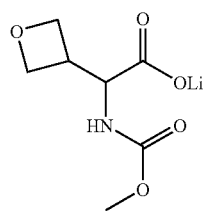

Cap-171

A solution of methyl 2-(benzyloxycarbonylamino)-2-(oxetan-3-ylidene)acetate (200 mg, 0.721 mmol; Il Farmaco (2001), 56, 609-613) in ethyl acetate (7 ml) and CH$_2$Cl$_2$ (4.00 ml) was degassed by bubbling nitrogen for 10 min. Dimethyl dicarbonate (0.116 ml, 1.082 mmol) and Pd/C (20 mg, 0.019 mmol) were then added, the reaction mixture was fitted with a hydrogen balloon and allowed to stir at ambient temperature overnight at which time TLC (95:5 CH$_2$Cl$_2$/MeOH: visualized with stain made from 1 g Ce(NH$_4$)$_2$SO$_4$, 6 g ammonium molybdate, 6 ml sulfuric acid, and 100 ml water) indicated complete conversion. The reaction was filtered through celite and concentrated. The residue was purified via Biotage® (load with dichloromethane on 25 samplet; elute on 25S column with dichloromethane for 3CV then 0 to 5% MeOH/dichloromethane over 250 ml then hold at 5% MeOH/dichloromethane for 250 ml; 9 ml fractions). Collected fractions containing desired material and concentrated to 120 mg (81%) of methyl 2-(methoxycarbonylamino)-2-(oxetan-3-yl)acetate as a colorless oil. $^1$H NMR (500 MHz, CHLOROFORM-D) δ ppm 3.29-3.40 (m, J=6.71 Hz, 1H) 3.70 (s, 3H) 3.74 (s, 3H) 4.55 (t, J=6.41 Hz, 1H) 4.58-4.68 (m, 2H) 4.67-4.78 (m, 2H) 5.31 (br s, 1H). LC/MS: Anal. Calcd. for [M+H]$^+$ C$_8$H$_{14}$NO$_5$: 204.2; found 204.0.

To methyl 2-(methoxycarbonylamino)-2-(oxetan-3-yl)acetate (50 mg, 0.246 mmol) in THF (2 mL) and water (0.5 mL) was added lithium hydroxide monohydrate (10.33 mg, 0.246 mmol). The resultant solution was allowed to stir overnight at ambient temperature. TLC (1:1 EA/Hex; Hanessian stain [1 g Ce(NH$_4$)$_2$SO$_4$, 6 g ammonium molybdate, 6 ml sulfuric acid, and 100 ml water]) indicated ~10% starting material remaining. Added an additional 3 mg LiOH and allowed to stir overnight at which time TLC showed no starting material remaining. Concentrated in vacuo and placed on high vac overnight providing 55 mg lithium 2-(methoxycarbonylamino)-2-(oxetan-3-yl)acetate as a colorless solid. $^1$H NMR (500 MHz, MeOD) δ ppm 3.39-3.47 (m, 1H) 3.67 (s, 3H) 4.28 (d, J=7.93 Hz, 1H) 4.64 (t, J=6.26 Hz, 1H) 4.68 (t, J=7.02 Hz, 1H) 4.73 (d, J=7.63 Hz, 2H).

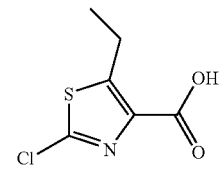

Cap-172

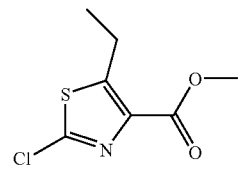

Cap-172, step a

The following diazotization step was adapted from Barton, A.; Breukelman, S. P.; Kaye, P. T.; Meakins, G. D.; Morgan, D. J. *J. C. S. Perkin Trans I* 1982, 159-164: A solution of NaNO$_2$ (166 mg, 2.4 mmol) in water (0.6 mL) was added slowly to a stirred, cold (0° C.) solution of methyl 2-amino-5-ethyl-1,3-thiazole-4-carboxylate (186 mg, 1.0 mmol), CuSO$_4$.5H$_2$O (330 mg, 1.32 mmol), NaCl (260 mg, 4.45 mmol) and H$_2$SO$_4$ (5.5 mL) in water (7.5 mL). The mixture was stirred at 0° C. for 45 min and allowed to warm up to room temperature where it stirred further for 1 h before CuCl (118 mg) was added. This mixture was stirred further at room temperature for 16 h before it was diluted with brine and extracted with ether twice. The organic layers were combined, dried over MgSO$_4$ and concentrated to give methyl 2-chloro-5-ethylthiazole-4-carboxylate (i.e. Cap-172, step a) (175 mg, 85%) as an orange oil (80% pure) which was used directly in the next reaction. $R_t$=1.99 min (Cond.-MD1); LC/MS: Anal. Calcd. for [M+H]$^+$ C$_7$H$_9$ClNO$_2$S: 206.01; found: 206.05.

Cap-172

To a solution of methyl 2-chloro-5-ethylthiazole-4-carboxylate (175 mg) in THF/H$_2$O/MeOH (20 mL/3 mL/12 mL) was added LiOH (305 mg, 12.76 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-172 (60 mg, 74%) as a red solid which was used without further purification. $^1$H NMR (300 MHz, DMSO-d$_6$) δ ppm 13.03-13.42 (1H, m), 3.16 (2H, q, J=7.4 Hz), 1.23 (3H, t, J=7.5 Hz). $R_t$=1.78 min (Cond.-MD1); LC/MS: Anal. Calcd. for [M+H]$^+$ C$_6$H$_7$ClNO$_2$S: 191.99; found: 191.99.

Cap-173

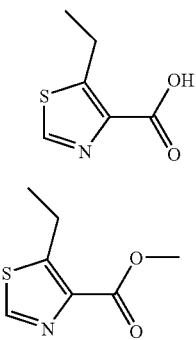

Cap-173, step a

The following diazotization step was adapted from Barton, A.; Breukelman, S. P.; Kaye, P. T.; Meakins, G. D.; Morgan, D. J. *J. C. S. Perkin Trans I* 1982, 159-164: A solution of NaNO$_2$ (150 mg, 2.17 mmol) in water (1.0 mL) was added dropwise to a stirred, cold (0° C.) solution of methyl 2-amino-5-ethyl-1,3-thiazole-4-carboxylate (186 mg, 1.0 mmol) in 50% H$_3$PO$_2$ (3.2 mL). The mixture was stirred at 0° C. for 1 h and allowed to warm up to room temperature where it stirred further for 2 h. After recooling to 0° C., the mixture was treated slowly with a solution of NaOH (85 mg) in water (10 mL). The mixture was then diluted with saturated NaHCO$_3$ solution and extracted twice with ether. The organic layers were combined, dried over MgSO$_4$ and concentrated to give methyl 5-ethylthiazole-4-carboxylate (i.e. Cap-173, step a) (134 mg, 78%) as an orange oil (85% pure) which was used directly in the next reaction. $R_t$=1.58 min (Cond.-MD1); LC/MS: Anal. Calcd. for [M+H]$^+$ C$_7$H$_{10}$NO$_2$S: 172.05; found: 172.05.

Cap-173

To a solution of methyl 5-ethylthiazole-4-carboxylate (134 mg) in THF/H$_2$O/MeOH (18 mL/2.7 mL/11 mL) was added LiOH (281 mg, 11.74 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-173 (90 mg, 73%) as an orange solid which was used without further purification. $^1$H NMR (300 MHz, DMSO-d$_6$) δ ppm 12.74-13.04 (1H, m), 3.20 (2H, q, J=7.3 Hz), 1.25 (3H, t, J=7.5 Hz). $R_t$=1.27 min (Cond.-MD1); LC/MS: Anal. Calcd. for [M+H]$^+$ C$_6$H$_8$NO$_2$S: 158.03; found: 158.04.

Cap-174

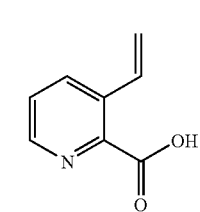

Cap-174, step a

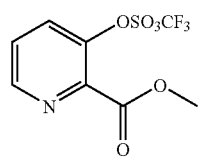

Triflic anhydride (5.0 g, 18.0 mmol) was added dropwise to a cold (0° C.) solution of methyl 3-hydroxypicolinate (2.5 g, 16.3 mmol) and TEA (2.5 mL, 18.0 mmol) in CH$_2$Cl$_2$ (80 mL). The mixture was stirred at 0° C. for 1 h before it was allowed to warm up to room temperature where it stirred for an additional 1 h. The mixture was then quenched with saturated NaHCO$_3$ solution (40 mL) and the organic layer was separated, washed with brine, dried over MgSO$_4$ and concentrated to give methyl 3-(trifluoromethylsulfonyloxy)picolinate (i.e. Cap-174, step a) (3.38 g, 73%) as a dark brown oil (>95% pure) which was used directly without further purification. $^1$H NMR (300 MHz, CDCl$_3$) δ ppm 8.72-8.79 (1H, m), 7.71 (1H, d, J=1.5 Hz), 7.58-7.65 (1H, m), 4.04 (3H, s). $R_t$=1.93 min (Cond.-MD1); LC/MS: Anal. Calcd. for [M+H]$^+$ C$_8$H$_7$F$_3$NO$_5$S: 286.00; found: 286.08.

Cap-174

To a solution of methyl 3-(trifluoromethylsulfonyloxy)picolinate (570 mg, 2.0 mmol) in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. overnight before a saturated solution of KF (20 mL) was added to the reaction mixture at room temperature. This mixture was stirred for 4 h before it was filtered through Celite and the pad of Celite was washed with ethyl acetate. The aqueous phase of the filtrate was then separated and concentrated down in vacuo. The residue was treated with 4N HCl in dioxanes (5 mL) and the resulting mixture was extracted with methanol, filtered and evaporated to afford Cap-174 (260 mg) as a green solid which was slightly contaminated with inorganic salts but was used without further purification. $^1$H NMR (300 MHz, DMSO-d$_6$) δ ppm 8.21 (1H, d, J=3.7 Hz), 7.81-7.90 (1H, m), 7.09 (1H, dd, J=7.7, 4.8 Hz), 6.98 (1H, dd, J=17.9, 11.3 Hz), 5.74 (1H, dd, J=17.9, 1.5 Hz), 5.20 (1H, d, J=11.0 Hz). $R_t$=0.39 min (Cond.-MD1); LC/MS: Anal. Calcd. for [M+H]$^+$ C$_8$H$_8$NO$_2$: 150.06; found: 150.07.

Cap-175

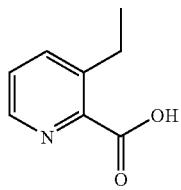

Cap-175, step a

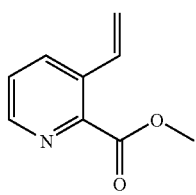

To a solution of methyl 3-(trifluoromethylsulfonyloxy)picolinate (i.e. Cap 173, step a) (570 mg, 2.0 mmol), an intermediate in the preparation of Cap-174, in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. for 4 h before the solvent was removed in vacuo. The residue was taken up in acetonitrile (50 mL) and hexanes (50 mL) and the resulting mixture was washed twice with hexanes. The acetonitrile layer was then separated, filtered through Celite, and evaporated. Purification of the residue by flash chromatography on a Horizon instrument (gradient elution with 25% ethyl acetate in hexanes to 65% ethyl acetate in hexanes) afforded methyl 3-vinylpicolinate (i.e. Cap-175, step a) (130 mg, 40%) as a yellow oil. $^1$H NMR (300 MHz, CDCl$_3$) δ ppm 8.60 (1H, dd, J=4.6, 1.7 Hz), 7.94 (1H, d, J=7.7 Hz), 7.33-7.51 (2H, in), 5.72 (1H, d, J=17.2 Hz), 5.47 (1H, d, J=11.0 Hz), 3.99 (3H, s). R$_f$=1.29 min (Cond.-MD1); LC/MS: Anal. Calcd. for [M+H]$^+$ C$_9$H$_{10}$NO$_2$: 164.07; found: 164.06.

Cap-175, step b

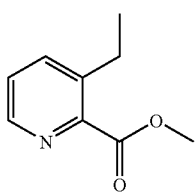

Palladium on carbon (10%, 25 mg) was added to a solution of methyl 3-vinylpicolinate (120 mg, 0.74 mmol) in ethanol (10 mL). The suspension was stirred at room temperature under an atmosphere of hydrogen for 1 h before it was filtered through Celite and the pad of Celite was washed with methanol. The filtrate was concentrated down to dryness to yield methyl 3-ethylpicolinate (i.e. Cap-175, step b) which was taken directly into the next reaction. R$_f$=1.15 min (Cond.-MD 1); LC/MS: Anal. Calcd. for [M+H]$^+$ C$_9$H$_{12}$NO$_2$: 166.09; found: 166.09.

Cap-175

To a solution of methyl 3-ethylpicolinate in THF/H$_2$O/MeOH (5 mL/0.75 mL/3 mL) was added LiOH (35 mg, 1.47 mmol). The mixture was stirred at room temperature for 2 d before additional LiOH (80 mg) was added. After an additional 24 h at room temperature, the mixture was filtered and the solvent was removed in vacuo. The residue was then treated with 4N HCl in dioxanes (5 mL) and the resulting suspension was concentrated down to dryness to yield Cap-175 as a yellow solid which was used without further purification. $^1$H NMR (300 MHz, DMSO-d$_6$) δ ppm 8.47 (1H, dd, J=4.8, 1.5 Hz), 7.82-7.89 (1H, m), 7.53 (1H, dd, J=7.7, 4.8 Hz), 2.82 (2H, q, J=7.3 Hz), 1.17 (3H, t, J=7.5 Hz). R$_f$=0.36 min (Cond.-MD1); LC/MS: Anal. Calcd. for [M±H]$^+$ C$_8$H$_{10}$NO$_2$: 152.07; found: 152.10.

Cap-176

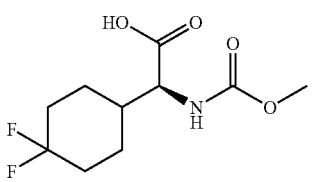

Cap-176, step a

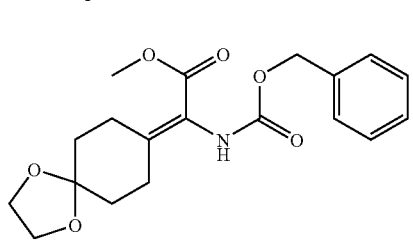

A solution of 1,4-dioxaspiro[4.5]decan-8-one (15 g, 96 mmol) in EtOAc (150 mL) was added to a solution of methyl 2-(benzyloxycarbonylamino)-2-(dimethoxyphosphoryl)acetate (21.21 g, 64.0 mmol) in 1,1,3,3-tetramethylguanidine (10.45 mL, 83 mmol) and EtOAc (150 mL). The resulting solution was the stirred at ambient temperature for 72 h and then it was diluted with EtOAc (25 mL). The organic layer was washed with 1N HCl (75 mL), H2O (100 mL) and brine (100 mL), dried (MgSO$_4$), filtered and concentrated. The residue was purified via Biotage (5% to 25% EtOAc/Hexanes; 300 g column). The combined fractions containing the product were then concentrated under vacuum and the residue was re-crystallized from hexanes/EtOAc to give white crystals that corresponded to methyl 2-(benzyloxycarbonylamino)-2-(1,4-dioxaspiro[4.5]decan-8-ylidene)acetate (6.2 g) $^1$H NMR (400 MHz, CDCl$_3$-d) δ ppm 7.30-7.44 (5H, m), 6.02 (1H, br. s.), 5.15 (2H, s), 3.97 (4H, s), 3.76 (3H, br. s.), 2.84-2.92 (2H, m), 2.47 (2H, t, J=6.40 Hz), 1.74-1.83 (4H, m). LC (Cond. OL1): R$_f$=2.89 min. LC/MS: Anal. Calcd. For [M+Na]$^+$ C$_{19}$H$_{23}$NNaO$_6$: 745.21; found: 745.47

Cap-176, step b

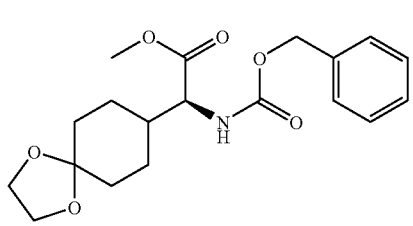

Ester Cap 176, step b was prepared from alkene Cap 176, step a according to the method of Burk, M. J.; Gross, M. F. and Martinez J. P. (*J. Am. Chem. Soc.*, 1995, 117, 9375-9376 and references therein): A 500 mL high-pressure bottle was charged with alkene Cap 176, step a (3.5 g, 9.68 mmol) in degassed MeOH (200 mL) under a blanket of N$_2$. The solution was then charged with (−)1,2-Bis((2S,5S)-2,5-dimethylphospholano)ethane(cyclooctadiene)rhodium (1) tetrafluoroborate (0.108 g, 0.194 mmol) and the resulting mixture was flushed with $N_2$ (3×) and charged with $H_2$ (3×). The solution was shaken vigorously under 70 psi of $H_2$ at ambient temperature for 72 h. The solvent was removed under reduced pressure and the remaining residue was taken up in EtOAc. The brownish solution was then filtered through a plug of Silica Gel and eluted with EtOAc. The solvent was concentrated under vacuum to afford a clear oil corresponding to ester Cap 176, step b (3.4 g) $^1$H NMR (500 MHz, $CDCl_3$-d) δ ppm 7.28-7.43 (5H, m), 5.32 (1H, d, J=9.16 Hz), 5.06-5.16 (2H, m), 4.37 (1H, dd, J=9.00, 5.04 Hz), 3.92 (4H, t, J=3.05 Hz), 3.75 (3H, s), 1.64-1.92 (4H, m), 1.37-1.60 (5H, m). LC (Cond. OL1): $R_t$=1.95 min. LC/MS: Anal. Calcd. For $[M+H]^+$ $C_{19}H_{26}NO_6$: 364.18; found: 364.27.

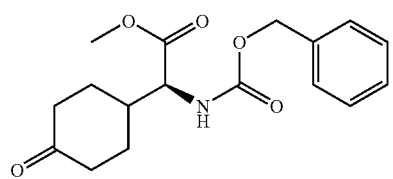

Cap-176, step c

Ester Cap 176, step b (4.78 g, 13.15 mmol) was dissolved in THF (15 mL) followed by sequential addition of water (10 mL), glacial acetic acid (26.4 mL, 460 mmol) and dichloroacetic acid (5.44 mL, 65.8 mmol). The resulting mixture was stirred for 72 h at ambient temperature, and the reaction was quenched by slow addition of solid $Na_2CO_3$ with vigorous stirring until the release of gas was no longer visible. Crude product was extracted into 10% ethyl acetate-dichloromethane and the organic layers were combined, dried ($MgSO_4$) filtered and concentrated. The resulting residue was purified via Biotage (0 to 30% EtOAc/Hex; 25 g column) to afford ketone Cap 176, step c (3.86 g) as a clear oil. $^1$H NMR (400 MHz, $CDCl_3$-d) δ ppm 7.28-7.41 (5H, m), 5.55 (1H, d, J=8.28 Hz), 5.09 (2H, s), 4.46 (1H, dd, J=8.16, 5.14 Hz), 3.74 (3H, s), 2.18-2.46 (5H, m), 1.96-2.06 (1H, m), 1.90 (1H, ddd, J=12.99, 5.96, 2.89 Hz), 1.44-1.68 (2H, m, J=12.36, 12.36, 12.36, 12.36, 4.77 Hz). LC (Cond. OL1): $R_t$=1.66 min. LC/MS; Anal. Calcd. For $[M+Na]^+$ $C_{17}H_{21}NNaO_5$: 342.13; found: 342.10.

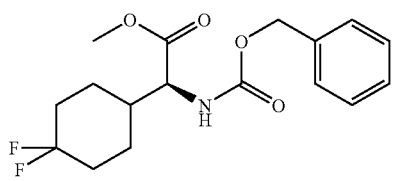

Cap 176, step d

Deoxo-Fluor® (3.13 mL, 16.97 mmol) was added to a solution of ketone Cap 176, step c (2.71 g, 8.49 mmol) in $CH_2Cl_2$ (50 mL) followed by addition of a catalytic amount of EtOH (0.149 mL, 2.55 mmol). The resulting yellowish solution was stirred at rt overnight. The reaction was quenched by addition of sat. aq. $NaHCO_3$ (25 mL) and the mixture was extracted with EtOAc (3×75 mL)). The combined organic layers were dried ($MgSO_4$), filtered and dried to give a yellowish oil. The residue was purified via Biotage chromatography (2% to 15% EtOAc/Hex; 90 g column) and a white solid corresponding to the difluoro amino acid dilforide Cap 176, step d (1.5 g) was recovered. $^1$H NMR (400 MHz, $CDCl_3$-d) δ ppm 7.29-7.46 (5H, m), 5.34 (1H, d, J=8.28 Hz), 5.12 (2H, s), 4.41 (1H, dd, J=8.66, 4.89 Hz), 3.77 (3H, s), 2.06-2.20 (2H, m), 1.83-1.98 (1H, m), 1.60-1.81 (4H, m), 1.38-1.55 (2H, $^{19}$F NMR (376 MHz, $CDCl_3$-d) δ ppm −92.15 (1F, d, J=237.55 Hz), −102.44 (1F, d, J=235.82 Hz). LC (Cond. OL1): $R_t$=1.66 min. LC/MS: Anal. Calcd. For $[2M+Na]^+$ $C_{34}H_{42}F_4N_2NaO_8$: 705.28; found: 705.18.

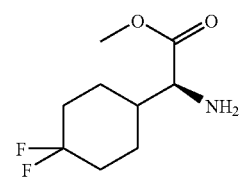

Cap 176, step e

Difluoride Cap 176, step d (4 g, 11.72 mmol) was dissolved in MeOH (120 mL) and charged with Pd/C (1.247 g, 1.172 mmol). The suspension was flushed with $N_2$ (3×) and the reaction mixture was placed under 1 atm of $H_2$ (balloon). The mixture was stirred at ambient temperature for 48 h. The suspension was then filtered though a plug of Celite and concentrated under vacuum to give an oil that corresponded to amino acid Cap 176, step e (2.04 g) and that was used without further purification. $^1$H NMR (400 MHz, DMSO-$d_6$) δ ppm 3.62 (3H, s), 3.20 (1H, d, J=5.77 Hz), 1.91-2.09 (2H, m), 1.50-1.88 (7H, m), 1.20-1.45 (2H, m). $^{19}$F NMR (376 MHz, DMSO-$d_6$) δ ppm −89.39 (1F, d, J=232.35 Hz), −100.07 (1F, d, J=232.35 Hz). $^{13}$C NMR (101 MHz, DMSO-$d_6$) δ ppm 175.51 (1C, s), 124.10 (1C, t, J=241.21, 238.90 Hz), 57.74 (1C, s), 51.39 (1C, s), 39.23 (1C, br. s.), 32.02-33.83 (2C, m), 25.36 (1C, d, J=10.02 Hz), 23.74 (1C, d, J=9.25 Hz). LC (Cond. OL2): $R_t$=0.95 min. LC/MS: Anal. Calcd. For $[2M+H]^+$ $C_{18}H_{31}F_4N_2O_2$: 415.22; found: 415.40.

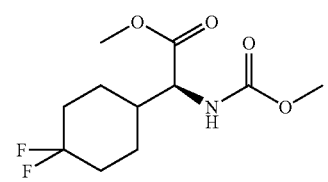

Cap 176, step f

Methyl chloroformate (1.495 mL, 19.30 mmol) was added to a solution of amino acid Cap 176, step e (2 g, 9.65 mmol) and DIEA (6.74 mL, 38.6 mmol) in $CH_2Cl_2$ (100 mL). The resulting solution was stirred at rt for 3 h and volatiles were removed under reduced pressure. The residue was purified via Biotage (0% to 20% EtOAc/Hex; 90 g column). A clear oil that solidified upon standing under vacuum and corresponding to carbamate Cap-176, step f (2.22 g) was recovered. $^1$H NMR (500 MHz, $CDCl_3$-d) δ ppm 5.27 (1H, d, J=8.55 Hz), 4.39 (1H, dd, J=8.85, 4.88 Hz), 3.77 (3H, s), 3.70 (3H, s), 2.07-2.20 (2H, m), 1.84-1.96 (1H, m), 1.64-1.82 (4H, m), 1.39-1.51 (2H, m). $^{19}$F NMR (471 MHz, $CDCl_3$-d) δ ppm −92.55 (1F, d, J=237.13 Hz), −102.93 (1F, d, J=237.12 Hz). $^{13}$C NMR (126 MHz, $CDCl_3$-d) δ ppm 171.97 (1C, s), 156.69 (1C, s), 119.77-125.59 (1C, m), 57.24 (1C, br. s.), 52.48 (1C, br. s.), 52.43 (1C, s), 39.15 (1C, s), 32.50-33.48 (2C, m), 25.30 (1C, d, J=9.60 Hz), 24.03 (1C, d, J=9.60 Hz). LC (Cond. OL1): $R_t$=1.49 min. LC/MS: Anal. Calcd. For [M+Na]$^+$ $C_{11}H_{17}F_2NNaO_4$: 288.10; found: 288.03.

Cap-176

A solution of LiOH (0.379 g, 15.83 mmol) in Water (25 mL) was added to a solution of carbamate Cap-176, step f (2.1 g, 7.92 mmol) in THF (75 mL) and the resulting mixture was stirred at ambient temperature for 4 h. THF was removed under vacuum and the remaining aqueous phase was acidified with 1N HCl solution (2 mL) and then extracted with EtOAc (2×50 mL). The combined organic layers were dried (MgSO$_4$), filtered and concentrated to give a white foam corresponding to Cap-176 (1.92 g). $^1$H NMR (400 MHz, DMSO-d$_6$) δ ppm 12.73 (1H, s), 7.50 (1H, d, J=8.78 Hz), 3.97 (1H, dd, J=8.53, 6.02 Hz), 3.54 (3H, s), 1.92-2.08 (2H, m), 1.57-1.90 (5H, m), 1.34-1.48 (1H, m), 1.27 (1H, qd, J=12.72, 3.26 Hz). $^{19}$F NMR (376 MHz, DMSO-d$_6$) δ ppm −89.62 (1F, d, J=232.35 Hz), −99.93 (1F, d, J=232.35 Hz). LC (Cond. OL2): $R_t$=0.76 min. LC/MS: Anal. Calcd. For [M−H]$^+$ $C_{10}H^{14}F_2NO_4$: 250.09; found: 250.10.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400, or 500 MHz spectrometer; the chemical shifts (δ) are reported in parts per million.

Purity assessment and low resolution mass analysis were conducted on a Shimadzu LC system coupled with Waters Micromass ZQ MS system. It should be noted that retention times may vary slightly between machines. Unless noted otherwise, the LC conditions employed in determining the retention time ($R_t$) were:

| Cond.-J1 | |
|---|---|
| Column = | Phenomenex-Luna 3.0 × 50 mm S10 |
| Start % B = | 0 |
| Final % B = | 100 |
| Gradient time = | 2 min |
| Stop time = | 3 min |
| Flow Rate = | 4 mL/min |
| Wavelength = | 220 nm |
| Slovent A = | 0.1% TFA in 10% methanol/90% water |
| Solvent B = | 0.1% TFA in 90% methanol/10% water |

| Cond.-J2 | |
|---|---|
| Column = | Phenomenex-Luna 3.0 × 50 mm S10 |
| Start % B = | 0 |
| Final % B = | 100 |
| Gradient time = | 4 min |
| Stop time = | 5 min |
| Flow Rate = | 4 mL/min |
| Wavelength = | 220 nm |
| Slovent A = | 0.1% TFA in 10% methanol/90% water |
| Solvent B = | 0.1% TFA in 90% methanol/10% water |

| Cond.-J3 | |
|---|---|
| Column = | XTERRA C18 S7 (3.0 × 50 mm) |
| Start % B = | 0 |
| Final % B = | 100 |
| Gradient time = | 2 min |
| Stop time = | 3 min |
| Flow Rate = | 5 mL/min |
| Wavelength = | 220 nm |
| Slovent A = | 0.1% TFA in 10% methanol/90% water |
| Solvent B = | 0.1% TFA in 90% methanol/10% water |

| Cond.-D1 | |
|---|---|
| Column = | Phenomenex-Luna 3.0 × 50 mm S10 |
| Start % B = | 0 |
| Final % B = | 100 |
| Gradient time = | 3 min |
| Stop time = | 4 min |
| Flow Rate = | 4 mL/min |
| Wavelength | 220 nm |
| Slovent A = | 0.1% TFA in 10% methanol/90% water |
| Solvent B = | 0.1% TFA in 90% methanol/10% water |

| Cond.-D2 | |
|---|---|
| Column = | Phenomenex-Luna 4.6 × 50 mm S10 |
| Start % B = | 0 |
| Final % B = | 100 |
| Gradient time = | 3 min |
| Stop time = | 4 min |
| Flow Rate = | 4 mL/min |
| Wavelength = | 220 nm |
| Slovent A = | 0.1% TFA in 10% methanol/90% water |
| Solvent B = | 0.1% TFA in 90% methanol/10% water |

| Cond.-JB-1 | |
|---|---|
| Column = | Waters Sunfire 5u C18 4.6 × 30 mm |
| Start % B = | 0 |
| Final % B = | 100 |
| Gradient time = | 3 min |
| Stop time = | 4 min |
| Flow Rate = | 4 mL/min |
| Wavelength = | 220 nm |
| Slovent A = | 0.1% TFA in 10% acetonitrile/90% water |
| Solvent B = | 0.1% TFA in 90% acetonitirle/10% water |

Synthetic Route 1:

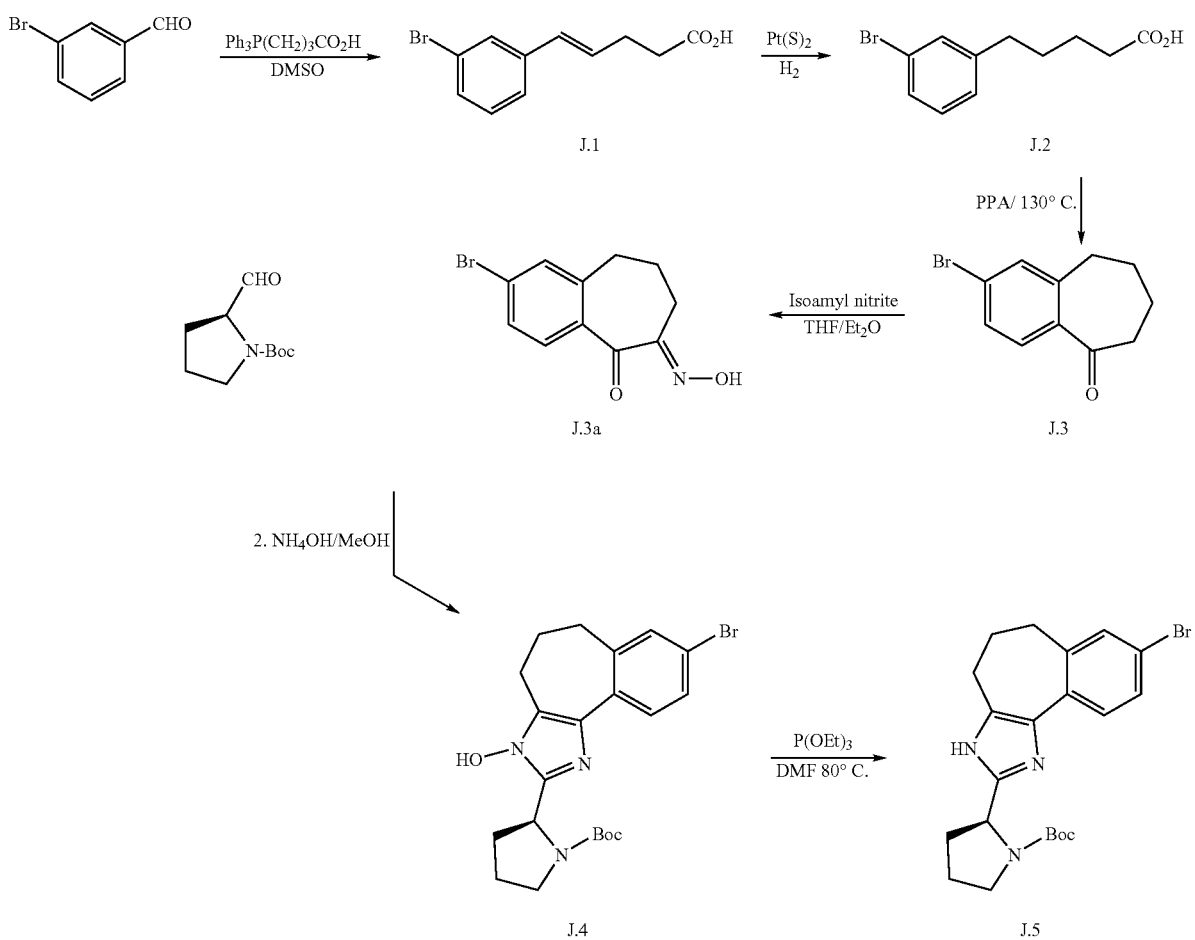

Reference: J. Med. Chem. (2005) 48, 7351.

Examples J.1-J.5

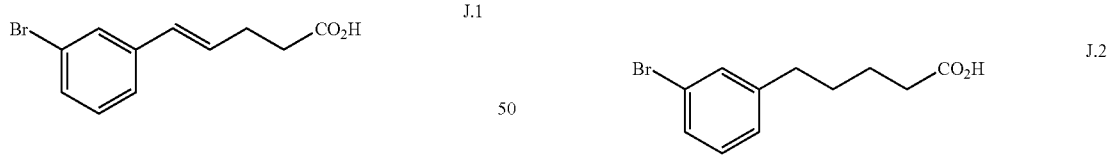

A 1M solution of potassium tert-butoxide in tetrahydrofuran (80 mL) was added dropwise to (3-carboxypropyl)triphenylphosphonium bromide (17 g, 40 mol) in anhydrous DMSO (20 mL) under nitrogen at 24° C., and the solution was stirred 30 min. before addition of 3-bromobenzaldehyde (4.7 mL, 40 mmol). After several minutes a precipitate was observed and an additional 20 mL of DMSO was added to aid solvation, and the reaction was stirred 18 h. The solution was poured onto water (120 mL) and washed with chloroform. The aqueous layer was acidified with conc. HCl and extracted with chloroform (3×250 mL). The organic phase was concentrated and applied to a 65i Biotage silica gel column, gradient elution from 15-65% B (A=Hexanes; B=ethyl acetate) over 2 L to give J.1, (E)-5-(3-bromophenyl)pent-4-enoic acid, 8.2 g (82%). $^1$H NMR (300 MHz, CDCl$_3$) δ 7.45 (t, J=1.5 Hz, 1H), 7.30 (dt, J=7.7, 1.5 Hz, 1H), 7.2-7.16 (m, 1H), 7.12 (t, J=7.7 Hz, 1H), 6.40-6.32 (m, 1H), 6.23-6.14 (m, 1H), 2.52 (s, 4H). LC (Cond.-J1): RT=2.0 min; LRMS: Anal. Calcd. for [M−H]$^-$ C$_{11}$H$_{11}$BrO$_2$: 252.97; found: 252.98.

J.1, (E)-5-(3-Bromophenyl)pent-4-enoic acid (4 g, 15.8 mmol) was dissolved in absolute ethanol (200 mL) and flushed with nitrogen before addition of 5% platinum sulfide on carbon (2.5 g). The solution was flushed with hydrogen at atmospheric pressure and stirred 5 h. The catalyst was removed by filtration over diatomaceous earth (Celite®) and the solvent immediately removed by rotory evaporation (in order to minimized esterification) to give J.2, 5-(3-bromophenyl)pentanoic acid 4 g (99%) which was carried forward without further purification. $^1$H NMR (500 MHz, CDCl$_3$) δ 7.31-7.30 (m, 2H), 7.13 (t, J=7.6 Hz, 1H), 7.09-7.07 (d, J=7.6 Hz, 1H), 2.60 (t, J=7.0 Hz, 2H), 2.37 (t, J=7.0 Hz, 2H), 1.68-1.65 (m, 4H). LC (Cond.-J1): RT=2.1 min; LRMS: Anal. Calcd. for [M−H]$^-$ C$_{11}$H$_{13}$BrO$_2$: 255.00; found: 254.99.

J.3

J.2, 5-(3-bromophenyl)pentanoic acid (4 g, 15.6 mmol) was taken up in polyphosphoric acid (15 g) and heated to 140° C. for 8 h in a 150 mL pressure vessel, capped to prevent product loss due to sublimation. The reaction mixture was partitioned between 150 mL of water and dichloromethane (600 mL). [Caution is necessary to avoid boiling of dichloromethane.] The organic phase was washed with water, brine, and concentrated. The crude product was applied to a 40 (S) Biotage silica gel column and gradient eluted from 5-60% (ethyl acetate/hexanes) and gave J.3 2-bromo-6,7,8,9-tetrahydro-5H-benzo[7]annulen-5-one 1.7 g (40%). $^1$H NMR (300 MHz, CDCl$_3$) δ 7.56 (d, J=8.1 Hz, 1H), 7.41 (dd, J=8.4 Hz, 1.8 Hz, 1H), 7.35 (d, J=1.8 Hz, 1H), 2.86 (t, J=5.9 Hz, 2H), 2.69 (t, J=5.8 Hz, 2H), 1.90-1.73 (m, 4H). LC (Cond.-J1): RT=2.1 min; LRMS: Anal. Calcd. for [M+H]$^+$ C$_{11}$H$_{11}$BrO: 239.00; found: 239.14.

J.3a

J.3, 2-Bromo-6,7,8,9-tetrahydro-5H-benzo[7]annulen-5-one (1.5 g, 5.9 mmol) was dissolved in 2:1 ether/tetrahydrofuran (120 mL) and 1N HCl in ether (9 mL) was added. The solution was cooled to 0° C. before addition of isoamyl nitrite (1.2 mL, 9 mmol) and the reaction was stirred 18 h at 24° C., concentrated, and applied to 25 (M) Biotage silica gel column. Gradient elution from 15-100% B (A=Hexanes; B=ethyl acetate) over 1 L and gave J.3a (E)-2-bromo-6-(hydroxyimino)-6,7,8,9-tetrahydro-5H-benzo[7]annulen-5-one 1 g (64%). LC (Cond.-J1); RT=1.9 min; LC/MS: Anal. Calcd. for [M+H]$^+$ C$_{11}$H$_{10}$NBrO$_2$: 268; found: 268.

J.4

Concentrated ammonium hydroxide (12 mL, 28%) was added to a solution of J.3a(E)-2-bromo-6-(hydroxyimino)-6,7,8,9-tetrahydro-5H-benzo[7]annulen-5-one (1 g, 3.7 mmol) and N-Boc-L-prolinal (850 mg, 4.3 mmol) in methanol (35 mL) and the reaction stirred 18 h at 24° C. The reaction mixture was concentrated to remove methanol, the aqueous solution extracted with dichloromethane, and the organic phase washed with water. Application of the crude product in dichloromethane to a 40 (S) Biotage silica gel column and subjection to gradient elution; Segment 1. 15%-30% B over 300 mL; Segment 2. 30%-100% B over 700 mL (A=1:1 hexanes/dichloromethane; B=ethyl acetate) gave J.4 700 mg (44%). $^1$H NMR (300 MHz, DMSO-d$_6$) δ 11.3 (br. s, 1H), 7.91 (d, J=8.4 Hz, 1H), 7.35 (dd, J=8.4, 1.5 Hz, 1H), 7.31 (d, J=1.8 Hz, 1H), 5.0/4.87 (m, 1H), 3.51-3.46 (m, 1H), 3.42-3.36 (m, 1H), 2.90-2.70 (m, 4H), 2.27-1.80 (m, 6H), 1.38/1.11 (s, 9H). LC (Cond.-J1): RT=1.9 min; LRMS: Anal. Calcd. For [M+H]$^+$ C$_{21}$H$_{26}$BrN$_3$O$_3$: 488.12; found: 488.14. HRMS: Anal. Calcd. for [M+H]$^+$ C$_{21}$H$_{26}$BrN$_3$O$_3$: 488.1236; found: 488.1242.

J.5

Triethyl phosphite (0.78 mL, 4.7 mmol) was added to a solution of J.4 (700 mg, 1.57 mmol) in dimethylformamide (2 mL) and the solution heated at 80° C. for 18 h under a nitrogen atmosphere. The reaction mixture was taken up in ethyl acetate (100 mL) and washed with water and brine. After concentration the crude product was applied to a 40 (S) Biotage silica gel column and subjected to gradient elution; Segment 1. 5%-15% B over 300 mL; Segment 2. 15%-100% B over 600 mL (A=dichloromethane; B=ethyl acetate) to give J.5 675 mg (100%). $^1$H NMR (300 MHz, DMSO-d$_6$) δ 11.7 (br. s, 1H), 7.92 (d, J=8.4 Hz, 1H), 7.82 (d, J=8.4 Hz, 1H), 7.29 (s, 1H), 4.78/4.69 (br s, 1H), 3.57-3.48 (m, 1H), 3.38-3.32 (m, 1H), 2.85-2.78 (m, 4H), 2.28-1.77 (m, 6H), 1.39/1.14 (s, 9H). LC (fond.-J1): RT=1.9 min; LRMS: Anal. Calcd. for [M+H]$^+$ C$_{21}$H$_{26}$BrN$_3$O$_2$: 432.13; found: 432.14.

Synthetic Route 2

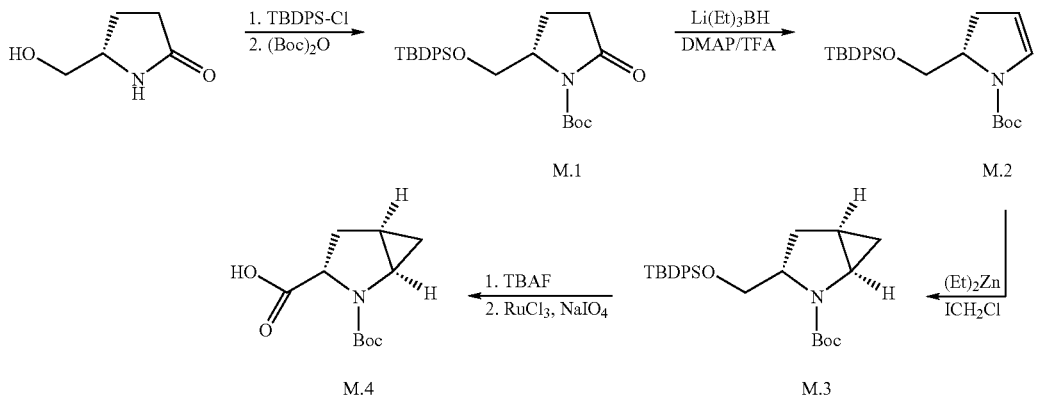

Examples M.1-M.4

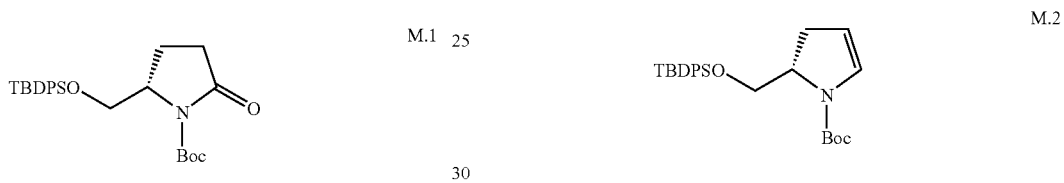

To a solution of (S)-5-(hydroxymethyl)pyrrolidin-2-one (10 g, 87 mmol) in dichloromethane (50 mL) was added tert-butylchlorodiphenylsilane (25.6 g, 93 mmol), Et$_3$N (12.1 mL, 87 mmol) and DMAP (1.06 g, 8.7 mmol). The mixture was stirred at room temperature until the starting pyrrolidinone was completely consumed, and then it was diluted with dichloromethane (50 mL) and washed with water (50 mL). The organic layer was dried (Na$_2$SO$_4$), filtered, and concentrated in vacuo, and the crude material was submitted to flash chromatography (silica gel; 30 to 100% of ethyl acetate/hexanes) to afford the silyl ether as a colorless oil (22.7 g, 74% yield). $^1$H-NMR (400 MHz, DMSO-d$_6$, δ=2.5 ppm) 7.69 (br s, 1H), 7.64-7.61 (m, 4H), 7.50-7.42 (m, 6H), 3.67-3.62 (m, 1H), 3.58-3.51 (m, 2H), 2.24-2.04 (m, 3H), 1.87-1.81 (m, 1H), 1.00 (s, 9H). LC/MS [M+H]$^+$=354.58.

Di-tert-butyl dicarbonate (38.5 g, 177 mmol) was added in portions as a solid over 10 min to a dichloromethane (200 mL) solution of silyl ether (31.2 g, 88.3 mmol), Et$_3$N (8.93 g, 88 mmol), and DMAP (1.08 g, 8.83 mmol) and stirred for 18 h at 24° C. Most of the volatile material was removed in vacuo and the crude material taken up in 20% ethyl acetate/hexanes and applied to a 2 L funnel containing 1.3 L of silica gel and then eluted with 3 L of 20% ethyl acetate/hexane and 2 L of 50% ethyl acetate). Upon concentration of the desired fractions in a rotary evaporator, a white slurry of solid formed which was filtered, washed with hexaness and dried in vacuo to afford carbamate M.1 as a white solid (32.65 g, 82% yield). $^1$H NMR (400 MHz, DMSO-d$_6$, δ=2.5 ppm) 7.61-7.59 (m, 2H), 7.56-7.54 (m, 2H), 7.50-7.38 (m, 6H), 4.18 (m, 1H), 3.90 (dd, J=10.4, 3.6, 1H), 3.68 (dd, J=10.4, 2.1, 1H), 2.68-2.58 (m, 1H), 2.40-2.33 (m, 1H), 2.22-2.12 (m, 1H), 2.01-1.96 (m, 1H), 1.35 (s, 9H), 0.97 (s, 9H). LC/MS [M−Boc+H]$^+$=354.58. Calcd. 454.24.

A three-necked flask equipped with a thermometer and a nitrogen inlet was charged with carbamate M.1 (10.05 g, 22.16 mmol) and toluene (36 mL), and lowered into −55° C. cooling bath. When the internal temperature of the mixture reached −50° C., lithium triethylborohydride (23 mL of 1.0 M/tetrahydrofuran, 23.00 mmol) was added dropwise over 30 min and the mixture stirred for 35 min while maintaining the internal temperature between −50° C. and −45° C. Hunig's base (16.5 mL, 94 mmol) was added dropwise over 10 min. Then, DMAP (34 mg, 0.278 mmol) was added in one batch, followed by the addition of trifluoroacetic anhydride (3.6 mL, 25.5 mmol) over 15 min, while maintaining the internal temperature between −50° C. and −45° C. The bath was removed 10 min later, and the reaction mixture was stirred for 14 h while allowing it to rise to ambient temperature. It was diluted with toluene (15 mL), cooled with an ice-water bath, and treated slowly with water (55 mL) over 5 min. The phases were separated and the organic layer washed with water (50 mL, 2×) and concentrated in vacuo. The crude material was purified by flash chromatography (silica gel; 5% ethyl acetate/hexanes) to afford dihydropyrrole M.2 as a colorless viscous oil (7.947 g, 82% yield). Rt=2.41 min under the following HPLC conditions: Solvent gradient from 100% A: 0% B to 0% A 100% B (A=0.1% TFA in 1:9 methanol/water; B=0.1% TFA in 9:1 methanol/water) over 2 min and hold for 1 min; detection @ 220 nm; Phenomenex-Luna 3.0×50 mm S10 column. $^1$H-NMR (400 MHz, DMSO-d$_6$, δ =2.5 ppm) 7.62-7.58 (m, 4H), 7.49-7.40 (m, 6H), 6.47 (br s, 1H), 5.07/5.01 (overlapping br d, 1H), 4.18 (br s, 1H), 3.89 (br s, 0.49H), 3.69 (br s, 1.51H), 2.90-2.58 (br in, 2H), 1.40/1.26 (overlapping br s, 9H), 0.98 (s, 9H). LC/MS: [M+Na]$^+$=460.19.

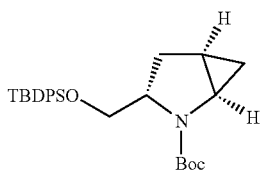

M.3

Diethylzinc (19 mL of ~1.1 M in toluene, 20.9 mmol) was added dropwise over 15 min to a cooled (−30° C.) toluene (27 mL) solution of dihydropyrrole M.2 (3.94 g, 9.0 mmol). Chloroiodomethane (stabilized over copper; 3.0 mL, 41.2 mmol) was added dropwise over 10 min, and stirred while maintaining the bath temperature at −25° C. for 1 h and between −25° C. and −21° C. for 18.5 h. The reaction mixture was opened to the air and quenched by the slow addition of 50% saturated NaHCO$_3$ solution (40 mL), and then removed from the cooling bath and stirred at ambient temperature for 20 min. It was filtered through a filter paper and the white cake was washed with 50 mL of toluene. The organic phase of the filtrate was separated and washed with water (40 mL, 2×), dried (MgSO$_4$), filtered, and concentrated in vacuo. The crude material was purified using a Biotage system (350 g silica gel; sample was loaded with 7% ethyl acetate/hexanes; eluted with 7-20% ethyl acetate/hexanes) to afford a mixture of methanopyrrolidines (M.3 predominates) as a colorless viscous oil (3.69 g, 90.7%). [Note: the exact cis/trans-isomer ratio was not determined at this stage]. Rt=2.39 min under the following HPLC conditions: Solvent gradient from 100% A: 0% B to 0% A: 100% B (A=0.1% TFA in 1:9 methanol/water; B=0.1% TFA in 9:1 methanol/water) over 2 min, and hold for 1 min; detection @ 220 nm; Phenomenex-Luna 3.0×50 mm S10 column. $^1$H-NMR (400 MHz, DMSO-d$_6$, δ =2.5 ppm) 7.62-7.60 (m, 4H), 7.49-7.40 (m, 6H), 3.77/3.67 (overlapping br s, 3H), 3.11-3.07 (m, 1H), 2.23 (app br s, 1H), 2.05-2.00 (m, 1H), 1.56-1.50 (m, 1H), 1.33 (very broad s, 9H), 1.00 (s, 9H), 0.80 (m, 1H), 0.30 (m, 1H). LC/MS: [M+Na]$^+$=474.1

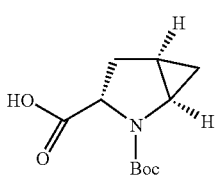

M.4

TBAF (7.27 mL of 1.0 M in tetrahydrofuran, 7.27 mmol) was added dropwise over 5 min to a tetrahydrofuran (30 mL) solution of silyl ethers M.3 (3.13 g, 6.93 mmol) and the mixture stirred at ambient temperature for 4.75 h. After the addition of saturated ammonium chloride solution (5 mL), most of the volatile material was removed in vacuo and the residue partitioned between dichloromethane (70 mL) and 50% saturated ammonium chloride solution (30 mL). The aqueous phase was extracted with dichloromethane (30 mL), and the combined organic phase was dried (MgSO$_4$), filtered, concentrated in vacuo and then exposed to high vacuum overnight. The crude material was purified using a Biotage (silica gel; 40-50% ethyl acetate/hexanes) to afford a mixture of alcohols, contaminated with traces of a lower Rf spot, as a colorless oil (1.39 g, ~94% yield). [Note: the exact cis/trans isomer ratio was not determined at this stage.] $^1$H-NMR (400 MHz, dimethylsulfoxide-d$_6$, δ =2.5 ppm) 4.70 (t, J=5.7, 1H), 3.62-3.56 (m, 1H), 3.49-3.44 (m, 1H), 3.33-3.27 (m, 1H), 3.08-3.04 (m, 1H), 2.07 (br m, 1H), 1.93-1.87 (m, 1H), 1.51-1.44 (m, 1H), 1.40 (s, 9H), 0.76-0.71 (m, 1H), 0.26 (m, 1H). LC/MS [M+Na]$^+$=236.20.

A semi-solution of sodium periodate (6.46 g, 30.2 mmol) in water (31 mL) was added to a solution of alcohols (2.15 g, 10.08 mmol) in acetonitrile (20 mL) and carbon tetrachloride (20 mL). Ruthenium trichloride (0.044 g, 0.212 mmol) was added immediately and the heterogeneous reaction mixture was stirred vigorously for 75 min. The reaction mixture was diluted with water (60 mL) and extracted with dichloromethane (50 mL, 3×). The combined organic phase was treated with 1 mL methanol, allowed to stand for about 5 min, and then filtered through diatomaceous earth. The pad was washed with dichloromethane (50 mL), and the filtrate was concentrated in vacuo to afford a light charcoal-colored solid. The crude material was dissolved in ethyl acetate (~10 mL) with heating and allowed to stand at ambient temperature with seeding. About 15 min into the cooling phase, a rapid crystal formation was observed. About 1 h later, hexanes (~6 mL) was added and the mixture refrigerated overnight (it did not appear that additional material precipitated out). The mixture was filtered and washed with ice/water-cooled hexanes/ethyl acetate (2:1 ratio; 20 mL) and dried under high vacuum to afford the first crop of acid M.4 (off-white crystals, 1.222 g). The mother liquor was concentrated in vacuo, and the residue dissolved in ~3 mL of ethyl acetate with heating, allowed to stand at ambient temperature for 1H, and then 3 mL hexanes was added and stored in a refrigerator for ~15 h. A second crop of acid M.4 was retrieved similarly (grey crystals, 0.133 g), for a combined yield of 59%. Rt=1.48 min under the following HPLC conditions: Solvent gradient from 100% A: 0% B to 0% A: 100% B (A=0.1% TFA in 1:9 methanol/water; B=0.1% TFA in 9:1 methanol/water) over 3 min; detection @ 220 nm; Phenomenex-Luna 3.0×50 mm S10 column. MP (dec.) for the first crop=147.5-149.5° C. $^1$H-NMR (400 MHz, DMSO-d$_6$, S=2.5 ppm) δ =12.46 (s, 1H), 3.88 (app br s, 1H), 3.27 (app br s, 1H; overlapped with water signal), 2.28 (br m, 1H), 2.07 (app br 5, 1H), 1.56 (app s, 1H), 1.40/1.34 (two overlapped s, 9H), 0.71 (m, 1H), 0.45 (m, 1H). $^{13}$C-NMR (100.6 MHz, DMSO-d$_6$, δ=39.21 ppm) 172.96, 172.60, 154.45, 153.68, 78.74, 59.88, 59.58, 36.91, 31.97, 31.17, 27.77, 27.52, 14.86, 14.53, 13.69. LC/MS [M+Na]$^+$=250.22. Anal. Calcd. For C11H17NO4: C, 58.13; H, 7.54; N, 6.16. Found (for first crop): C, 58.24; H, 7.84; N, 6.07. Optical rotation (10 mg/mL in CHCl3): [α] D=−216 and −212For the first and second crop, respectively.

Example M.4a

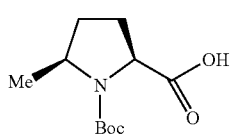

M.4a

The synthesis of acid M.4a is reported in patent application: US2009/0068140.

Synthetic Route 3

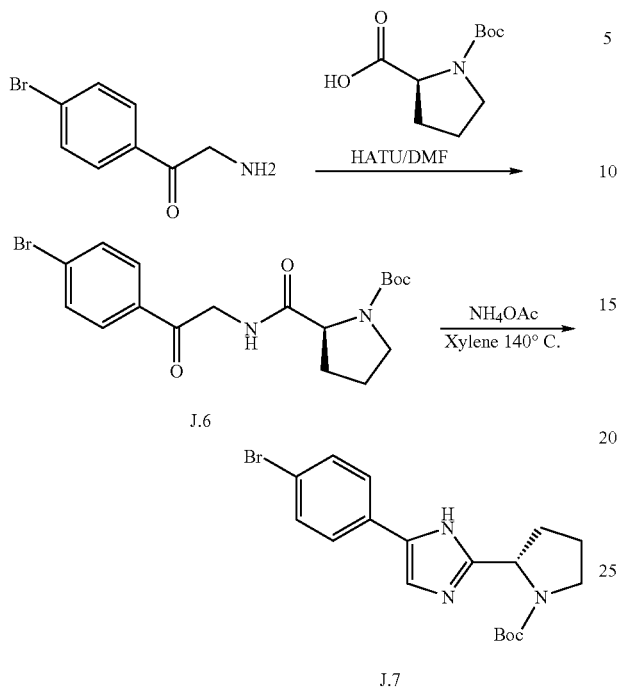

J.6

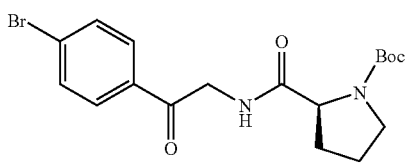

Examples J.6–J.7b

J.6

N,N-Diisopropylethylamine (18 mL, 103.3 mmol) was added dropwise, over 15 minutes, to a heterogeneous mixture of N-Boc-L-proline (7.139 g, 33.17 mmol), HATU (13.324 g, 35.04 mmol), the HCl salt of 2-amino-1-(4-bromo-phenyl)ethanone (8.127 g, 32.44 mmol), in dimethylformamide (105 mL) and stirred at ambient condition for 55 minutes. Dimethylformamide was removed in vacuo, and the resulting residue was partitioned between ethyl acetate (300 mL) and water (200 mL). The organic layer was washed with water (200 mL) and brine, dried (MgSO$_4$), filtered, and concentrated. A silica gel mesh was prepared from the residue and submitted to flash chromatography (silica gel; 50-60% ethyl acetate/hexanes) to provide J.6 (S)-tert-butyl 2-(2-(4-bromophenyl)-2-oxoethyl-carbamoyl)pyrrolidine-1-carboxylate as a white solid (12.8 g). NMR (DMSO-d$_6$, δ=2.5 ppm, 400 MHz): δ8.25-8.14 (m, 1H), 7.92 (br d, J=8.0, 2H), 7.75 (br d, J=8.6, 2H), 4.61 (dd, J=18.3, 5.7, 1H), 4.53 (dd, J=18.1, 5.6, 1H), 4.22-4.12 (m, 1H), 3.43-3.35 (m, 1H), 3.30-3.23 (m, 1H), 2.18-2.20 (m, 1H), 1.90-1.70 (m, 3H), 1.40/1.34 (two app br s, 9H). LC (Cond.-31): RT=1.70 min; LCMS: Anal. Calcd. For [M+Na]$^+$ C$_{18}$H$_{23}$BrN$_2$NaO$_4$: 433.07; found 433.09.

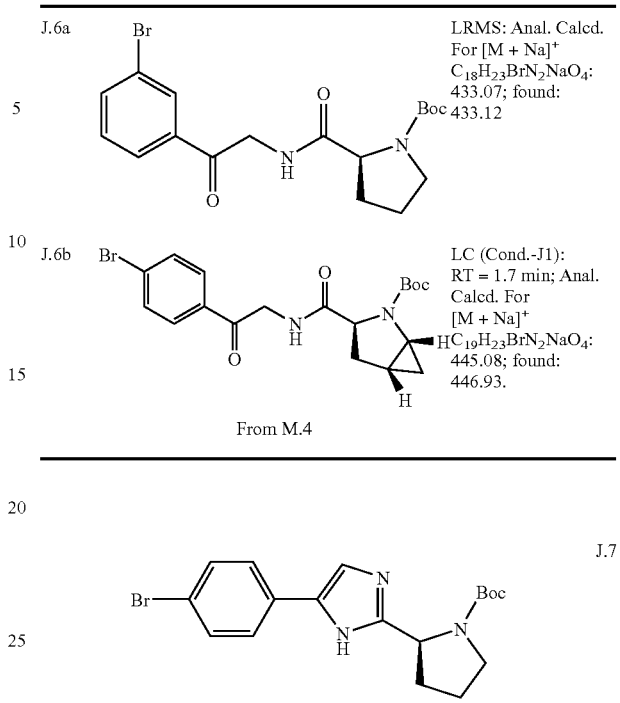

| | | |
|---|---|---|
| J.6a | | LRMS: Anal. Calcd. For [M + Na]$^+$ C$_{18}$H$_{23}$BrN$_2$NaO$_4$: 433.07; found: 433.12 |
| J.6b | From M.4 | LC (Cond.-J1): RT = 1.7 min; Anal. Calcd. For [M + Na]$^+$ HC$_{19}$H$_{23}$BrN$_2$NaO$_4$: 445.08; found: 446.93. |

J.7

A mixture J.6 (S)-tert-butyl 2-(2-(4-bromophenyl)-2-oxo-ethylcarbamoyl)-pyrrolidine-1-carboxylate (12.8 g, 31.12 mmol) and ammonium acetate (12.0 g, 155.7 mmol) in xylenes (155 mL) was heated in a sealed tube at 140° C. for 2 hours. The volatile component was removed in vacuo, and the residue was partitioned carefully between ethyl acetate and water, whereby enough saturated NaHCO$_3$ solution was added so as to make the pH of the aqueous phase slightly basic after the shaking of the biphasic system. The layers were separated, and the aqueous layer was extracted with an additional ethyl acetate. The combined organic phase was washed with brine, dried (MgSO$_4$), filtered, and concentrated. The resulting material was recrystallized from ethyl acetate/hexanes to provide two crops of J.7 (S)-tert-butyl 2-(5-(4-bromophenyl)-1H-imidazol-2-yl)pyrrolidine-1-carboxylate, 5.85 g. The mother liquor was concentrated in vacuo and submitted to a flash chromatography (silica gel; 30% ethyl acetate/hexanes) to provide an additional 2.23 g. $^1$H NMR (DMSO-d$_6$, δ=2.5 ppm, 400 MHz): δ 12.17/11.92/11.86 (m, 1H), 7.72-7.46/7.28 (m, 5H), 4.86-4.70 (m, 1H), 3.52 (app br s, 1H), 3.36 (m, 1H), 2.30-1.75 (m, 4H), 1.40/1.15 (app br s, 9H). LC (Cond.-J1): RT=1.71 min; LC/MS: Anal. Calcd. For [M+H]$^+$ C$_{18}$H$_{23}$BrN$_3$O$_2$: 392.10; found 391.96. HRMS: Anal. Calcd. For [M+H]$^+$ C$_{18}$H$_{23}$BrN$_3$O$_2$: 392.0974; found 392.0959.

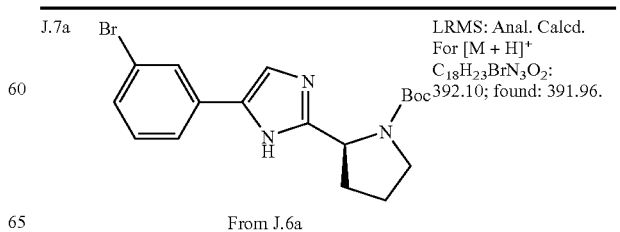

J.7a — From J.6a — LRMS: Anal. Calcd. For [M + H]$^+$ C$_{18}$H$_{23}$BrN$_3$O$_2$: 392.10; found: 391.96.

J.7b 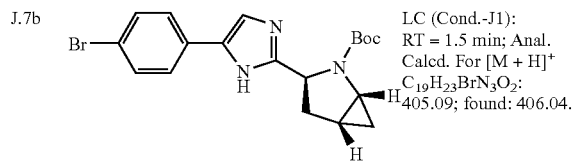
From J.6b

LC (Cond.-J1): RT = 1.5 min; Anal. Calcd. For [M + H]+ $C_{19}H_{23}BrN_3O_2$: 405.09; found: 406.04.

-continued

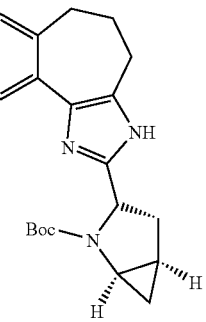

J.9

Synthetic Route 4

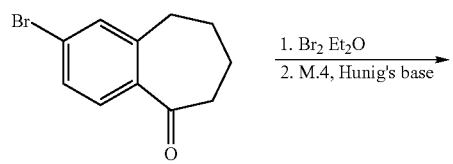
J.3

1. Br₂ Et₂O
2. M.4, Hunig's base

Examples J.8-J.9e

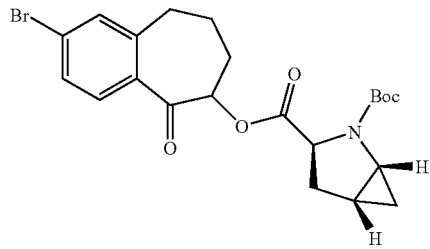
J.8

Bromine (0.23 mL, 4.18 mmol) was added dropwise to a solution of J.3 2-Bromo-6,7,8,9-tetrahydro-5H-benzo[7]annulen-5-one (1.0 g, 4.18 mmol) in ether (50 mL), after being cooled to 0° C. The solution was stirred 3 h and a few drops of additional bromine was and while the reaction was followed by TLC until complete. The solvent was removed by rotary evaporation, the residue was taken up in acetonitrile (25 mL), M.4 (950 mg, 4.18 mmol), and Hunig's base (1.4 mL) added dropwise. The reaction was stirred 18 hours at 60° C. prior to removal of the solvent by rotory evaporation. The crude product charged (dichloromethane) to a 40 g Thompson silica gel cartridge and gradient elution 15-100% B over 1 L (A/B hexanes/ethyl acetate) gave J.8 (1R,3S,5R)-3-(2-bromo-5-oxo-6,7,8,9-tetrahydro-5H-benzo[7]annulen-6-yl) 2-tert-butyl 2-azabicyclo[3.1.0]hexane-2,3-dicarboxylate 1 g (51.5%) as an oil. RT=2.2 minutes (Cond.-J1). LCMS: Anal. Calcd. for $C_{22}H_{26}BrNO_5Na$: 48610; found: 486.07 (M+Na)+.

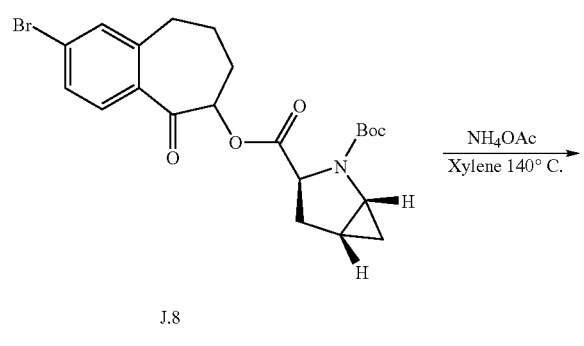
J.8

NH₄OAc
Xylene 140° C.

| | | |
|---|---|---|
| J.8a (Derived from 6-bromo tetral-1-one purchased from J & W PharmLab, LLC) | 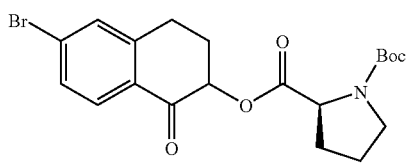 [SMILES: CC(C)(C)OC(=O)N1CCC[C@H]1C(=O)OC1CCc2cc(Br)ccc2C1=O] | RT = 3.1 min (Cond.-D2); LC/MS: Anal. Calcd. for [M + H]+ $C_{20}H_{25}BrNO_5$: 438; found: 438. |
| J.8b (Derived from 6-bromo tetral-1-one purchased from J & W PharmLab, LLC) | 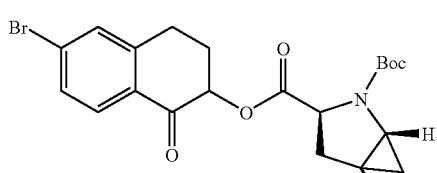 From M.4 | RT = 2.99 min (Cond. D2), LCMS: Calcd for $C_{21}H_{25}BrNO_5$ [M + Na]+ 472.07; found: 472.10 |

-continued

| | | |
|---|---|---|
| J.8c (Derived from 4-bromo 2-fluoroacetophenone) | 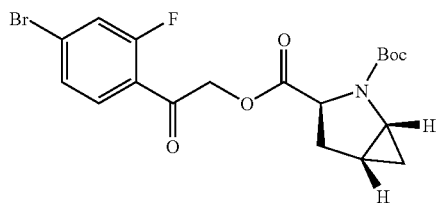 From M.4 | RT = 2.87 min (Cond. D2), LCMS: Calcd for $C_{29}H_{22}BrFNO_5$ $[M + H]^+$ 464.05; found: 463.98 |
| J.8d Derived from 1-(4-bromophenyl)butan-1-one) | 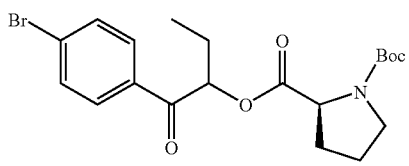 [SMILES: CCC(OC(=O)[C@@H]1CCCN1C(=O)OC(C)(C)C)C(=O)c1ccc(Br)cc1] | RT = 2.2 min, (Cond.-J1); Calcd for $C_{20}H_{27}BrNO_5$ $[M-Boc]^+$ 340.11; found: 340.02. |
| J.8e Derived from 1-(4-bromophenyl)-4,4,4-trifluorobutan-1-one | 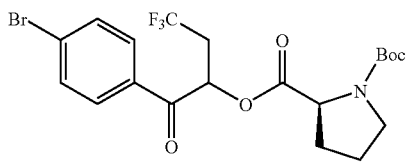 | RT = 2.21 min, (Cond.-J1); Calcd for $C_{20}H_{24}BrF_3NO_5$ $[M-Boc]^+$ 394.08; found: 394.03. |

J.9

Ammonium acetate (1.7 g, 21.54 mmol) was added to a solution of J.8 (1.0 g, 2.15 mmol) in xylene (15 mL) and the reaction mixture stirred at 140° C. for 3 h in a screw-cap pressure vessel. After being cooled, the reaction mixture was partitioned between ethyl acetate and sat'd $NaHCO_3$ soln, and the aqueous layer was extracted with ethyl acetate. The combined organic layers were washed with brine, concentrated, and the residue applied to 20 g Thomson silica gel column. Gradient elution (10-50% B over 1 L; A/B hexanes/ethyl acetate). The major and less polar product (oxazole 450 mg) was separated away to afford J.9 192 mg (20%) as a diastereomeric mixture (favoring 3.9; a 3:1 mixture of SIR proline). $^1$H NMR (300 MHz, $CDCl_3$) δ 10.6/10.3 (br. s, 1H), 8.06 (d, J=8.2 Hz, 0.6H), 7.34 (dd, J=6.4, 1.8 Hz, 1H), 7.28 (s, 0.3H), 7.21 (d, J=1.8 Hz, 0.7H), 7.11 (d, J=8.6 Hz, 0.3H), 4.83-4.77 (m, 1H), 3.48 (m, 0.68H), 3.23 (m, 1.2H), 2.98 (t, J=6.4 Hz, 0.65H), 2.88 (t, H=6.7 Hz, 1.35H), 2.82-2.79 (m, 2H), 2.33 (t, J=9.1 Hz, 1H), 2.01-1.95 (m, 2.4H), 1.76-1.72 (m, 1H), 1.57/1.48 (s, 9H), 0.87-0.83 (m, 1.3H), 0.44 (br. s, 1H). LC (Cond.-J1): RT=1.7 min; LCMS: Anal. Calcd. for $[M+H]^+$ $C_{22}H_{26}BrN_3O_2$: 444.13; found: 444.07.

| | | |
|---|---|---|
| J.9a | 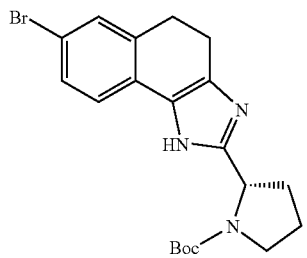 From J.8a | RT = 2.4 min (Cond.-D2); LC/MS: Anal. Calcd. for $[M + H]^+$ $C_{20}H_{25}BrN_3O_2$: 418.11; found: 418.10. |

| | | |
|---|---|---|
| J.9b | 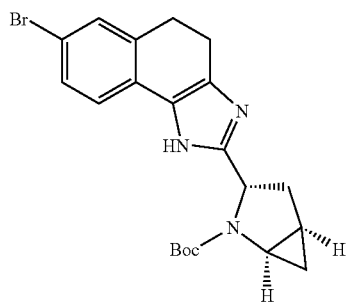<br>From J.8b | RT = 2.3 min (Cond.-D2);<br>LC/MS: Anal. Calcd. for<br>[M + H]⁺ $C_{21}H_{25}BrN_3O_2$:<br>430.11; found: 430.16.<br>HRMS: Anal. Calcd. for<br>[M + H]⁺ $C_{21}H_{25}BrN_3O_2$:<br>430.1125; found 430.1123. |
| J.9c | 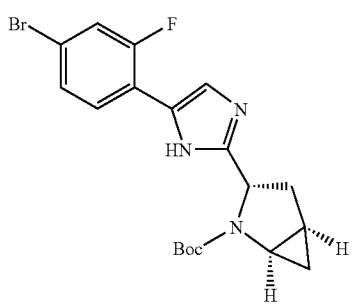<br>From J.8c | RT = 2.2 min (Cond.-D2);<br>LC/MS: Anal. Calcd. for<br>[M + H]⁺ $C_{19}H_{22}BrFN_3O_2$:<br>422.09; found: 422.10.<br>HRMS: Anal. Calcd. for<br>[M + H]⁺ $C_{19}H_{22}BrFN_3O_2$:<br>422.0877; found 422.0874. |
| J.9d | 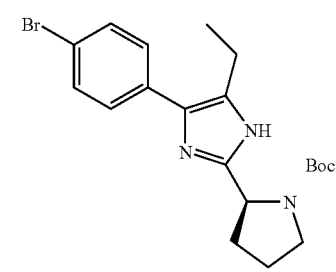<br>From J.8d | RT = 1.69 min (Cond.-J1);<br>Calcd for $C_{20}H_{27}BrN_3O_2$<br>[M + H]⁺ 420.13; found:<br>420.13. |
| J.9e<br>Obtained as the more polar product of a ~1:1 mixture containing the $CF_3$ analog. | 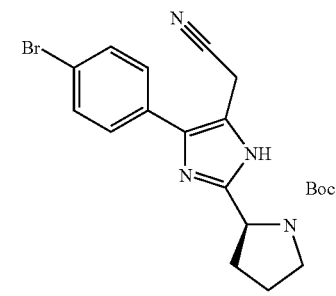<br>From J.8e | RT = 1.55 min, (Cond.-J1);<br>Calcd for $C_{20}H_{24}BrN_4O_2$<br>[M + H]⁺ 431.11; found:<br>431.15. |

Example J.9f

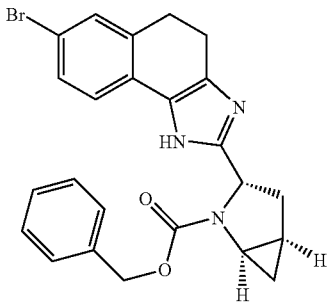 [SMILES: O=C(OCc1ccccc1)N1[C@@H]2C[C@@H]2C[C@H]1c1nc2c([nH]1)-c1ccc(Br)cc1CC2]

A cold (0° C.) solution of HCl (0.871 mL, 3.49 mmol, 4N in dioxanes) was added to a solution of J9b (1.5 g, 3.49 mmol) in MeOH (20 mL). The mixture was stirred for 2 h before it was concentrated to dryness. The tan solid was taken up in dioxane (20 mL) and water (20 mL), cooled to 0° C., and treated with sodium carbonate (0.369 g, 3.49 mmol) and CBZ-Cl (0.498 mL, 3.49 mmol). The reaction mixture was allowed to warm up to room temperature, stirred for 5 h, diluted with ethyl acetate, and washed with saturated sodium bicarbonate solution. The organic phase was washed with brine and dried over sodium sulfate to yield J.1.9f (0.97 g, 60%) as a tan foam, RT=2.47 min (Cond.-D1); LC/MS: Anal. Calcd. for $[M+H]^+$ $C_{24}H_{23}BrN_3O_2$: 464.10 and 466.10; found: 463.95 and 465.98.

Synthetic Route 4.a

Examples J.9g1-J.9g

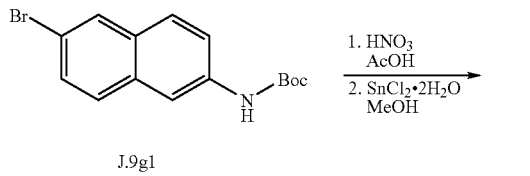

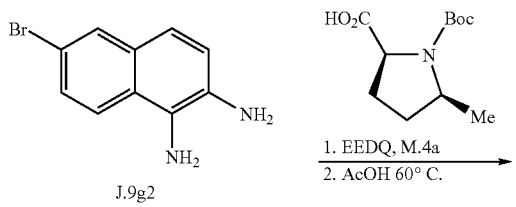

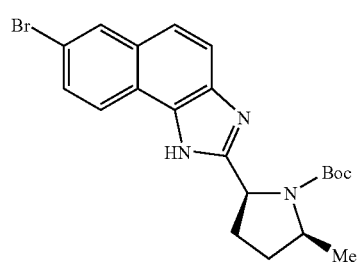

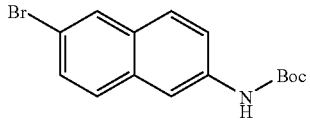

Diphenylphosphoryl azide (17.09 mL, 79 mmol) was added to a solution of 6-bromo-2-naphthoic acid (16.5 g, 65.7 mmol), triethylamine (18.32 mL, 131 mmol), and tert-butylalcohol (7.54 mL, 79 mmol) in toluene (225 mL) and stirred for 4 h at 100° C. The volatiles were removed by rotary evaporation and the residue taken up in EtOAc (500 mL) and washed with water and brine. A precipitate formed upon concentration which was isolated by filtration and washed with 1:1 $Et_2O$/Hex to give Example J.9g1 (10.5 g). A second crop of less pure product was isolated upon concentration of the mother liquor (9.8 g); combined yield (93%). LC/MS (Cond. J2): RT=3.44 min. LC/MS Anal. Calcd. for $[M+Na]^+$ $C_{15}H_{16}BrNO_2$: 345.02; found 345.03.

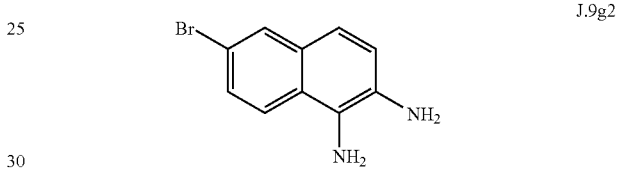

Example J.9g1 (5 g, 15.52 mmol) was diluted in acetic acid (50 mL) and fuming nitric acid (2.3 mL) was added dropwise over 20 min. The reaction was stirred for 2 h and the product, isolated by filtration, was partitioned between $CH_2Cl_2$ and sat'd $NaHCO_3$ soln. The organic layer was concentrated to provide tert-butyl 6-bromo-1-nitronaphthalen-2-ylcarbamate 5.7 g (quant). LC/MS (Cond. J2): RT=3.52 min. LC/MS Anal. Calcd. for $[M+Na]^+$ $C_{15}H_{15}BrN_2O_4$: 390.02; found 390.99.

Tin(II)chloride dehydrate (3 g, 16.34 mmol) was added to a solution of tert-butyl 6-bromo-1-nitronaphthalen-2-ylcarbamate (2 g, 5.47 mmol) in MeOH (100 mL) and the solution was stirred for 18 h at 70° C. The solvent was removed by rotary evaporation and Example J.9g2 (assume theoretical 1.25 g) was dried under high vacuum LC/MS (Cond. J2): RT=1.49 min. LC/MS Anal. Calcd. for $[M+H]^+$ $C_{10}H_9BrN_2$: 237.00; found 236.96.

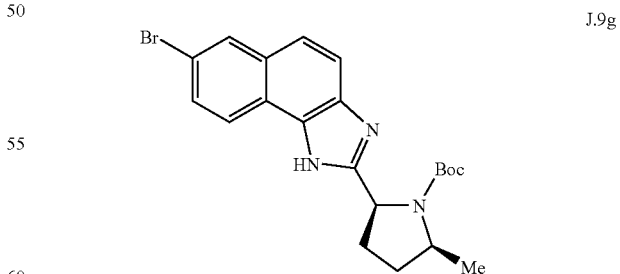

EEDQ (1.67 g, 6.75 mmol) was added to a solution of Example J.9g2 (1.6 g, 6.75 mmol) and M.4a (1.55 g, 6.75 mmol) in DCM (100 mL) and stirred for 6 h. (Note: The dianiline was not completely soluble). The reaction mixture was diluted with DCM (1 vol) and washed with half sat'd $NaHCO_3$ soln. Concentration gave a solid (2.5 g). LC/MS (Cond. J2): RT 3.07 min. LC/MS Anal. Calcd. for [M+H]$^+$ C$_{21}$H$_{27}$BrN$_3$O$_3$: 448.13; found 448.11.

The crude solid (2.5 g, 5.58 mmol) was taken up in AcOH (200 mL) and stirred for 18 h at 60° C. Concentration under high vacuum removed the solvent. The residue was taken up in DCM, washed with sat'd NaHCO$_3$ soln, and concentrated. The residue was charged (DCM) to a 80 g Thompson silica gel cartridge and gradient elution was performed from 15% to 100% B over 750 mL. (A/B Hex/EtOAc) to give Example J.9g (2.6 g). $^1$H NMR (MeOD, 500 MHz, δ): 8.36-8.35 (m, 2H), 8.0 (d, J=9Hz, 1H), 7.91 (dd, J=9, 2 Hz, 1H), 7.87 (d, J×9 Hz, 1H), 5.31-5.28 (m, 1H), 4.17 (br. s, 1H), 2.59-2.56 (m, 1H), 2.39-2.31 (m, 2H) 1.86-1.83 (m, 1H), 1.52-1.19 (m, 12H). LC/MS (Cond. J2): RT=2.57 min. LC/MS Anal. Calcd. for [M+H]$^+$ C$_{21}$H$_{25}$BrN$_3$O$_2$: 430.12; found 430.09.

Synthetic Route 5

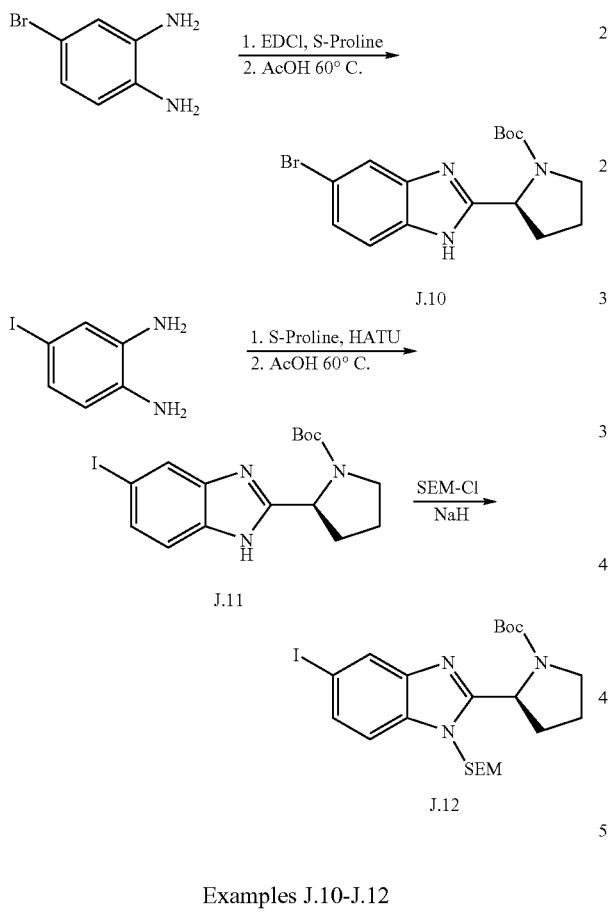

Examples J.10-J.12 mL), and stirred at ambient conditions for 19 h. The mixture was then diluted with dichloromethane, to washed with water (2×), dried (brine; MgSO$_4$), filtered, and concentrated in vacuo to provide a brown foam. Acetic acid (40 mL) was added to the foam, and the mixture was heated at 65° C. for 90 min. The volatile component was removed in vacuo, and the residue was dissolved in ethyl acetate and washed carefully with saturated NaHCO$_3$ solution (2×), and the organic phase was dried (brine; MgSO$_4$), filtered, and concentrated in vacuo. The resultant crude material was submitted to flash chromatography (silica gel; ethyl acetate) to provide 3.10 as a tan foam (2.5 g). $^1$H NMR (DMSO-d$_6$, δ=2.5 ppm, 400 MHz): 12.49-12.33 (four br s, 1H), 7.71 (d, J=2, 0.54H), 7.60 (app br s, 0.46H), 7.50 (d, J=8.6, 0.45H), 7.40 (d, J=8.4, 0.55H), 7.26 (m, 1H), 4.96-4.87 (m, 1H), 164-3.51 (m, 1H), 3.44-3.38 (m, 1H), 2.38-2.21 (m, 1H), 1.99-1.85 (m, 3H), 1.39 (s, 3.7H), 1.06 (s, 5.3H). (Cond.-D2) LC/MS: Anal. Calcd. for [M+H]+ C$_{16}$H$_{21}$I3BrN$_3$O$_2$: 368.03; found: 368.18.

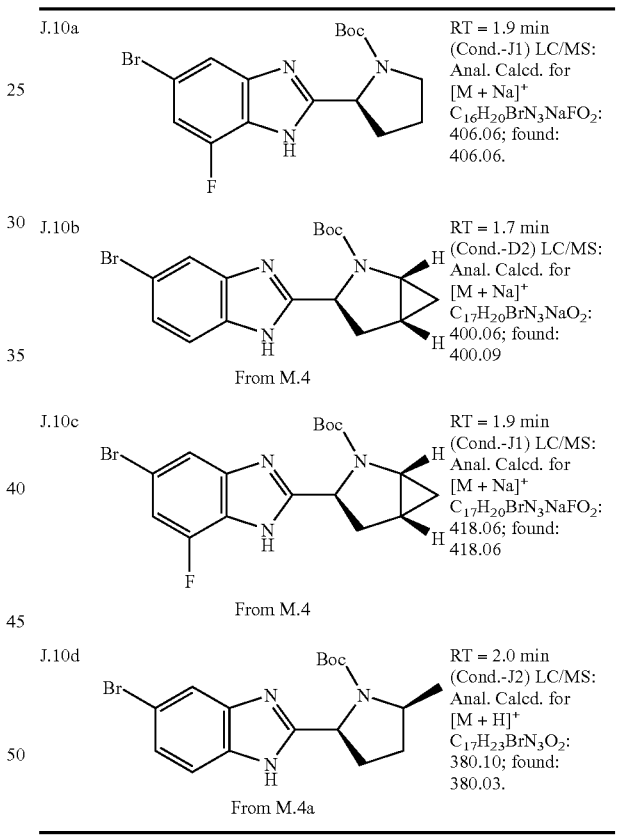

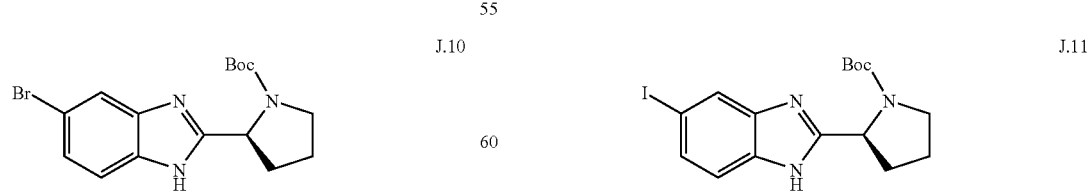

EDCI.HCl (2.35 g, 12.25 mmol) was added to a mixture of 4-bromobenzene-1,2-diamine (2.078 g, 11.11 mmol), N-Boc-L-proline (2.311 g, 10.74 mmol) and 1-hydroxybenzotriazole (1.742 g, 12.89 mmol) in dichloromethane (40

4-Iodo-2-nitroaniline (35.2 g, 0.133 mol) was added in batches via an open funnel over 25 mM to a heated (65° C.) mixture of SnCl$_2$.2H$_2$O (106.86 g, 0.465 mol) and 12N HCl (200 ml). An additional 12N HCl (30 ml) was added and the reaction mixture was heated at 65° C. for an additional 1 h, and stirred at room temperature for 1 h. It was placed in a refrigerator for 15 h, and the precipitate was filtered. The resultant solid was transferred into a flask containing water (210 ml), cooled (ice/water), and a solution of NaOH (aq) (35 g in 70 ml of water) was added to it over 10 min with stirring. The cooling bath was removed, and vigorous stirring was continued for 45 min. The mixture was filtered and the solid was washed with water and dried in vacuo to provide 4-iodobenzene-1,2-diamine as a tan solid (25.4 g). The product was used in the next step without further purification. $^1$H NMR (DMSO-d$_6$, $\delta$=2.5 ppm, 500 MHz): 6.79 (d, J=2.1H), 6.63 (dd, J=1.9, 8.1, 1H), 6.31 (d, J=8.1, 1H), 4.65 (br s, 2H), 4.59 (br s, 2H). LC/MS: Anal. Calcd. for [M+H]+ C$_6$R$_8$IN$_2$: 234.97; found: 234.9.

HATU (6.5 g, 17.1 mmol) was added to a solution of 4-iodobenzene-1,2-diamine (4 g, 17.1 mmol), (S)-1-(tent-butoxycarbonyl)pyrrolidine-2-carboxylic acid (3.67 g, 17.1 mmol), and Hunig's base (3 mL) in dimethylformamide (100 mL). The reaction mixture was stirred for 4 h before being diluted with ethyl acetate (300 mL) and washed with sat'd NaHCO$_3$, brine, and dried (Na$_2$SO$_4$). The aqueous phase was extracted twice more with ethyl acetate and combined with the initial organic extract prior to drying. Concentration gave a residue which was taken up in glacial acetic acid (100 mL) and heated at 65° C. for 2 h. The cooled mixture was concentrated in vacuo, diluted with ethyl acetate (300 mL) and 1N NaOH solution (to pH=10), washed with brine, and dried (Na$_2$SO$_4$). The crude product was applied to a 65 (i) Biotage silica gel cartridge. Segment 1. Hold 15% B for 450 mL; Segment 2. Gradient elution from 15% to 100% B over 4.5 L (A=hexane; B=ethyl acetate); Segment 3. Hold 100% B for 2.5 L to give J.11 tert-butyl 2-(5-iodo-1H-benzo[d]imidazol-2-yl)pyrrolidine-1-(S)-carboxylate 7.0 g (99%). $^1$H NMR (500 MHz, DMSO-d$_6$) $\delta$ 7.85 (br.s, 1H), 7.42 (d, J=8.2 Hz, 1H), 7.34 (br. s, 1H), 4.97-4.84 (m, 1H), 3.6 (br. s, 1H), 3.44-3.40 (m, 1H), 2.37-2.25 (m, 1H), 1.99-1.87 (m, 3H), 1.4/1.07 (s, 9H). LC (Cond.-D2): 2.1 min; LCMS: Anal. Calcd. for [M+H]+ C$_{16}$H$_{20}$IN$_3$O$_2$: 414.07; found: 414.08.

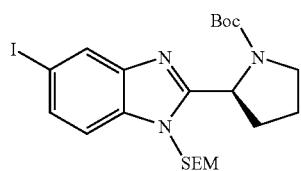

J.12

Unwashed 60% sodium hydride (48 mg, 1.21 mmol) was added in one portion to a stirred solution of J.11 tert-butyl 2-(5-iodo-1H-benzo[d]imidazol-2-yl)pyrrolidine-1-(S)-carboxylate (500 mg, 1.21 mmol) in dry dimethylformamide (10 mL) under nitrogen. The mixture was stirred 5 min before addition of SEM-Cl (0.21 mL, 1.21 mmol), stirred for 3H, quenched with sat'd ammonium chloride (1 mL), diluted with ethyl acetate (50 mL), and the organic phase was washed with sat'd NaHCO$_3$ soln and brine. The aqueous phase was extracted twice more with ethyl acetate and combined with the initial organic extract prior to drying. Concentration gave a residue applied which was applied (dichloromethane) to a 40 (i) Biotage silica gel cartridge. Segment 1. Hold 5% B for 150 mL; Segment 2. Gradient elution from 5% to 100% B over 2.5 L (A=hexane; B=ethyl acetate) B to give regioisomeric products (SEM location) J.12 316 mg (48%). $^1$H NMR (500 MHz, DMSO-d$_5$) $\delta$ 7.99 (d, J=5.8 Hz, 1H), 7.54-7.49 (m, 2H), 5.77-5.64 (m, 2H), 5.20-5.11 (m, 1H), 3.61-3.43 (m, 4H), 2.89-2.05 (m, 2H), 1.98-1.87 (m, 2H), 1.36/1.04 (s, 9H), 0.91-0.81 (m, 2H), −0.06 (s, 9H). LC (Cond.-D2): RT=3.1 min; LRMS: Anal. Calcd. for [M+H]+ C$_{22}$H$_{34}$IN$_3$O$_3$Si: 544.15; found: 544.15.

Synthetic Route 6.

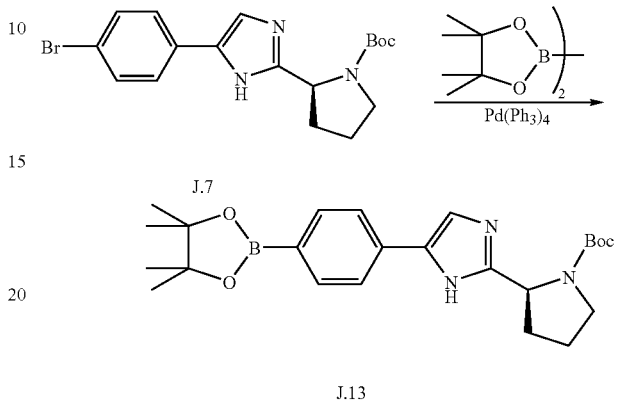

Examples J.13-J.13f

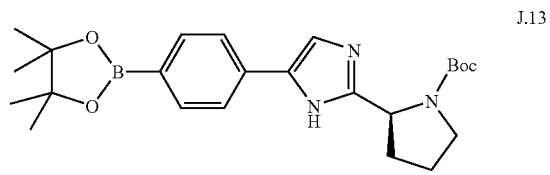 [SMILES: CC(C)(C)OC(=O)N1CCC[C@H]1c1ncc(-c2ccc(B3OC(C)(C)C(C)(C)O3)cc2)[nH]1]

J.13

Pd(Ph$_3$P)$_4$ (469 mg, 0.406 mmol) was added to a pressure tube containing a mixture of J.7 (S)-tert-butyl 2-(5-(4-bromophenyl)-1H-imidazol-2-yl)pyrrolidine-1-carboxylate (4 g, 10.22 mmol), bis(pinacolato)diboron (5.4 g, 21.35 mmol), potassium acetate (2.6 g, 26.21 mmol) and 1,4-dioxane (80 mL). The reaction flask was purged with nitrogen, capped and heated (oil bath 80° C.) for 16 hours. The reaction mixture was filtered and the filtrate was concentrated in vacuo. The crude material was partitioned carefully between dichloromethane (150 mL) and an aqueous medium (50 mL water+ 10 mL saturated NaHCO$_3$ solution). The aqueous layer was extracted with dichloromethane, and the combined organic phase was dried (MgSO$_4$), filtered, and concentrated in vacuo. The resulting material was purified with flash chromatography (sample was loaded with eluting solvent; 20-35% ethyl acetate/dichloromethane) to provide J.13 (S)-test-butyl 2-(5-(4-(4,4,5,5-tetramethyl-1,3,2-dioxaborolan-2-yl)phenyl)-1H-imidazol-2-yl)pyrrolidine-1-carboxylate, contaminated with pinacol, as an off-white dense solid; the relative mole ratio of J.13 to pinacol was about 10:1 ($^1$H NMR). The sample weighed 3.9 g after ~2.5 days exposure to high vacuum. $^1$H NMR (DMSO-d$_6$, $\delta$=2.5 ppm, 400 MHz): 12.22/ 11.94/11.87 (m, 1H), 7.79-7.50/7.34-7.27 (m, 5H), 4.86-4.70 (m, 1H), 3.52 (app br s, 1H), 3.36 (m, 1H), 2.27-1.77 (m, 4H), 1.45-1.10 (m, 21H). LC (Cond.-J1): RT=1.64 min; LC/MS: Anal. Calcd. for [M+H]+ C$_{24}$H$_{35}$BN$_3$O$_4$: 440.27; found 440.23.

| | | |
|---|---|---|
| J.13a | 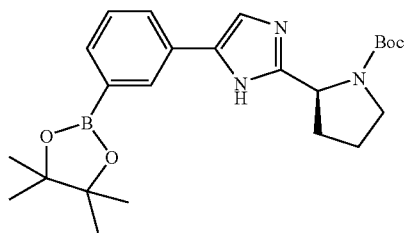<br>From J.7a | RT = 1.6 min (Cond.-J1);<br>LC/MS: Anal. Calcd. for<br>[M + H]+ C24H35BN3O4:<br>440.27; found: 440.36. |
| J.13b | 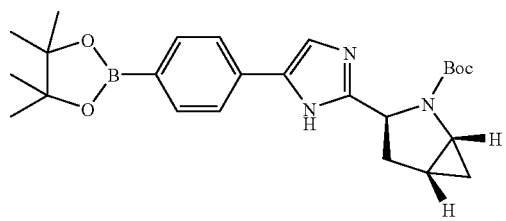<br>From J.7b | RT = 1.6 min (Cond.-J1);<br>LC/MS: Anal. Calcd. for<br>[M + H]+ C25H35BN3O4:<br>452.27; found: 452.17. |
| J.13c | 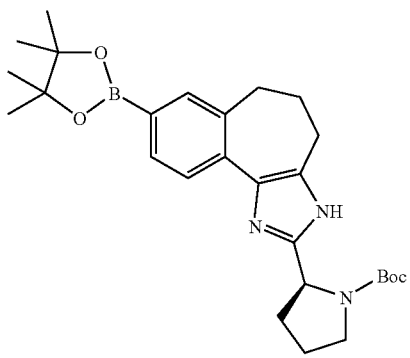<br>From J.5 | RT = 1.9 min (Cond.-D2);<br>LC/MS: Anal. Calcd. for<br>[M + H]+ C27H38BN3O4:<br>480; found: 480. |
| J.13d | 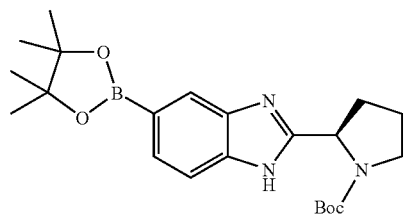<br>From J.10 | RT = 1.7 (Cond.-J1)<br>LCMS: Anal. Calcd. for<br>[M + H]+<br>C22H33BN3O4 414.25;<br>found: 414.28. |
| J.13e | 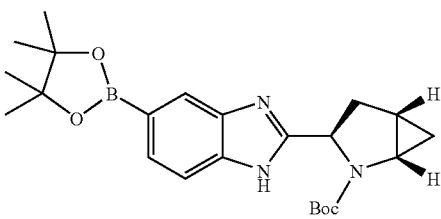<br>From J.10a | RT = 2.1 (Cond.-D2)<br>LCMS: Anal. Calcd. for<br>[M + H]+<br>C23H33BN3O4 426.29;<br>found: 426.21. |

J.13f

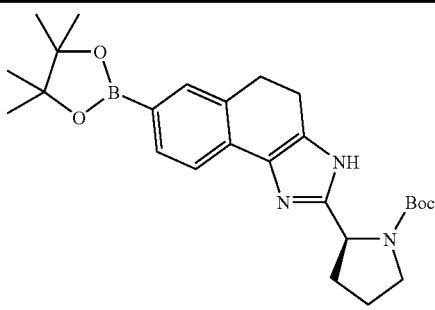

From J.9a

RT = 2.46 (Cond.-D2)
LCMS: Anal. Calcd. for
[M + H]⁺ $C_{26}H_{37}BN_3O_4$
466.28; found: 466.33.

Synthetic Route 7

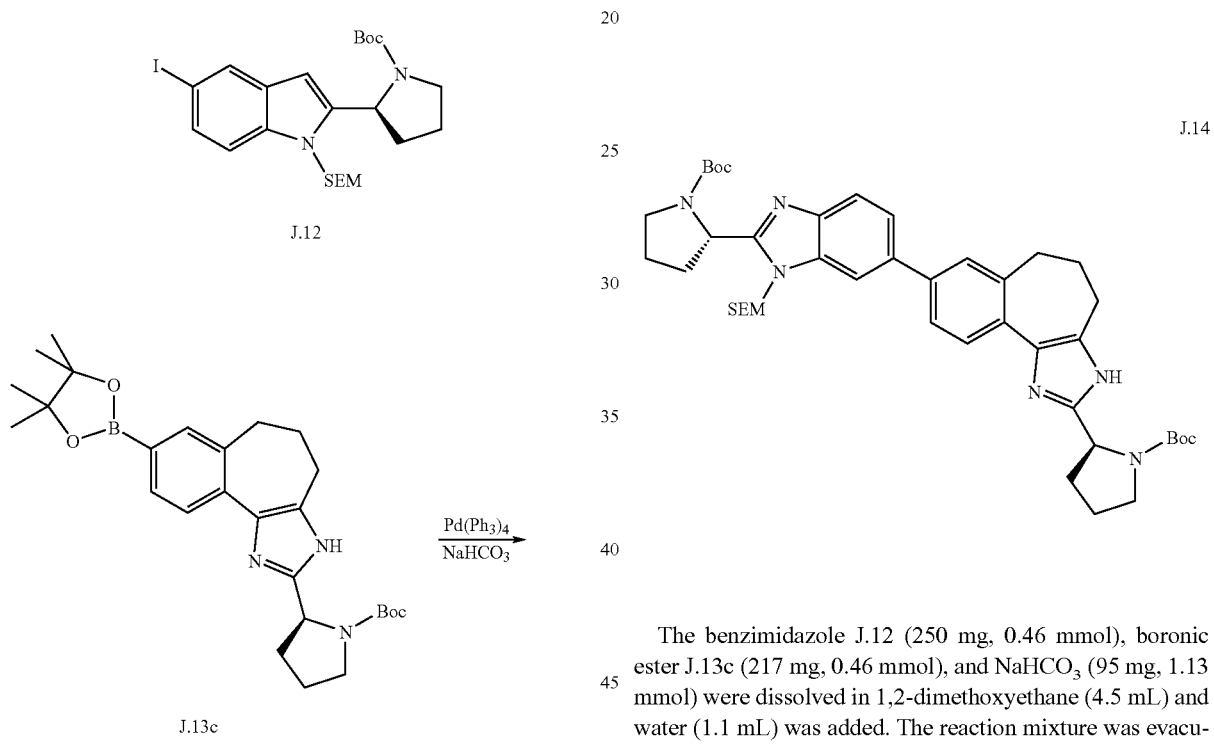

Examples J.14-J.14f.1

The benzimidazole J.12 (250 mg, 0.46 mmol), boronic ester J.13c (217 mg, 0.46 mmol), and NaHCO₃ (95 mg, 1.13 mmol) were dissolved in 1,2-dimethoxyethane (4.5 mL) and water (1.1 mL) was added. The reaction mixture was evacuated and flushed with nitrogen (3×), Pd(Ph₃P)₄ (26 mg, 0.022 mmol) was added, and the mixture heated (oil bath at 80° C.) in a capped pressure vessel for 14 h. After being cooled, the solution was partitioned into ethyl acetate/water and the organic layer washed with sat'd NaHCO₃, brine, and dried (Na₂SO₄). Concentration gave a residue which was applied to a 25M Biotage SiO₂ column pre-equilibrated with 25% B (300 mL). Gradient elution; Segment 1: 25% 13 (60 mL); Segment 2: 25-100% B (1440 mL); Segment 3: Hold at 100% (600 mL). A=Hexanes; B=ethyl acetate gave J.14, 101.1 mg (29%). ¹H NMR (500 MHz, DMSO-d₆) δ8 8.10-8.09 (m, 1H), 7.96/7.91 (s, 1H), 7.65-7.47 (m, 4H), 5.85-5.70 (m, 2H), 5.12/5.14 (s, 1H), 4.83/4.73 (s, 1H), 3.62-3.54 (m, 4H), 3.48-3.26 (m, 2H), 2.90 (br. s, 4H), 2.37-1.84 (m, 10H), 1.42/1.08 (s, 9H), 1.37/1.06 (s, 9H), 0.92-0.83 (m, 2H), 0.06 (s, 9H). LC (Cond.-D2): 2.8 min; LCMS: Anal. Calcd. for [M+H]⁺ $C_{43}H_{61}N_6O_5Si$ 769.45; found: 769.43. HRMS: Anal. Calcd. for [M+H]⁺ $C_{43}H_{61}N_6O_5Si$: 769.4473; found 769.4484.

| | | |
|---|---|---|
| J.14a | 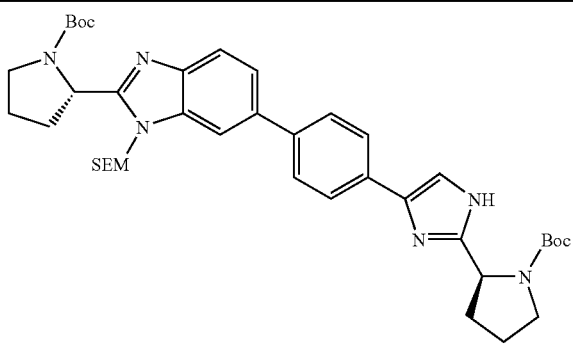<br>From J.12 and J.13 | RT = 2.71 min (Cond.-D2); LCMS: Anal. Calcd. for [M + H]$^+$ C$_{40}$H$_{57}$N$_6$O$_5$Si 729.42; found: 729.43. HRMS: Anal. Calcd. for [M + H]$^+$ C$_{40}$H$_{57}$N$_6$O$_5$Si: 729.4160; found: 729.4188. |
| J.14b | 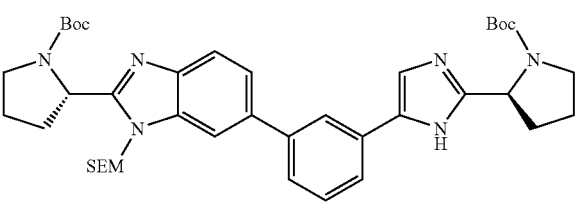<br>From J.12 and J.13a | RT = 2.75 min (Cond.-D2); LCMS: Anal. Calcd. for [M + H]$^+$ C$_{40}$H$_{57}$N$_6$O$_5$Si 729.42; found: 729.44. HRMS: Anal. Calcd. for [M + H]$^+$ C$_{40}$H$_{57}$N$_6$O$_5$Si: 729.4160; found: 729.4191. |
| J.14c | 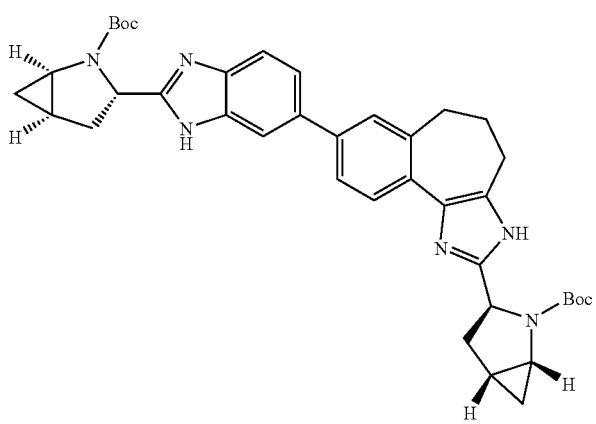<br>From J.13e and J.9 | RT = 1.6 min (Cond.-J1); LCMS: Anal. Calcd. for [M + H]$^+$ C$_{39}$H$_{46}$N$_6$O$_4$ 663.37; found: 663.46. HRMS: Anal. Calcd. for [M + H]$^+$ C$_{39}$H$_{46}$N$_6$O$_4$ 663.3653; found: 663.3648. |
| J.14d | 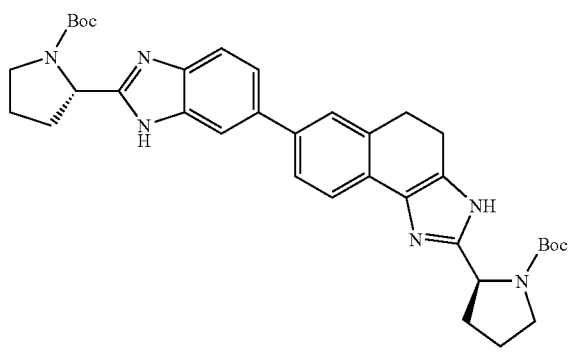<br>From J.13d and J.9a | RT = 2.11 min, (Cond.-D2); Calcd for C$_{36}$H$_{45}$N$_6$O$_4$ [M + H]$^+$ 625.35; found: 625.42. HRMS: Calcd for C$_{36}$H$_{45}$N$_6$O$_4$ [M + H]$^+$ 625.3497; found: 625.3486. |
| J.14e | 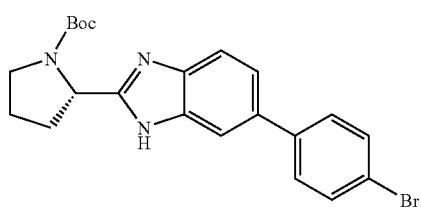<br>From J.13d and 1,4-dibromobenzene | RT = 1.83 min, (Cond.-J1); Calcd for C$_{22}$H$_{25}$BrN$_3$O$_2$ [M + H]$^+$ 442.12; found: 442.20. |

| | | |
|---|---|---|
| J.14e.1 | 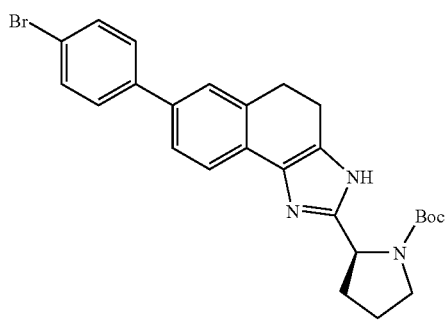<br>From J.13f and 1,4-dibromobenzene | RT = 2.40 min, (Cond.-D2); Calcd for $C_{26}H_{29}BrN_3O_2$ $[M + H]^+$ 494.15; found: 494.14. |
| J.14f | 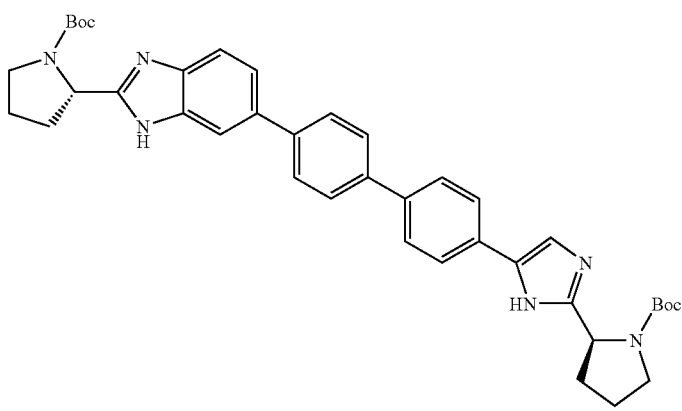<br>From J.14e and J.13 | RT = 1.66 min, (Cond.-J1); Calcd for $C_{40}H_{47}N_6O_4$ $[M + H]^+$ 675.36; found: 675.52. |
| J.14f.1 | 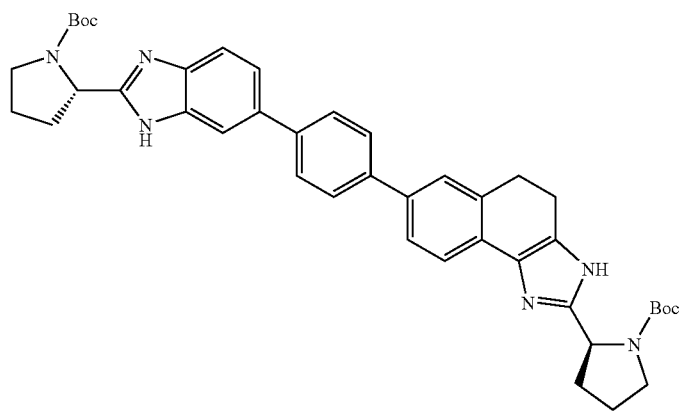<br>From J.13d and J.14e.1 | RT: 2.15 min, (Cond.-D1); Calcd for $C_{42}H_{49}N_6O_4$ $[M + H]^+$ 701.38; found: 701.35. |

Synthetic Route 8

Examples J.14g-J.14g.1

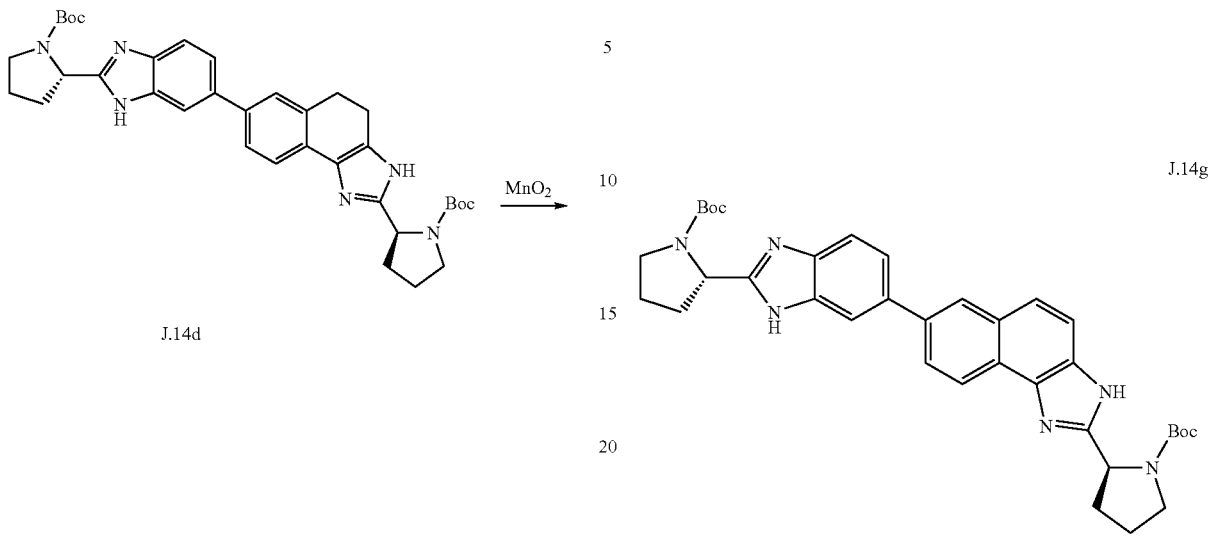

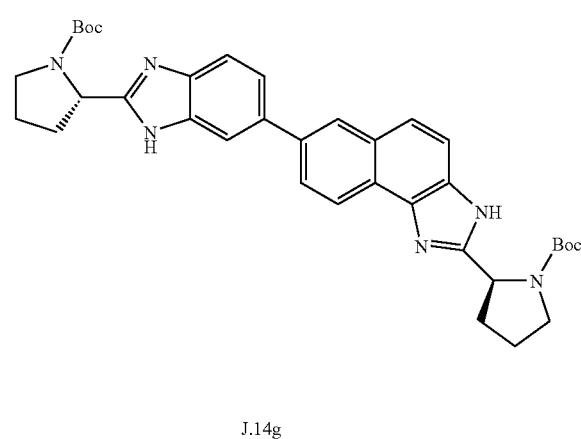

Activated manganese dioxide (122 mg, 1.409 mmol) was added in one portion to a stirred solution of J.14d (S)-tert-butyl 2-(7-(2-((S)-1-(tert-butoxycarbonyl)pyrrolidin-2-yl)-1H-benzo[d]imidazol-5-yl)-4,5-dihydro-1H-naphtho[1,2-d]imidazol-2-yl)pyrrolidine-1-carboxylate (88 mg, 0.141 mmol) in dry dichloromethane (2 mL). The suspension was stirred for 14 h and additional manganese dioxide (1.5 g) was added. The suspension was stirred for 16 h and manganese dioxide (1.5 g) was added again and allowed to continue stirring for 24 h. The reaction mixture was filtered through diatomaceous earth (Celite), concentrated, and placed on high vacuum for 1 h. There was isolated 3.14 g (85.0 mg, 92%) as a yellowish-orange solid, LCMS: 2.14 min (Cond.-D2) Calcd. for $C_{36}H_{43}N_6O_4$ [M+H]$^+$ 623.33; found: 623.46. HRMS: Calcd for $C_{36}H_{43}N_6O_4$ [M+H]$^+$ 623.3340; found: 623.3327.

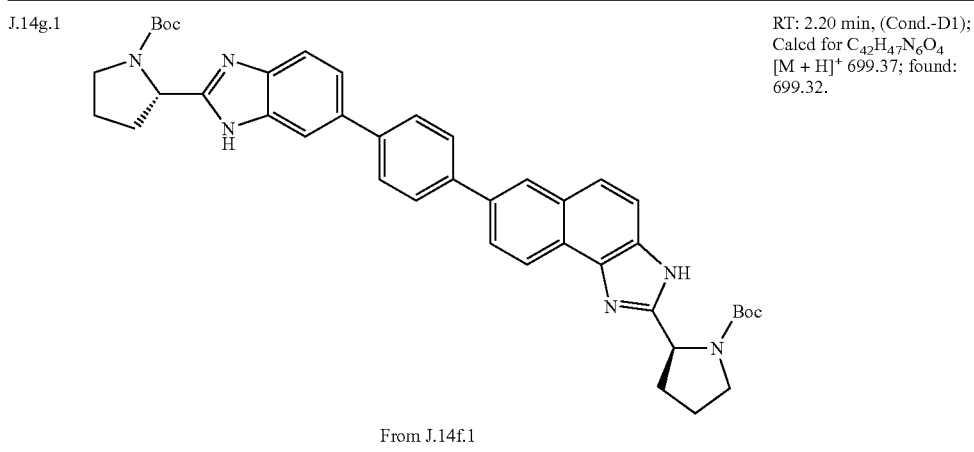

From J.14f.1

RT: 2.20 min, (Cond.-D1); Calcd for $C_{42}H_{47}N_6O_4$ [M + H]$^+$ 699.37; found: 699.32.

Synthetic Route 8a

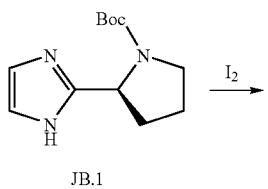

JB.1

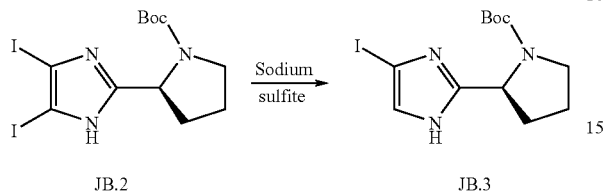

JB.2    JB.3

Examples JB.1-JB.3

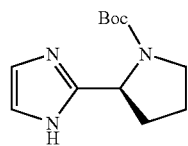

JB.1

Glyoxal (2.0 mL of 40% in water) was added dropwise over 11 minutes to a methanol solution of NH₄OH (32 mL) and (S)-Boc-prolinal (8.56 g, 43.0 mmol) and stirred at ambient temperature for 19 hours. The volatile component was removed in vacuo and the residue was purified by a flash chromatography (silica gel, EtOAc) followed by a recrystallization (EtOAc, room temperature) to provide (S)-tort-butyl 2-(1H-imidazol-2-yl)pyrrolidine-1-carboxylate (4.43 g) as a white fluffy solid. $^1$H NMR (DMSO-d₆, 400 MHz): 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39/1.15 (s, 9H), RT=0.87 min (Cond.-JB.1) LC/MS: Anal. Calcd. for [M+H]⁺ C₁₂H₂₀N₃O₂: 238.16; found 238.22. The compound shown to have a 98.9 ee % when analyzed under the chiral HPLC conditions noted below. Column: Chiralpak AD, 10 um, 4.6×50 mm Solvent: 1.7% ethanol/heptane (isocratic) Flow rate: 1 mL/min Wavelength: either 220 or 256 nm. Relative retention time: 3.25 min (R), 5.78 minutes (S)

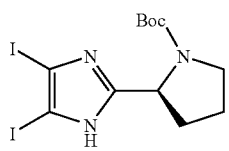

JB.3

Iodine was (16.17 g, 63.7 mmol) was added to a solution of Example JB.1 (6.87 g, 29.0 mmol) and sodium carbonate (9.21 g, 87 mmol) in dioxane (72 mL) and water (72 mL) at ambient temperature. The flask was covered with aluminum foil and stirred for 16 hours. The reaction mixture was diluted with EtOAc and a saturated aqueous solution of sodium thiosulfate. The mixture was stirred for 15 minutes and the phases were separated. The layers were separated and the aqueous phase was extracted several times with ethyl acetate. The combined organic phases were dried (Na₂SO₄), filtered and concentrated in vacuo to afford (S)-tert-butyl 2-(4,5-diiodo-1H-imidazol-2-yl)pyrrolidine-1-carboxylate (12.5 g) as a tan solid. $^1$H NMR (500 MHz, MeOD) δ ppm 4.72-4.84 (m, 1H), 3.58-3.70 (m, 1H), 3.43-3.54 (m, 1H), 2.36 (br s, 1H), 1.88-2.08 (m, 3H), 1.47 (br s, 3H), 1.27 (br s, 6H). RT=1.40 min (Cond.-JB.1) LC/MS: Anal. Calcd. for [M+H]⁺ C₁₂H₁₇I₂N₃O₂: 488.94 found; 489.96.

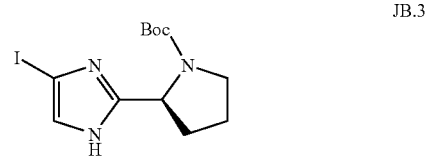 [SMILES: CC(C)(C)OC(=O)N1CCC[C@H]1c1nc(I)c[nH]1]

JB.3

Sodium sulfite (10.31 g, 82 mmol) was added to a solution of Example JB.2 (4.0 g, 8.2 mmol) in ethanol (75 mL) and water (75 mL). The suspension was heated with an oil bath at 100° C. for 4 hours and at 90° C. for 16 h. The reaction was diluted with EtOAc and water. The layers were separated and the aqueous layer was extracted several times with EtOAc. The combined organic phases were dried (brine, Na₂SO₄), filtered and concentrated in vacuo. The residue was purified by a flash chromatography (sample was dry loaded on silica gel and eluted with, 0 to 40% ethyl acetate/CH₂Cl₂) to afford (S)-tert-butyl 2-(5-iodo-1H-imidazol-2-yl)pyrrolidine-1-carboxylate (2.17 g) as a white solid. $^1$H NMR (500 MHz, MeOD) δ ppm 7.52-7.64 (m, 1H), 4.95-5.10 (m, 1H), 3.57-3.70 (m, 1H), 3.47-3.57 (m, 1H), 2.37-2.55 (m, 1H), 1.94-2.10 (m, 3H), 1.46 (s, 4H), 1.27 (s, 5H). RT=0.93 min (Cond.-JB.1) LC/MS: Anal. Calcd. for [M+H]⁺ C₁₂H₁₈1N₃O₂363.04; found: 364.06.

Synthetic Route 9

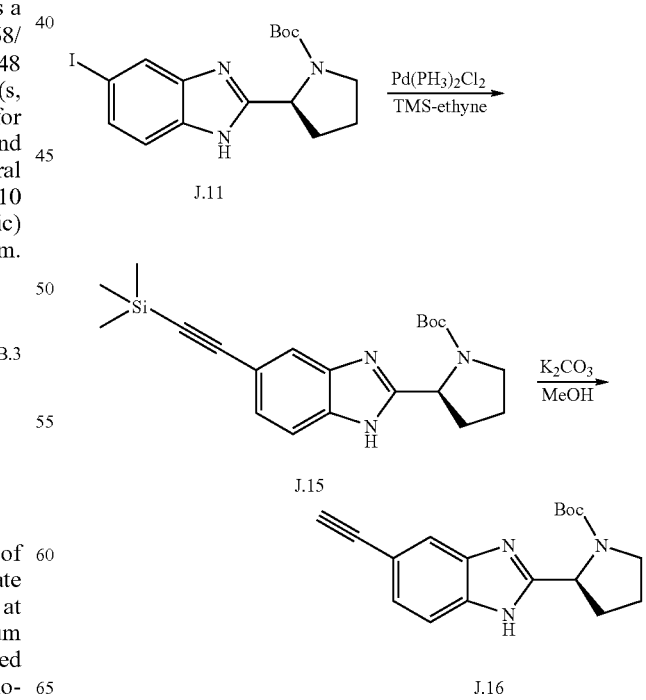

J.11

J.15

J.16

Examples J.15-JB.4

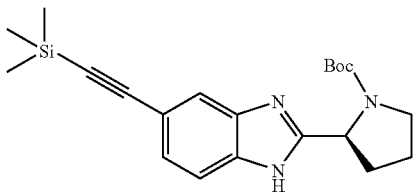

J.15

A mixture of copper iodide (299.6 mg, 48.1 mmol) and Pd(PPh$_3$)$_2$Cl$_2$ (1.29 g, 4.41 mmol) was added to a dimethylformamide (200 ml) solution of J.11 (16.0 g, 38.7 mmol), (trimethylsilyl)acetylene (6.8 ml, 48.1 mmol), and triethylamine (16 ml), and the reaction mixture was stirred at ~25° C. for 19.5 h. The volatile component was removed in vacuo and a silica gel mesh was prepared from the residue and submitted to a flash chromatography (silica gel; eluting with 40% ethyl acetate/hexanes) to provide alkyne J.15 as a tan foam (13.96 g). $^1$H NMR (DMSO-d$_6$, δ=2.5 ppm, 500 MHz): 12.52-12.38 (m, 1H), 7.62-7.41 (m, 2H), 7.24-7.19 (m, 1H), 5.01-4.85 (m, 1H), 3.64-3.51 (m, 1H), 3.46-3.35 (m, 1H), 2.38-2.21 (m, 1H), 2.07-1.81 (m, 3H), 1.39 (s, 4H), 1.04 (s, 51-1), 0.23 (s, 9H). RT=2.09 min (Cond.-J1) LC/MS: Anal. Calcd. for [M+H]$^+$ C$_{21}$H$_{30}$N$_3$O$_2$Si: 384.21; found: 384.27.

J.15a

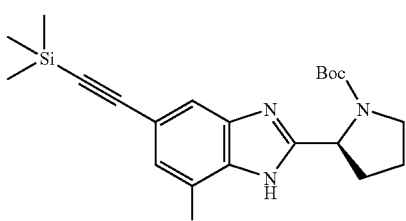

From J.10a

RT = 1.89 min, (Cond.-J1); Calcd for C$_{21}$H$_{29}$N$_3$O$_2$Si [M + H]$^+$ 402.20; found: 402.26.

J.15b

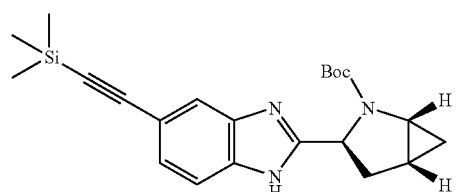

From J.10b

RT = 1.92 min, (Cond.-J1); Calcd for C$_{22}$H$_{30}$N$_3$O$_2$Si [M + H]$^+$ 396.21; found: 396.22.

J.15c

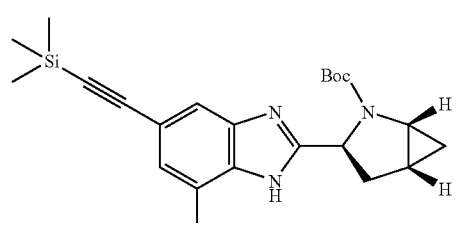

From J.10c

RT = 2.2 min, (Cond.-J1); Calcd for C$_{22}$H$_{29}$FN$_3$O$_2$Si [M + H]$^+$ 414.20; found: 414.26.

J.15d

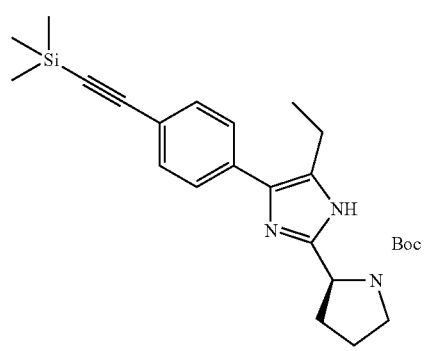

From J.9d

RT = 1.70 min, (Cond.-J1); Calcd for C$_{25}$H$_{36}$N$_3$O$_2$Si [M + H]$^+$ 438.26; found: 438.33.

| | | |
|---|---|---|
| J.15d.1 | 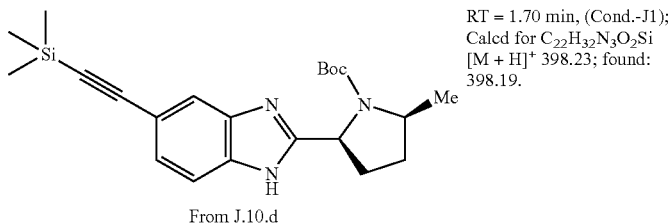<br>From J.10.d | RT = 1.70 min, (Cond.-J1); Calcd for $C_{22}H_{32}N_3O_2Si$ $[M + H]^+$ 398.23; found: 398.19. |
| J.15e | 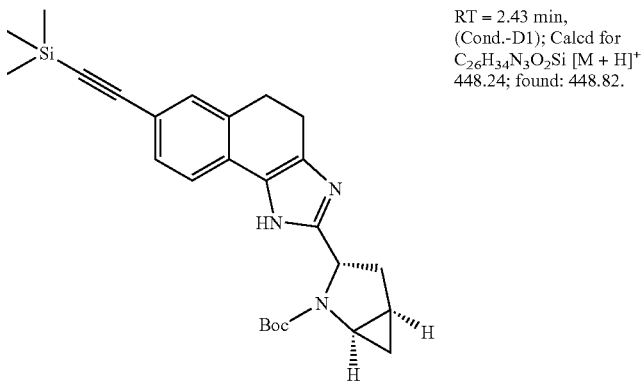<br>From J.9b | RT = 2.43 min, (Cond.-D1); Calcd for $C_{26}H_{34}N_3O_2Si$ $[M + H]^+$ 448.24; found: 448.82. |
| J.15f | 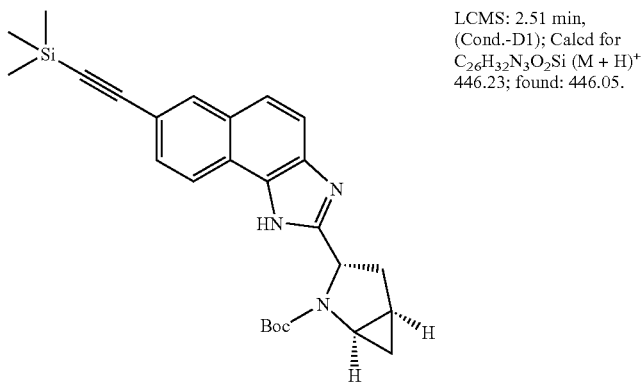<br>From J.15e according to the procedure described for J.14g. | LCMS: 2.51 min, (Cond.-D1); Calcd for $C_{26}H_{32}N_3O_2Si$ $(M + H)^+$ 446.23; found: 446.05. |
| JB.4 | 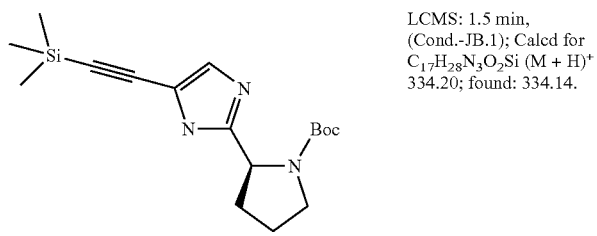<br>From JB.3 | LCMS: 1.5 min, (Cond.-JB.1); Calcd for $C_{17}H_{28}N_3O_2Si$ $(M + H)^+$ 334.20; found: 334.14. |

Examples J.16-JB.5

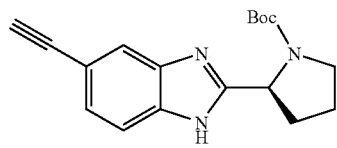

J.16

Potassium carbonate (0.5526 g, 4 mmol) was added to solution of alkyne J.15 (13.9 g, 36.2 mmol) in methanol (200 ml) and the mixture was stirred at room temperature for 17 h. The volatile component was removed in vacuo, and the residue was partitioned between ethyl acetate and saturated ammonium chloride (aq) solution, and the organic layer was separated and washed with brine, dried (MgSO$_4$), filtered, and concentrated in vacuo to provide alkyne J.16 as a tan foam (9.3 g). $^1$H NMR (DMSO-d$_6$, δ=2.5 ppm, 500 MHz): 12.58-12.30 (br s, 1H), 7.72-7.36 (two overlapping app br s, 2H), 7.23 (d, J=8.1, 1H), 4.97-4.88 (m, 1H), 4.02 (s, 1H), 3.64-3.52 (m, 1H), 3.44-3.36 (m, 1H), 2.40-2.20 (m, 1H), 2.06-1.81 (m, 3H), 1.39 (s, 4H), 1.05 (s, 5H). LC/MS: Anal. Calcd. for [M+Na]$^+$ C$_{18}$H$_{21}$N$_3$NaO$_2$: 334.15; found: 334.24.

| | | |
|---|---|---|
| J.16a | 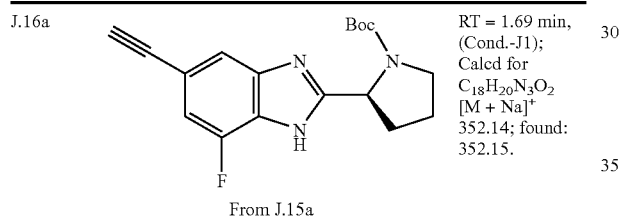 From J.15a | RT = 1.69 min, (Cond.-J1); Calcd for C$_{18}$H$_{20}$N$_3$O$_2$ [M + Na]$^+$ 352.14; found: 352.15. |
| J.16b | 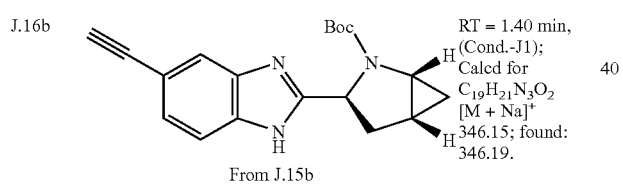 From J.15b | RT = 1.40 min, (Cond.-J1); Calcd for C$_{19}$H$_{21}$N$_3$O$_2$ [M + Na]$^+$ 346.15; found: 346.19. |
| J.16c | 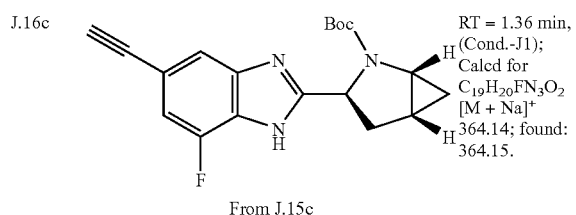 From J.15c | RT = 1.36 min, (Cond.-J1); Calcd for C$_{19}$H$_{20}$FN$_3$O$_2$ [M + Na]$^+$ 364.14; found: 364.15. |
| J.16d | 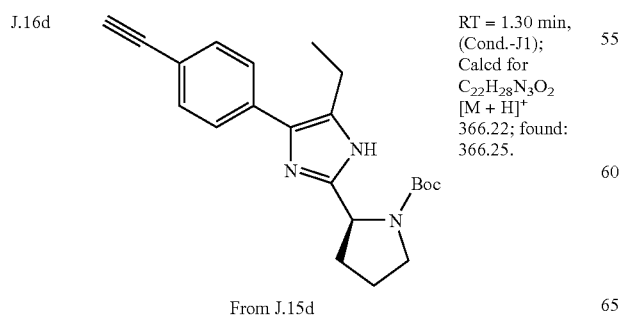 From J.15d | RT = 1.30 min, (Cond.-J1); Calcd for C$_{22}$H$_{28}$N$_3$O$_2$ [M + H]$^+$ 366.22; found: 366.25. |
| J.16d.1 | 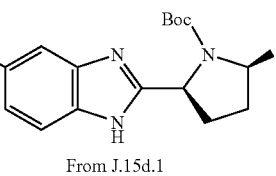 From J.15d.1 | RT = 2.74 min, (Cond.-J2); Calcd for C$_{19}$H$_{24}$N$_3$O$_2$ [M + H]$^+$ 326.19; found: 326.13. |
| J.16e | 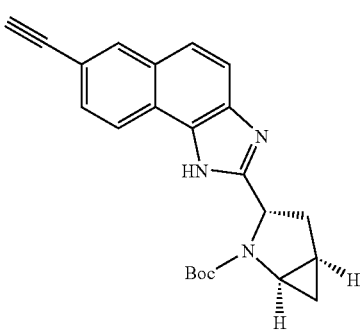 From J.15f | LCMS: 1.88 min, (Cond.-D1) Calcd for C$_{23}$H$_{24}$N$_3$O$_2$ (M + H)$^+$ 374.19; found: 374.04. |
| JB.5 | From JB.4 | LCMS: 0.88 min, (Cond.-JB-1) Calcd for C$_{10}$H$_{11}$N$_3$O$_2$ (M + H; −tBu)$^+$ 206.10; found: 206.05. |

Synthetic Route 9a

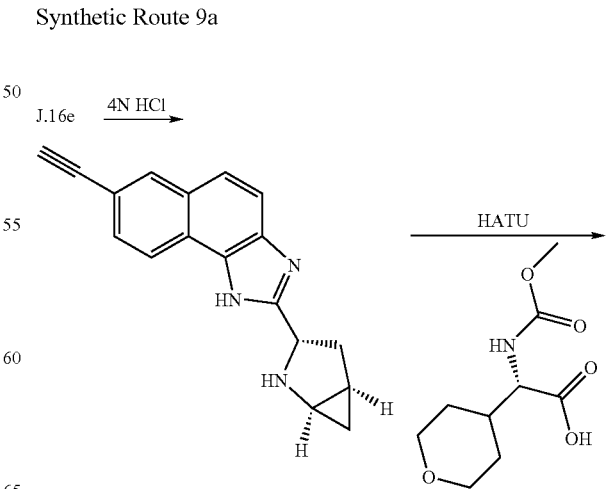

159

-continued

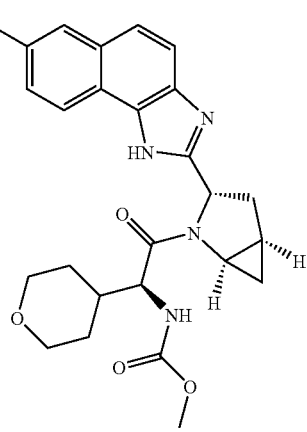

J.16f

Example J.16f

J.16f

Example J.16f was obtained from Example J.16e according to the two step procedure described below. Deprotection as in the preparation of J.19 to formed an HCl salt which was coupled with cap-170 with HATU according the preparation of J.21 below to give J.16f RT=1.59 min, (Cond.-D1); Calcd for $C_{27}H_{29}N_4O_4$ [M+H]$^+$ 473.22; found: 473.06.

Synthetic Route 10

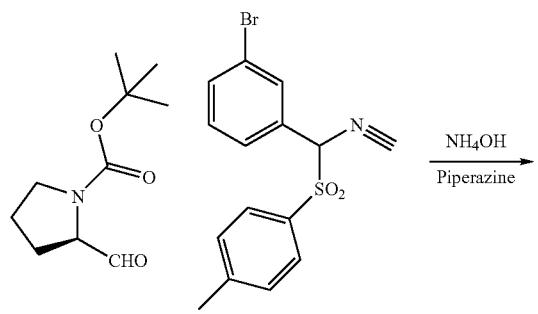

160

-continued

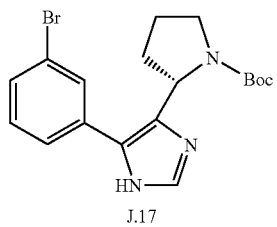

J.17

Example J.17-17.a

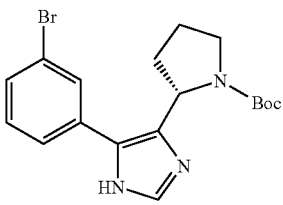

J.17

The ammonium hydroxide (4 mL) was added to a solution of (S)-prolinal (650 mg, 3.26 mmol) in tetrahydrofuran (15 mL) and stirred for 6 h at 48° C. in a sealed pressure vessel. α-tosyl-(3-bromobenzyl) isocyanide (974 mg, 2.77 mmol) and piperazine (281 mg, 3.26 mmol) were added and the reaction mixture stirred 18 h at 48° C. After being cooled, the reaction mixture was diluted with ethyl acetate (200 mL) and washed with water and brine and concentrated. The crude product was taken up in dichloromethane and charged to a 40 g Thomson silica gel cartridge. Gradient elution was performed from 20-100% B over 750 mL gave J.17 (S)-tert-butyl 2-(5-(3-bromophenyl)-1H-imidazol-4-yl)pyrrolidine-1-carboxylate 413 mg (31%). $^1$H NMR (CDCl$_3$, δ500 MHz): 10.36/9.90 (br s, 1H), 7.75 (br s, 1H), 7.53 (br. s, 2H), 7.38 (br. s, 1H), 7.24 (br. s, 1H), 5.11 (br. s, 1H), 3.54 (br. s, 2H), 2.32/2.19 (m, 1H), 1.95-1.85 (m, 2H), 1.74 (s, 1H), 1.45/1.18 (s, 9H). RT=1.7 (Cond.-J1) LC/MS: Anal. Calcd. for [M+H]$^+$ $C_{18}H_{23}BrN_3O_2$: 392.09; found: 392.13.

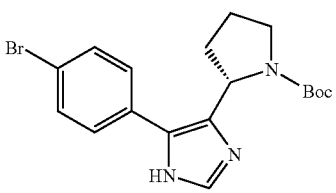

J.17a  RT = 1.7 min, (Cond.-J1); Calcd for $C_{18}H_{23}BrN_3O_2$ [M + H]$^+$ 392.09; found: 392.13.

From α-tosyl-(4-bromobenzyl) isocyanide

Synthetic Route 11.

Examples J.18-JB.6

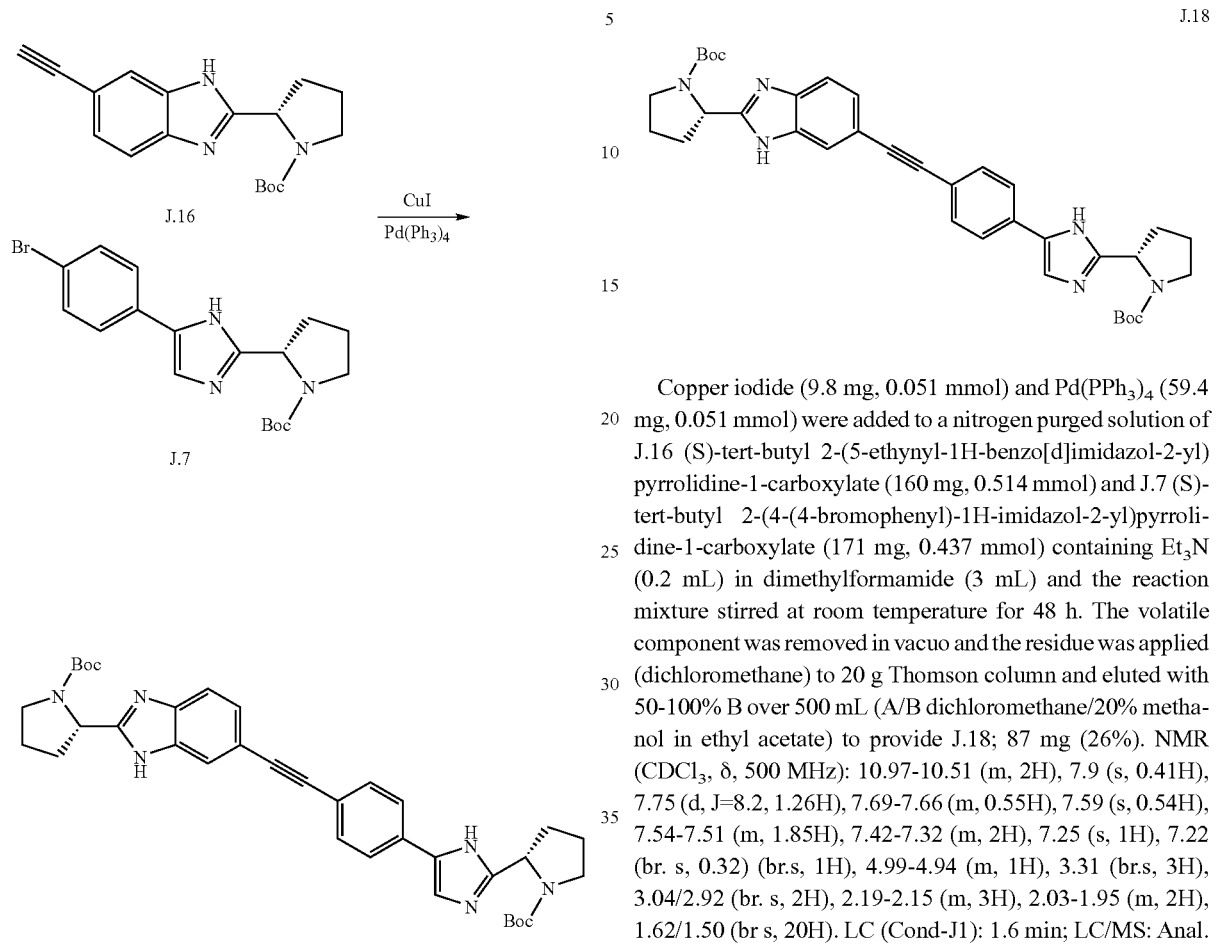

Copper iodide (9.8 mg, 0.051 mmol) and Pd(PPh$_3$)$_4$ (59.4 mg, 0.051 mmol) were added to a nitrogen purged solution of J.16 (S)-tert-butyl 2-(5-ethynyl-1H-benzo[d]imidazol-2-yl)pyrrolidine-1-carboxylate (160 mg, 0.514 mmol) and J.7 (S)-tert-butyl 2-(4-(4-bromophenyl)-1H-imidazol-2-yl)pyrrolidine-1-carboxylate (171 mg, 0.437 mmol) containing Et$_3$N (0.2 mL) in dimethylformamide (3 mL) and the reaction mixture stirred at room temperature for 48 h. The volatile component was removed in vacuo and the residue was applied (dichloromethane) to 20 g Thomson column and eluted with 50-100% B over 500 mL (A/B dichloromethane/20% methanol in ethyl acetate) to provide J.18; 87 mg (26%). NMR (CDCl$_3$, δ, 500 MHz): 10.97-10.51 (m, 2H), 7.9 (s, 0.41H), 7.75 (d, J=8.2, 1.26H), 7.69-7.66 (m, 0.55H), 7.59 (s, 0.54H), 7.54-7.51 (m, 1.85H), 7.42-7.32 (m, 2H), 7.25 (s, 1H), 7.22 (br. s, 0.32) (br.s, 1H), 4.99-4.94 (m, 1H), 3.31 (br.s, 3H), 3.04/2.92 (br. s, 2H), 2.19-2.15 (m, 3H), 2.03-1.95 (m, 2H), 1.62/1.50 (br s, 20H). LC (Cond-J1): 1.6 min; LC/MS: Anal. Calcd. for [M+H]$^+$ C$_{36}$H$_{43}$N$_6$O$_4$: 623.34; found: 623.52; HRMS: Anal. Calcd. for [M+H]$^+$ C$_{36}$H$_{43}$N$_6$O$_4$: 623.3340; found: 623.3344.

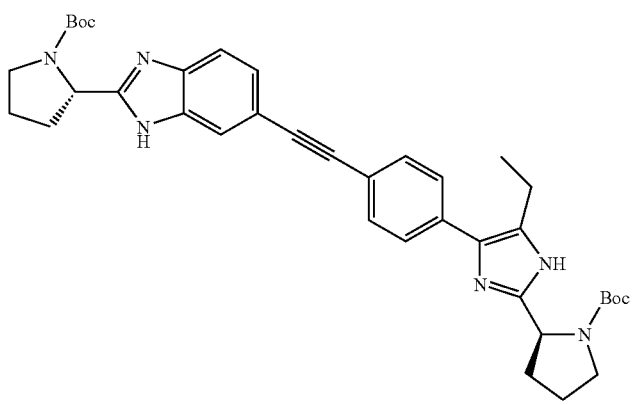

J.18.1

From J.10 and J.16d

RT = 1.4 min (Cond.-J1); LCMS:
Anal. Calcd. for [M + H]$^+$
C$_{38}$H$_{47}$N$_6$O$_4$ 651.36; found: 651.46.

-continued
| | | |
|---|---|---|
| J.18.2 | 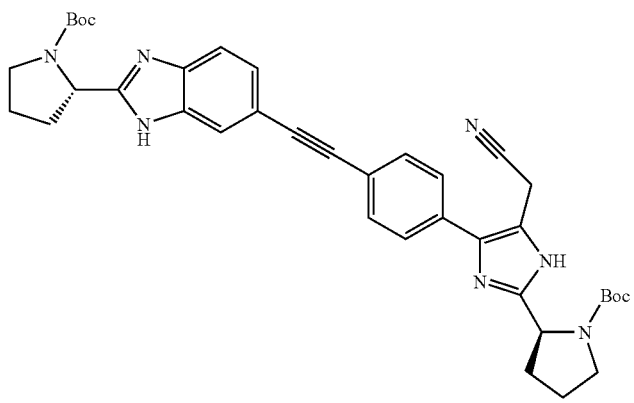
From J.16 and J.9e | RT = 1.34 min (Cond.-J1); LCMS: Anal. Calcd. for [M + H]$^+$ C$_{38}$H$_{44}$N$_7$O$_4$ 662.35; found: 662.35. |
| J.18a | 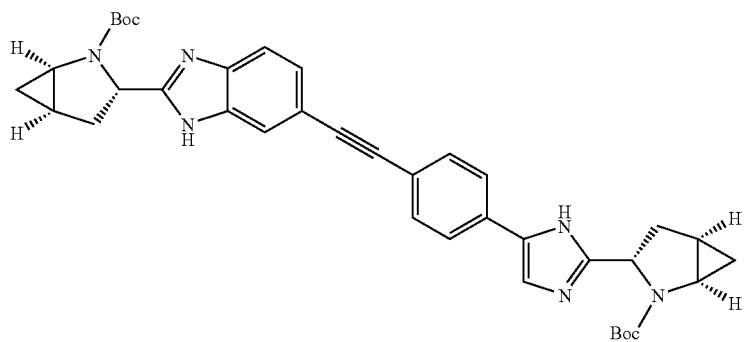
From J.16b and J.7b | RT = 1.6 min (Cond.-J1); LCMS: Anal. Calcd. for [M + H]$^+$ C$_{38}$H$_{43}$N$_6$O$_4$ 647.33; found: 647.39. |
| J.18b | 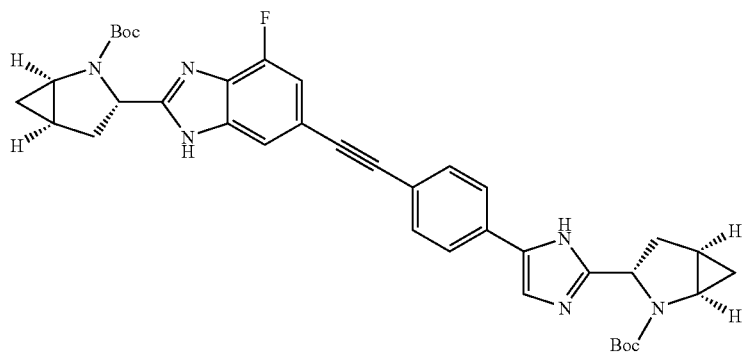
From J.16c and J.7b | RT = 1.57 min (Cond.-J1); LCMS: Anal. Calcd. for [M + H]$^+$ C$_{38}$H$_{42}$FN$_6$O$_4$ 665.33; found: 665.49. |
| J.18c | 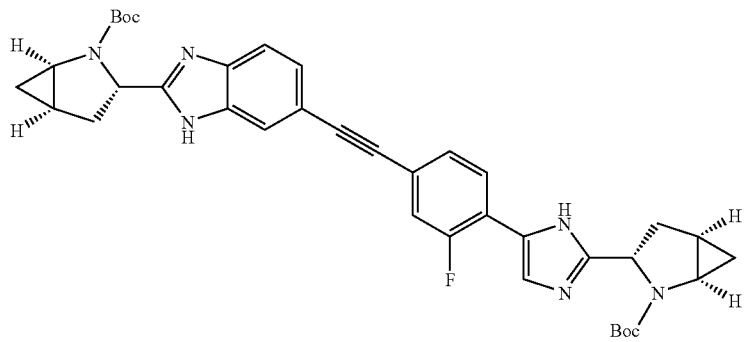
From J.16b and J.9c | RT = 1.42 min (Cond.-J1); LCMS: Anal. Calcd. for [M + H]$^+$ C$_{38}$H$_{42}$FN$_6$O$_4$ 665.33; found: 665.49. |

| | | |
|---|---|---|
| J.18d | 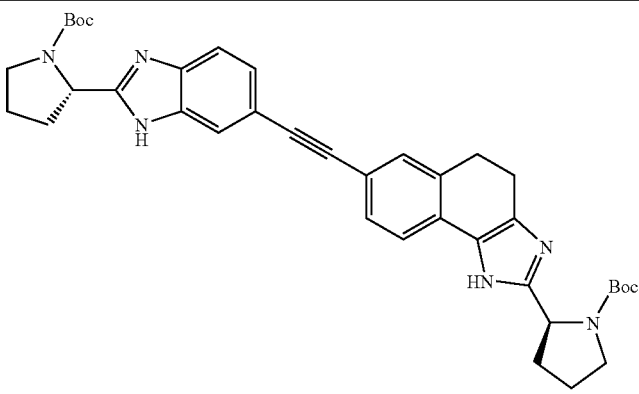<br>From J.16 and J.9a | RT: 2.27 min, (Cond.-D2); Calcd for $C_{38}H_{45}N_6O_4$ $[M + H]^+$ 649.35; found: 649.49.<br>HRMS: Calcd for $C_{38}H_{45}N_6O_4$ $[M + H]^+$ 649.3497; found: 649.3484. |
| J.18e | 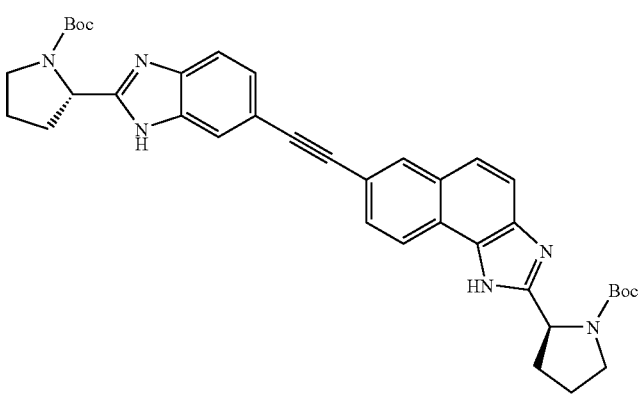<br>From J.18d according to the procedure described for J.14g. | RT: 2.31 min, (Cond.-D2); Calcd for $C_{38}H_{43}N_6O_4$ $[M + H]^+$ 647.33; found: 647.46.<br>HRMS: Calcd for $C_{38}H_{43}N_6O_4$ $[M + H]^+$ 647.3340; found: 647.3328. |
| J.18f | 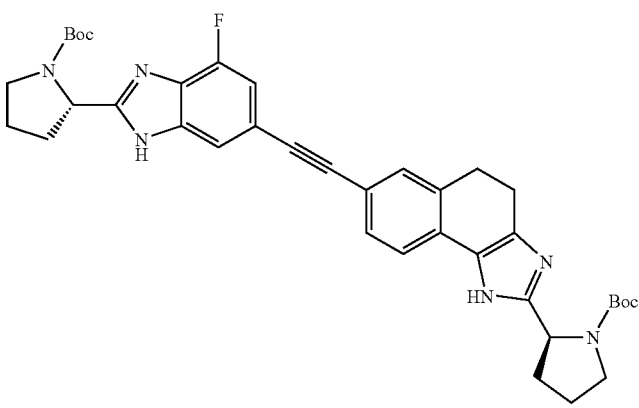<br>From J.16a and J.9a | RT: 1.61 min, (Cond.-J1); Calcd for $C_{38}H_{44}FN_6O_4$ $[M + H]^+$ 667.34; found: 667.46. |

| | | |
|---|---|---|
| J.18g | 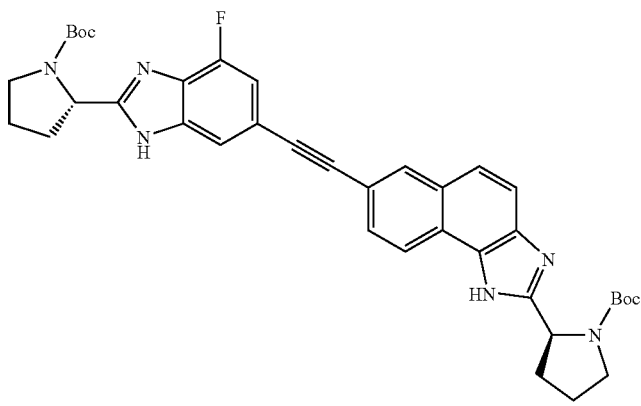<br>From J.18f according to the procedure described for J.14g. | RT: 1.64 min, (Cond.-J1); Calcd for $C_{38}H_{42}FN_6O_4$ [M + H]$^+$ 665.33; found: 665.49. |
| J.18h | 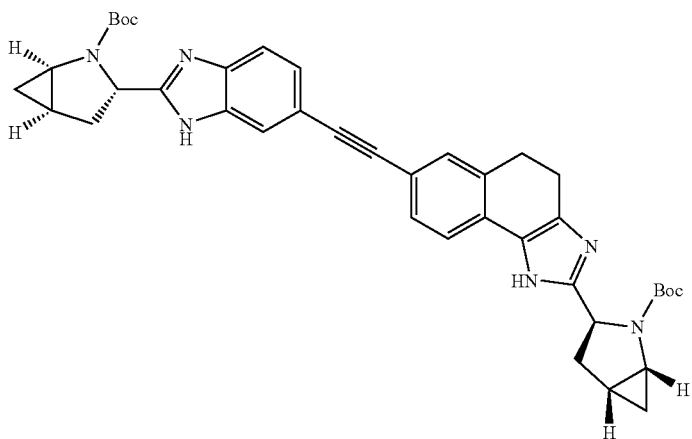<br>From J.16b and J.9b | RT: 1.44 min, (Cond.-J1); Calcd for $C_{40}H_{45}N_6O_4$ [M + H]$^+$ 673.35; found: 673.43. |
| J.18i | 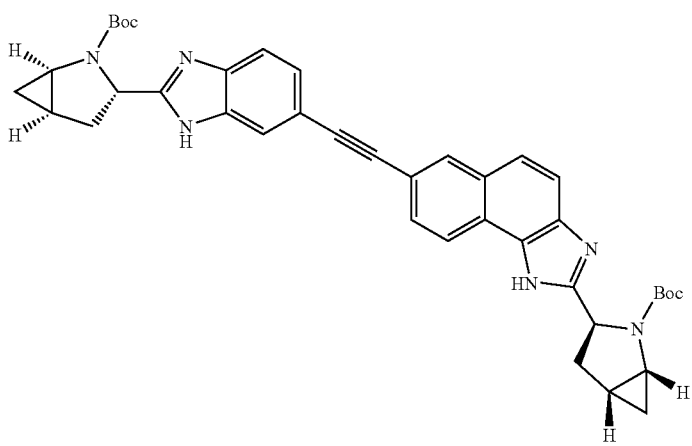<br>From J.18h according to the procedure described for J.14g. | RT: 1.48 min, (Cond.-J1); Calcd for $C_{40}H_{43}N_6O_4$ [M + H]$^+$ 670.34; found: 670.46. |

-continued
J.18i.1 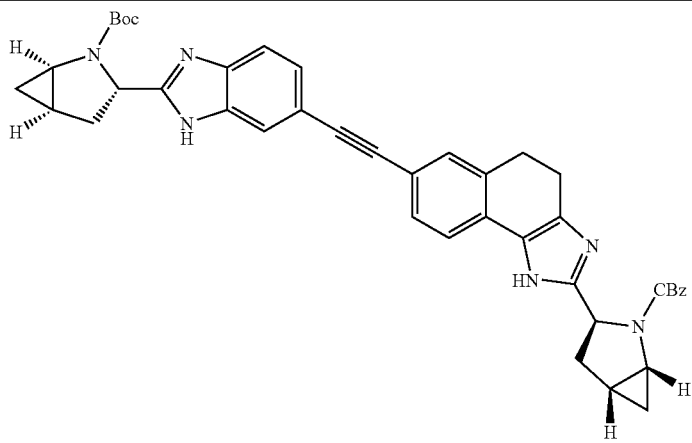
From J.16b and J.9f
RT: 2.03 min, (Cond.-D1); Calcd for C$_{43}$H$_{43}$N$_6$O$_4$ [M + H]$^+$ 707.34; found: 707.28.
J.18i.2 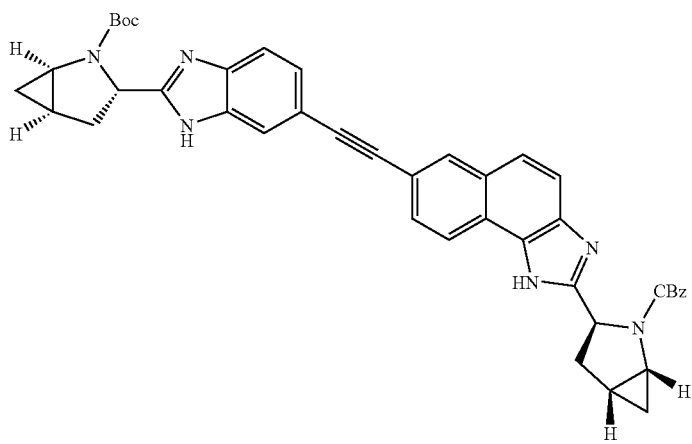
From J.18i.1 according to the procedure described for J.14g.
RT: 2.10 min, (Cond.-D1); Calcd for C$_{43}$H$_{41}$N$_6$O$_4$ [M + H]$^+$ 705.32; found: 705.19.
J.18i.3 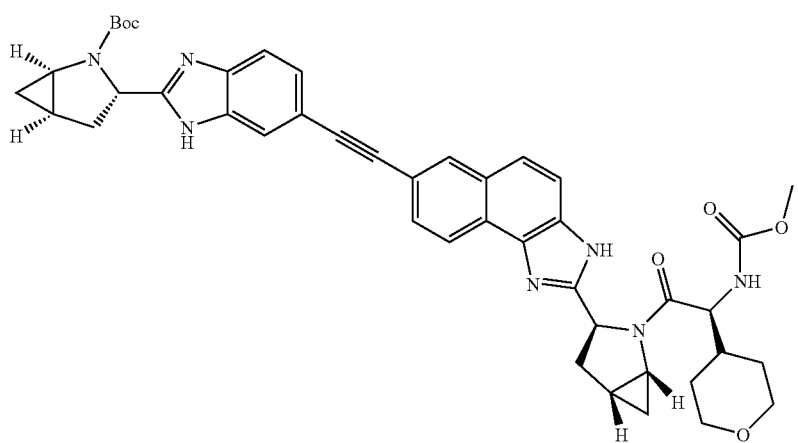
From J.16f and J.10b
RT = 1.92 min (Cond.-D1); LCMS: Calcd for C$_{44}$H$_{48}$N$_7$O$_6$ (M + H)$^+$ 770.37; found: 770.29.

| | | |
|---|---|---|
| J.18j | 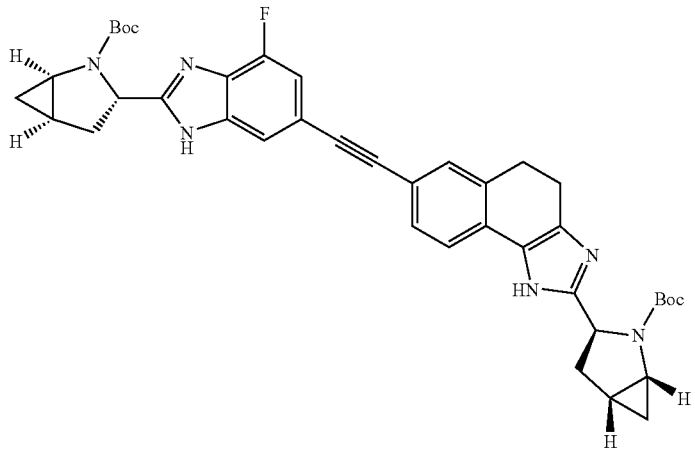<br>From J.16c and J.9b | RT: 1.62 min, (Cond.-J1); Calcd for $C_{40}H_{44}FN_6O_4$ [M + H]$^+$ 691.34; found: 691.46. |
| J.18k | 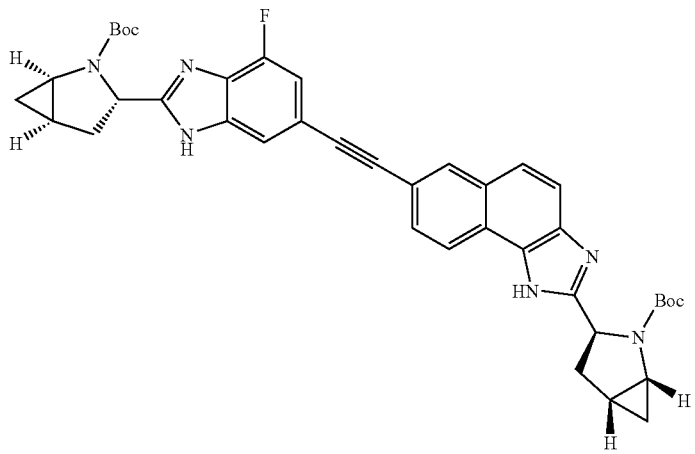<br>From J.18j according to the procedure described for J.14g. | RT: 1.66 min, (Cond.-J1); Calcd for $C_{40}H_{42}FN_6O_4$ [M + H]$^+$ 689.33; found: 689.43. |
| J.18k.1 | 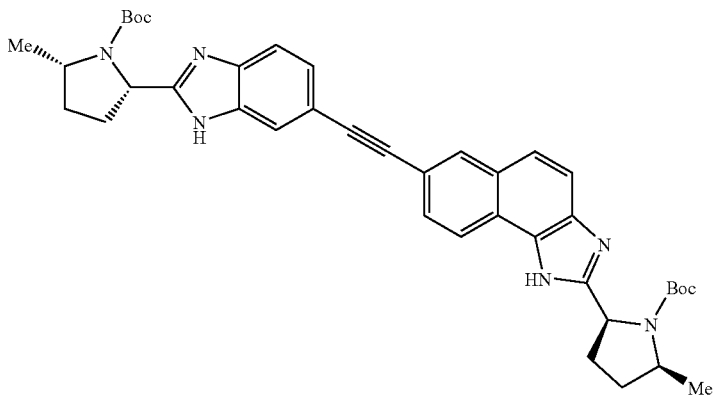<br>From J.16d.1 and J.9g | RT: 3.44 min, (Cond.-J2); Calcd for $C_{40}H_{47}N_6O_4$ [M + H]$^+$ 675.37; found: 675.33 |
| J.18l | 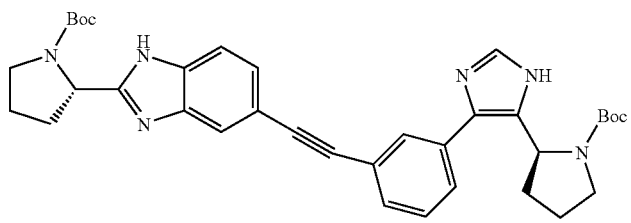<br>From J.16 and J.17 | RT = 1.67 min, (Cond.-J1); Calcd for $C_{36}H_{43}N_6O_4$ [M + H]$^+$ 623.34; found: 623.46. |

J.18m 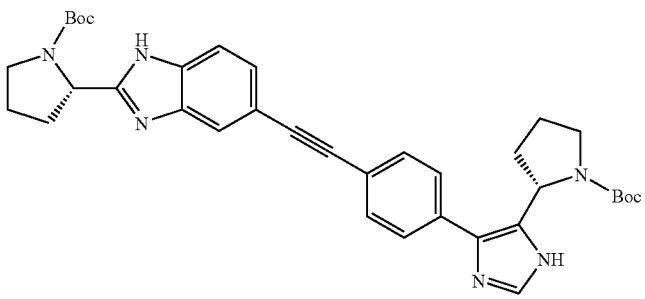

From J.16 and J.17a

RT = 1.67 min, (Cond.-J1); Calcd for C$_{36}$H$_{43}$N$_6$O$_4$ [M + H]$^+$ 623.34; found: 623.46.

JB.6 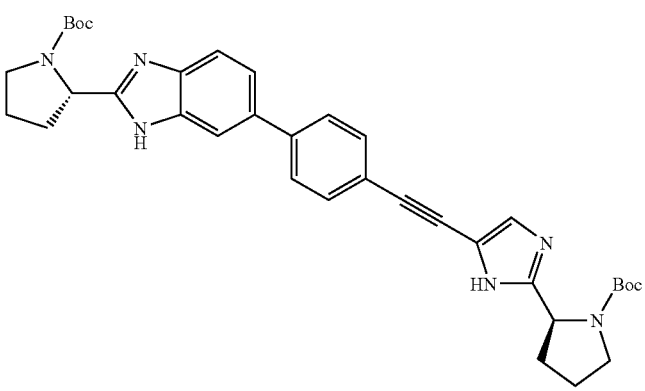

From J.14e and JB.5

RT = 1.33 min, (Cond.-JB.1); Calcd for C$_{36}$H$_{43}$N$_6$O$_4$ [M + H]$^+$ 623.34; found: 623.24.

Synthetic Route 12

Examples J.19-JB.7

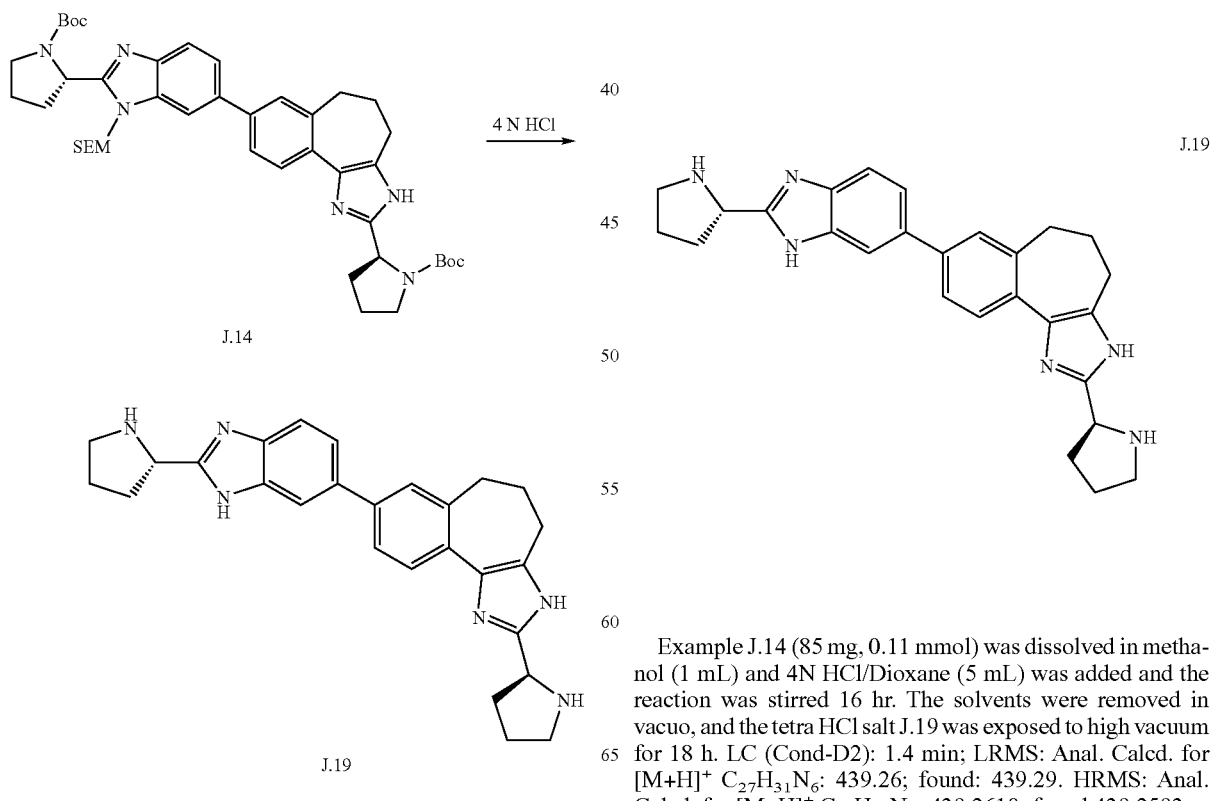

Example J.14 (85 mg, 0.11 mmol) was dissolved in methanol (1 mL) and 4N HCl/Dioxane (5 mL) was added and the reaction was stirred 16 hr. The solvents were removed in vacuo, and the tetra HCl salt J.19 was exposed to high vacuum for 18 h. LC (Cond-D2): 1.4 min; LRMS: Anal. Calcd. for [M+H]$^+$ C$_{27}$H$_{31}$N$_6$: 439.26; found: 439.29. HRMS: Anal. Calcd. for [M+H]$^+$ C$_{27}$H$_{31}$N$_6$: 439.2610; found 439.2593.

| | | |
|---|---|---|
| J.19a | 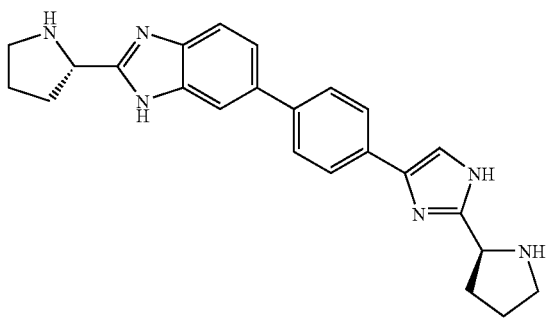<br>From J.14a | RT = 1.34 min (Cond.-D2) LCMS:<br>Anal. Calcd. for [M + H]$^+$ C$_{24}$H$_{27}$N$_6$:<br>399.23; found: 399.24.<br>HRMS: Anal. Calcd. for [M + H]$^+$<br>C$_{24}$H$_{27}$N$_6$: 399.2297; found:<br>399.2316. |
| J.19b | 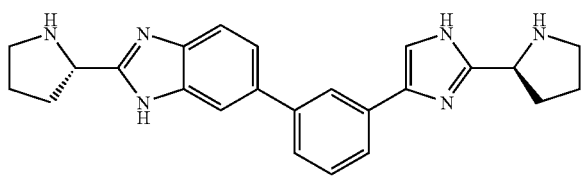<br>From J.14b | RT = 1.46 min (Cond.-D2) LCMS:<br>Anal. Calcd. for [M + H]$^+$ C$_{24}$H$_{27}$N$_6$:<br>399.23; found: 399.24.<br>HRMS: Anal. Calcd. for [M + H]$^+$<br>C$_{24}$H$_{27}$N$_6$: 399.2297; found:<br>399.2298. |
| J.19c | 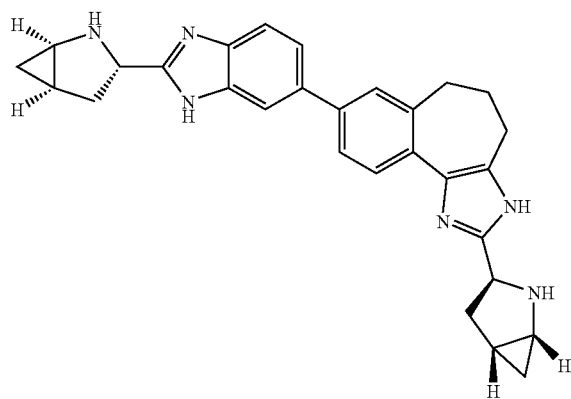<br>From J.14c | RT = 1.13 min (Cond.-J1) LCMS:<br>Anal. Calcd. for [M + H]$^+$ C$_{29}$H$_{30}$N$_6$:<br>463.26; found: 463.38. |
| J.19d | 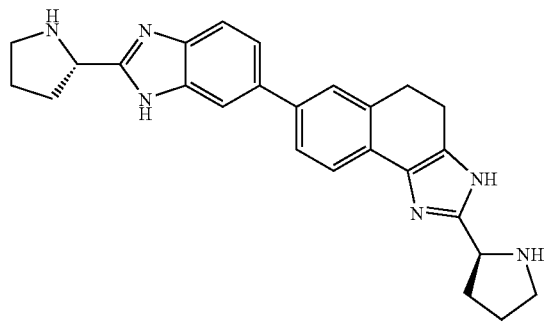<br>From J.14d | RT = 1.27 min, (Cond.-D2) LCMS:<br>Calcd for C$_{26}$H$_{29}$N$_6$ [M + H]$^+$<br>425.24; found: 425.28.<br>HRMS: Calcd for C$_{26}$H$_{29}$N$_6$<br>[M + H]$^+$ 425.2448; found:<br>425.2444. |

| | | |
|---|---|---|
| J.19e | 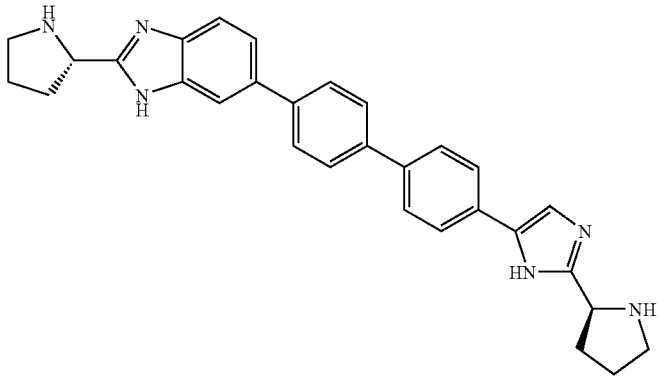<br>From J.14f | RT = 1.30 min, (Cond.-J1) LCMS: Calcd for $C_{30}H_{31}N_6$ [M + H]$^+$ 475.26; found: 475.25. |
| J.19f | 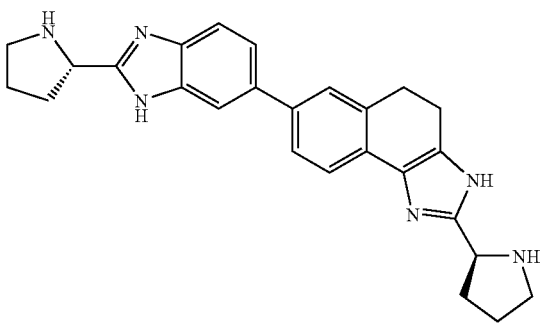<br>From J.14g | RT = 1.46 min, (Cond.-D2) LCMS: Calcd for $C_{26}H_{27}N_6$ [M + H]$^+$ 423.23; found: 423.31.<br>HRMS: Calcd for $C_{26}H_{27}N_6$ [M + H]$^+$ 423.2292; found: 423.2287. |
| J.19f.1 | 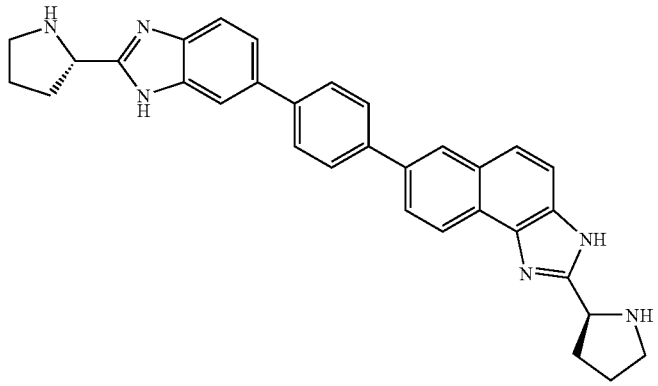<br>From J.14g.1 | RT: 1.73 min, (Cond.-D1); Calcd for $C_{32}H_{31}N_6$ [M + H]$^+$ 499.26; found: 499.22. |
| J.20 | 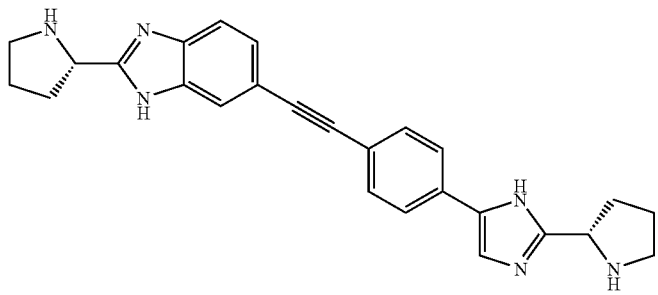<br>From J.18 | RT = 1.18 min, (Cond.-J1) LCMS: Calcd for $C_{26}H_{27}N_6$ [M + H]$^+$ 423.23; found: 423.24. |

| | | |
|---|---|---|
| J.20.1 | 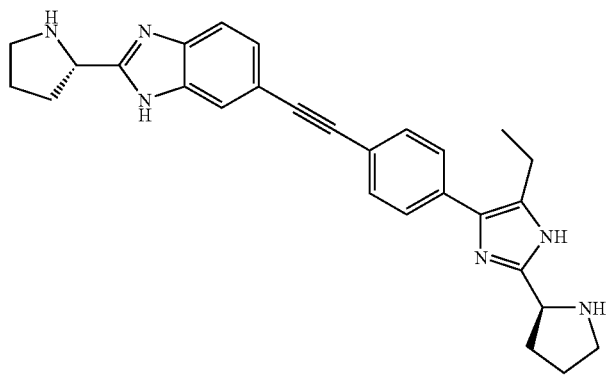<br>From J.18.1 | RT = 0.99 min (Cond.-J1); LCMS Calcd for $C_{28}H_{31}N_6$ $(M + H)^+$ 451.25; found: 451.28. |
| J.20.2 | 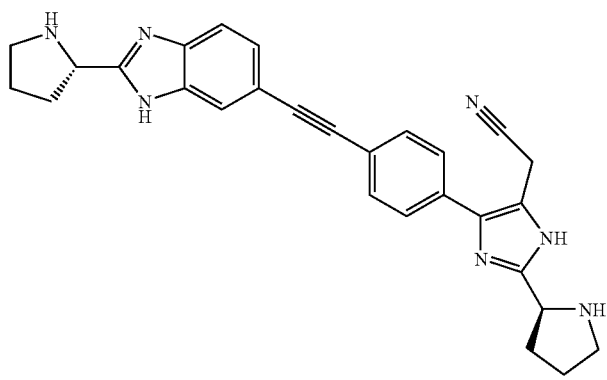<br>From J.18.2 | RT = 0.98 min (Cond.-J1); LCMS Calcd for $C_{28}H_{28}N_7$ $(M + H)^+$ 462.24; found: 462.24. |
| J.20a | 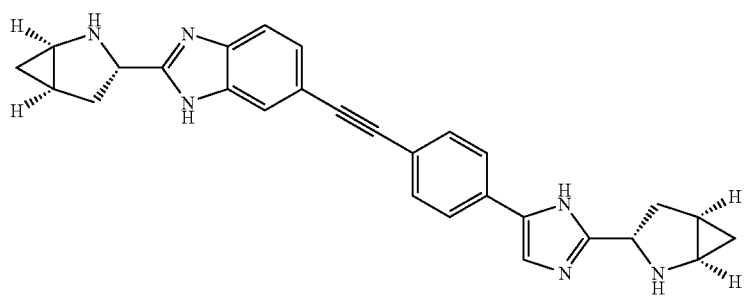<br>From J.18a | RT = 1.21 min, (Cond.-J1) LCMS: Calcd for $C_{28}H_{27}N_6$ $[M + H]^+$ 447.23; found: 447.18. |
| J.20b | 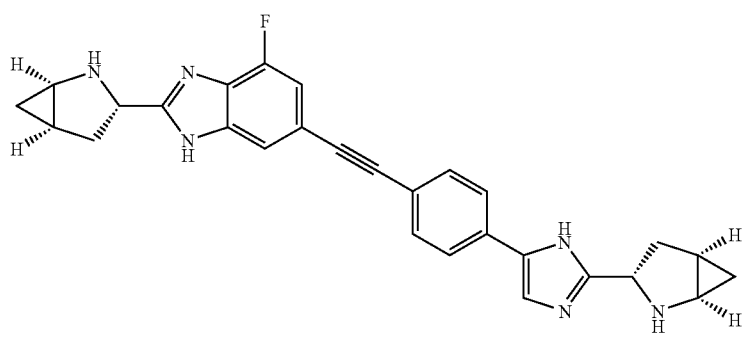<br>From J.18b | RT = 1.04 min, (Cond.-J1) LCMS: Calcd for $C_{28}H_{26}FN_6$ $[M + H]^+$ 465.21; found: 465.28. |

| | | |
|---|---|---|
| J.20c | 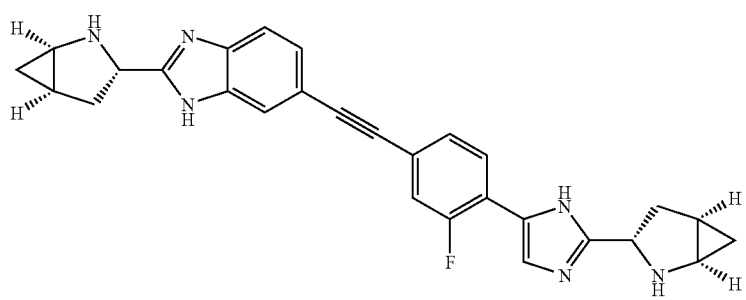<br>From J.18c | RT = 1.07 min, (Cond.-J1) LCMS:<br>Calcd for $C_{28}H_{26}FN_6$ $[M + H]^+$<br>465.21; found: 465.28. |
| J.20d | 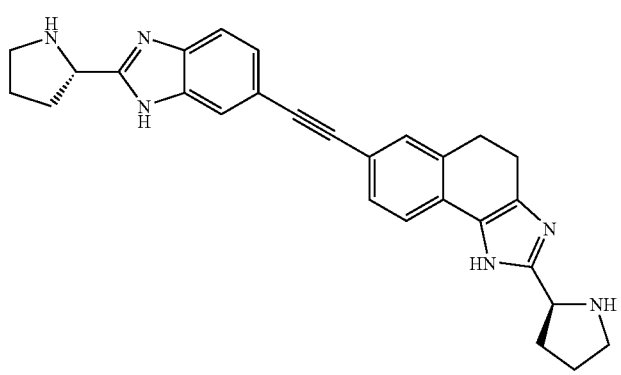<br>From J.18d | RT = 1.60 min, (Cond.-D2) LCMS:<br>Calcd for $C_{28}H_{29}N_6$ $[M + H]^+$<br>449.24; found: 449.28. |
| J.20e | 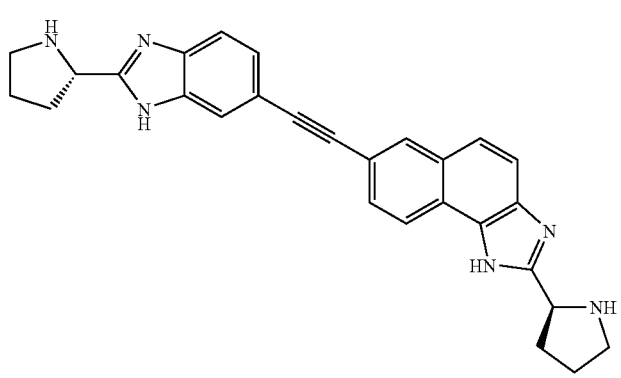<br>From J.18e | RT = 1.78 min, (Cond.-D2) LCMS:<br>Calcd for $C_{28}H_{27}N_6$ $[M + H]^+$<br>447.23; found: 447.25. |
| J.20f | 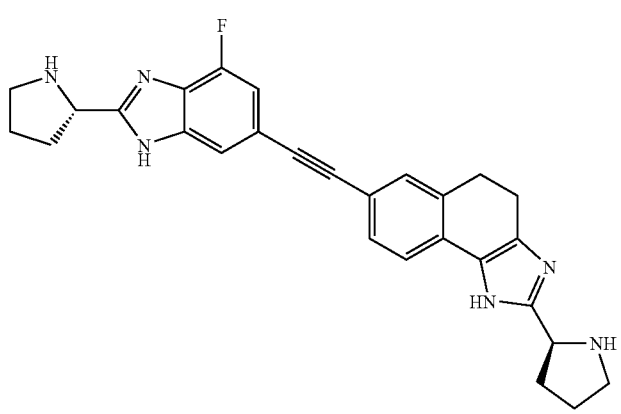<br>From J.18f | RT = 1.07 min, (Cond.-J1) LCMS:<br>Calcd for $C_{28}H_{28}FN_6$ $[M + H]^+$<br>467.24; found: 467.25. |

| | | |
|---|---|---|
| J.20g | 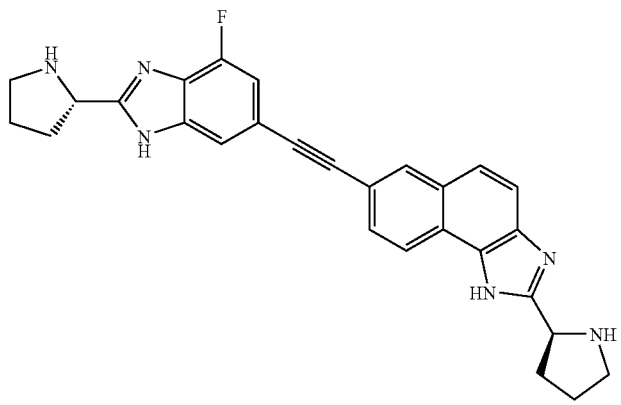<br>From J.18g | RT = 1.17 min, (Cond.-J1) LCMS:<br>Calcd for $C_{28}H_{26}FN_6$ [M + H]$^+$<br>465.22; found: 465.28. |
| J.20g.1 | 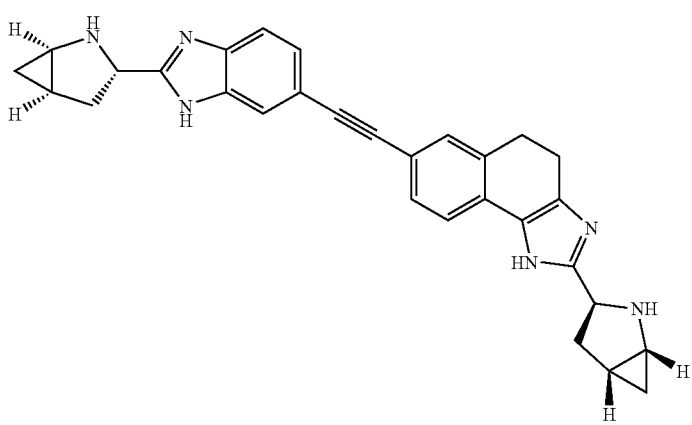<br>From J.18h | RT = 1.43 min, (Cond.-D1) LCMS:<br>Calcd for $C_{30}H_{29}N_6$ [M + H]$^+$<br>473.25; found: 473.13. |
| J.20h | 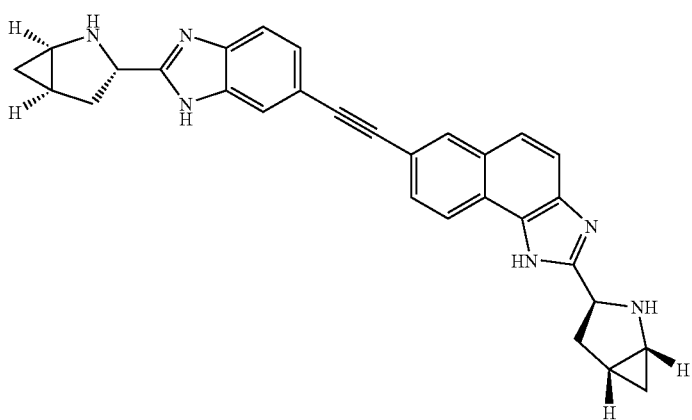<br>From J.18i | RT = 1.09 min, (Cond.-J1) LCMS:<br>Calcd for $C_{30}H_{27}N_6$ [M + H]$^+$<br>471.23; found: 471.25. |

-continued
| | | |
|---|---|---|
| J.20h.1 | 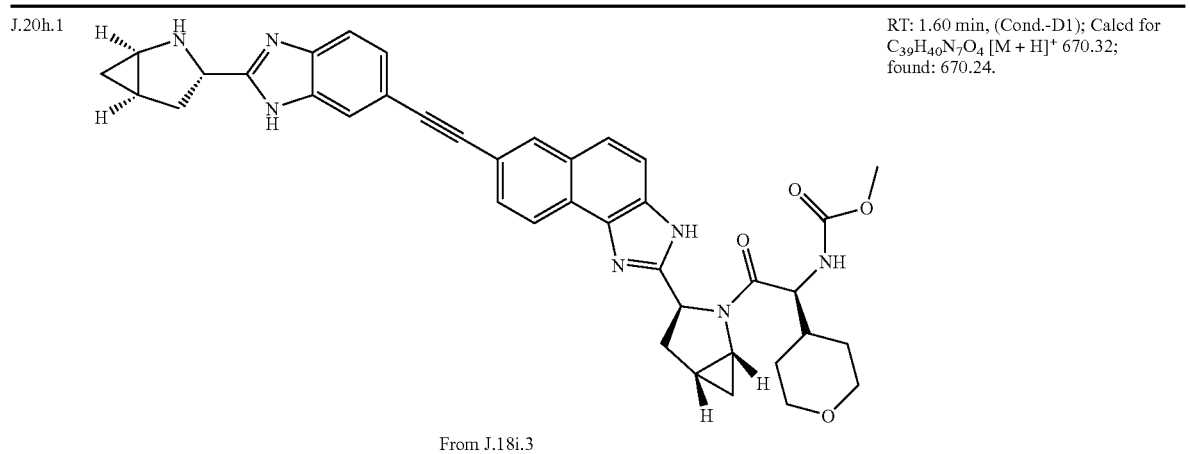<br>From J.18i.3 | RT: 1.60 min, (Cond.-D1); Calcd for C$_{39}$H$_{40}$N$_7$O$_4$ [M + H]$^+$ 670.32; found: 670.24. |
| J.20h.2 | 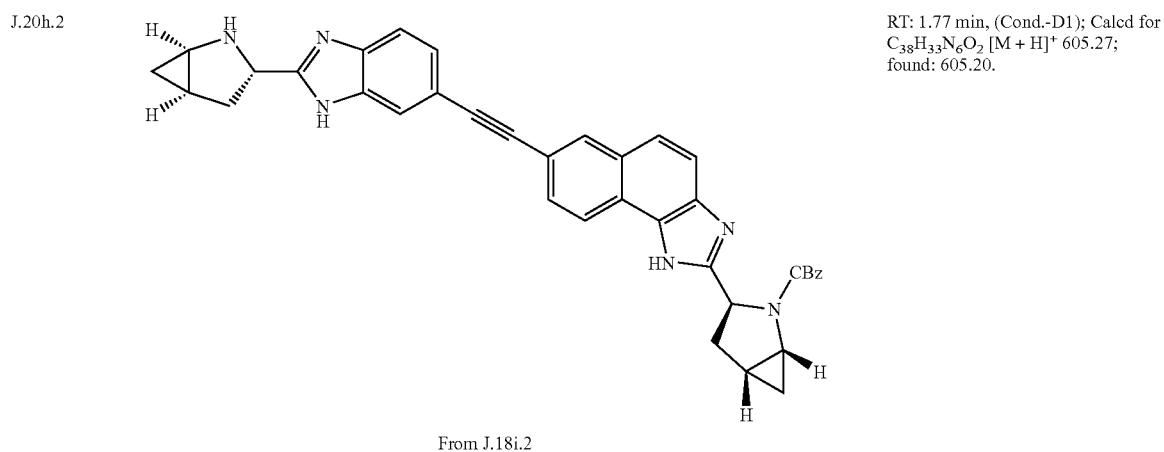<br>From J.18i.2 | RT: 1.77 min, (Cond.-D1); Calcd for C$_{38}$H$_{33}$N$_6$O$_2$ [M + H]$^+$ 605.27; found: 605.20. |
| J.20i | 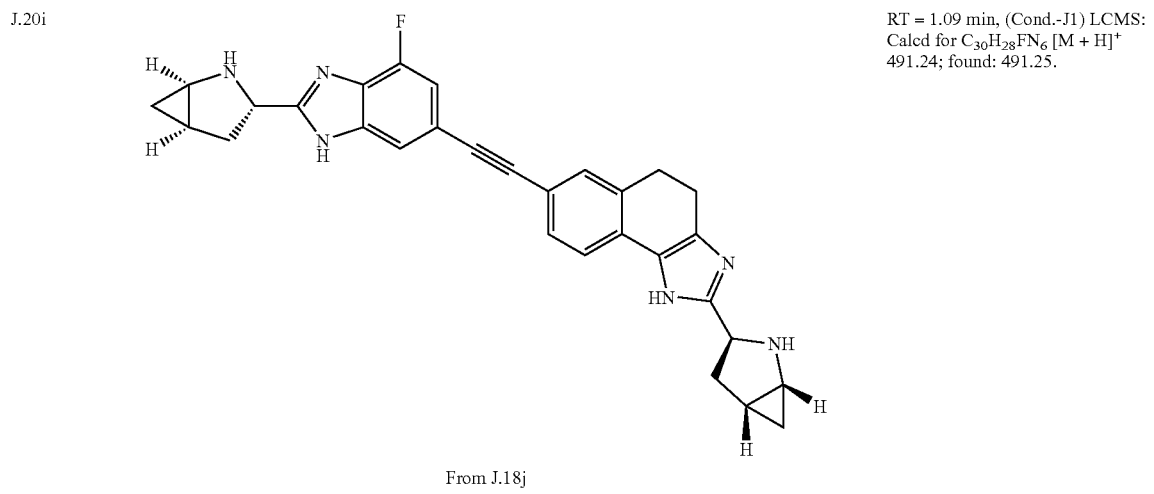<br>From J.18j | RT = 1.09 min, (Cond.-J1) LCMS: Calcd for C$_{30}$H$_{28}$FN$_6$ [M + H]$^+$ 491.24; found: 491.25. |

| | | |
|---|---|---|
| J.20j | 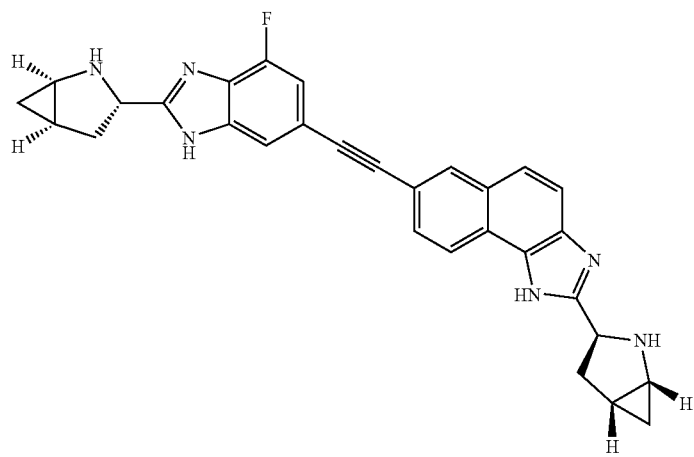 From J.18k | RT = 1.17 min, (Cond.-J1) LCMS: Calcd for $C_{30}H_{26}FN_6$ $[M + H]^+$ 489.22; found: 489.22. |
| J.20j.1 | 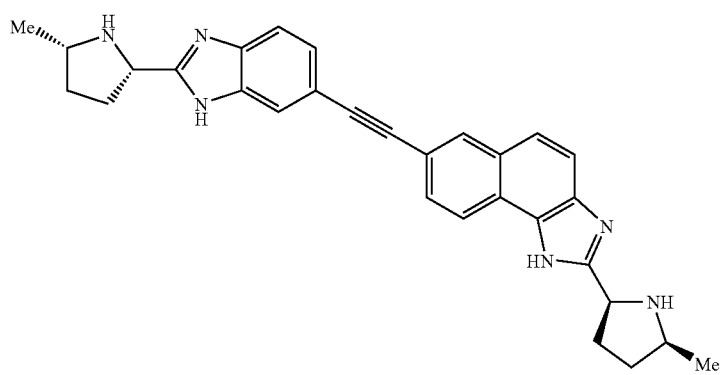 From J.18k.1 | RT = 2.73 min, (Cond.-J2) LCMS: Calcd for $C_{30}H_{31}N_6$ $[M + H]^+$ 475.26; found: 475.17. |
| J.20k | 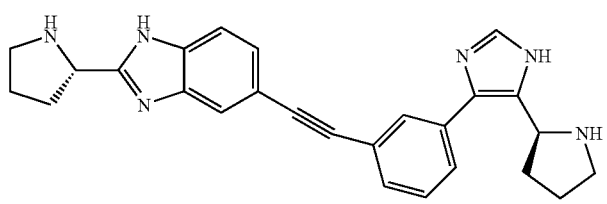 From J.18l | RT = 1.0 min (Cond.-J1) LCMS: Calcd for $C_{26}H_{27}N_6$ $[M + H]^+$ 423.23; found: 423.24. |
| J.20l | 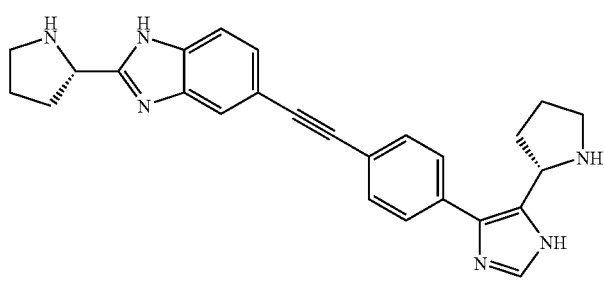 From J.18m | RT = 1.01 min (Cond.-J1) LCMS: Calcd for $C_{26}H_{27}N_6$ $[M + H]^+$ 423.23; found: 423.31. |

-continued
JB.7 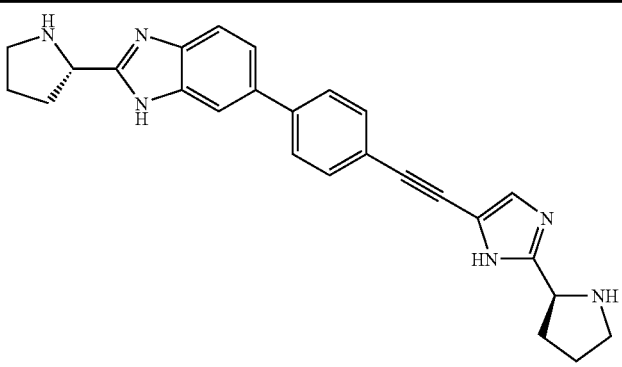
RT = 1.0 min (Cond.-JB.1) LCMS: Calcd for $C_{26}H_{27}N_6$ [M + H]$^+$ 423.23; found: 423.17.
From JB.6
Synthetic Route 13.
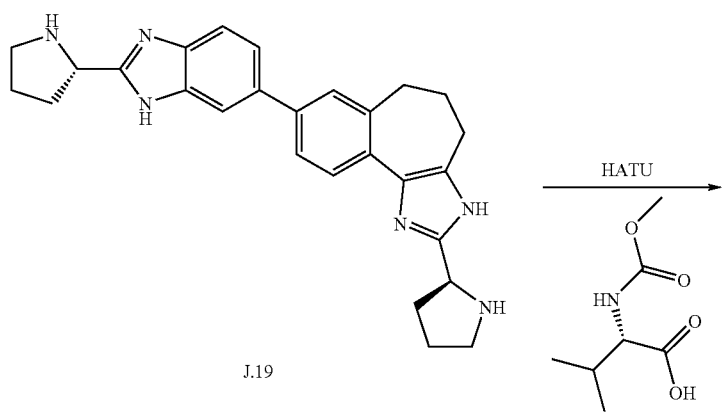
J.19
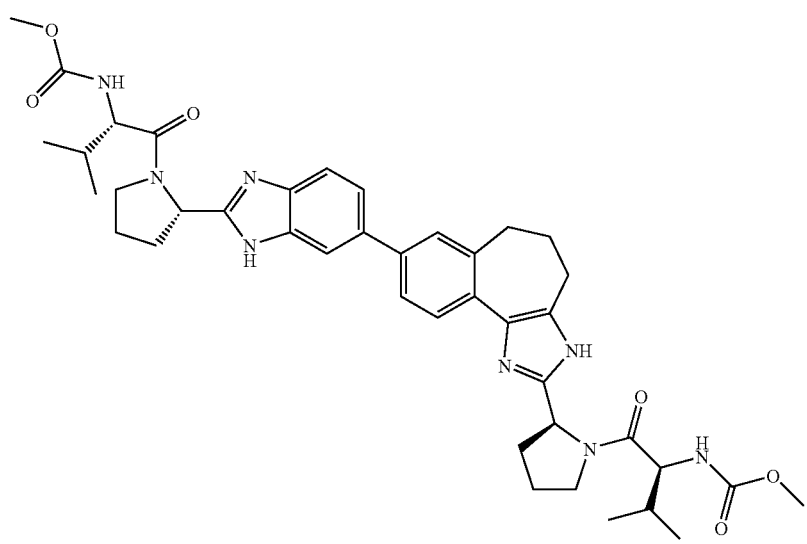
J.21

Examples J.21-JB.12

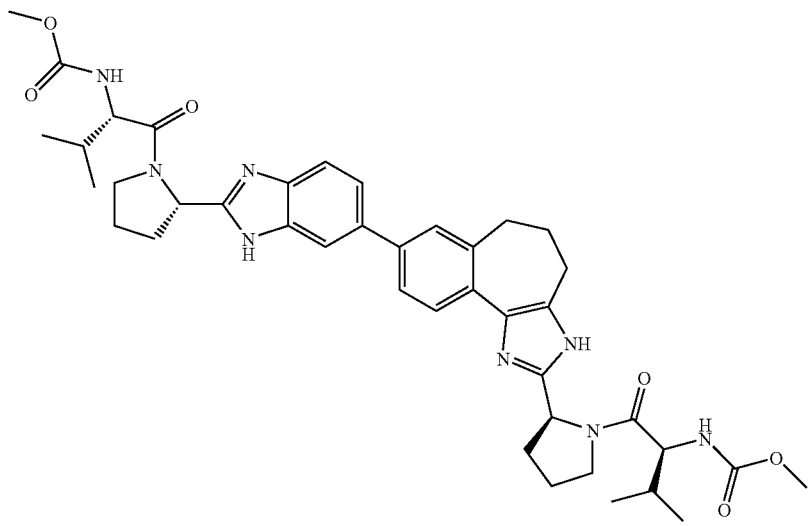

J.21

HATU (60 mg, 0.16 mmol) was added to a rapidly stirred solution of example J.19 (38.18 mg, 0.075 mmol), N-methoxycarbonyl-L-valine (26.2 mg, 0.15 mmol), and Hunig's base (0.095 mL, 0.54 mmol) in dimethylformamide (1.5 mL). The reaction mixture was stirred for 2 h and the solvent was removed under purge of nitrogen. The residue was diluted with methanol and subjected to prep. HPLC (Phenomenex LUNA C18 (30×100 mm); 5%-100% B over 40 min; Flow Rate=40 mL/min; Wavelength=220 nm; Solvent A=0.1% TFA in 10% methanol/90% water; Solvent B=0.1% TFA in 90% methanol/10% water) to give the bis TFA salt of J.21, 17.6 mg (24%). $^1$H NMR (500 MHz, DMSO-$d_6$) δ 7.91-7.84 (m, 1H), 7.72-7.57 (series m, 5H), 7.30-6.8 (m, 2H), 5.50-5.17 (series m, 4H), 4.20 (m, 1H), 4.10 (br. s, 1H), 3.34-3.25 (m, 6H), 3.17 (s, 6H), 3.14-2.90 (series m, 4H), 2.23-2.20 (m, 2H), 2.13-1.93 (m, 8H), 1.32-1.03 (m, 12H). LC (Cond.-D2): 1.8 min; LCMS: Anal. Calcd. for [M+H]$^+$ $C_{41}H_{53}N_8O_6$ 753.41; found: 753.55. HRMS: Anal. Calcd. for [M+H]$^+$ $C_{41}H_{53}N_8O_6$ 753.4088; found: 753.4108.

J.21a

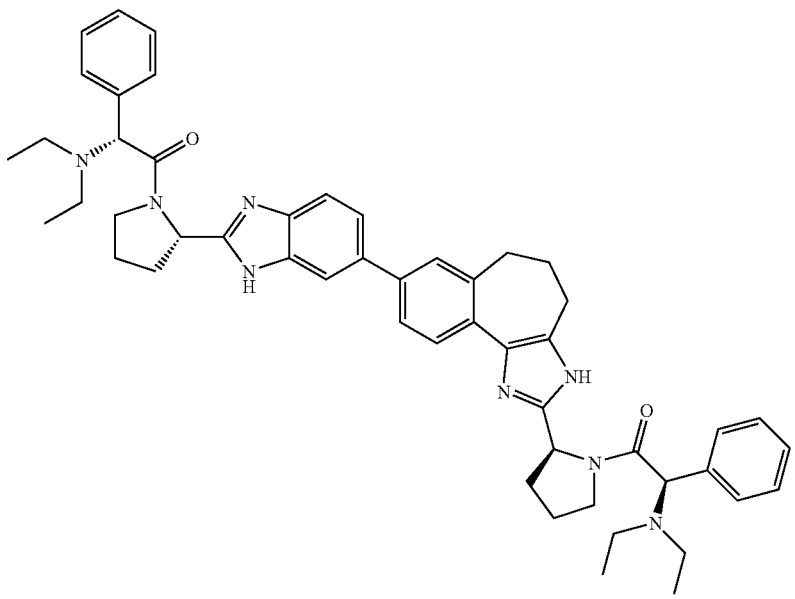

From J.19

RT = 2.1 min (Cond.-D2); LCMS: Anal. Calcd. for [M + H]$^+$ $C_{51}H_{61}N_8O_2$: 817.49; found: 817.63. HRMS: Anal. Calcd. for [M + H]$^+$ $C_{51}H_{61}N_8O_2$: 817.4917; found: 817.4927.

J.22 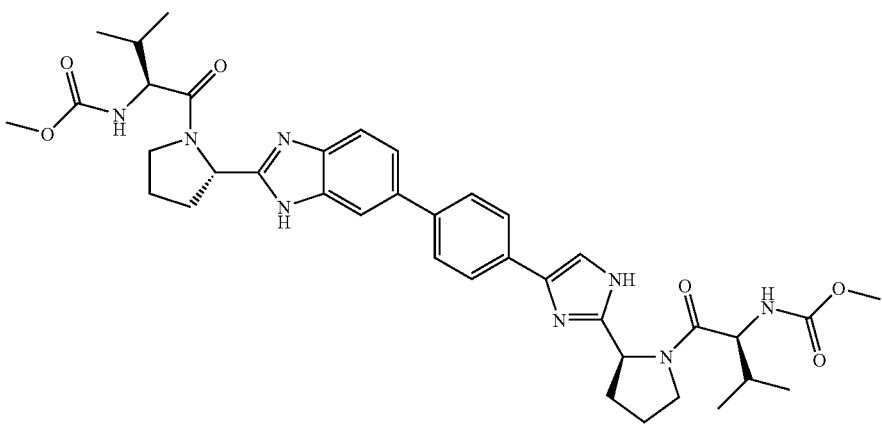
From J.19a
RT = 1.88 min (Cond.-D2) LCMS: Anal. Calcd. for [M + H]⁺ $C_{38}H_{49}N_8O_6$: 713.38; found: 713.31. HRMS: Anal. Calcd. for [M + H]⁺ $C_{38}H_{49}N_8O_6$: 713.3775; found: 713.3804.
J.22a 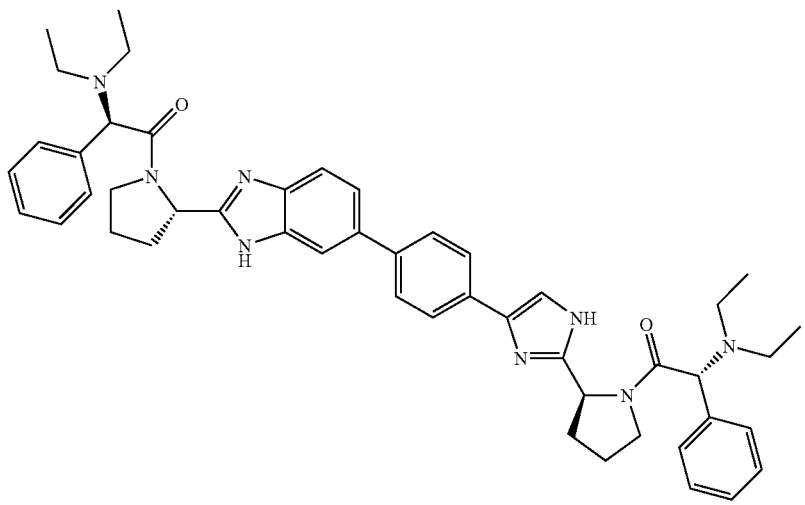
From J.19a
RT = 1.65 min (Cond.-D2) LCMS: Anal. Calcd. for [M + H]⁺ $C_{48}H_{56}N_8O_2$: 777.46; found: 777.48. HRMS: Anal. Calcd. for [M + H]⁺ $C_{48}H_{56}N_8O_2$: 777.4604; found: 777.4636.
J.22b 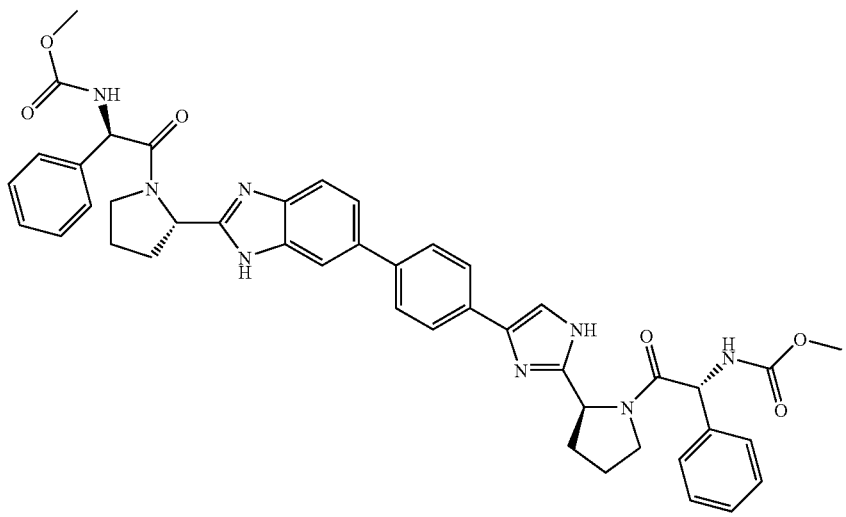
From J.19a
RT = 1.99 min (Cond.-D2); LCMS: Anal. Calcd. for [M + H]⁺ $C_{44}H_{45}N_8O_6$: 781.35; found: 781.37. HRMS: Anal. Calcd. for [M + H]⁺ $C_{44}H_{45}N_8O_6$: 781.3462; found: 781.3483.

| | | |
|---|---|---|
| J.23 | 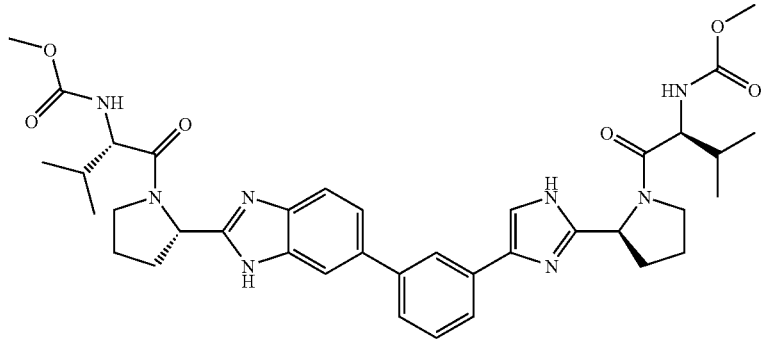<br>From J.19b | RT = 1.92 min (Cond.-D2); LCMS: Anal. Calcd. for [M + H]⁺ $C_{38}H_{49}N_8O_6$: 713.38; found: 713.40. HRMS: Anal. Calcd. for [M + H]⁺ $C_{38}H_{49}N_8O_6$: 713.3804; found: 713.3798. |
| J.23a | 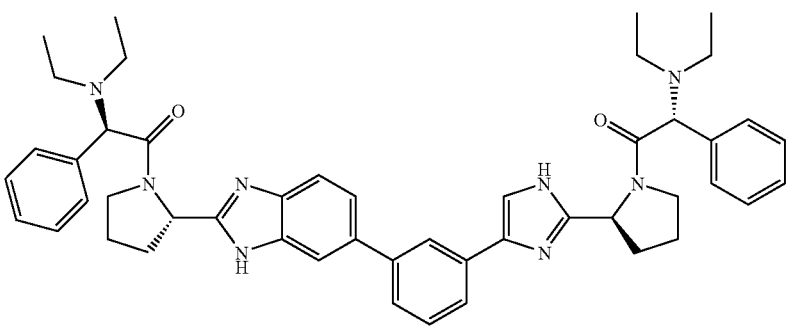<br>From J.19b | RT = 1.72 min (Cond.-D2); LCMS: Anal. Calcd. for [M + H]⁺ $C_{48}H_{56}N_8O_2$: 777.46; found: 777.48. HRMS: Anal. Calcd. for [M + H]⁺ $C_{48}H_{56}N_8O_2$: 777.4604; found: 777.4579. |
| J.23b | 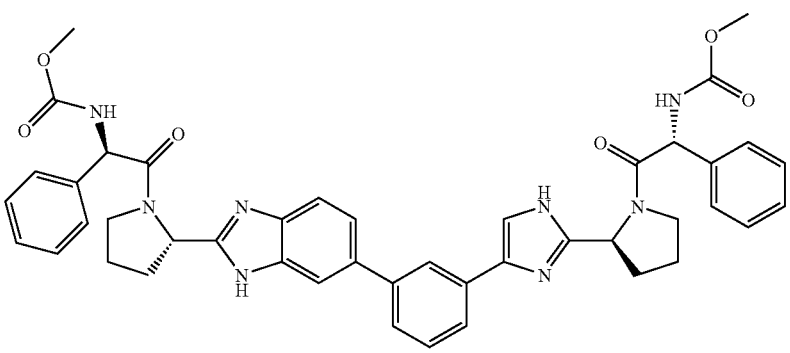<br>From J.19b | RT = 2.02 min (Cond.-D2); LCMS: Anal. Calcd. for [M + H]⁺ $C_{44}H_{45}N_8O_6$: 781.35; found: 781.37. HRMS: Anal. Calcd. for [M + H]⁺ $C_{44}H_{45}N_8O_6$: 781.3462; found: 781.3497. |

| | | |
|---|---|---|
| J.24 | 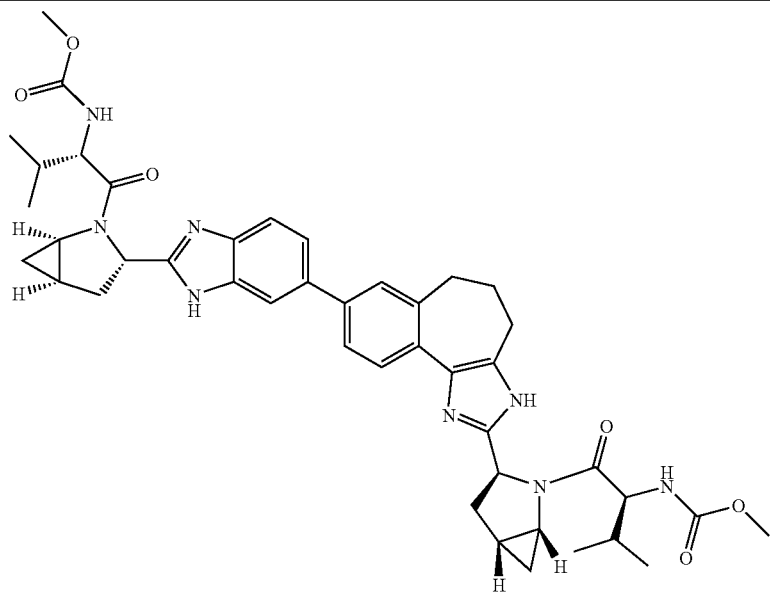
From J.19c | RT = 1.5 min (Cond.-J1); 87%, LCMS: Calcd for C$_{43}$H$_{53}$N$_8$O$_6$ (M + H)$^+$ 777.41; found: 777.49. HRMS: Calcd for C$_{43}$H$_{53}$N$_8$O$_6$ (M + H)$^+$ 777.4083; found: 777.4088. |
| J.25 | 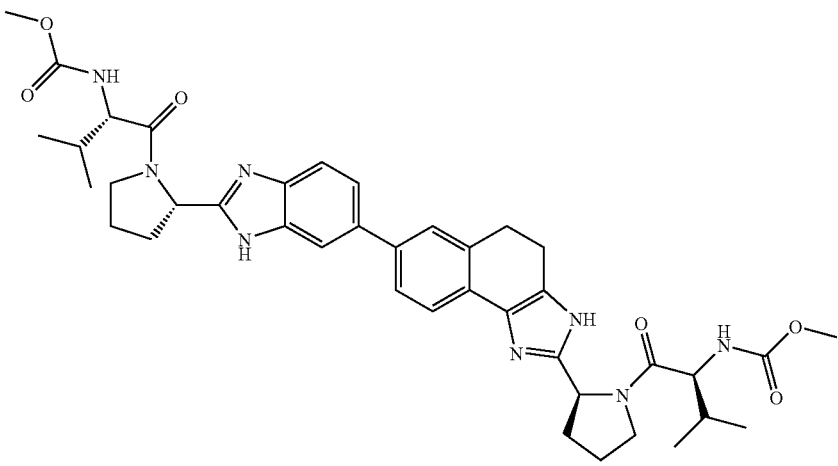
From J.19d | RT = 1.83 min (Cond.-D2); LCMS: 95%, Calcd for C$_{40}$H$_{51}$N$_8$O$_6$ (M + H)$^+$ 739.39; found: 739.59. HRMS: Calcd for C$_{40}$H$_{51}$N$_8$6 (M + H)$^+$ 739.3926; found: 739.3916. |
| J.25.a | 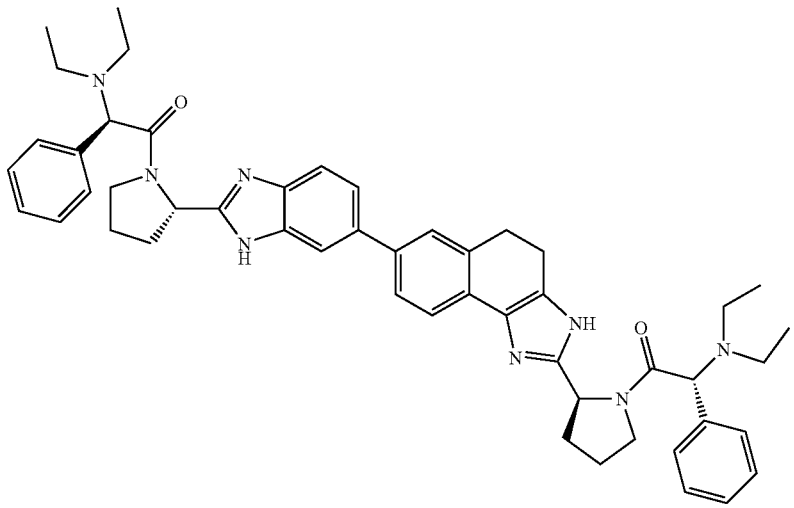
From J.19d | RT = 1.58 min (Cond.-D2); LCMS: Calcd for C$_{50}$H$_{59}$N$_8$O$_2$ (M + H)$^+$ 803.47; found: 803.65. HRMS: Calcd for C$_{50}$H$_{59}$N$_8$O$_2$ (M + H)$^+$ 803.4755; found: 803.4749. |

| J.26 | 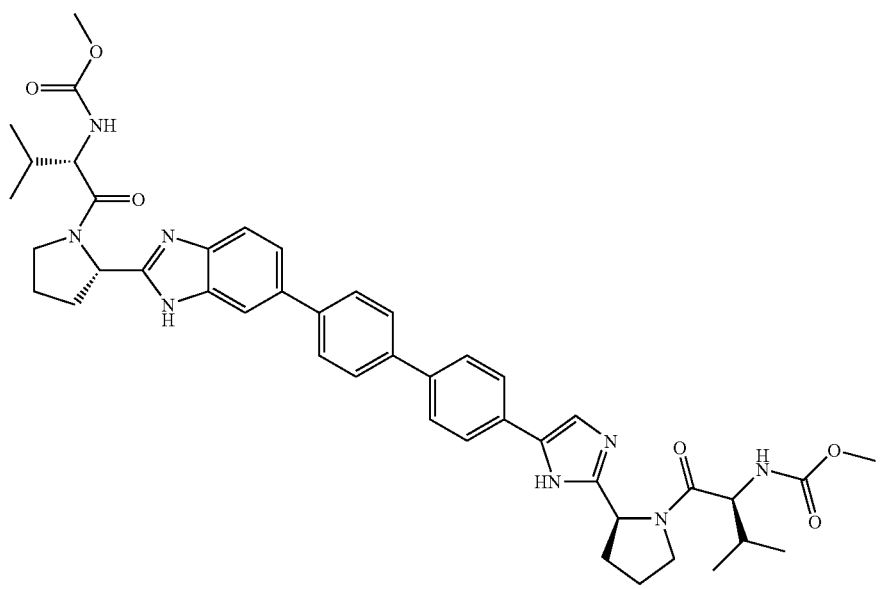<br>From J.19e | RT = 1.51 min (Cond.-J1);<br>LCMS Calcd for<br>$C_{44}H_{53}N_8O_6$<br>$(M + H)^+$ 789.41;<br>found: 789.55. |
|---|---|---|
| J.27 | 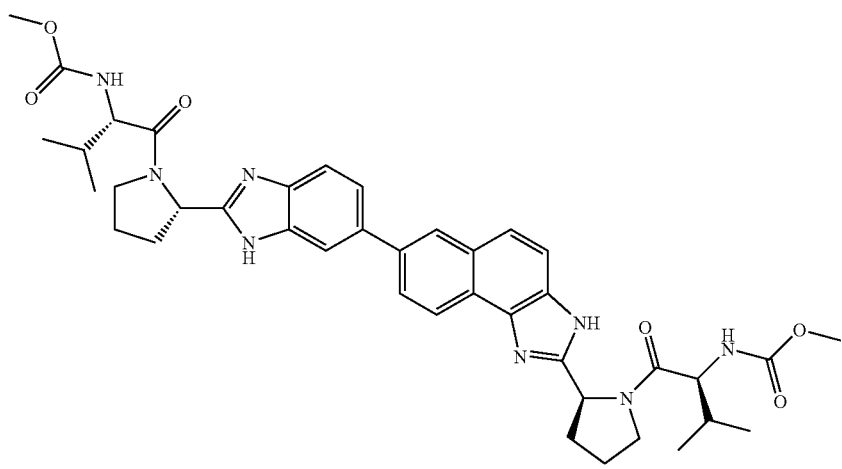<br>From J.19f | RT = 1.94 min (Cond.-D2);<br>LCMS: 95%,<br>Calcd for<br>$C_{40}H_{49}N_8O_6$<br>$(M + H)^+$ 737.38;<br>found: 737.56.<br>HRMS: Calcd for<br>$C_{40}H_{49}N_8O_6$<br>$(M + H)^+$<br>737.3770; found:<br>737.3756. |

J.27a 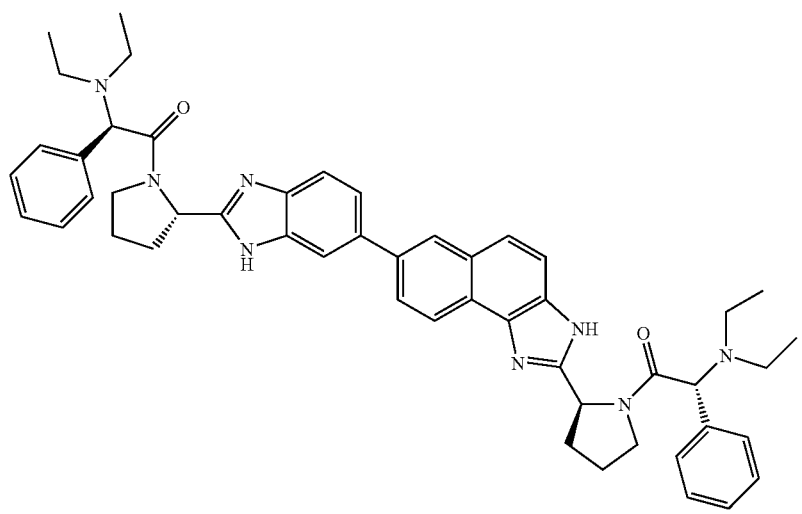
From J.19f
RT = 1.67 min (Cond.-D2); LCMS: Calcd for $C_{50}H_{57}N_8O_2$ $(M + H)^+$ 801.46; found: 801.68. HRMS: Calcd for $C_{50}H_{57}N_8O_2$ $(M + H)^+$ 801.4599; found: 801.4592.
J.27b 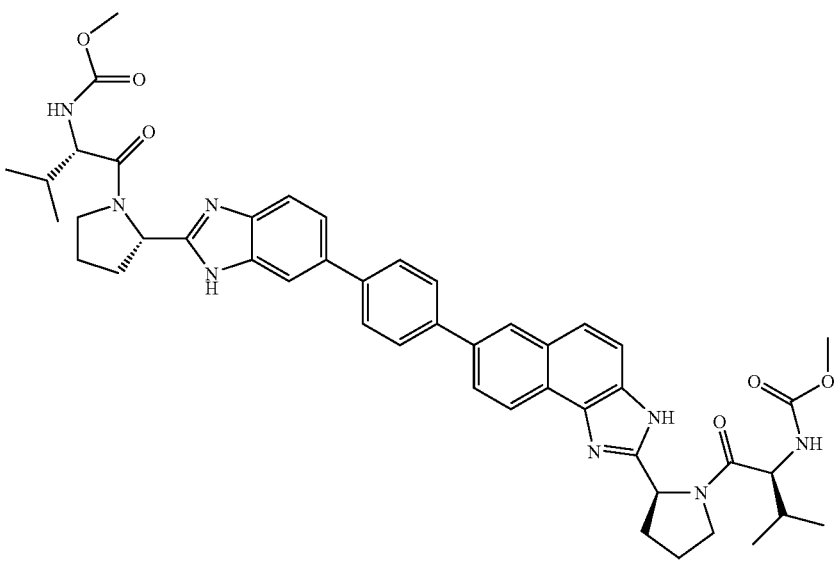
From J.19f.1
RT = 1.94 min (Cond.-D1); LCMS: Calcd for $C_{46}H_{53}N_8O_6$ $(M + H)^+$ 813.41; found: 813.46.

-continued
J.27c
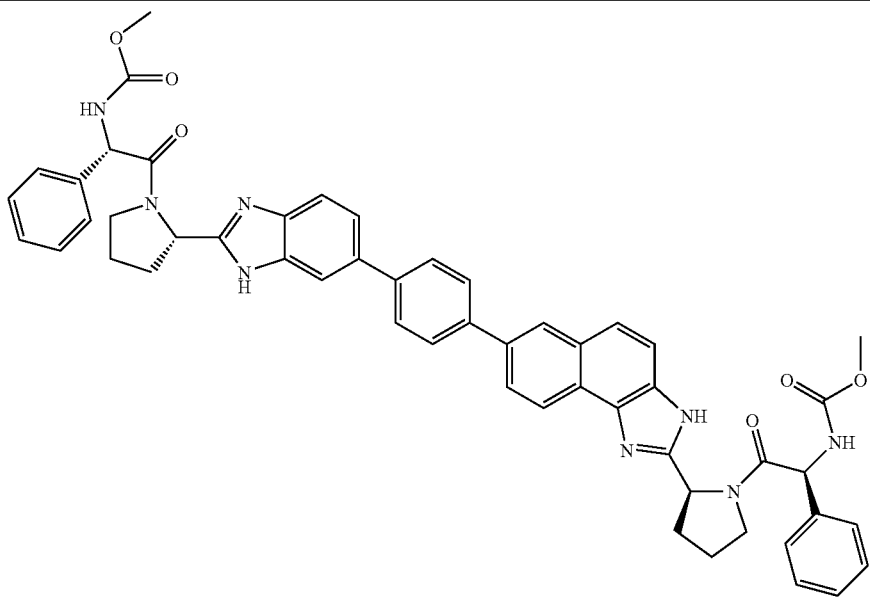
From J.19f.1
RT = 2.01 min (Cond.-D1);
LCMS: Calcd for C$_{52}$H$_{49}$N$_8$O$_6$ (M + H)$^+$ 881.38; found: 881.37.
J.28
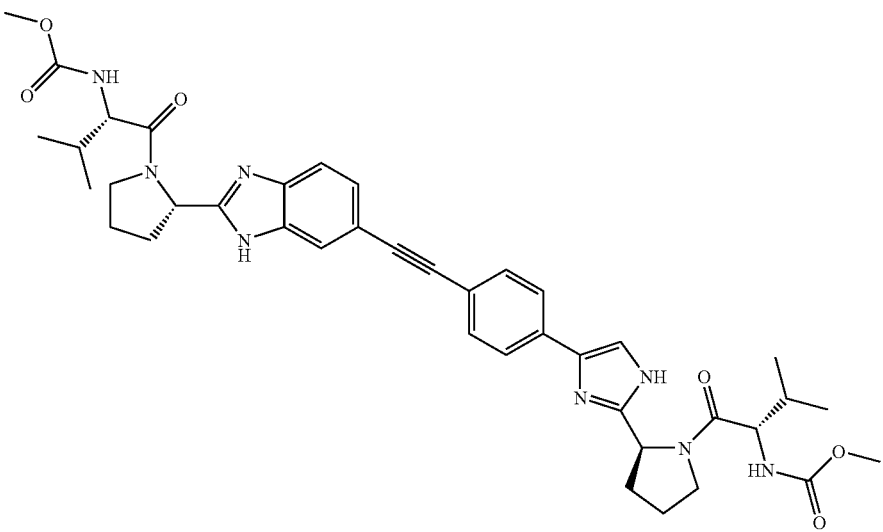
From J.20
RT = 1.46 min (Cond.-J1);
LCMS Calcd for C$_{40}$H$_{49}$N$_8$O$_6$ (M + H)$^+$ 737.38; found: 737.42.
HRMS: Calcd for C$_{40}$H$_{49}$N$_8$O$_6$ (M + H)$^+$ 737.3770; found: 737.3774.

| | | |
|---|---|---|
| J.28a | 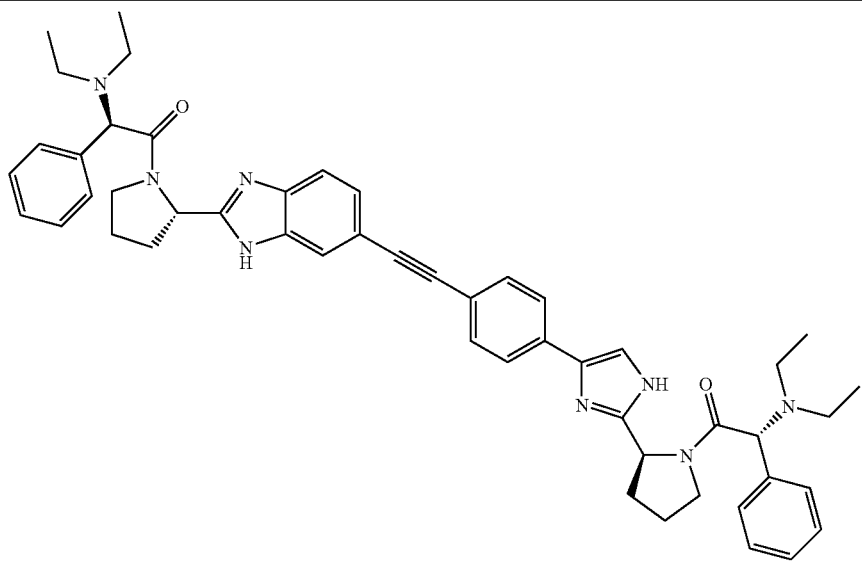<br>From J.20 | RT = 1.30 min (Cond.-J1);<br>LCMS Calcd for C$_{50}$H$_{57}$N$_8$O$_2$ (M + H)$^+$ 801.46; found: 801.62.<br>HRMS: Calcd for C$_{50}$H$_{57}$N$_8$O$_2$ (M + H)$^+$ 801.4599; found: 801.4585. |
| J.28a.1 | 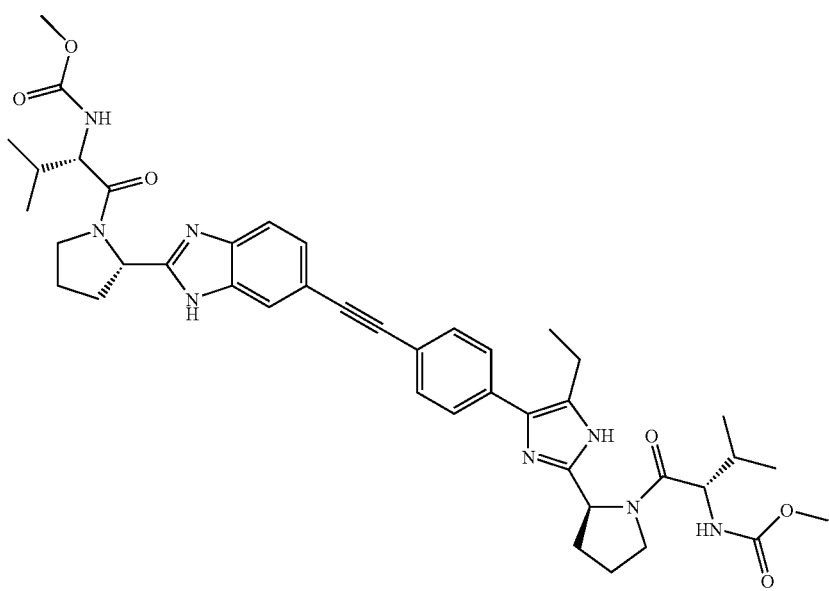<br>From 20.1 | RT = 1.29 min (Cond.-J1);<br>LCMS Calcd for C$_{42}$H$_{53}$N$_8$O$_6$ (M + H)$^+$ 765.41; found: 765.49. |

| J.28a.2 | 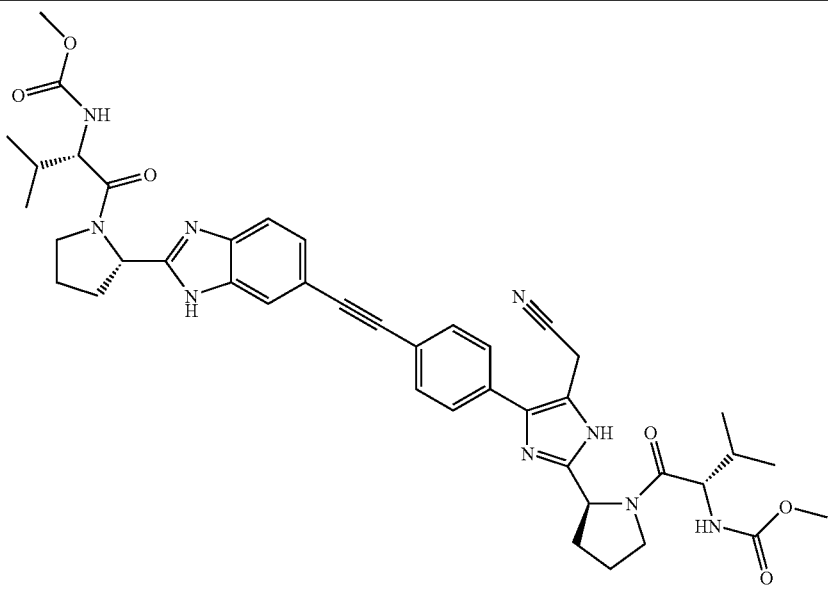 From 20.2 | RT = 1.22 min (Cond.-J1); LCMS Calcd for C$_{42}$H$_{50}$N$_9$O$_6$ (M + H)$^+$ 776.39; found: 776.42. |
|---|---|---|
| J.28b | 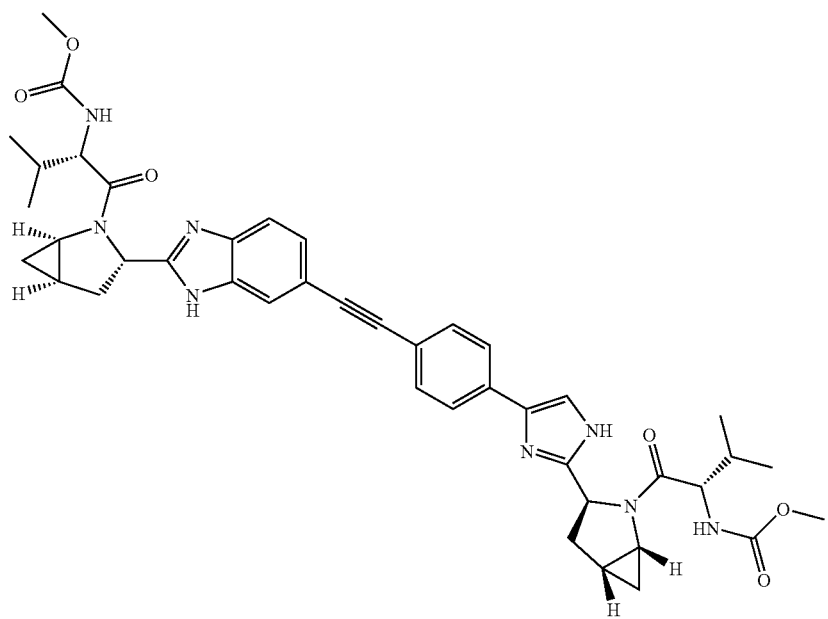 From J.20a | RT = 1.25 min (Cond.-J1); LCMS Calcd for C$_{42}$H$_{49}$N$_8$O$_6$ (M + H)$^+$ 761.38; found: 761.49. |

J.28c
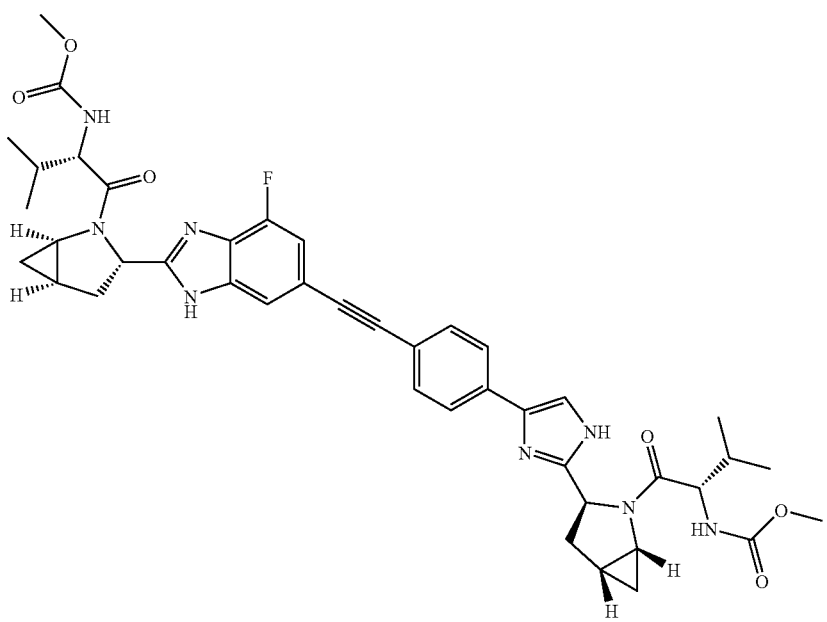
From J.20b
RT = 1.44 min
(Cond.-J1);
LCMS Calcd for
$C_{42}H_{48}FN_8O_6$
$(M + H)^+$ 779.37;
found: 779.45.
J.28d
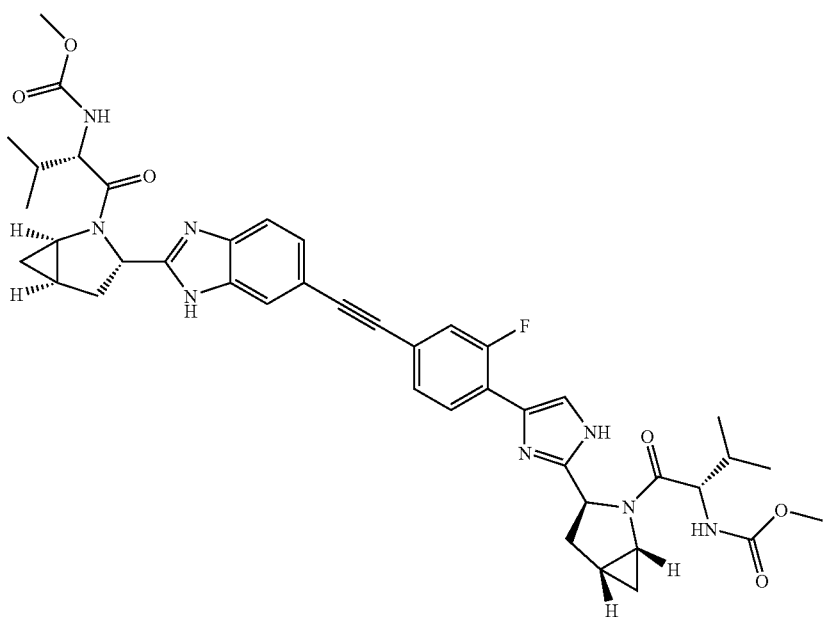
J.20c
RT = 1.30 min
(Cond.-J1);
LCMS Calcd for
$C_{42}H_{48}FN_8O_6$
$(M + H)^+$ 779.37;
found: 779.45.

-continued
| | | |
|---|---|---|
| J.28e | 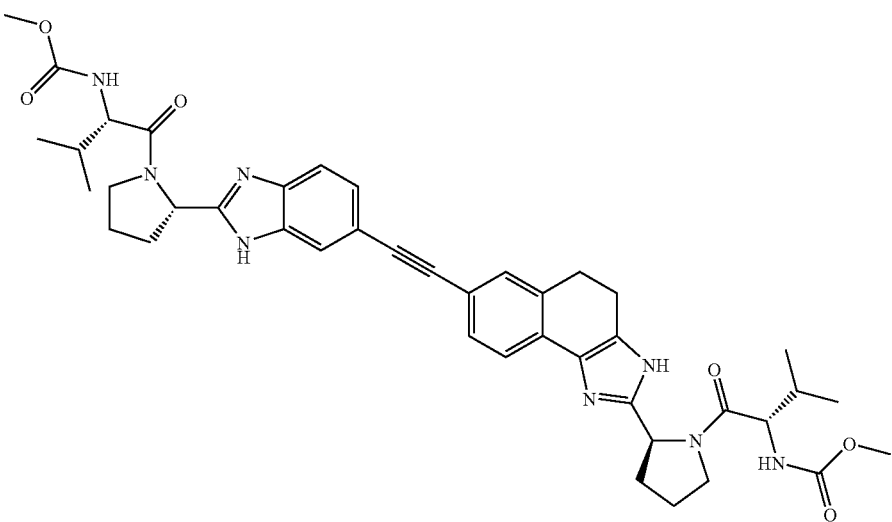 From J.20d | RT = 2.02 min (Cond.-D2); 95%, Calcd for $C_{42}H_{51}N_8O_6$ $(M + H)^+$ 763.39; found: 763.59. HRMS: Calcd for $C_{42}H_{51}N_8O_6$ $(M + H)^+$ 763.3926; found: 763.3918. |
| J.28e.1 | 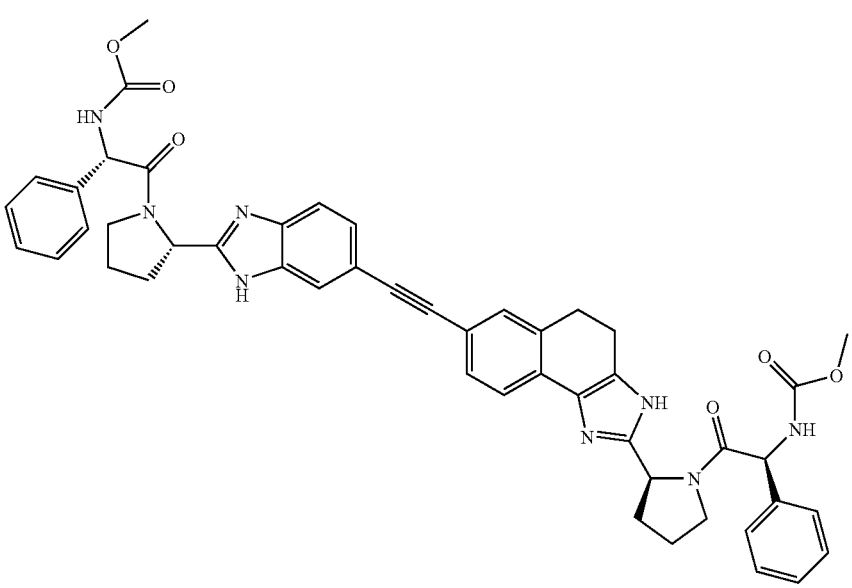 From J.20d | RT = 1.97 min (Cond.-D1); LCMS: Calcd for $C_{48}H_{47}N_8O_6$ $(M + H)^+$ 831.43; found: 831.36. |

J.28f
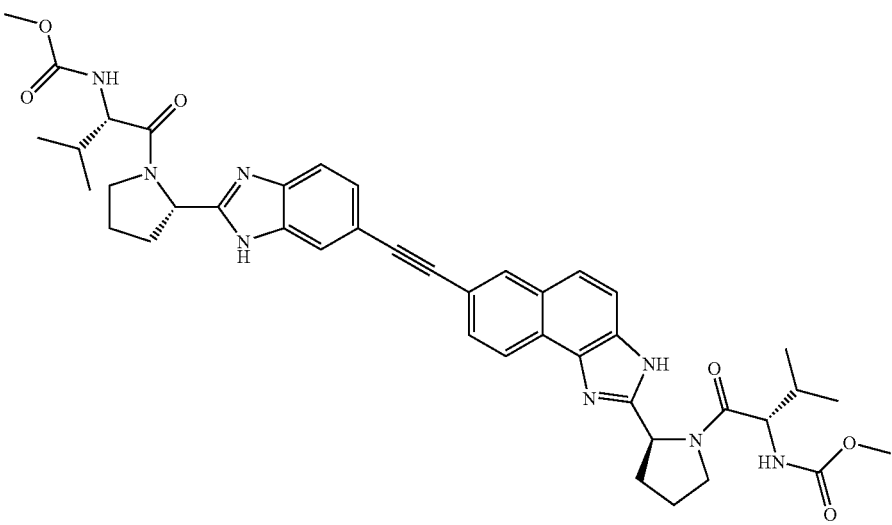
From J.20e
RT = 2.10 min (Cond.-D2); 95%, Calcd for $C_{42}H_{49}N_8O_6$ $(M + H)^+$ 761.38; found: 761.55. HRMS: Calcd for $C_{42}H_{49}N_8O_6$ $(M + H)^+$ 761.3770; found: 761.3765.
J.28f.1
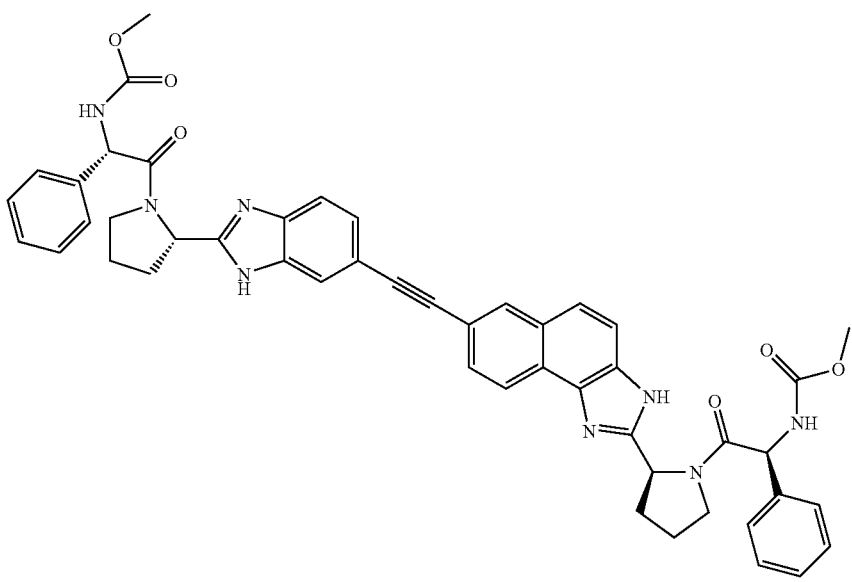
From J.20e
RT = 1.95 min (Cond.-D1); LCMS: Calcd for $C_{48}H_{45}N_8O_6$ $(M + H)^+$ 829.35; found: 829.45.

-continued
J.28g
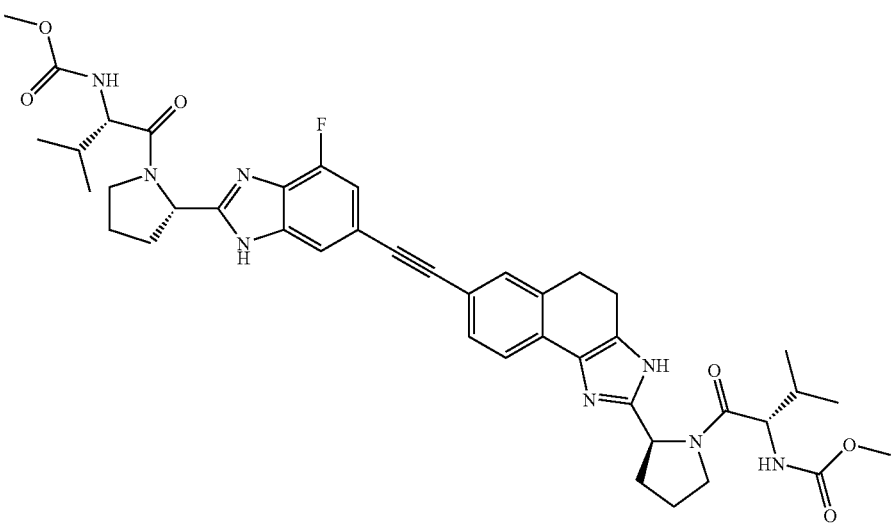
From J.20f
RT = 1.46 min (Cond.-J1); LCMS Calcd for $C_{42}H_{50}FN_8O_6$ $(M + H)^+$ 781.39; found: 781.49.
J.28h
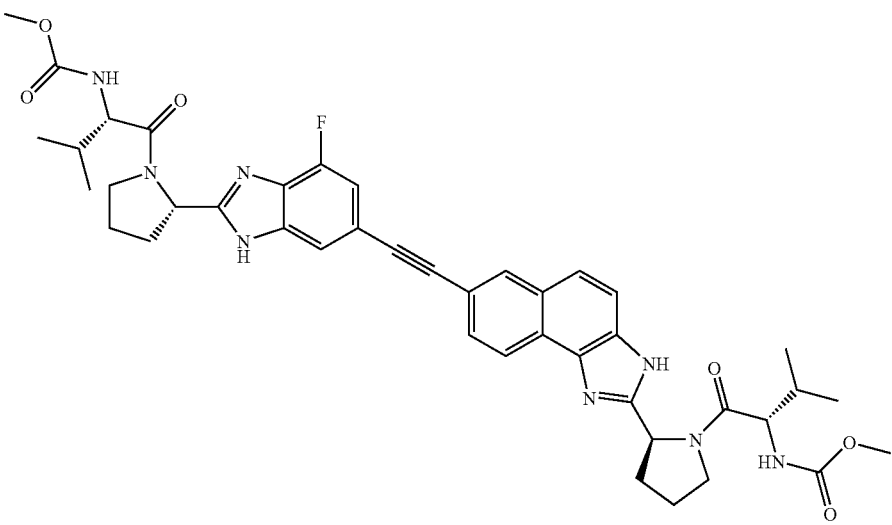
From J.20g
RT: 1.52 min, (Cond.-J1); Calcd for $C_{42}H_{48}FN_8O_6$ $[M + H]^+$ 779.37; found: 779.52.

-continued
| J.28h.1 | 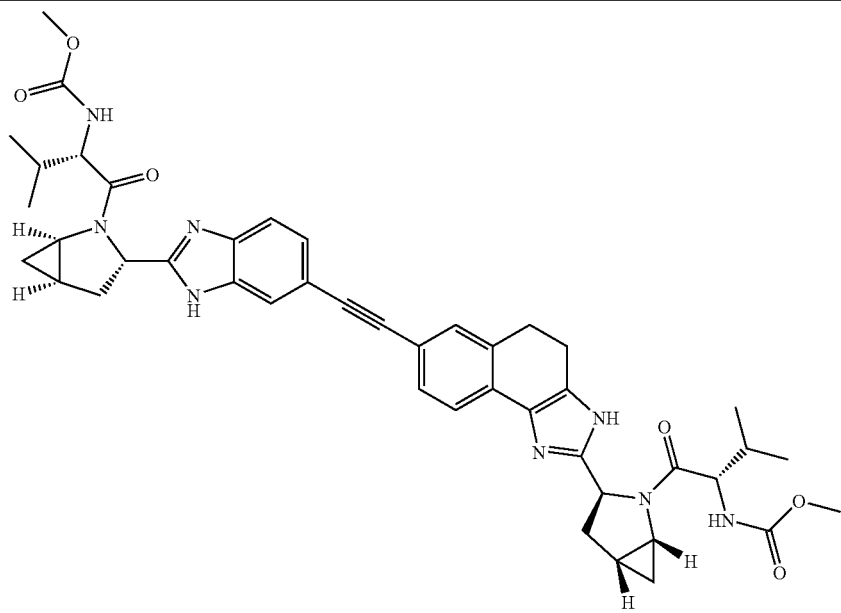 | RT = 1.83 min (Cond.-D1); LCMS: Calcd for $C_{44}H_{51}N_8O_6$ $(M + H)^+$ 787.23; found: 787.40. |
From J.20g.1
| J.28h.2 | 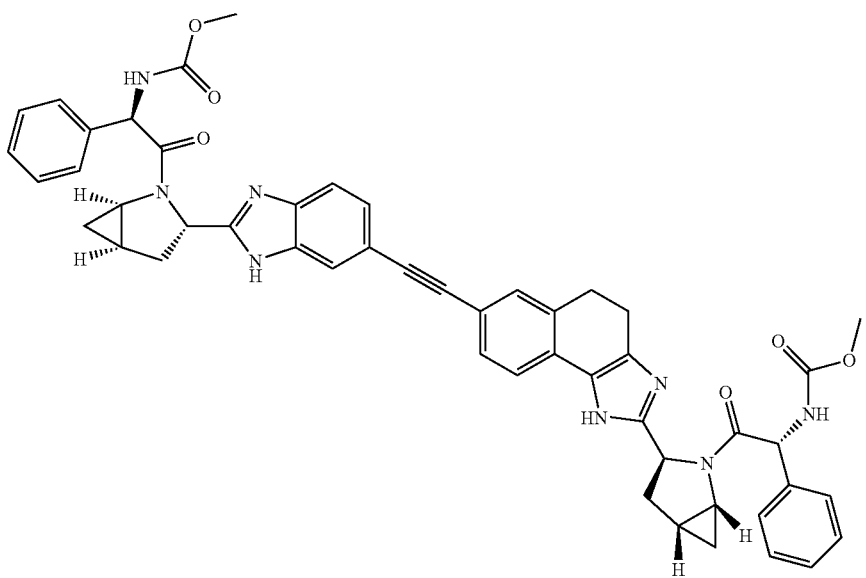 | RT = 1.92 min (Cond.-D1); LCMS: Calcd for $C_{50}H_{47}N_8O_6$ $(M + H)^+$ 855.36; found: 855.21. |
From J.20g.1

J.28i
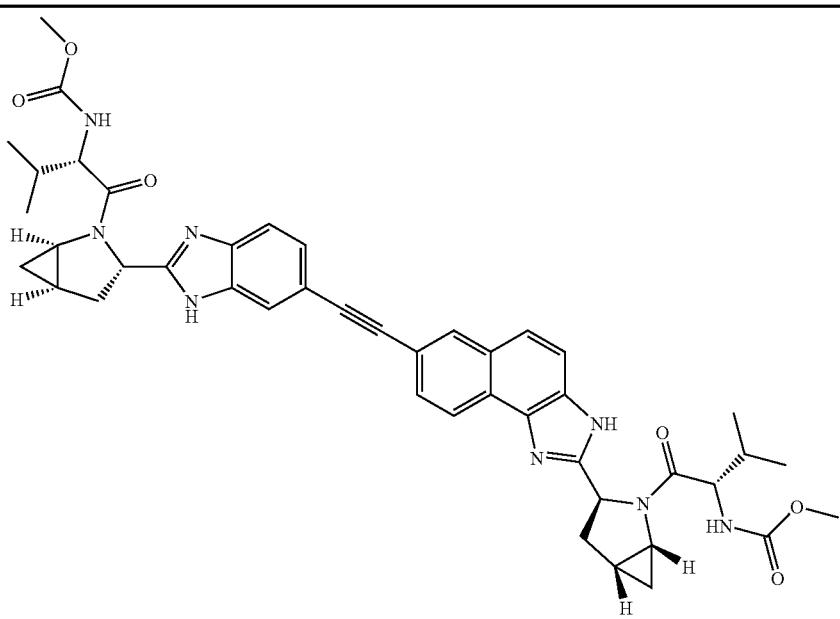
From J.20h
RT: 1.34 min, (Cond.-J1); Calcd for $C_{44}H_{49}N_8O_6$ $[M + H]^+$ 785.38; found: 785.55.
J.28i.1
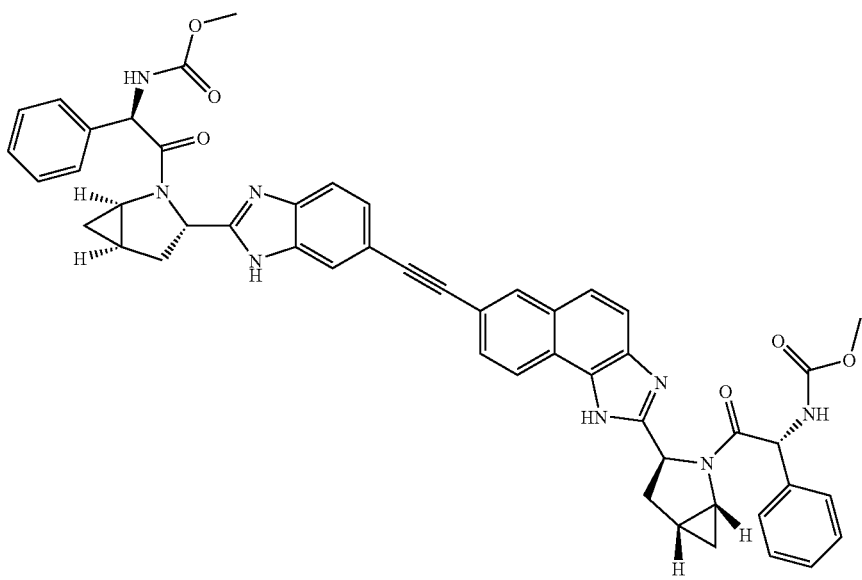
From J.20h
RT = 2.01 min (Cond.-D1); LCMS: Calcd for $C_{50}H_{45}N_8O_6$ $(M + H)^+$ 853.35; found: 853.25.

| | | |
|---|---|---|
| J.28i.2 | 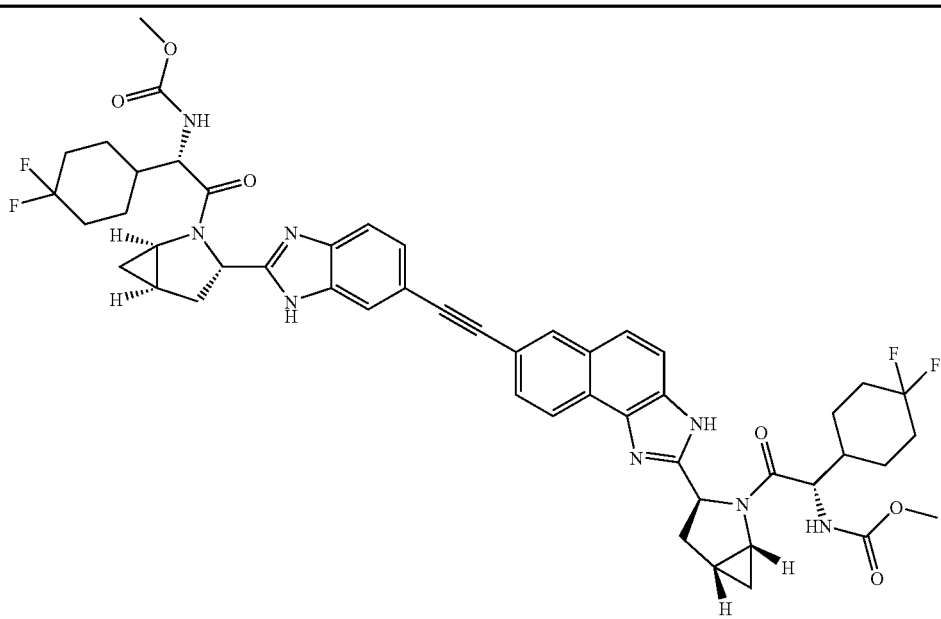<br>From J.20h | RT = 2.14 min (Cond.-D1); LCMS: Calcd for $C_{50}H_{55}F_2N_8O_6$ $(M + H)^+$ 937.40; found: 937.46. |
| J.28i.3 | 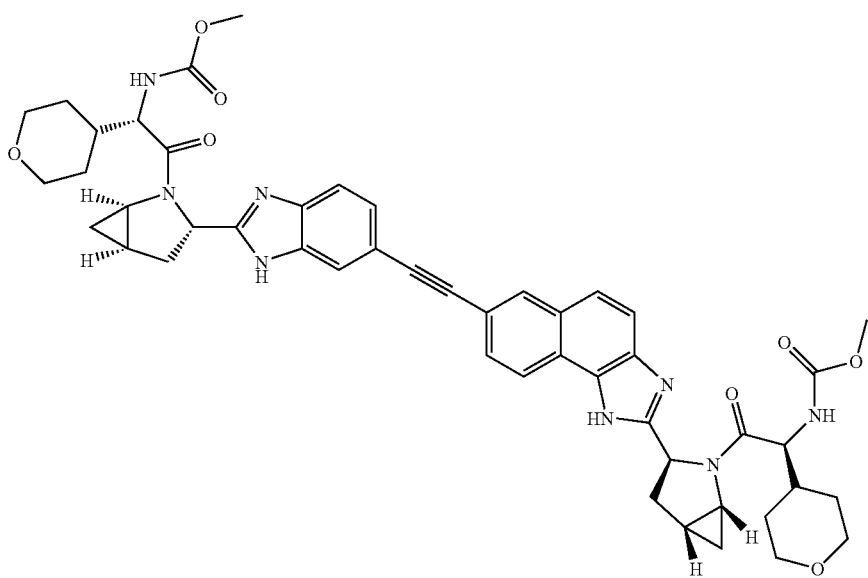<br>From J.20h | RT = 2.83 min (Cond.-D1); LCMS: Calcd for $C_{48}H_{53}N_8O_8$ $(M + H)^+$ 869.40; found: 869.35. |

| J.28i.4 | 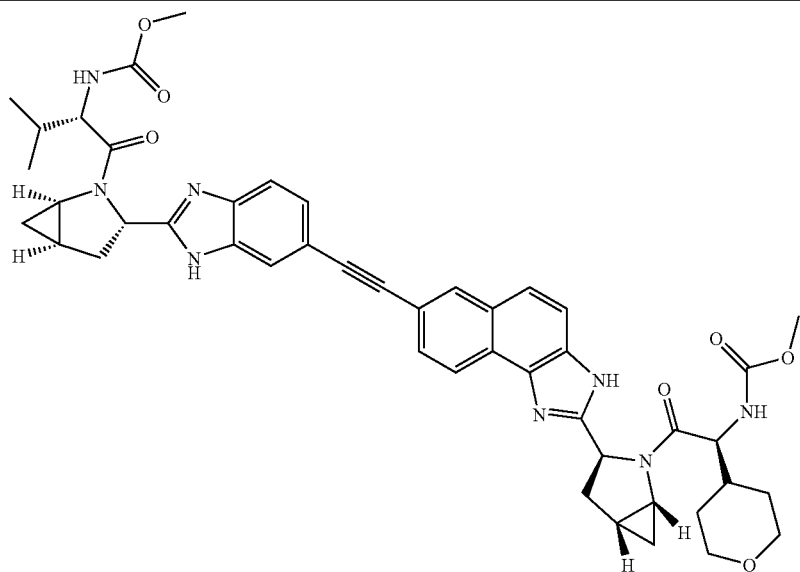 From J.20h.1 | RT = 1.81 min (Cond.-D1); LCMS: Calcd for $C_{46}H_{51}N_8O_7$ $(M + H)^+$ 827.39; found: 827.26. |
| J.28j | 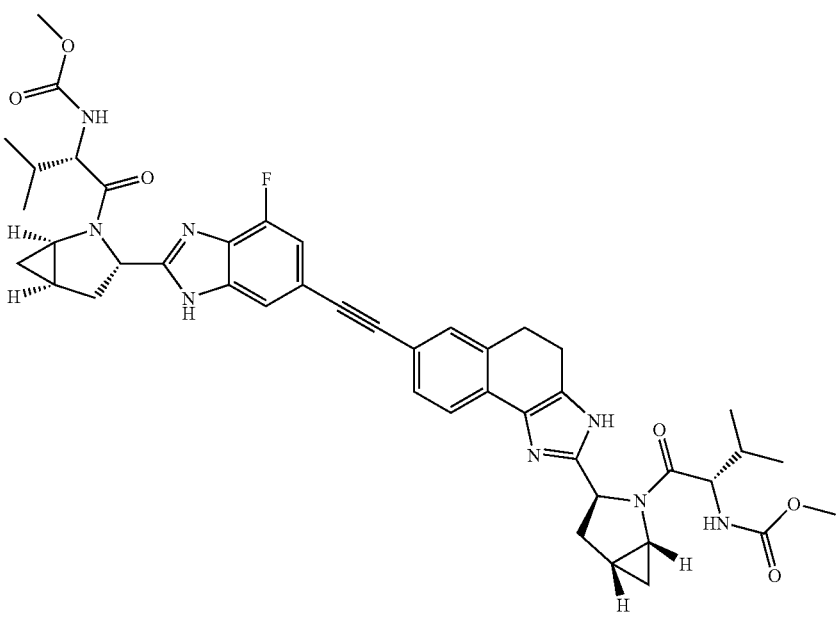 From J.20i | RT: 1.49 min, (Cond.-J1); Calcd for $C_{44}H_{50}FN_8O_6$ $[M + H]^+$ 805.39; found: 805.55. |

| J.28k | 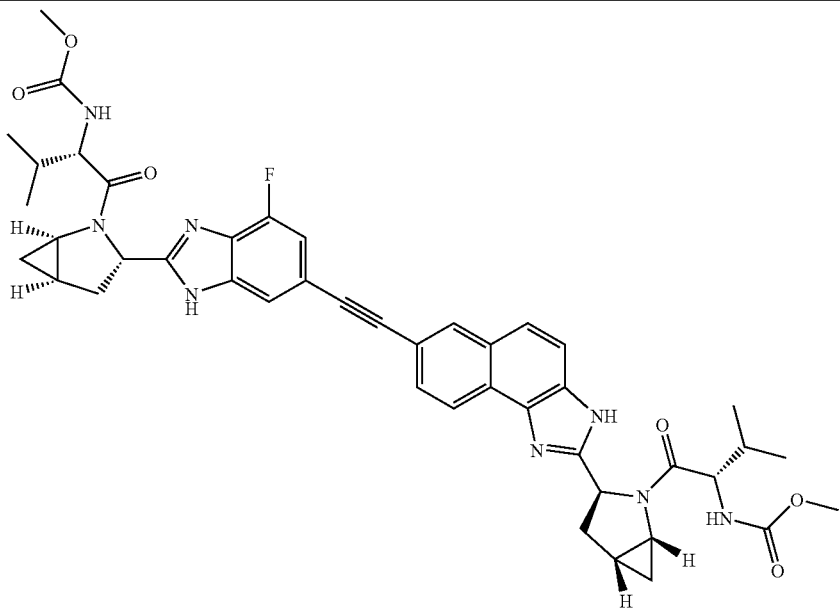
From J.20j | RT: 1.54 min, (Cond.-J1); Calcd for C₄₄H₄₈FN₈O₆ [M + H]⁺ 803.37; found: 803.58. |
| J.28k.1 | 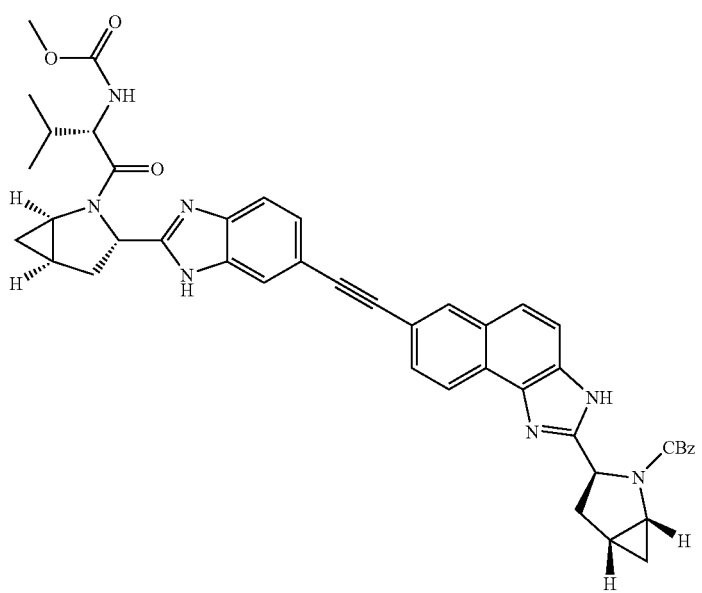
From J.20h.2 | RT: 2.01 min, (Cond.-D1); Calcd for C₄₅H₄₄N₇O₅ [M + H]⁺ 762.34; found: 762.16. |

| | | |
|---|---|---|
| J.28l | 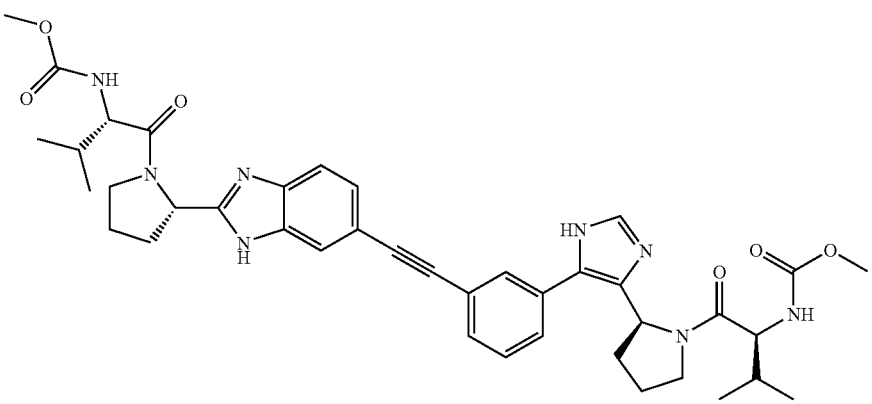<br>From J.20k | RT = 1.46 min (Cond.-J1); LCMS Calcd for $C_{40}H_{49}N_8O_6$ $(M + H)^+$ 737.38; found: 737.56. HRMS: Calcd for $C_{40}H_{49}N_8O_6$ $(M + H)^+$ 737.3770; found: 737.3760. |
| J.28m | 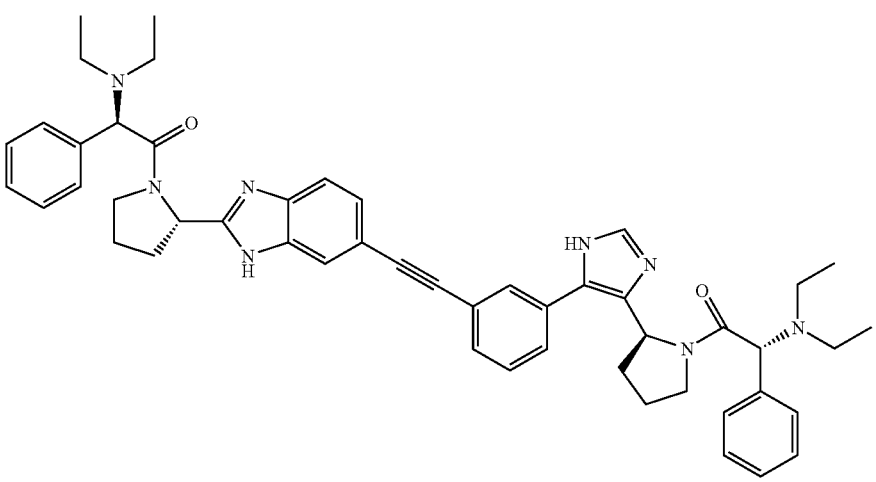<br>From J.20k | RT = 1.36 min (Cond.-J1); LCMS Calcd for $C_{50}H_{57}N_8O_2$ $(M + H)^+$ 801.46; found: 801.62. HRMS: Calcd for $C_{50}H_{57}N_8O_2$ $(M + H)^+$ 801.4599; found: 801.4597. |
| J.28n | 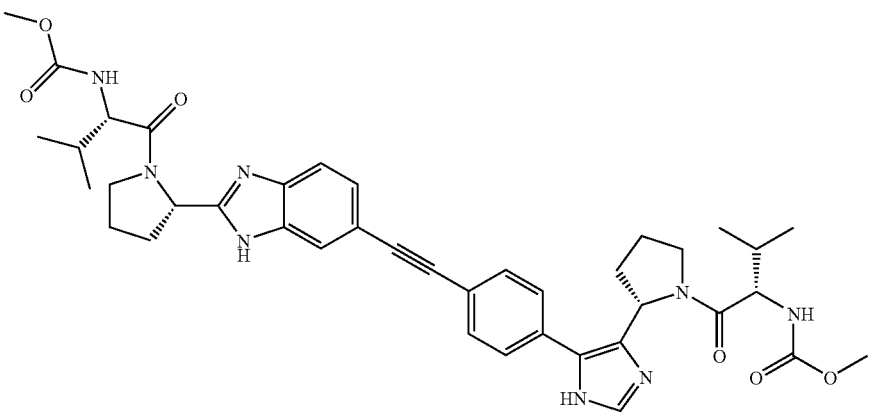<br>From J.20l | RT = 1.43 min (Cond.-J1); LCMS Calcd for $C_{40}H_{49}N_8O_6$ $(M + H)^+$ 737.38; found: not apparent. HRMS: Calcd for $C_{40}H_{49}N_8O_6$ $(M + H)^+$ 737.3770; found: 737.3759. |

J.28o
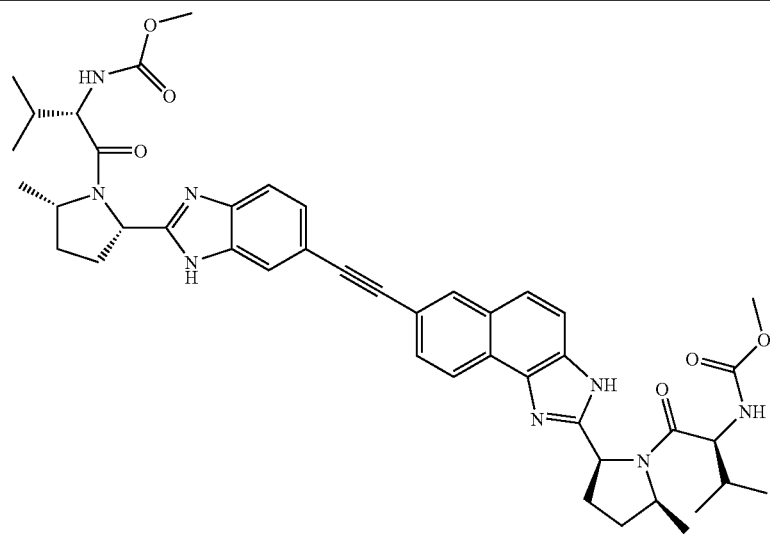
From J.20j.1
RT: 1.88 min, (Cond.-J2); Calcd for $C_{44}H_{53}N_8O_6$ [M + H]$^+$ 789.41; found: 789.36.
J.28p
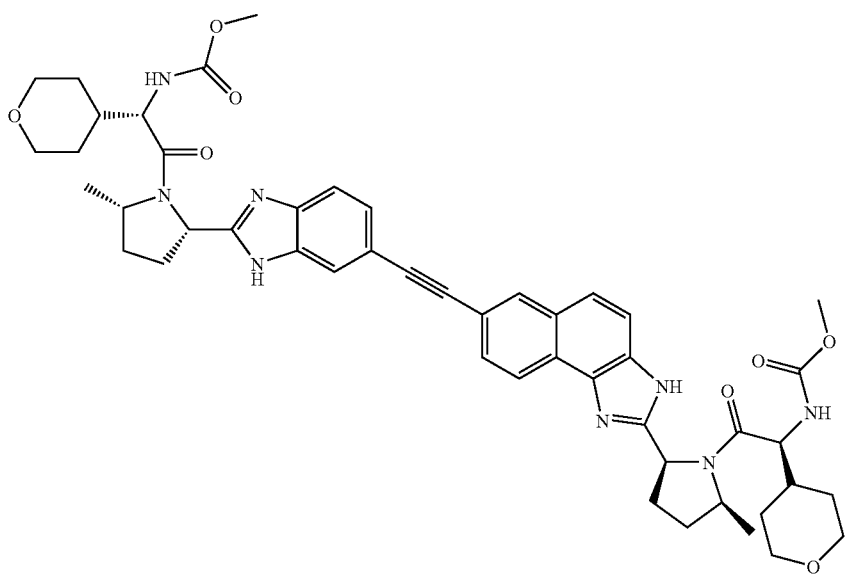
From J.20j.1
RT: 1.76 min, (Cond.-J2); Calcd for $C_{48}H_{57}N_8O_8$ [M + H]$^+$ 873.43; found: 873.43.
JB.8
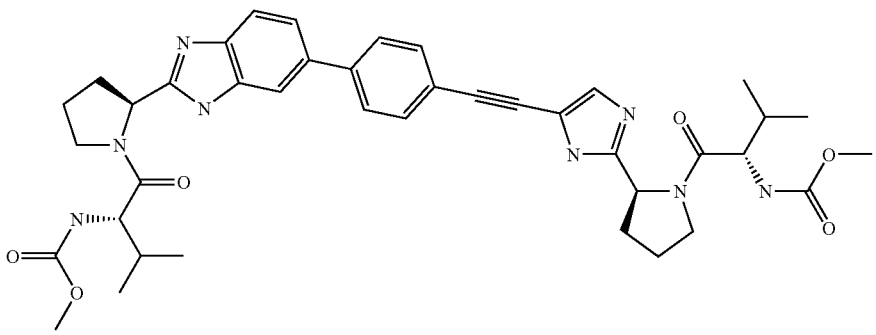
From JB.7
RT: 1.17 min, (Cond.-JB.1); Calcd for $C_{40}H_{49}N_8O_6$ [M + H]$^+$ 737.38; found: 737.31.

| | | |
|---|---|---|
| JB.8.1 | 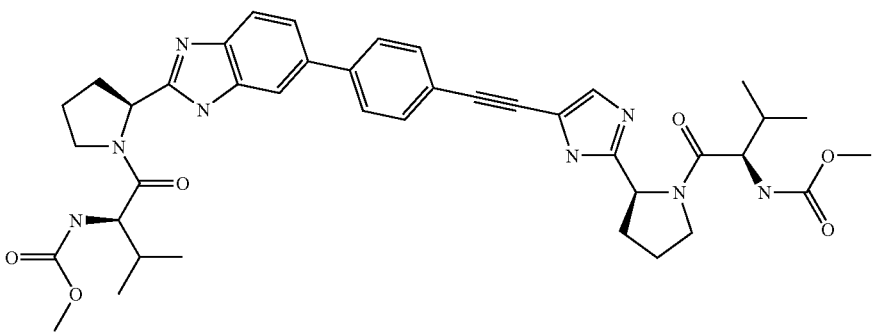<br>From JB.7 | RT: 1.23 min, (Cond.-JB.1); Calcd for $C_{40}H_{49}N_8O_6$ [M + H]$^+$ 737.38; found: 737.33. |
| JB.9 | 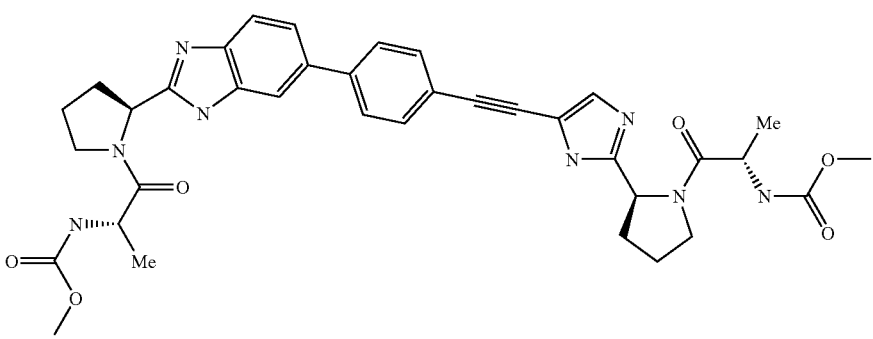<br>From JB.7 | RT: 1.39 min, (Cond.-JB.1); Calcd for $C_{36}H_{41}N_8O_6$ [M + H]$^+$ 681.32; found: 681.21. |
| JB.10 | 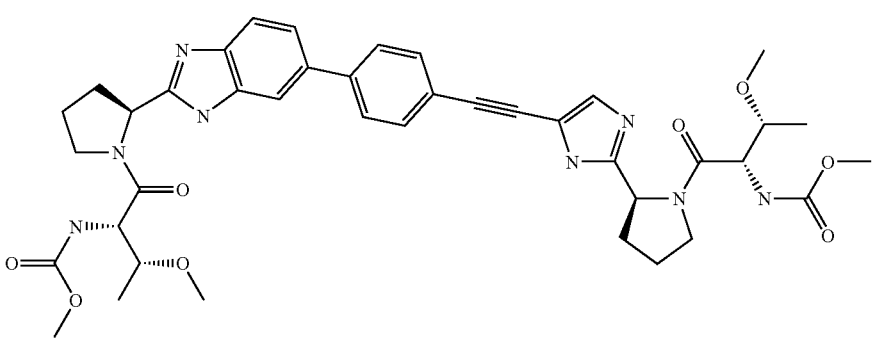<br>From JB.7 | RT: 1.08 min, (Cond.-JB.1); Calcd for $C_{40}H_{49}N_8O_8$ [M + H]$^+$ 769.37; found: 769.31. |
| JB.11 | 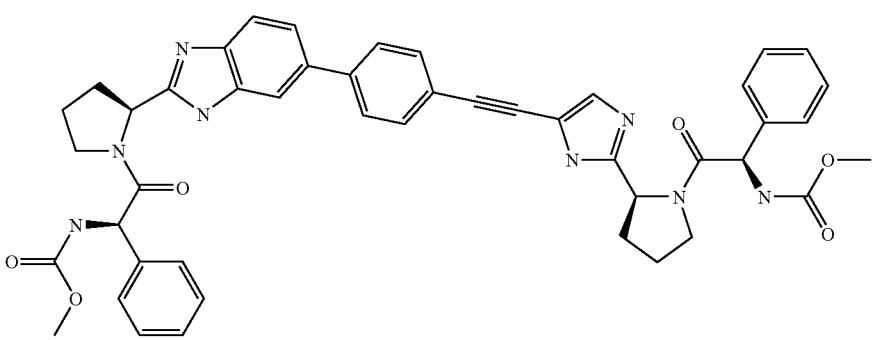<br>From JB.7 | RT: 1.33 min, (Cond.-JB.1); Calcd for $C_{46}H_{45}N_8O_6$ [M + H]$^+$ 805.35; found: 805.27. |

-continued
JB.12
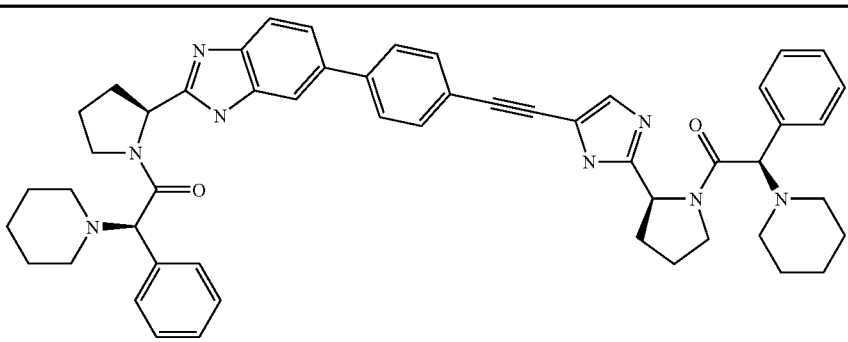
From JB.7
RT: 1.35 min,
(Cond.-JB.1);
Calcd for
$C_{52}H_{56}N_8O_2$
$[M + H]^+$ 825.46;
found: 825.34.
Synthetic Route 13a.
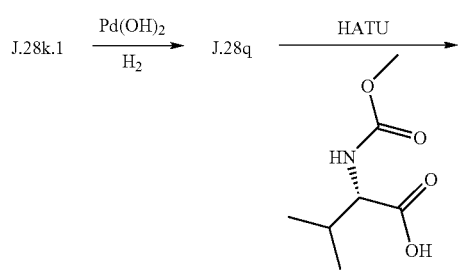
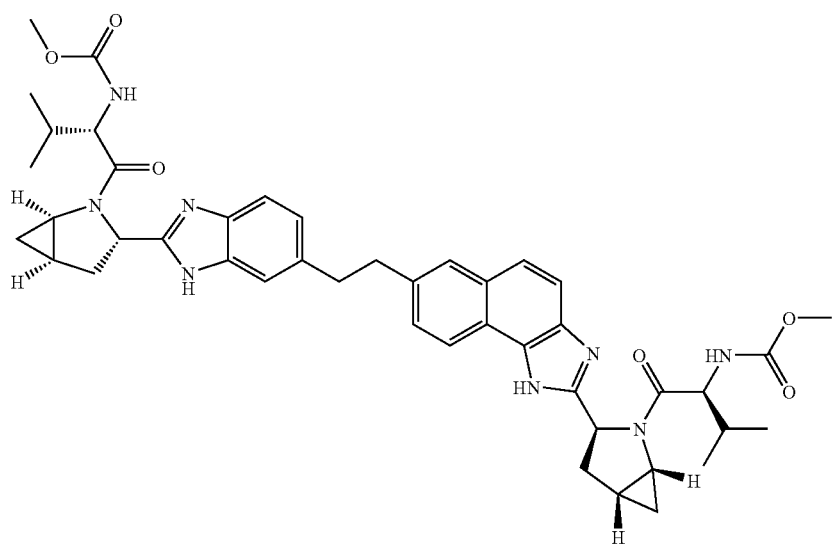
J.28r

Examples J.28q-JB.13

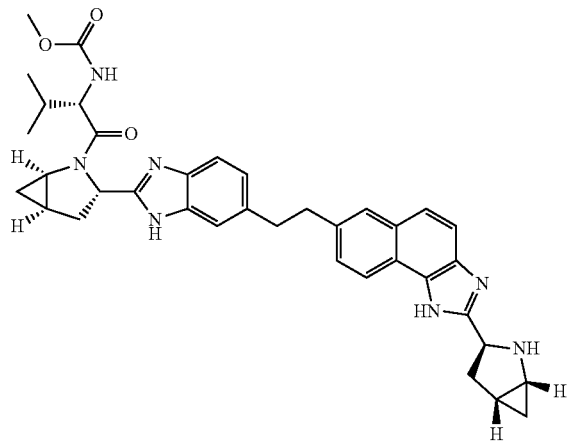

J.28q

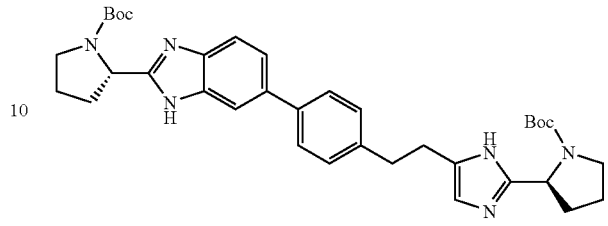

JB.13

A solution of Example J.28k.1 (286.6 mg, 0.376 mmol) in MeOH (2 mL) was added to a stirred suspension of 20% palladium hydroxide on carbon (52.8 mg, 0.376 mmol) and potassium carbonate (104 mg, 0.752 mmol) in MeOH (4 mL) under an atmosphere of nitrogen. The flask was evacuated and charged with hydrogen (3×; balloon, 14 psi) and stirred for 3 h. Note: Significant amounts of N-methylated product form if allowed to go over 3 h. The mixture was filtered over celite, and the celite pad washed with MeOH (100 mL), methylene chloride (50 mL), and MeOH (100 mL) again. The filtrate was concentrated and placed under high vacuum for 0.5 h before it was taken up in MeOH and passed through a nylon syringe fit (to remove traces of catalyst). Example, J.28q was obtained (202 mg, 85% yield) as a yellow solid. RT: 1.62 min, (Cond.-D1); Calcd for $C_{37}H_{42}N_7O_2$ [M+H]$^+$ 632.34; found: 632.21.

10% Pd/C (50 mg, 0.470 mmol) was added in one portion to a suspension of a TFA salt of Example JB.6 (100 mg, 0.118 mmol) in MeOH (10 mL). The reaction mixture was purged with hydrogen and stirred under a balloon of hydrogen overnight at rt. The reaction mixture was filtered through Celite and concentrated. The residue was purified by prep HPLC (Waters Sunfire C18 column 30×150 mm 5 u eluted with a gradient of 10 to 100% ACN-Water+0.1% TFA) to yield a TFA salt of tert-butyl(2S)-2-(4-(2-(4-(2-((2S)-1-(tert-butoxycarbonyl)-2-pyrrolidinyl)-1H-benzimidazol-5-yl)phenyl)ethyl)-1H-imidazol-2-yl)-1-pyrrolidinecarboxylate (70 mg) as a white solid. $^1$H NMR (500 MHz, MeOD) δ ppm 7.95 (d, J=9.5 Hz, 1H), 7.85 (d, J=9.2 Hz, 2H), 7.66 (br s, 2H), 7.31-7.44 (m, 2H), 7.26 (s, 0.5H), 7.14 (s, 0.5H), 5.29 (br s, 1H), 5.04 (br s, 1H), 3.73-3.82 (m, 1H), 3.64 (br s, 2H), 3.55 (br s, 1H), 3.02-3.15 (m, 4H), 2.56-2.70 (m, 1H), 2.41-2.55 (m, 1H), 2.24 (br s, 1H), 2.08-2.18 (m, 2H), 2.03 (br s, 3H), 1.49 (d, J=7.9 Hz, 9H), 1.26 (br s, 4.5H), 1.22 (br s, 4.5H). RT: 1.16 min, (Cond.-JB-1); Calcd for $C_{36}H_{46}N_6O_4$ [M+H]$^+$ 627.37; found: 627.31 [M+H]$^+$.

Examples J.28r-JB.15

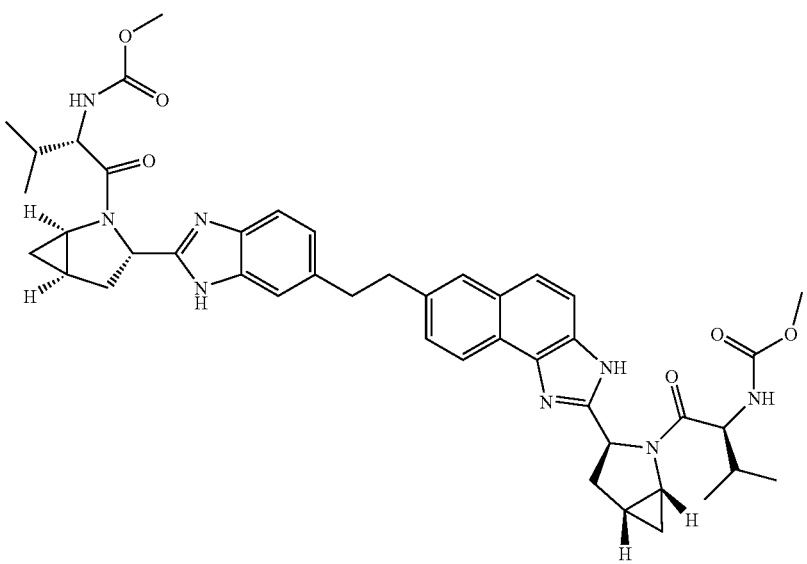

J.28r

RT = 1.78 min (Cond.-D1); LCMS: Calcd for $C_{44}H_{53}N_8O_6$ (M + H)$^+$ 789.41; found: 789.24.

From J.28q according to the procedure described for J.21

-continued
J.28s 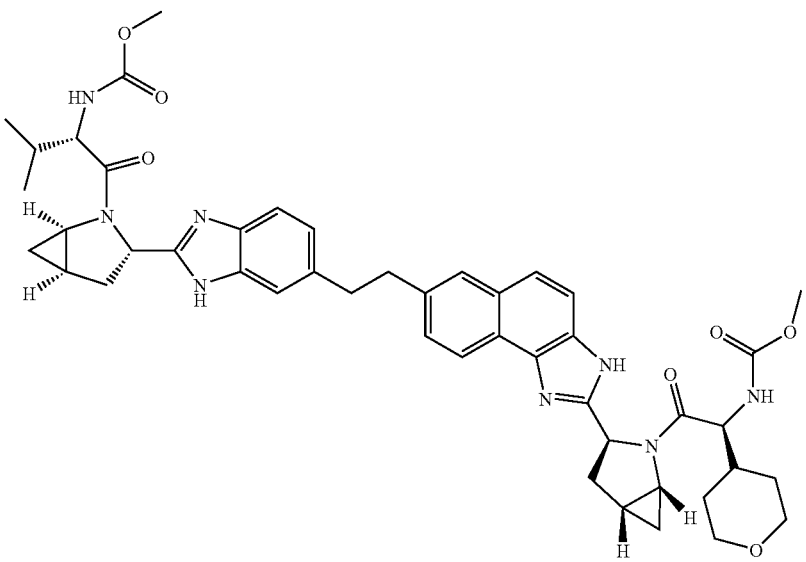
From J.28q according to the procedure described for J.21
RT = 1.67 min (Cond.-D1); LCMS: Calcd for $C_{46}H_{55}N_8O_7$ $(M + H)^+$ 831.42; found: 831.26.
JB.14 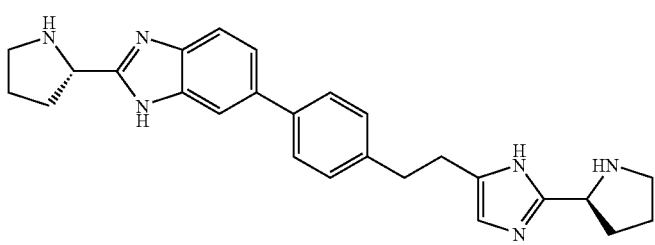
From JB.13 according to the procedure described for J.19
RT = 0.82 min (Cond.-JB-1); LCMS: Calcd for $C_{26}H_{31}N_6$ $(M + H)^+$ 427.26; found: 427.28.
JB.15 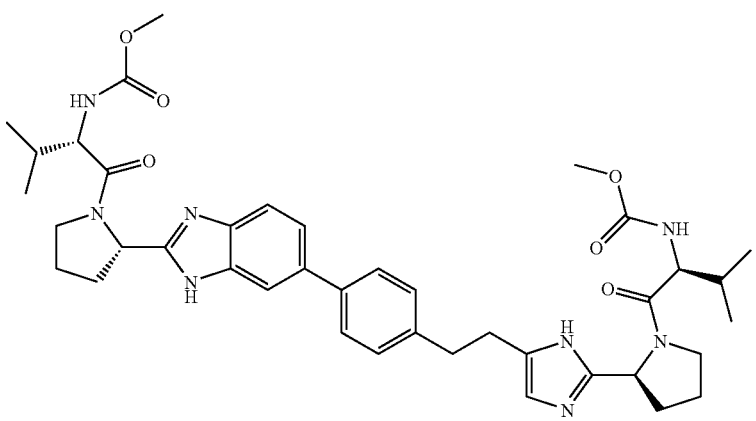
From JB.14 according to the procedure described for J.21
RT = 1.06 min (Cond.-JB-1); LCMS: Calcd for $C_{40}H_{56}N_6O_6$ $(M + H)^+$ 741.41; found: 741.39.

Synthetic Route 14.

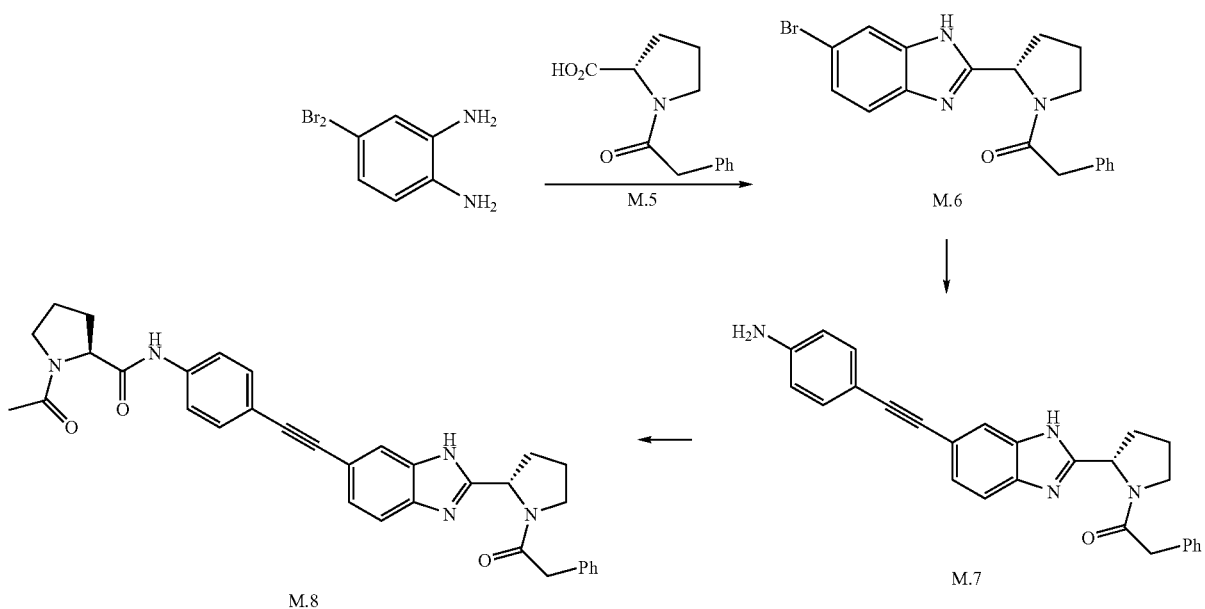

Examples M.5-M.9

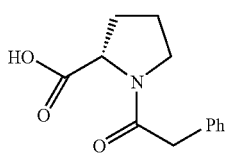

M.5

Example M.5 was prepared from L-proline according to the procedure described in Gudasheva, et al. Eur. J. Med. Chem. 1996, 31, 151.

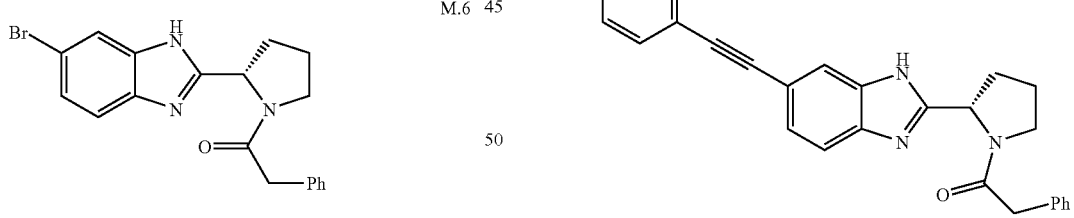

M.6

EDCI.HCl (1.76 g, 9.22 mmol) was added to a mixture of 4-bromobenzene-1,2-diamine (1.50 g, 8.03 mmol), M.5 (1.88 g, 8.06 mmol) and 1-hydroxybenzotriazole (1.31 g, 9.70 mmol) in dichloromethane (30 mL), and stirred at ambient conditions for 19 h. The mixture was then diluted with dichloromethane, washed with water (2x), dried (brine; MgSO$_4$), filtered, and concentrated in vacuo to provide a brown foam. Acetic acid (30 mL) was added to the foam, and the mixture was heated at 65° C. for 90 min. The volatile component was removed in vacuo, and the residue was dissolved in ethyl acetate and washed carefully with saturated NaHCO$_3$ solution (2x), and the organic phase was dried (brine; MgSO$_4$), filtered, and concentrated in vacuo. The resultant crude material was submitted to flash chromatography (silica gel; ethyl acetate) to provide Example M.6 as a tan foam (1.67 g). $^1$H NMR (CDCl$_3$, δ =7.24 ppm, 500 MHz): 10.71/10.68 (overlapping br s, 1H), 7.85 (s, 0.48H), 7.56 (d, J=8.6, 0.52H), 7.50 (s, 0.52H), 7.35-7.22 (m, 6.48H), 5.38 (app br d, J=8.1, 1H), 3.73 (d, J=15.7, 1H), 3.67 (d, J=15.6, 1H), 3.64-3.51 (m, 2H), 3.12-3.04 (m, 1H), 2.41-2.28 (m, 1H), 2.20-2.08 (m, 2H). LC/MS: Anal. Calcd. for [M+H]$^+$ C$_{19}$H$_{18}$BrN$_3$O: 386.07; found: 386.10.

M.7

Pd(Ph$_3$P)$_2$Cl$_2$ (13.3 mg, 0.019 mmol) was added to a mixture of M.6 (152.9 mg, 0.40 mmol), 4-ethynylaniline (69.6 mg, 0.59 mmol), and Et$_3$N (2.20 mL) in dimethylformamide (2.0 mL) and the reaction was heated to 50° C. for 8.5 hr. The volatile component was removed in vacuo and the residue was submitted to flash chromatography (0-30% methanol/dichloromethane), then further purified on reverse phase HPLC (methanol/water/TFA) to afford the TFA salt of M.7 (50 mg). LC/MS: Anal. Calcd. for [M+H]$^+$ C$_{27}$H$_{25}$N$_4$O: 421.2; Found 421.21.

M.8

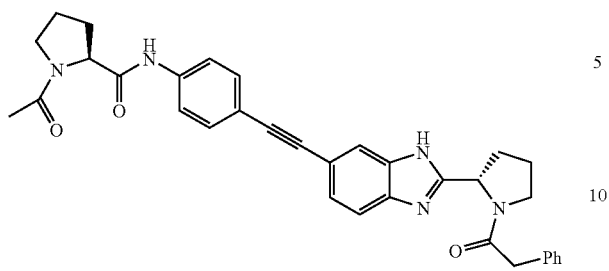

Dichloromethane (3.0 mL) was added to a mixture of M.7 (57.0 mg, 0.14 mmol), (S)-1-acetylpyrrolidine-2-carboxylic acid (23.3 mg, 0.15 mmol) and EEDQ (39.0 mg, 0.16 mmol) and stirred at ambient conditions for 16 hr. The volatile components were removed in vacuo, and the residue was dissolved in methanol and subjected to a reverse phase HPLC purification (methanol/water/TFA), followed by free-basing (SCX column; methanol wash; 2.0 M ammonia/methanol elution) and flash chromatography purification (5-15% methanol/ethyl acetate) to afford M.8 as a brown solid (38.0 mg). LC/MS: Anal. Calcd. for [M+H]$^+$ C$_{34}$H$_{34}$N$_5$O$_3$: 560.27; found: 560.28.

M.9

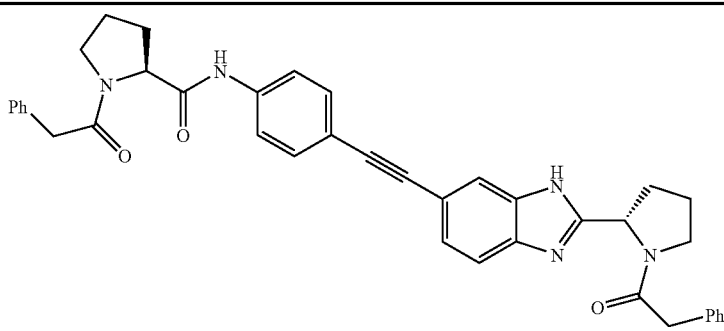

LC/MS: Anal. Calcd. for [M + H]$^+$ C$_{40}$H$_{37}$N$_5$O$_3$: 636.30; found: 636.29.

From M.5 and M.7

Examples M.10-M.11

M.10

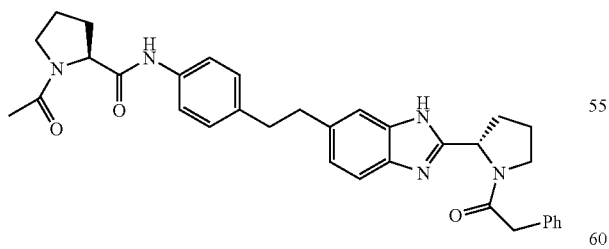

A mixture of M.8 (24.0 mg, 0.04 mmol) and Pd/C (10%, 14.1 mg) in methanol (3.0 mL) was stirred under a balloon of H$_2$ (1 atm) for 3 hr. The suspension was filtered through a pad of diatomaceous earth (Celite®) and concentrated in vacuo to afford M.10 as an off-white foam (22.0 mg). LC/MS: Anal. Calcd. for [M+H]+ C$_{34}$H$_{38}$N$_5$O$_3$: 564.30; found: 564.43.

M.11

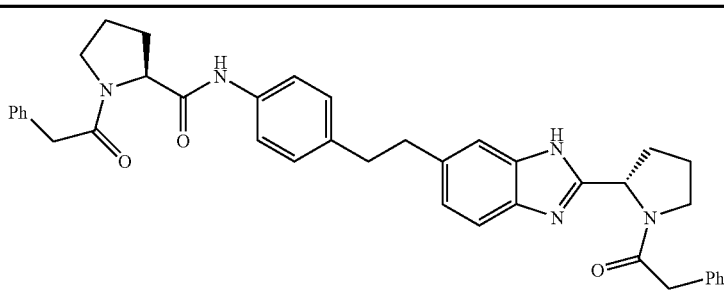

From M.9

LC/MS: Anal. Calcd. for [M + H]+ C40H42N5O3: 640.33; found: 640.35.

Synthetic Route 15

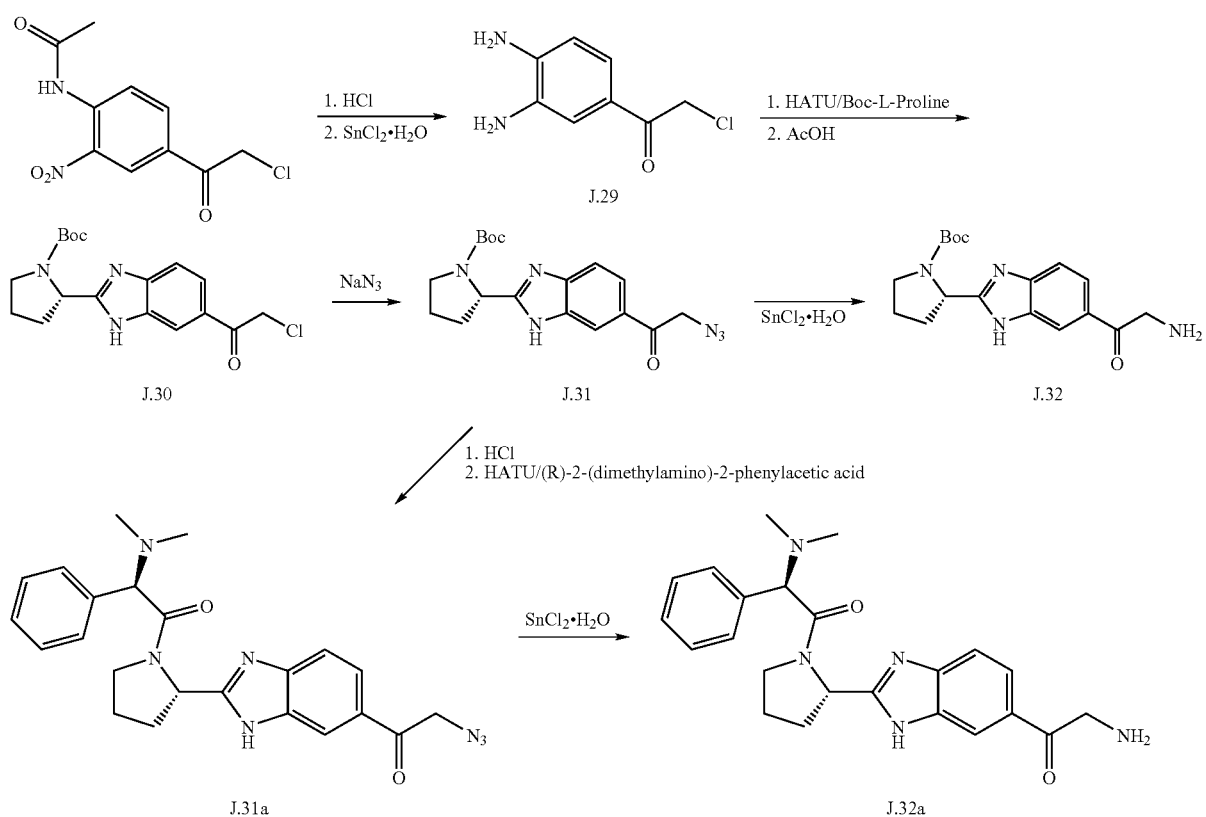

Examples J.29-J.32a

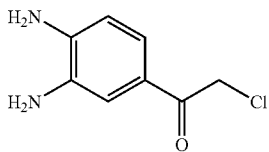

J.29

N-(4-(2-Chloroacetyl)-2-nitrophenyl)acetamide (25.7 g, 0.1 mol) was suspended in 250 mL of 3N HCl and heated at 80° C. in 1 L pressure vessel for 20 h. After being cooled to room temperature, 1-(4-amino-3-nitrophenyl)-2-chloroethanone.HCl (23.2 g, 92%) was isolated by vacuum filtration as a bright yellow solid. The salt (23.2 g, 0.092 mol) was suspended in methanol (600 mL) and tin chloride dihydrate (65 g, 0.29 mol) was added in one portion. The mixture was heated at 70° C. for 14 h while being vigorously stirred. An additional 20 g of tin chloride dihydrate was added and the reaction stirred 8 h. The solvent was removed by rotory evaporation and the residue was taken up in ethyl acetate/NaHCO3 soln (caution: much carbon dioxide evolution). The precipitated salts were removed by filtration and the organic layer was separated. The aqueous layer was extracted twice more (ethyl acetate) and the combined organic layers were washed with brine, dried (Na2SO4) and concentrated to ¼ volume. 2-Chloro-1-(3,4-diaminophenyl)ethanone, J.29, 10.03 g (59%) was isolated by vacuum filtration as a brick red solid. $^1$H NMR (400 MHz, DMSO-d$_6$) δ: 8.17 (dd, J=8.3, 2.3 Hz, 1H), 7.14 (d, J=2.0 Hz, 1H), 6.51 (d, J=8.0 Hz, 1H), 5.57 (br. s, 2H), 4.85 (s, 2H), 4.78 (br. s, 2H). LC (Cond.-D2); 0.65 min; LC/MS: Anal. Calcd. for [M+H]⁺ $C_8H_{10}ClN_2O$: 185.05; found: 185.02. HRMS: Anal. Calcd. for [M+H]⁺ $C_8H_{10}ClN_2O$: 185.0482; found: 185.0480. The reaction was repeated to supply more material.

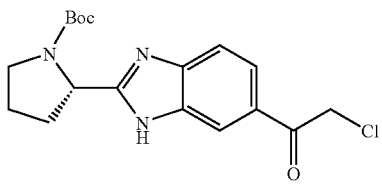
J.30

HATU (38.5 g, 101.3 mmol) was added portion wise to a vigorously stirred solution of J.29 (17.0 g, 92 mmol), N-Boc-L-proline (19.82 g, 92 mmol), and Hunig's base (17.6 mL, 101.3 mmol) in dimethylformamide (200 mL). After 6 h, the reaction mixture was concentrated in vacuo to remove solvent and the residue was taken up in ethyl acetate, washed with saturated NaHCO₃ solution, brine, and dried (Na₂SO₄). Concentration yielded a viscous brown oil which was taken up in glacial acetic acid (100 mL) and heated at 60° C. for 20 h. The solvent was removed in vacuo and the residue was taken up in ethyl acetate, washed with saturated NaHCO₃ solution (adjust with 1N NaOH soln until pH=9), brine, and dried (Na₂SO₄). The residue obtained upon concentration was pre-adsorbed onto SiO₂ (dichloromethane) and subjected to flash chromatography successively eluting with 50%, 75%, 100% ethyl acetate/hexanes to give J.30 (S)-tert-Butyl 2-(6-(2-chloroacetyl)-1H-benzo[d]imidazol-2-yl)pyrrolidine-1-carboxylate 22.37 g (67%) was obtained as a yellow foam. ¹H NMR (400 MHz, DMSO-d₆) δ: 8.20 (s, 1H), 7.81 (dd, J=8.3, 2.3 Hz, 1H), 7.59 (d, J=8.0 Hz, 1H), 5.24 (s, 2H), 4.99/4.93 (s, 1H), 3.60 (br. s, 1H), 3.46-3.41 (m, 1H), 2.36-2.30 (m, 1H), 2.01-1.89 (in, 3H), 1.39/1.06 (s, 9H). LC (Cond.-D2): 1.85 min; LC/MS: Anal. Calcd. for [M+H]⁺ $C_{18}H_{23}ClN_3O_3$: 364.14; found: 364.20. HRMS: Anal. Calcd. for [M+H]⁺ $C_{18}H_{23}ClN_3O_3$: 364.1428; found: 364.1427.

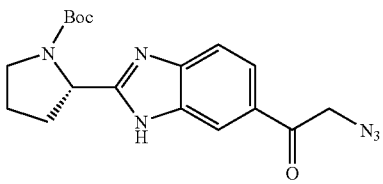
J.31

Sodium azide (1.79 g, 27.48 mmol) was added in one portion to a solution of J.30 (S)-tert-butyl 2-(6-(2-chloroacetyl)-1H-benzo[d]imidazol-2-yl)pyrrolidine-1-carboxylate (10.0 g, 27.48 mmol) in acetonitrile (200 mL) and stirred at 60° C. for 16 h. The reaction mixture was concentrated to ⅕ volume, diluted with ethyl acetate, and washed with water and brine prior to being dried (Na₂SO₄). Concentration gave J.31 (S)-tert-butyl 2-(6-(2-azidoacetyl)-1H-benzo[d]imidazol-2-yl)pyrrolidine-1-carboxylate 6.8 g (48%) as a golden orange foam. ¹H NMR (500 MHz, DMSO-d₆) δ: 8.22/8.03 (s, 1H), 7.80-7.75 (m, 1H), 7.65/7.56 (d, J=8.5 Hz, 1H), 4.99-4.93 (m, 3H), 3.60 (br. s, 1H), 3.46-3.41 (m, 1H), 2.38-2.27 (m, 1H), 2.01-1.89 (m, 3H), 1.40/1.06 (s, 9H). LC (Cond.-D2): 1.97 min; LC/MS: Anal. Calcd. for [M+H]⁺ $C_{18}H_{23}N_6O_3$: 371.19; found: 371.32. HRMS: Anal. Calcd. for [M+H]⁺ $C_{18}H_{23}N_6O_3$: 371.1832; found: 371.1825.

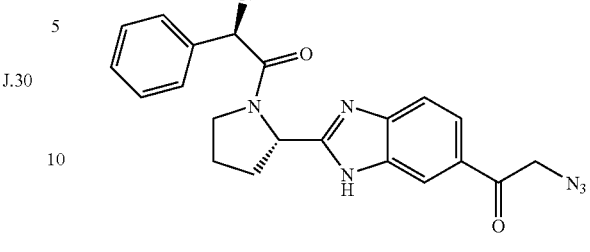
J.31a

To a solution of J.31 (1.8 g, 4.86 mmol) in ethyl acetate (5 mL) was added HCl/dioxane (10 mL of 4N), and the reaction was stirred 4 hr. The solvents were removed in vacuo, and the HCl salt was exposed to high vacuum for 18 h to give (S)-2-azido-1-(2-(pyrrolidin-2-yl)-1H-benzo[d]imidazol-6-yl) ethanone.2HCl a yellow solid. HATU (1.94 g, 5.10 mmol) was added to the HCl salt of (S)-2-azido-1-(2-(pyrrolidin-2-yl)-1H-benzo[d]imidazol-6-yl)ethanone (1.8 g, 4.86 mmol), (R)-2-(dimethylamino)-2-phenylacetic acid HCl salt (1.05 g, 4.86 mmol), and Hunig's base (3.4 mL, 19.4 mmol) in dimethylformamide (50 mL) while being rapidly stirred 6 h. The solvent was removed in vacuo and the reside was partitioned into two lots and separately pre-absorbed onto SiO₂ (dichloromethane), and subjected to flash chromatography on a 40 M Biotage silica gel column pre-equilibrated 2% B, and eluted with 2% B (150 mL); Segment 2: 2-40% B (1200 mL); Segment 3: 40-80% (600 mL). A=dichloromethane; B=25% methanol/dichloromethane to give J.31a (R)-1-((S)-2-(6-(2-azidoacetyl)-1H-benzo[d]imidazol-2-yl)pyrrolidin-1-yl)-2-(dimethylamino)-2-phenylethanone (combined lots: 1.05 g (50%)) as a yellow foam. ¹H NMR (500 MHz, DMSO-d₆) δ: 8.16 (s, 1H), 7.82 (dd, J=8.8, 1.5 Hz, 1H), 7.65 (d, J=8.5 Hz, 1H), 7.60-7.56 (m, 5H), 5.51 (s, 1H), 5.22 (dd, J=8.2, 2.8, 1H), 4.95 (m, 2H), 4.09-4.05 (m, 1H), 3.17-3.12 (m, 1H), 2.90/2.84 (br. s, 6H), 2.23-2.19 (m, 1H), 2.21-1.89 (m, 3H). LC (D-Cond. 1): RT=1.5 min; LC/MS: Anal. Calcd. for [M+H]⁺ $C_{23}H_{26}N_7O_2$: 432.22; found: 431.93. HRMS: Anal. Calcd. for [M+H]⁺ $C_{23}H_{26}N_7O_2$: 432.2148; found: 432.2127.

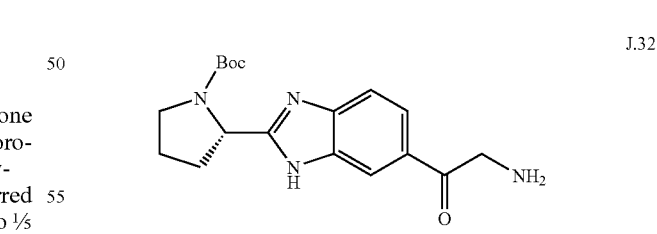
J.32

Tin(II)dichloride dehydrate (12.24 g, 54.26 mmol) was added to J.31 (6.8 g, 18.08 mmol) dissolved in methanol (200 mL). The reaction mixture was heated at 60° C. for 6 h and concentrated and dried under high vacuum to give the HCL salt of J.32 (S)-tert-butyl 2-(6-(2-aminoacetyl)-1H-benzo[d] imidazol-2-yl)pyrrolidine-1-carboxylate, 16.6 g which contained tin salts. LC (Cond.-D2): 1.21 min; LC/MS: Anal. Calcd. for [M+H]⁺ $C_{18}H_{25}N_4O_3$: 345.18; found: 345. The material was used without purification.

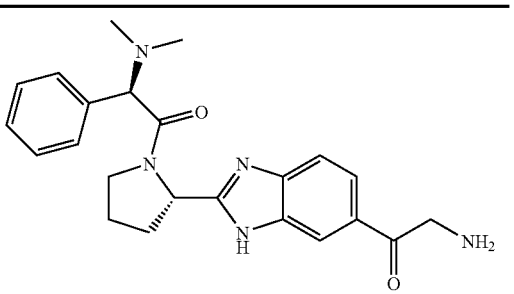

J.32a

Synthetic Route 16

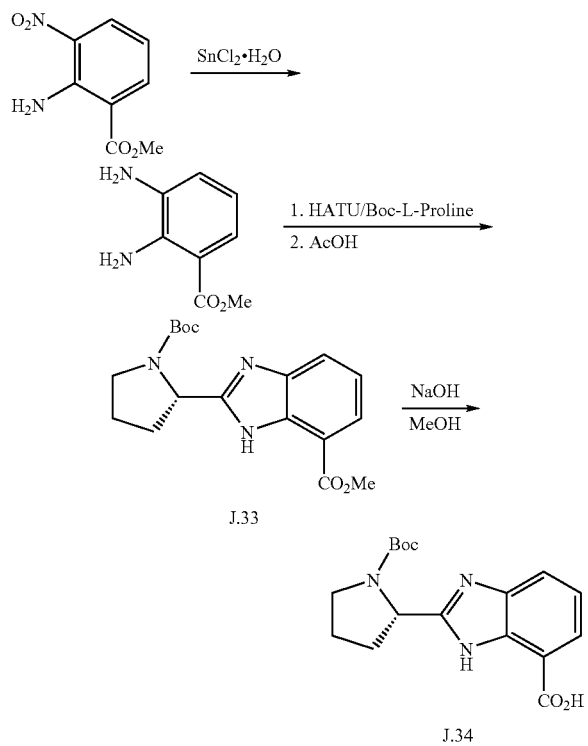

Examples J.33-J.34a

Tin(II)chloride dihydrate (17.25 g, 76.5 mmol) was added in one portion to methyl 2-amino-3-nitrobenzoate (5.0 g, 25.5 mmol) in methanol (100 mL) under nitrogen. The yellow mixture was vigorously stirred at 65° C. for 16 h, and the solvent was removed by rotory evaporation to near dryness. The residue was taken up in ethyl acetate and the solution was poured into a large beaker containing 1:1 ethyl acetate/NaHCO₃ soln. (300 mL) and stirred 15 min. The precipitates were removed by filtration and the organic layer was separated. The aqueous layer was extracted twice with ethyl acetate, and the combined organic layers were washed with saturated NaHCO₃ solution, brine, and dried (Na₂SO₄). Concentration gave methyl 2,3-diaminobenzoate as a deep red viscous oil 4.1 g (97%).

HATU (10.66 g, 28.0 mmol) was added in one portion to a stirred solution of methyl 2,3-diaminobenzoate (4.1 g, 24.7 mmol), N-Boc-L-proline (5.49 g, 25.5 mmol), and Hunig's base (4.9 mL, 28.0 mmol) in dimethylformamide (50 mL). The reaction mixture was stirred 3 h and solvent removed in vacuo, and the residue was diluted with ethyl acetate, washed with 0.1N HCl, sat'd NaHCO₃, brine, and dried (Na₂SO₄). Concentration gave a reddish brown viscous oil which was taken up in glacial acetic acid (60 mL) and heated at 60° C. for 16 h. The solvent was removed in vacuo, and the residue was diluted with ethyl acetate, washed with sat'd NaHCO₃ soln., brine, and dried (Na₂SO₄). Concentration gave a residue that was divided into two lots, and each lot pre-adsorbed onto SiO₂ (dichloromethane), applied to a 40 M Biotage SiO₂ column, and eluted by gradient 10%-100% B (1440 mL); A=hexanes; B=ethyl acetate to give J.33 (S)-methyl 2-(1-(tert-butoxycarbonyl)pyrrolidin-2-yl)-1H-benzo[d]imidazole-7-carboxylate 7.05 g (83%) as a reddish oil. $^1$H NMR (500 MHz, DMSO-$d_6$) δ: 7.86 (d, J=7.9 Hz, 1H), 7.78 (t, J=5 Hz, 1H), 7.28-7.24 (m, 1H), 5.20-5.11 (m, 1H), 3.95 (s, 3H), 3.60-3.52 (m, 1H), 3.43-3.38 (m, 1H), 2.33-2.22 (m, 1H), 2.15-2.0 (m, 2H), 1.91-1.86 (m, 1H), 1.40/1.05 (s, 9H). LC (Cond.-D2): RT=1.86 min; LC/MS: Anal. Calcd. for [M+H]$^+$ $C_{18}H_{24}N_3O_4$: 346.18; found 346.26; HRMS: Anal. Calcd. for [M+H]$^+$ $C_{18}H_{24}N_3O_4$: 346.1767; found: 346.1776.

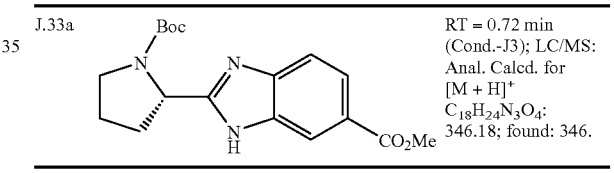

J.33a    RT = 0.72 min (Cond.-J3); LC/MS: Anal. Calcd. for [M + H]$^+$ $C_{18}H_{24}N_3O_4$: 346.18; found: 346.

Example J.34

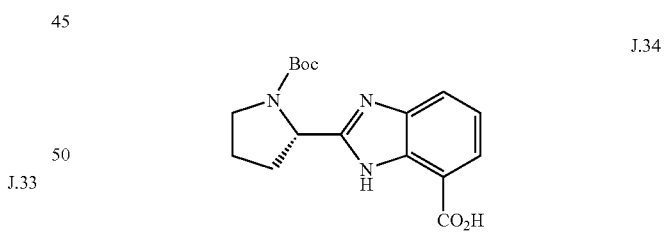

J.34

A solution of 5N sodium hydroxide (8 mL) was added to methyl ester J.33 (7.0 g, 20.3 mmol) in methanol (80 mL) and stirred 8 h. An additional 4 mL was added and stirring continued stirring for 18 h, at which time the reaction temperature was raised to 45° C. for a final 8 h to complete the hydrolysis. Most of the methanol was removed by rotory evaporation, and the basic aqueous solution was diluted with ethyl acetate. A precipitate formed and was isolated by filtration. The organic layer was separated and washed with brine. Additional lots of precipitate formed during partial concentration to ¼ vol, and the combined lots of J.34 (S)-2-(1-(tert-butoxycarbonyl)pyrrolidin-2-yl)-1H-benzo[d]imidazole-7-carboxylic acid totaled 5.49 g (82%). $^1$H NMR (500 MHz, DMSO-d$_6$) δ: 8.04-8.0 (m, 2H), 7.58 (br. s, 1H), 5.32 (s, 1H), 3.67-3.63 (m, 1H), 3.47-3.43 (m, 1H), 2.44-2.36 (m, 1H), 2.17-2.11 (m, 1H), 2.05-1.93 (m, 2H), 1.40/1.06 (s, 9H). LC (Cond.-D2): 1.68 min; LC/MS: Anal. Calcd. for [M+H]$^+$ C$_{17}$H$_{22}$N$_3$O$_4$: 332.16; found: 332.25. HRMS: Anal. Calcd. for [M+H]$^+$ C$_{17}$H$_{22}$N$_3$O$_4$: 322.1610; found: 322.1625.

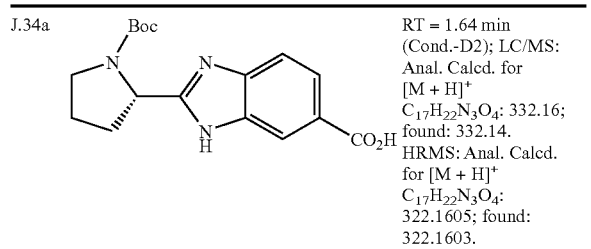

J.34a

RT = 1.64 min (Cond.-D2); LC/MS: Anal. Calcd. for [M + H]$^+$ C$_{17}$H$_{22}$N$_3$O$_4$: 332.16; found: 332.14. HRMS: Anal. Calcd. for [M + H]$^+$ C$_{17}$H$_{22}$N$_3$O$_4$: 322.1605; found: 322.1603.

Synthetic Route 17.

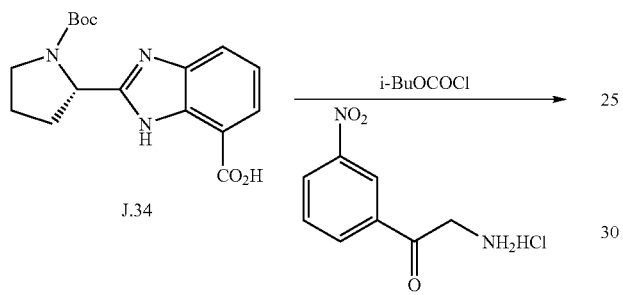

J.34

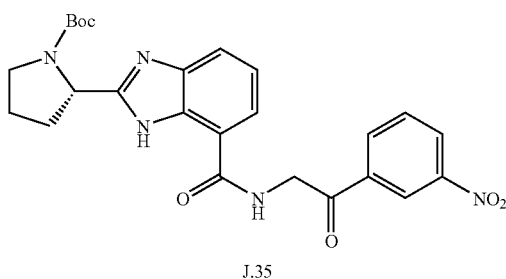

J.35

Examples J.35-J.35a

J.35

Iso-butyl chloroformate (0.45 mL, 3.4 mmol) was added dropwise to a solution of acid J.34 (1.0 g, 3.02 mmol) and N-methylmorpholine (1.2 mL, 10 mmol) in tetrahydrofuran (50 mL) cooled at 0° C. under nitrogen, and the ice bath was removed the reaction stirred 30 min. The solution was recooled and an additional 0.5 ml of base was added followed by of 2-nitrophenacylamine.HCl (700 mg, 3.2 mmol). The reaction mixture was stirred for 18 h at room temperature and diluted with ethyl acetate and sat'd NaHCO$_3$ soln. A precipitate was removed by filtration and the organic phase was concentrated. The residue was taken up in methanol and filtered to provide a second lot of precipitate. The combine lots of J.35, 796 mg (65%) were carried forward without further purification. $^1$H NMR (300 MHz, DMSO-d$_6$) δ: 10.5 (br. s, 1H), 8.73 (s, 1H), 8.52-8.49 (m, 1H), 7.88 (t, J=8.0 Hz, 1H), 7.80 (d, J=7.7 Hz, 1H), 7.65 (d, J=7.7 Hz, 1H), 7.25 (t, J=7.7 Hz, 1H), 5.11-5.05 (m, 3H), 3.70-3.33 (m, 2H), 2.39-2.31 (m, 1H), 2.14-1.89 (m, 3H), 1.38/1.07 (s, 9H). LC (Cond.-J1): 1.64 min; LRMS: Anal. Calcd. for [M+H]$^+$ C$_{25}$H$_{28}$N$_5$O$_6$: 494.21; found: 494.17

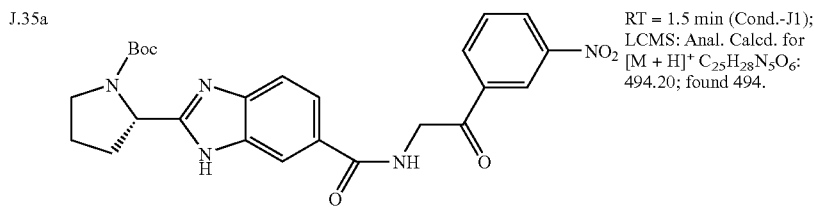

J.35a

RT = 1.5 min (Cond.-J1); LCMS: Anal. Calcd. for [M + H]$^+$ C$_{25}$H$_{28}$N$_5$O$_6$: 494.20; found 494.

From J.34a and 2-amino-1-(3-nitrophenyl)ethanone

Synthetic Route 18

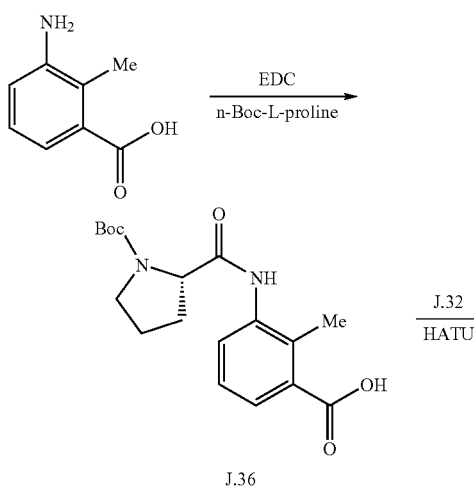

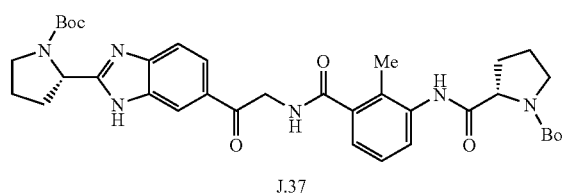

Examples J.36-J.37e

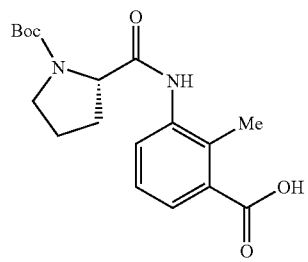

J.36

N-(3-Dimethylaminopropyl)-N-ethylcarbodimide.HCl salt (3.1 g, 16.6 mmol) was added to a suspension of 3-amino-2-methylbenzoic acid (2.5 g, 16.6 mmol) and N-Boc-L-proline (3.5 g, 16.6 mmol) in dichloromethane (40 mL). The reaction mixture was stirred under nitrogen for 18 h, diluted with solvent (1 vol) and washed with 1N HCl, brine, and dried (MgSO$_4$). Concentration gave a foam with was applied to a 40 M Biotage SiO$_2$ column, and eluted by gradient 20%-60% B (1000 mL); A=1% acetic acid/hexanes; B=1% acetic acid/ethyl acetate to give J.36 (S)-3-(1-(tert-butoxycarbonyl)pyrrolidine-2-carboxamido)-2-methylbenzoic acid 2.6 g (45%). $^1$H NMR (300 MHz, DMSO-d$_6$) δ: 12.5 (br. s, 1H), 9.52/9.46 (s, 1H), 7.57 (d, J=7.3 Hz, 1H), 7.44-7.40 (m, 1H), 7.29-7.24 (m, 1H), 4.32-4.28 (m, 1H), 3.47-3.48 (m, 1H), 3.34-3.29 (m, 1H), 2.33 (s, 3H), 1.93-1.80 (m, 4H), 1.41/1.36 (s, 9H). LC (Cond.-J1): 1.55 min; LCMS: Anal. Calcd. for [M+H]$^+$ C$_{18}$H$_{25}$N$_2$O$_5$: 349.18; found 349.33.

J.36a 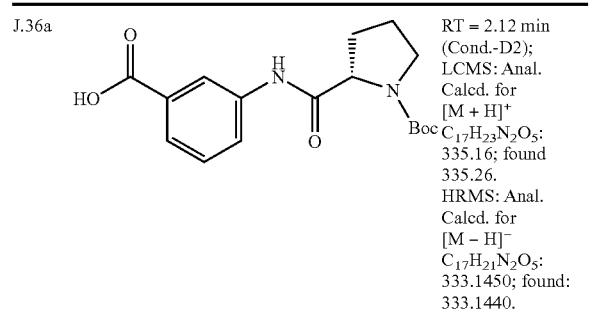
RT = 2.12 min (Cond.-D2); LCMS: Anal. Calcd. for [M + H]$^+$ C$_{17}$H$_{23}$N$_2$O$_5$: 335.16; found 335.26. HRMS: Anal. Calcd. for [M − H]$^-$ C$_{17}$H$_{21}$N$_2$O$_5$: 333.1450; found: 333.1440.

J.36b 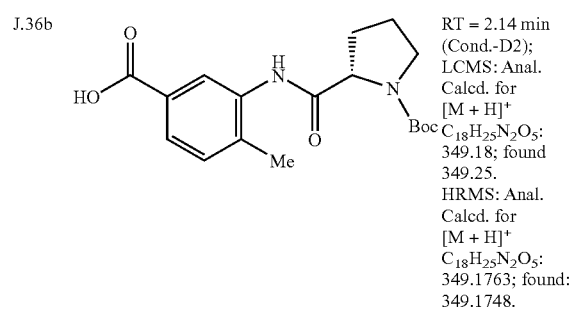
RT = 2.14 min (Cond.-D2); LCMS: Anal. Calcd. for [M + H]$^+$ C$_{18}$H$_{25}$N$_2$O$_5$: 349.18; found 349.25. HRMS: Anal. Calcd. for [M + H]$^+$ C$_{18}$H$_{25}$N$_2$O$_5$: 349.1763; found: 349.1748.

J.36c 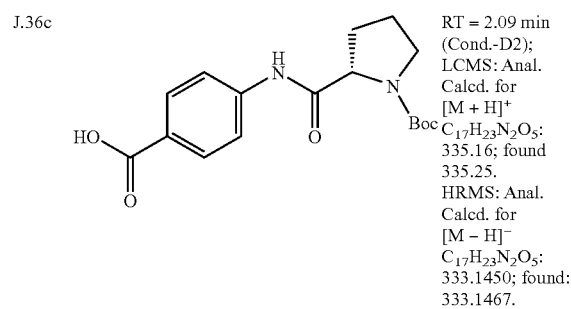
RT = 2.09 min (Cond.-D2); LCMS: Anal. Calcd. for [M + H]$^+$ C$_{17}$H$_{23}$N$_2$O$_5$: 335.16; found 335.25. HRMS: Anal. Calcd. for [M − H]$^-$ C$_{17}$H$_{23}$N$_2$O$_5$: 333.1450; found: 333.1467.

J.36d 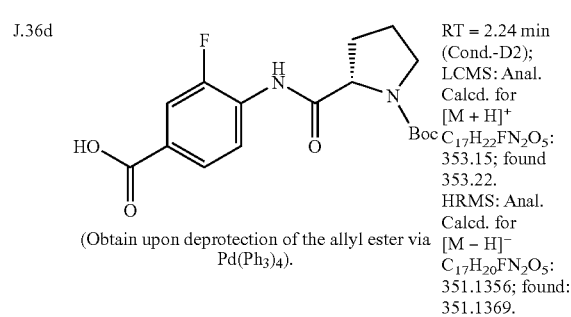
(Obtain upon deprotection of the allyl ester via Pd(Ph$_3$)$_4$).
RT = 2.24 min (Cond.-D2); LCMS: Anal. Calcd. for [M + H]$^+$ C$_{17}$H$_{22}$FN$_2$O$_5$: 353.15; found 353.22. HRMS: Anal. Calcd. for [M − H]$^-$ C$_{17}$H$_{20}$FN$_2$O$_5$: 351.1356; found: 351.1369.

J.37

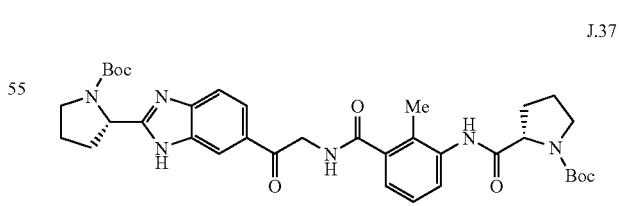

HATU (462 mg, 1.22 mmol) was added in one portion to a stirred solution of J.32 (450 mg, 1.22 mmol), J.36 (423 mg, 1.22 mmol), and Hunig's base (1.0 mL) in dimethylformamide (10 mL) and the reaction mixture was stirred 18 h. The solvent was removed in vacuo and the residue was applied to a 25 M Biotage SiO$_2$ column, and eluted by gradient 5%-60%

B (500 mL); A=ethyl acetate; B=10% methanol/ethyl acetate to give J.37, 439.6 mg (50%). ¹H NMR (300 MHz, DMSO-$d_6$) δ: 12.73-12.58 (m, 1H), 9.45/9.35 (s, 1H), 8.59 (br s, 1H), 8.33/8.12 (s, 1H) 7.86 (d, J=8.4 Hz, 1H), 7.66/7.56 (d, J=8.4 Hz, 1H), 7.40-7.36 (m, 1H), 7.25 (app br. s, 2H), 5.0-4.92 (m, 1H), 4.79 (d, J=4.8 H, 2H), 4.33-4.30 (m, 1H), 3.60 (br. s, 1H), 3.47-3.41 (m, 2H), 3.35-3.29 (m, 1H), 2.24 (s, 3H), 2.02-1.87 (m, 8H), 1.42-1.37/1.05 (m, 18H). LC (Cond.-J1): 1.65 min; LRMS: Anal. Calcd. for [M+H]⁺ $C_{36}H_{47}N_6O_7$: 675.35; found 675.30.
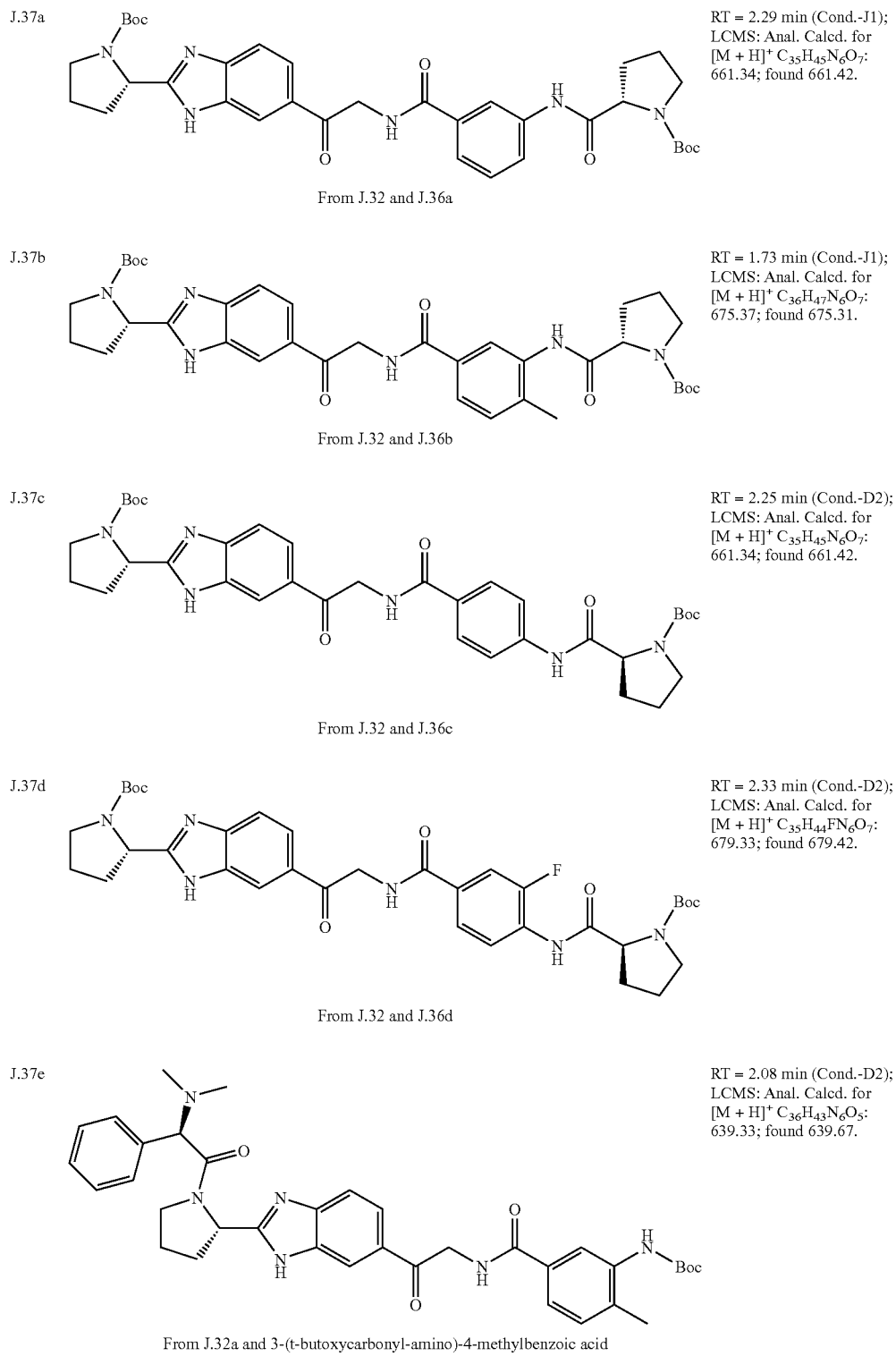

Synthetic Route 19

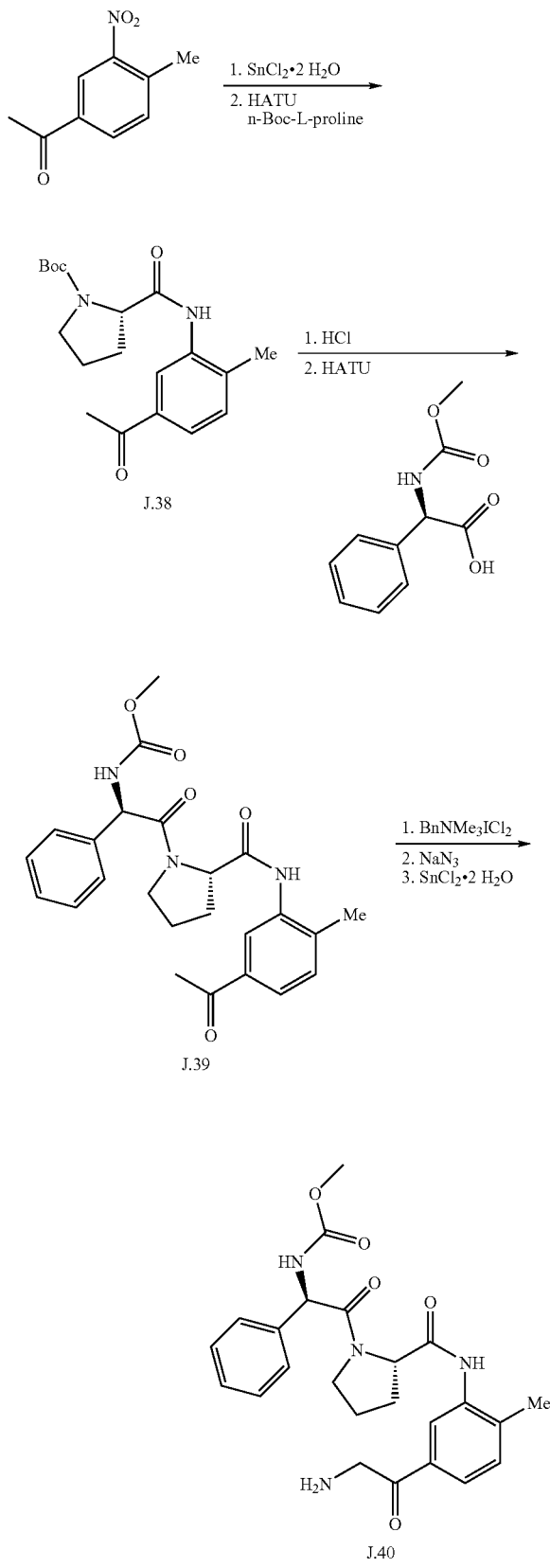

Examples J.38-J.40

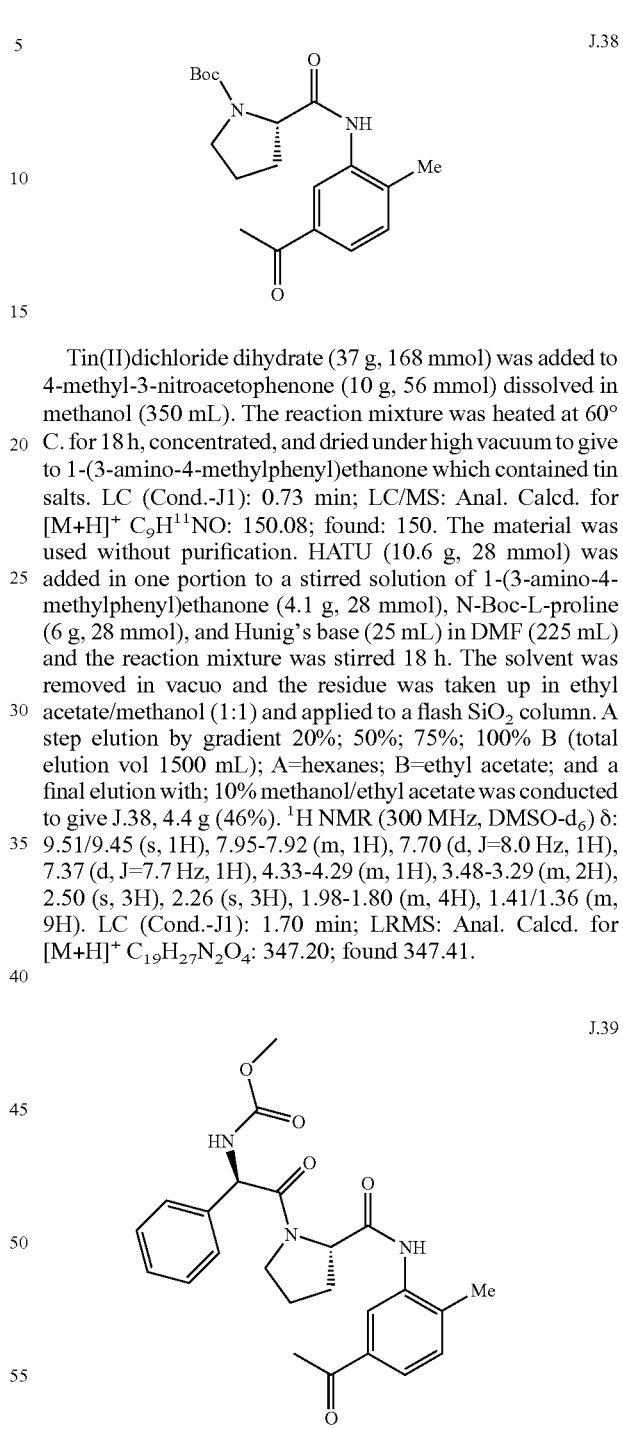

Tin(II)dichloride dihydrate (37 g, 168 mmol) was added to 4-methyl-3-nitroacetophenone (10 g, 56 mmol) dissolved in methanol (350 mL). The reaction mixture was heated at 60° C. for 18 h, concentrated, and dried under high vacuum to give to 1-(3-amino-4-methylphenyl)ethanone which contained tin salts. LC (Cond.-J1): 0.73 min; LC/MS: Anal. Calcd. for $[M+H]^+$ $C_9H^{11}NO$: 150.08; found: 150. The material was used without purification. HATU (10.6 g, 28 mmol) was added in one portion to a stirred solution of 1-(3-amino-4-methylphenyl)ethanone (4.1 g, 28 mmol), N-Boc-L-proline (6 g, 28 mmol), and Hunig's base (25 mL) in DMF (225 mL) and the reaction mixture was stirred 18 h. The solvent was removed in vacuo and the residue was taken up in ethyl acetate/methanol (1:1) and applied to a flash $SiO_2$ column. A step elution by gradient 20%; 50%; 75%; 100% B (total elution vol 1500 mL); A=hexanes; B=ethyl acetate; and a final elution with; 10% methanol/ethyl acetate was conducted to give J.38, 4.4 g (46%). $^1$H NMR (300 MHz, DMSO-$d_6$) δ: 9.51/9.45 (s, 1H), 7.95-7.92 (m, 1H), 7.70 (d, J=8.0 Hz, 1H), 7.37 (d, J=7.7 Hz, 1H), 4.33-4.29 (m, 1H), 3.48-3.29 (m, 2H), 2.50 (s, 3H), 2.26 (s, 3H), 1.98-1.80 (m, 4H), 1.41/1.36 (m, 9H). LC (Cond.-J1): 1.70 min; LRMS: Anal. Calcd. for $[M+H]^+$ $C_{19}H_{27}N_2O_4$: 347.20; found 347.41.

Example J.38 (3 g, 83 mmol) was dissolved in methanol (30 mL) and 4N HCl/dioxane (50 mL) was added and the reaction was stirred 18 hr. The solvents were removed in vacuo, and (S)—N-(5-acetyl-2-methylphenyl)pyrrolidine-2-carboxamide HCl salt was exposed to vacuum. LC (Cond-J1): 0.9 min. HATU (1.4 g, 3.5 mmol) was added in one portion to a stirred solution of (S)—N-(5-acetyl-2-methylphenyl)pyrrolidine-2-carboxamide.HCl (1.0 g, 3.5 mmol), (R)-2-(methoxycarbonylamino)-2-phenylacetic acid (740 mg, 3.5 mmol), and Hunig's base (2.9 mL) in dimethylformamide (25 mL) and the reaction mixture was stirred 18 h. The solvent was removed in vacuo and the residue was applied to a 40 M Biotage SiO$_2$ column, and eluted by gradient 50%-100% B (500 mL); A=hexanes; B=ethyl acetate to give J.39, methyl (R)-2-((S)-2-(5-acetyl-2-methylphenylcarbamoyl)pyrrolidin-1-yl)-2-oxo-1-phenylethylcarbamate 1.25 g (87%). $^1$H NMR (300 MHz, DMSO-d$_6$) δ: 9.42 (s, 1H), 7.95 (s, 1H), 7.75-7.69 (m, 2H), 7.43-7.19 (m, 6H), 5.50/5.40 (d, J=7.7 Hz, 1H), 4.49-4.47 (m, 1H), 3.87-3.81 (m, 1H), 3.58-3.54 (m, 1H), 3.50 (s, 3H), 2.54 (s, 3H), 2.27 (s, 3H), 1.99-1.83 (m, 4H). LC (Cond.-J1): 1.65 min; LRMS: Anal. Calcd. for [M+H]$^+$ C$_{24}$H$_{28}$N$_3$O$_5$: 438.20; found 438.20.

Reference: Synthesis (1988) p 545. (Chlorination).

Synthetic Route 20.

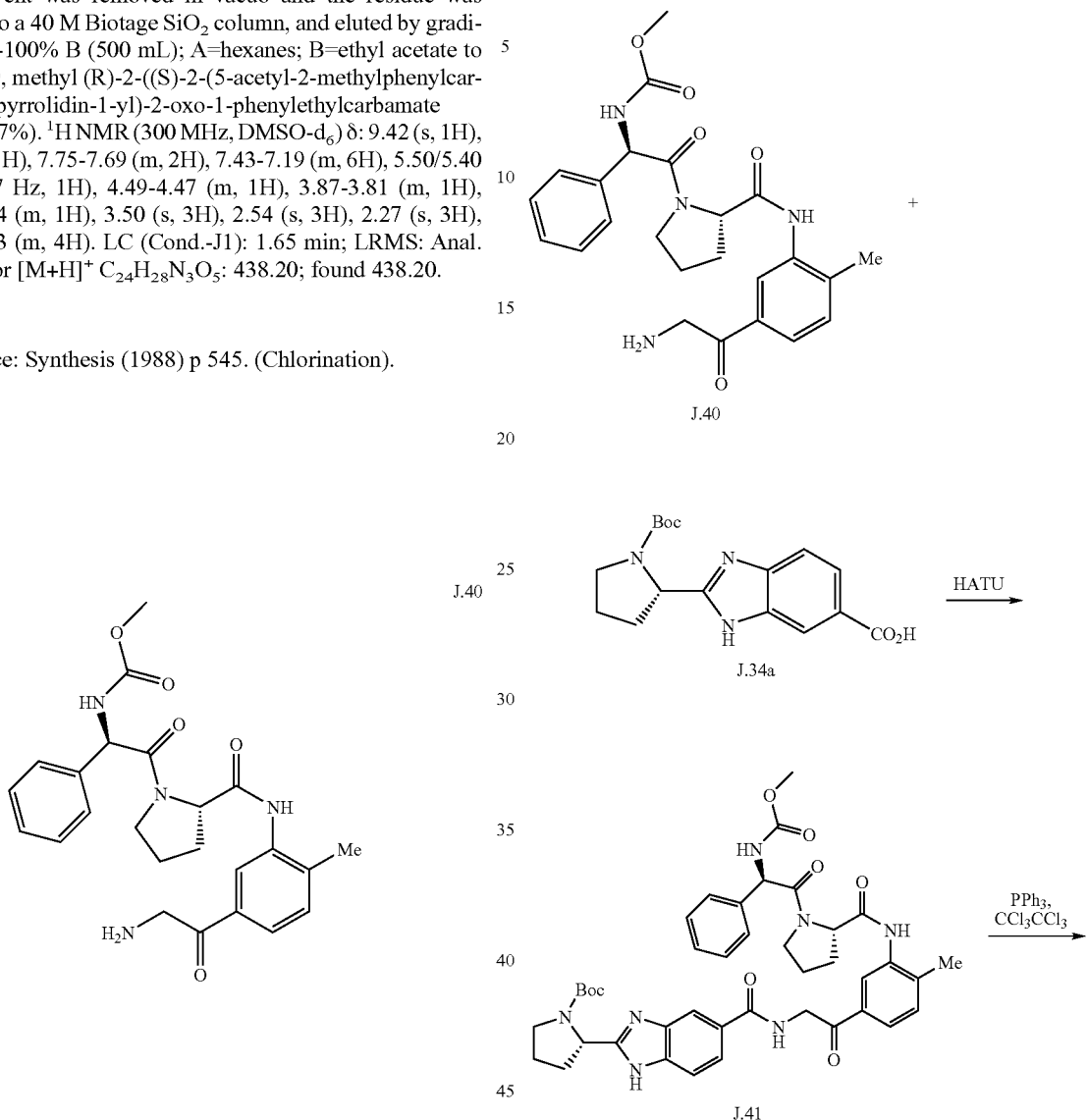

Benzyltrimethyldichloroiodate (2.0 g, 5.72 mmol) was added to a solution of J.39 (1.25 g, 2.86 mmol) in dichloromethane (65 mL) and methanol (20 mL). The reaction was heated for 3 h at 75° C. before being concentrated by rotory evaporation. The residue was taken up in ethyl acetate and washed with sodium thiosulfate soln, brine, and dried (MgSO$_4$) to afford an α-chloroketone. LC (Cond.-J1): 1.70 min; LC/MS: Anal. Calcd. for [M+H]$^+$ C$_{24}$H$_{27}$ClN$_3$O$_5$: 471.16; found: 471.

The α-chloroketone was converted to the α-aminoketone J.40 as described in example J.31. [α-azidoketone: LC (Cond.-J1): 1.70 min; LRMS: Anal. Calcd. for [M+H]$^+$ C$_{24}$H$_{27}$N$_6$O$_5$: 479.20; found: 479.20.] J.26 LC (Cond.-J1): 1.70 min; LRMS: Anal. Calcd. for [M+H]$^+$ C$_{24}$H$_{29}$N$_4$O$_5$: 453.21; found: 453.

Example J.41-J.42h

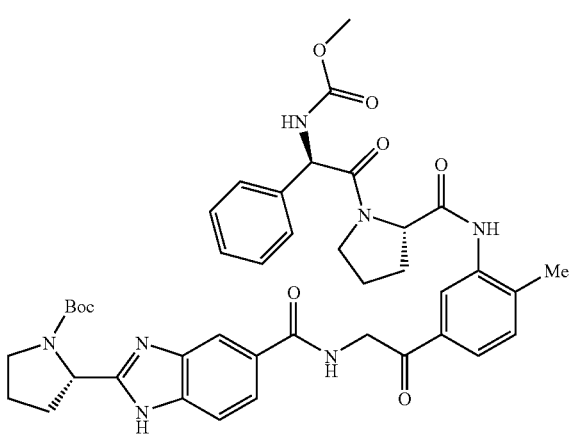

J.41

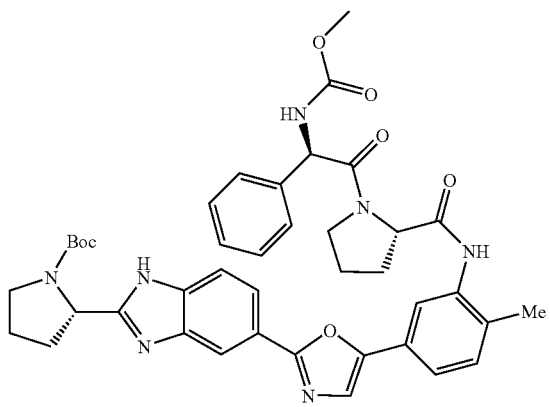

J.42

The α-aminoketone 3.40 was coupled with J.34a as described in example J.37 to give J.41: LC (Cond.-J1): 1.90 min; LRMS: Anal. Calcd. for [M+H]$^+$ C$_{41}$H$_{48}$N$_7$O$_8$: 766.36; found: 766.37.

A solution of J.41 (237 mg, 0.31 mmol), triphenylphosphine (162 mg, 0.62 mmol), and triethylamine (0.2 mL, 1.74 mmol) in dichloromethane (3 mL) was stirred about 5 min under nitrogen atmosphere before addition of hexachloroethane (146 mg, 0.62 mmol) in one portion. The reaction mixture was stirred 18 h, partially concentrated, and applied to a 12 M Biotage silica gel column and eluted by gradient 40%-100% B. A=hexanes; B=ethyl acetate to give J.42, 95 mg (41%). LC (Cond.-J1); 1.95 min; LRMS: Anal. Calcd. for [M+H]$^+$ C$_{41}$H$_{46}$N$_7$O$_7$: 748.36; found: 748.29.

J.41a

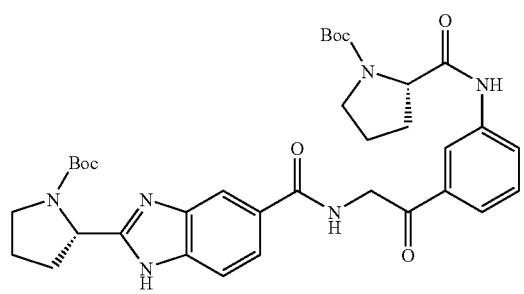

RT = 1.64 min (Cond.-J1); LCMS: Anal. Calcd. for [M + H]$^+$ C$_{35}$H$_{45}$N$_6$O$_7$: 661.34; found 661.30.

From J.35a and N-Boc-L-proline, prepared as described enroute to J.38.

J.41b

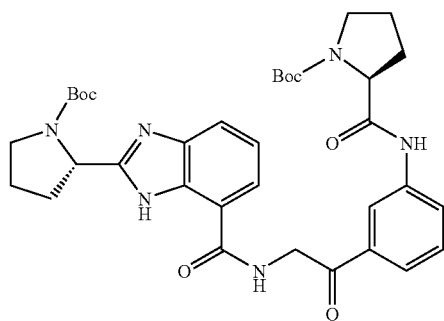

RT = 1.82 min (Cond.-J1); LCMS: Anal. Calcd. for [M + H]$^+$ C$_{35}$H$_{45}$N$_6$O$_7$: 661.34; found 661.32.

From J.35 and N-Boc-L-proline, prepared as described enroute to J.38.

| | | |
|---|---|---|
| J.42a | 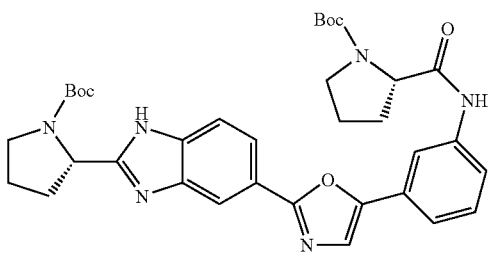 From J.41a | RT = 2.64 min (D-Cond. 2); LC/MS: Anal. Calcd. for [M + H]$^+$ C$_{35}$H$_{43}$N$_6$O$_6$: 643.32; found: 643.35. HRMS: Anal. Calcd. for [M + H]$^+$ C$_{35}$H$_{43}$N$_6$O$_6$: 643.3244; found 643.3242. |
| J.42b | 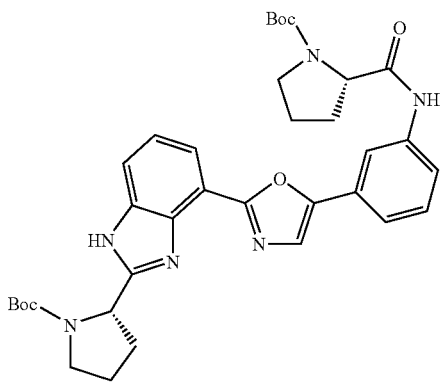 From J.41b | RT = 2.97 min (D-Cond. 2); LC/MS: Anal. Calcd. for [M + H]$^+$ C$_{35}$H$_{43}$N$_6$O$_6$: 643.32; found: 643.37. HRMS: Anal. Calcd. for [M + H]$^+$ C$_{35}$H$_{43}$N$_6$O$_6$: 643.3244; found 643.3265. |
| J.42c | 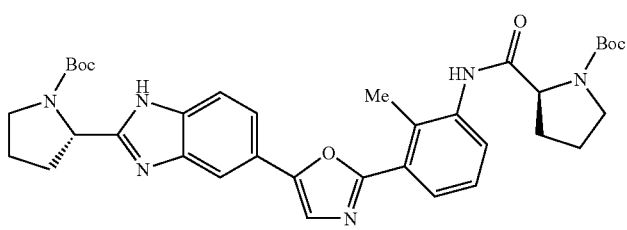 From J.37 | RT = 2.51 min (D-Cond. 2); LC/MS: Anal. Calcd. for [M + H]$^+$ C$_{36}$H$_{45}$N$_6$O$_6$: 657.34; found: 657.36. HRMS: Anal. Calcd. for [M + H]$^+$ C$_{36}$H$_{45}$N$_6$O$_6$: 657.3401; found 657.3407. |
| J.42d | 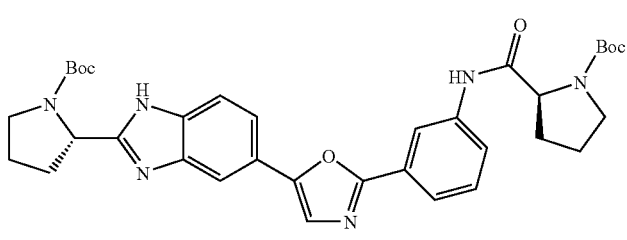 From J.37a | RT = 2.61 min (D-Cond. 2); LC/MS: Anal. Calcd. for [M + H]$^+$ C$_{35}$H$_{43}$N$_6$O$_6$: 643.32; found: 643.41. |
| J.42e | 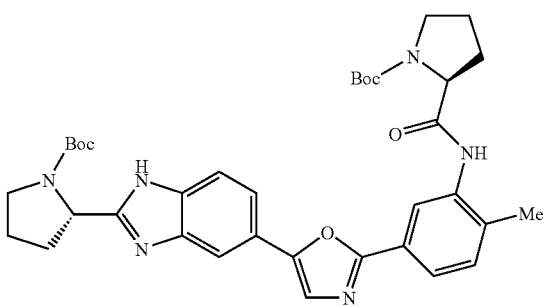 From J.37b | RT = 2.63 min (D-Cond. 2); LC/MS: Anal. Calcd. for [M + H]$^+$ C$_{36}$H$_{45}$N$_6$O$_6$: 657.34; found: 657.73. HRMS: Anal. Calcd. for [M + H]$^+$ C$_{36}$H$_{45}$N$_6$O$_6$: 657.3401; found 657.3397. |

| | | |
|---|---|---|
| J.42f | 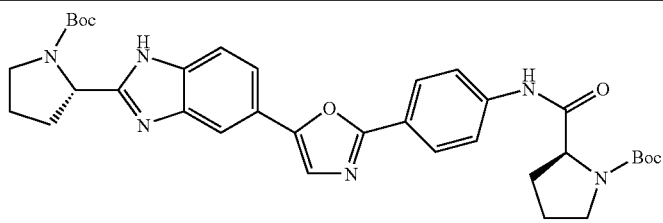<br>From J.37c | RT = 1.59 min (D-Cond. 2);<br>LC/MS: Anal. Calcd. for<br>[M + H]$^+$ C$_{35}$H$_{43}$N$_6$O$_6$:<br>643.32; found: 643.41. |
| J.42g | 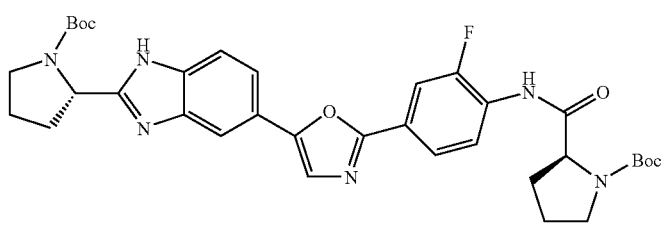<br>From J.37d | RT = 2.64 min (D-Cond. 2);<br>LC/MS: Anal. Calcd. for<br>[M + H]$^+$ C$_{35}$H$_{42}$FN$_6$O$_6$:<br>661.32; found: 661.40. |
| J.42h | 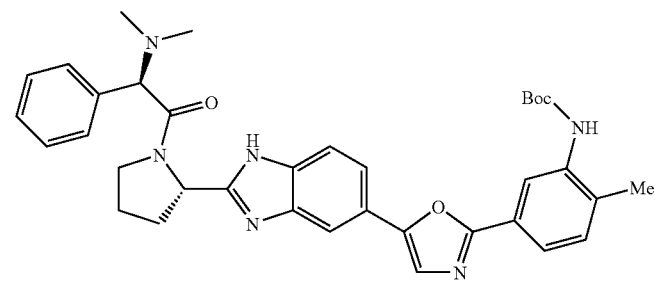<br>From J.37e | RT = 2.41 min (D-Cond. 2);<br>LC/MS: Anal. Calcd. for<br>[M + H]$^+$ C$_{36}$H$_{41}$N$_6$O$_4$:<br>621.32; found: 621.21. |

Examples J.43-J.43j

The pyrrolidines examples J.42-J.42h were treated with HCl as described in example J.39 to give examples J.43-J.43j as HCl salts.

| | | |
|---|---|---|
| J.43 | 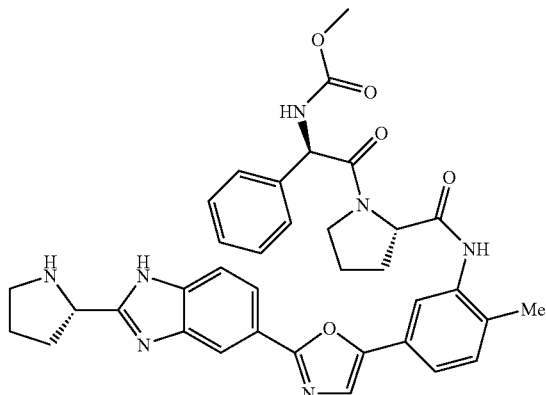<br>From J.42 | RT = 1.80 min (Cond.-J1)<br>LCMS: Anal. Calcd. for<br>[M + H]$^+$ C$_{36}$H$_{38}$N$_7$O$_5$:<br>648.29; found 648. |

| | | |
|---|---|---|
| J.43a | 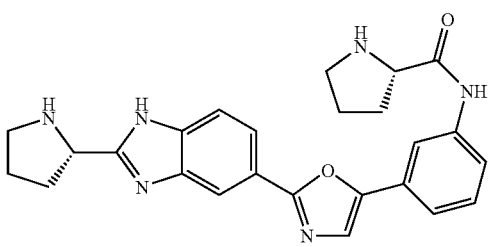<br>From J.42a | RT = 1.69 min (D-Cond. 2); LC/MS: Anal. Calcd. for [M + H]$^+$ C$_{25}$H$_{27}$N$_6$O$_2$: 443.22; found: 443.23. |
| J.43b | 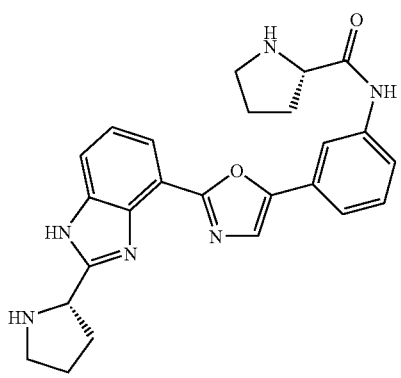<br>From J.42b | RT = 1.86 min (D-Cond. 2); LC/MS: Anal. Calcd. for [M + H]$^+$ C$_{25}$H$_{27}$N$_6$O$_2$: 443.22; found: 443.07. HRMS: Anal. Calcd. for [M + H]$^+$ C$_{25}$H$_{27}$N$_6$O$_2$: 443.2195; found 443.2213. |
| J.43c | 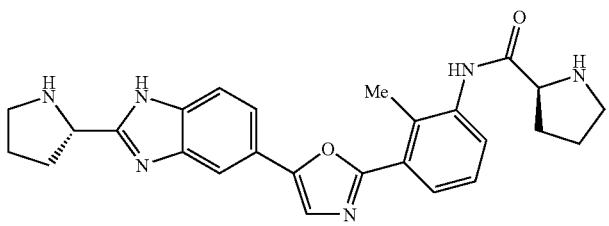<br>From J.42c | RT = 1.51 min (D-Cond. 2); LC/MS: Anal. Calcd. for [M + H]$^+$ C$_{26}$H$_{29}$N$_6$O$_2$: 457.24; found: 457.19. |
| J.43d | 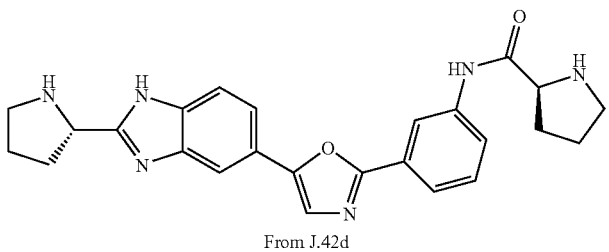 [SMILES: O=C(Nc1cccc(-c2ncc(-c3ccc4[nH]c([C@@H]5CCCN5)nc4c3)o2)c1)[C@@H]1CCCN1]<br>From J.42d | RT = 1.64 min (D-Cond. 2); LC/MS: Anal. Calcd. for [M + H]$^+$ C$_{25}$H$_{27}$N$_6$O$_2$: 443.22; found: 443.31. HRMS: Anal. Calcd. for [M + H]$^+$ C$_{25}$H$_{27}$N$_6$O$_2$: 443.2195; found 443.2205. |
| J.43e | 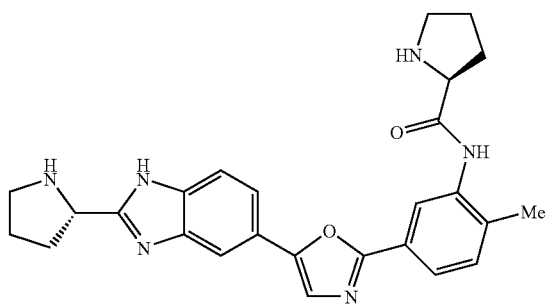<br>From J.42e | RT = 1.70 min (D-Cond. 2); LC/MS: Anal. Calcd. for [M + H]$^+$ C$_{26}$H$_{29}$N$_6$O$_2$: 457.24; found: 457.29. HRMS: Anal. Calcd. for [M + H]$^+$ C$_{26}$H$_{29}$N$_6$O$_2$: 457.2352; found 457.2332. |

-continued

| | | |
|---|---|---|
| J.43f | 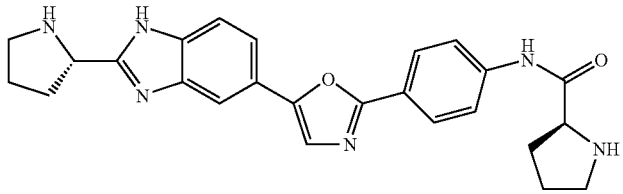<br>From J.42f | RT = 1.59 min (D-Cond. 2);<br>LC/MS: Anal. Calcd. for<br>[M + H]$^+$ C$_{25}$H$_{27}$N$_6$O$_2$:<br>443.22; found: 443.31.<br>HRMS: Anal. Calcd. for<br>[M + H]$^+$ C$_{25}$H$_{27}$N$_6$O$_2$:<br>443.2195; found 443.2206. |
| J.43g | 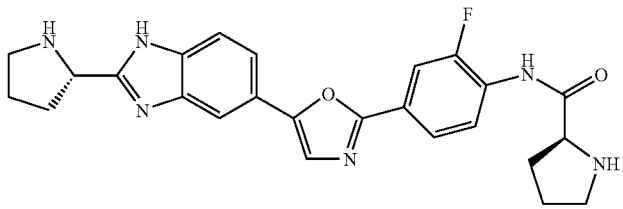<br>From J.42g | RT = 1.61 min (D-Cond. 2);<br>LC/MS: Anal. Calcd. for<br>[M + H]$^+$ C$_{25}$H$_{26}$FN$_6$O$_2$:<br>461.21; found: 461.31.<br>HRMS: Anal. Calcd. for<br>[M + H]$^+$ C$_{25}$H$_{26}$FN$_6$O$_2$:<br>461.2101; found: 461.2101. |
| J.43h | 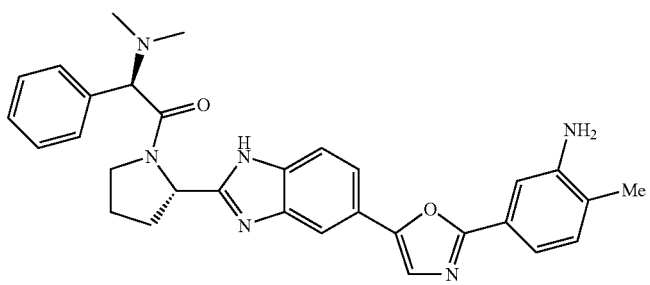<br>From J.42h | RT = 1.70 min (D-Cond. 2);<br>LC/MS: Anal. Calcd. for<br>[M + H]$^+$ C$_{31}$H$_{33}$N$_6$O$_2$:<br>521.27; found: 521.48.<br>HRMS: Anal. Calcd. for<br>[M + H]$^+$ C$_{31}$H$_{33}$N$_6$O$_2$:<br>521.2665; found 521.2673. |
| J.43i | 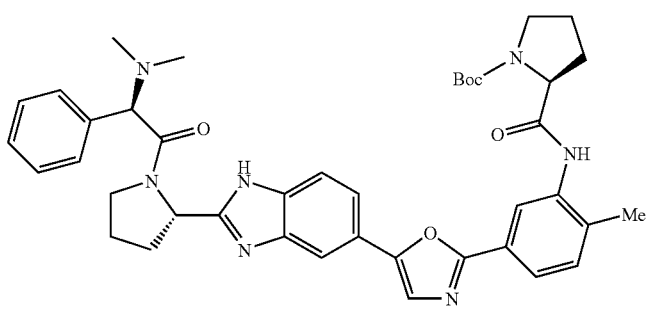<br>From J.43h and N-Boc-L-proline as described in example J.38. | RT = 2.33 min (D-Cond. 2);<br>LC/MS: Anal. Calcd. for<br>[M + H]$^+$ C$_{41}$H$_{48}$N$_7$O$_5$:<br>718.37; found: 718.19.<br>HRMS: Anal. Calcd. for<br>[M + H]$^+$ C$_{41}$H$_{48}$N$_7$O$_5$:<br>718.3717; found 718.3692. |
| J.43j | 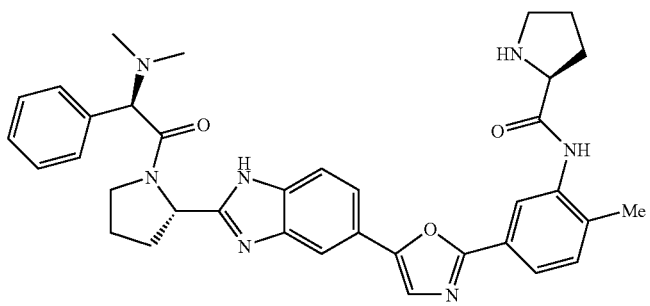<br>From J.43i as described in example J.39 | RT = 1.69 min (D-Cond. 2);<br>LC/MS: Anal. Calcd. for<br>[M + H]$^+$ C$_{36}$H$_{40}$N$_7$O$_3$:<br>618.32; found: 618.38. |

Examples J.44-J.53a

Examples J.44-J.53a were prepared as described in example J.21.

J.44

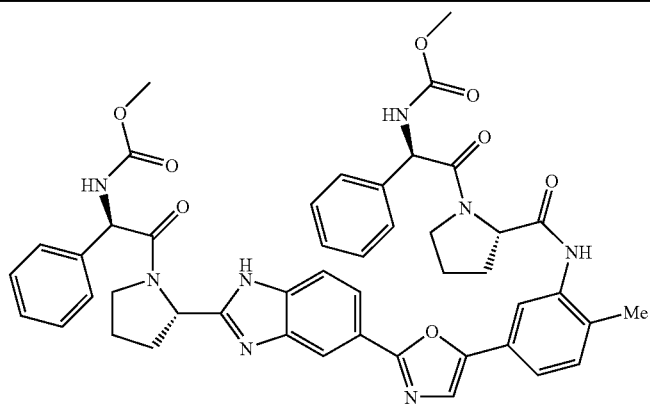

From J.43

RT = 1.91 min (Cond.-J1) LRMS: Anal. Calcd. for [M + H]+ $C_{46}H_{47}N_8O_8$: 839.35; found 839.29. HRMS: Anal. Calcd. for [M + H]+ $C_{46}H_{47}N_8O_8$: 839.3517; found 839.3492.

J.44a

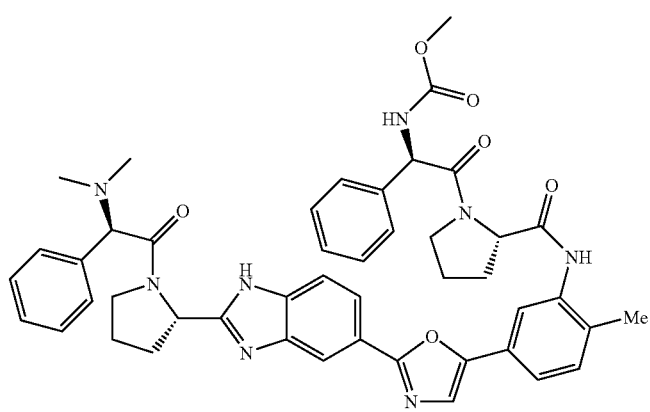

From J.43

RT = 1.80 min (Cond.-J1) LRMS: Anal. Calcd. for [M + H]+ $C_{46}H_{49}N_8O_6$: 809.38; found 809.29. HRMS: Anal. Calcd. for [M + H]+ $C_{46}H_{49}N_8O_8$: 809.3775; found 809.3768.

J.45

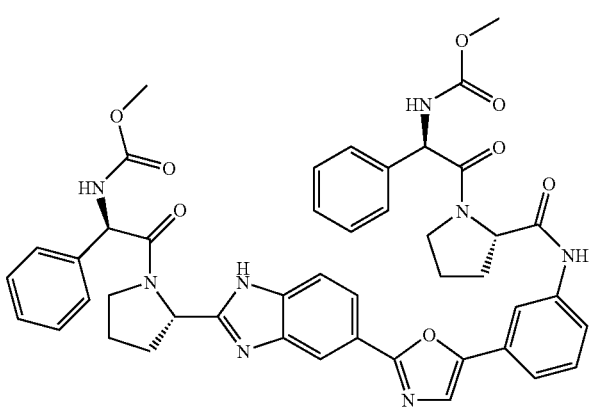

From J.43a

RT = 2.42 min (D-Cond. 2); LC/MS: Anal. Calcd. for [M + H]+ $C_{45}H_{45}N_8O_8$: 825.34; found: 825.40. HRMS: Anal. Calcd. for [M + H]+ $C_{45}H_{45}N_8O_8$: 825.3360; found 825.3366.

J.45a

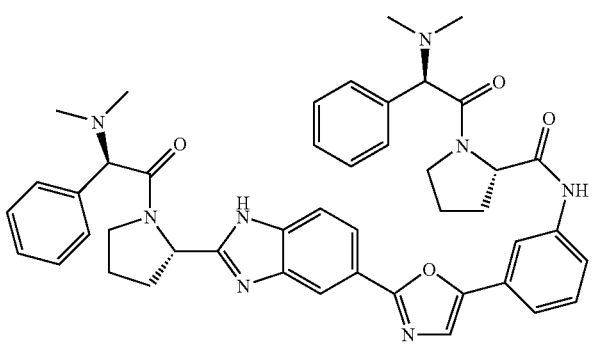

From J.43a

RT = 2.27 min (D-Cond. 2); LC/MS: Anal. Calcd. for [M + H]+ $C_{45}H_{49}N_8O_4$: 765.39; found: 765.36. HRMS: Anal. Calcd. for [M + H]+ $C_{45}H_{49}N_8O_4$: 765.3877; found 765.3879.

J.45b 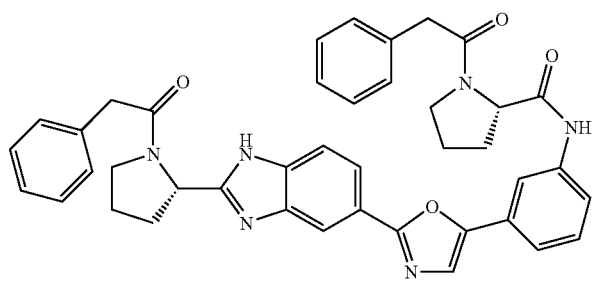
From J.43a

RT = 2.48 min (D-Cond. 2); LC/MS: Anal. Calcd. for [M + H]+ $C_{41}H_{39}N_6O_4$: 679.30; found: 679.37. HRMS: Anal. Calcd. for [M + H]+ $C_{41}H_{39}N_6O_4$: 679.3033; found 679.3037.

J.46 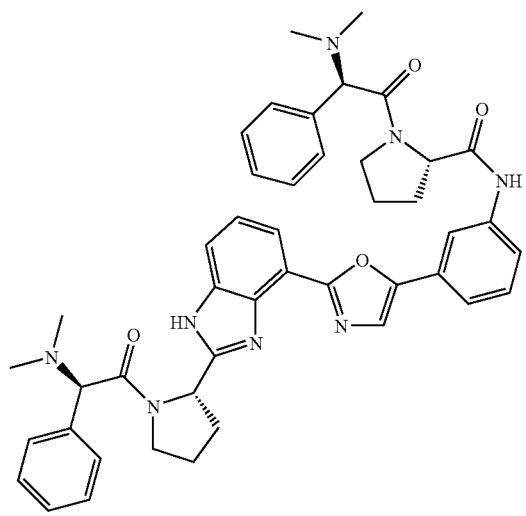
From J.43b

RT = 2.10 min (D-Cond. 2); LC/MS: Anal. Calcd. for [M + H]+ $C_{45}H_{49}N_8O_4$: 765.39; found: 765.72. HRMS: Anal. Calcd. for [M + H]+ $C_{45}H_{49}N_8O_4$: 765.3877; found 765.3899.

J.47 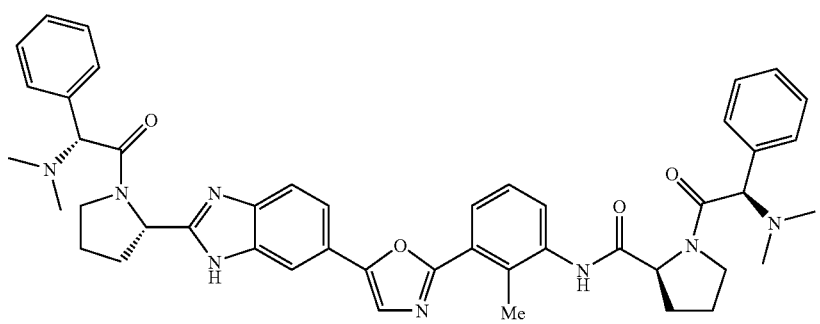
From J.43c

RT = 1.77 min (Cond.-D2); LC/MS: Anal. Calcd. for [M + H]+ $C_{46}H_{51}N_8O_4$: 779.40; found: 779.49. HRMS: Anal. Calcd. for [M + H]+ $C_{46}H_{51}N_8O_4$: 779.4033; found: 779.4042.

J.47a 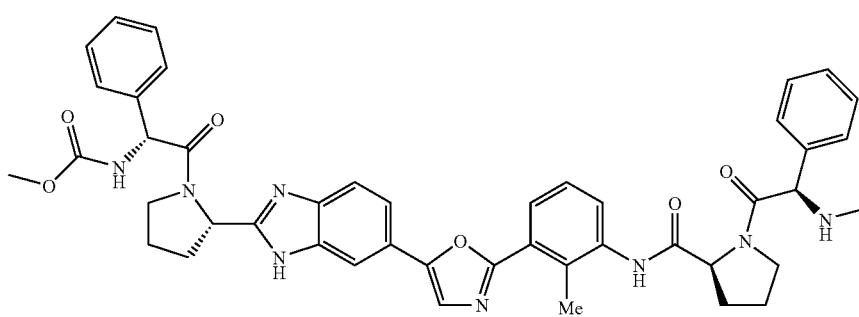
From J.43c

RT = 2.28 min (Cond.-D2); LC/MS: Anal. Calcd. for [M + H]+ $C_{46}H_{47}N_8O_8$: 839.35; found: 839.43. HRMS: Anal. Calcd. For [M + H]+ $C_{46}H_{47}N_8O_8$: 839.3517; found: 839.3519.

-continued

J.48 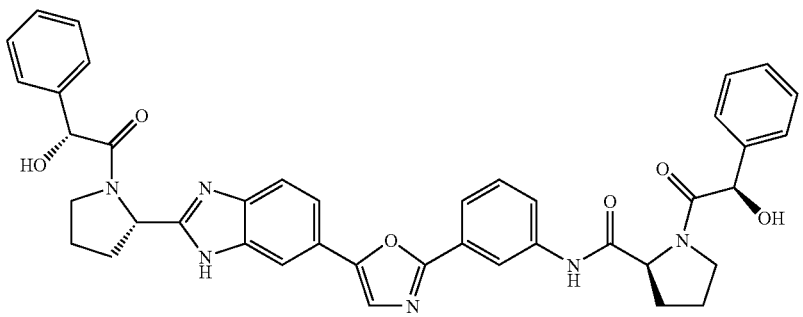
From J.43d

RT = 2.21 min (Cond.-D2); LC/MS: Anal. Calcd. for [M + H]+ $C_{41}H_{39}N_6O_6$: 711.29; found: 711.46. HRMS: Anal. Calcd. for [M + H]+ $C_{41}H_{39}N_6O_6$: 711.2931; found: 711.2942.

J.48a 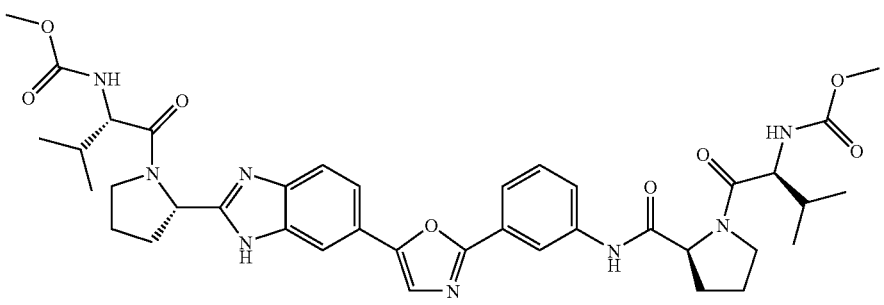
From J.43d

RT = 2.37 min (Cond.-D2); LC/MS: Anal. Calcd. for [M + H]+ $C_{39}H_{49}N_8O_8$: 757.37; found: 757.37. HRMS: Anal. Calcd. for [M + H]+ $C_{39}H_{49}N_8O_8$: 757.3673; found: 757.3705.

J.48b 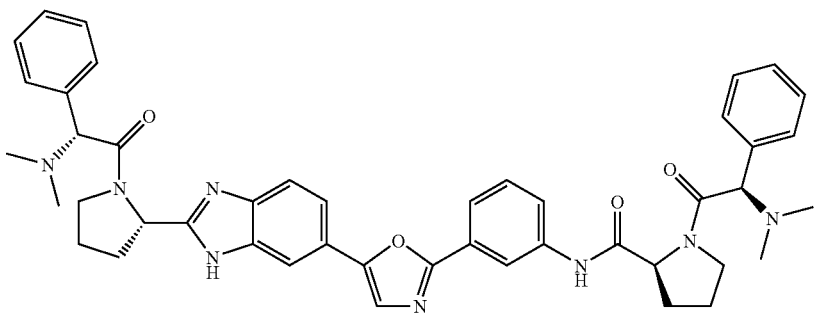
From J.43d

RT = 1.92 min (Cond.-D2); LC/MS: Anal. Calcd. for [M + H]+ $C_{45}H_{49}N_8O_4$: 765.39; found: 765.59. HRMS: Anal. Calcd. for [M + H]+ $C_{45}H_{49}N_8O_4$: 765.3877; found: 765.3841.

J.48c 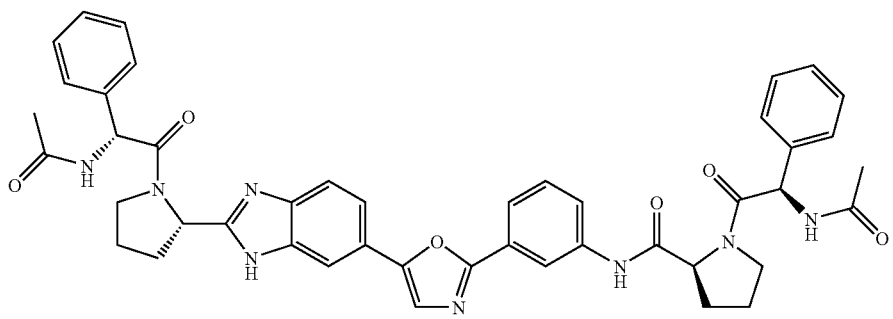
From J.43d

RT = 2.26 min (Cond.-D2); LC/MS: Anal. Calcd. for [M + H]+ $C_{45}H_{45}N_8O_6$: 793.35; found: 793.52. HRMS: Anal. Calcd. for [M + H]+ $C_{45}H_{45}N_8O_6$: 793.3462; found: 793.3452.

| | | |
|---|---|---|
| J.48d | 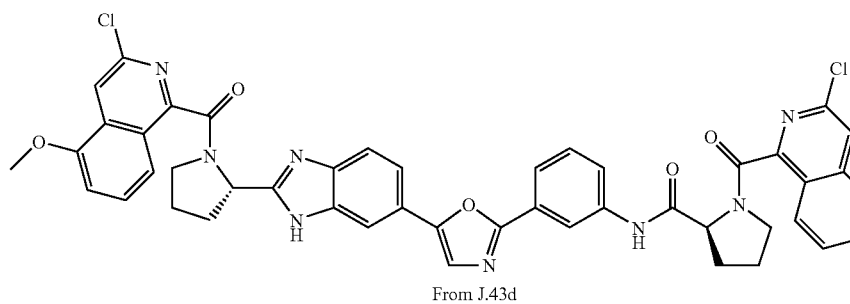 From J.43d | RT = 2.88 min (Cond.-D2); LC/MS: Anal. Calcd. for [M + H]$^+$ C$_{47}$H$_{39}$Cl$_2$N$_8$O$_6$: 881.24; found: 881.50. HRMS: Anal. Calcd. for [M + H]$^+$ C$_{47}$H$_{39}$Cl$_2$N$_8$O$_6$: 881.2370; found: 881.2347. |
| J.49 | 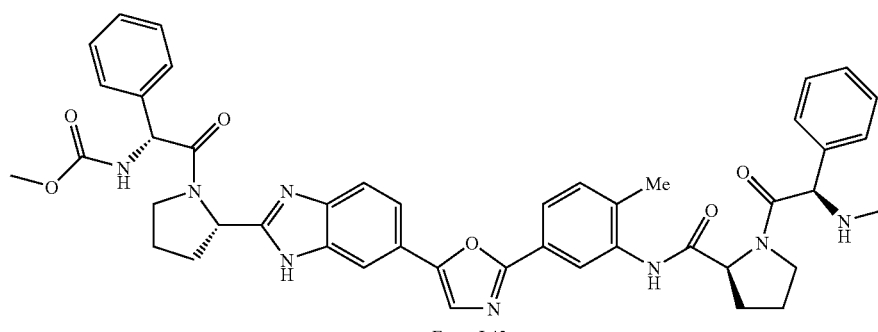 From J.43e | RT = 2.41 min (Cond.-D2); LC/MS: Anal. Calcd. for [M + H]$^+$ C$_{46}$H$_{47}$N$_8$O$_8$: 839.35; found: 839.27. HRMS: Anal. Calcd. for [M + H]$^+$ C$_{46}$H$_{47}$N$_8$O$_8$: 839.3517; found: 839.3535. |
| J.49a | 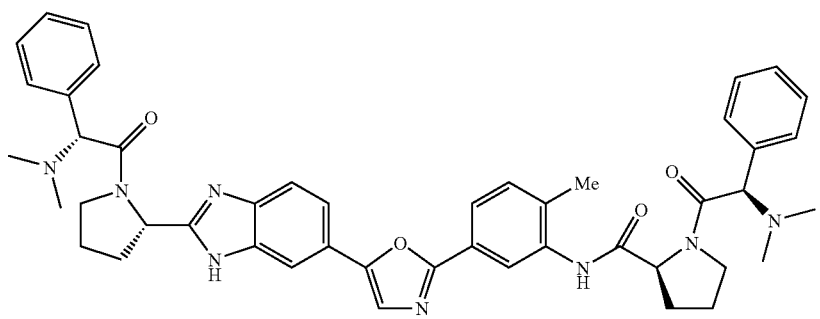 From J.43e | RT = 2.07 min (Cond.-D2); LC/MS: Anal. Calcd. for [M + H]$^+$ C45H51N8O4: 779.40; found: not apparent. HRMS: Anal. Calcd. for [M + H]$^+$ C46H51N8O4: 779.4033; found: 779.4014. |
| J.50 | 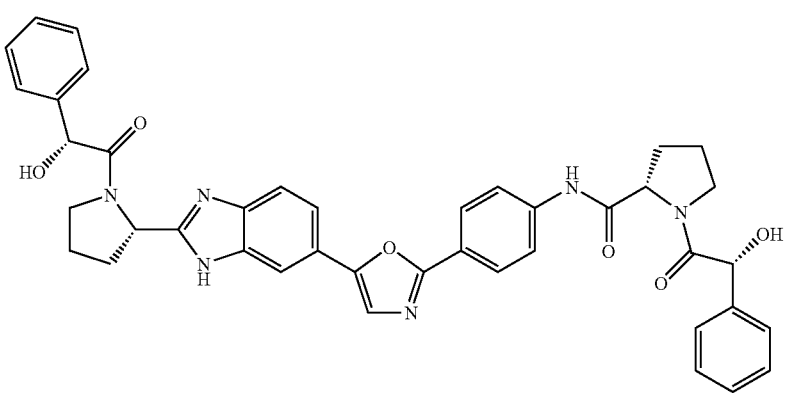 From J.43f | RT = 2.26 min (Cond.-D2); LC/MS: Anal. Calcd. for [M + H]$^+$ C41H39N6O6: 711.29; found: 711.39. HRMS: Anal. Calcd. for [M + H]$^+$ C41H39N6O6: 711.2931; found: 711.2958. |

| | | |
|---|---|---|
| J.50a | 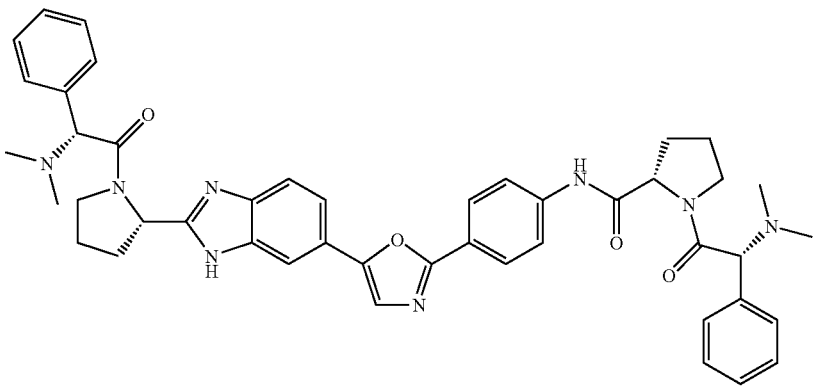<br>From J.43f | RT = 1.92 min (Cond.-D2); LC/MS: Anal. Calcd. for [M + H]+ C45H49N8O4: 765.39; found: 765.53. HRMS: Anal. Calcd. for [M + H]+ C45H49N8O4: 765.3877; found: 765.3843. |
| J.50b | 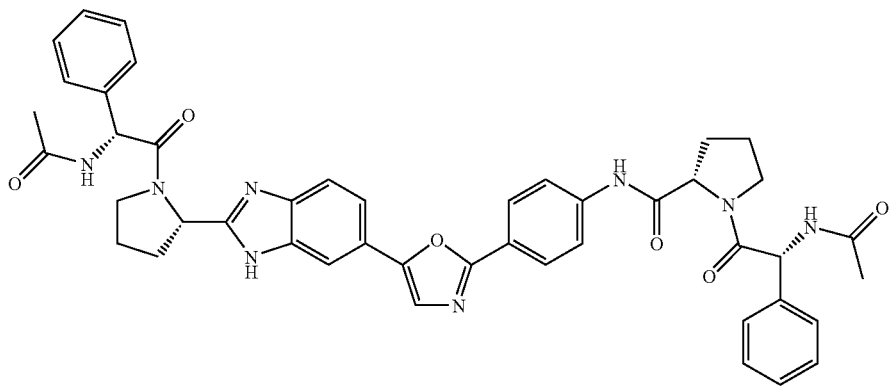<br>From J.43f | RT = 2.29 min (Cond.-D2); LC/MS: Anal. Calcd. for [M + H]+ C45H45N8O6: 793.35; found: 793.49. HRMS: Anal. Calcd. for [M + H]+ C45H45N8O6: 793.3462; found: 793.3442. |
| J.50c | 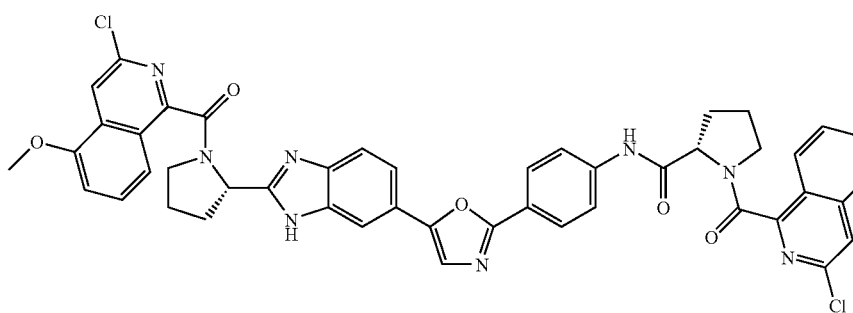<br>From J.43f | RT = 2.99 min (Cond.-D2); LC/MS: Anal. Calcd. for [M + H]+ C47H39Cl2N8O6: 881.24; found: 883.41. HRMS: Anal. Calcd. for [M + H]+ C47H39Cl2N8O6: 881.2370; found: 881.2349. |
| J.51 | 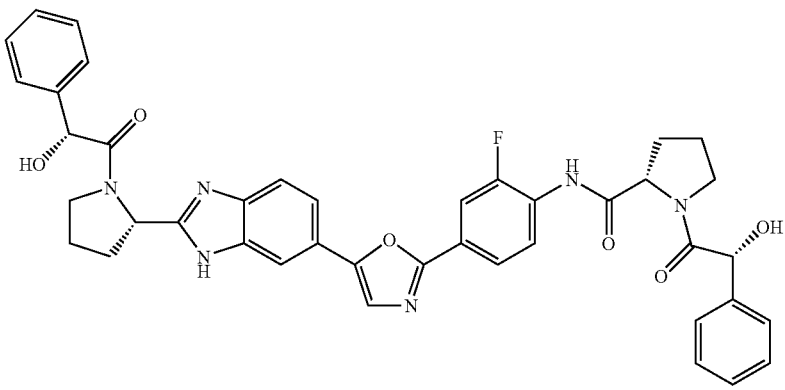<br>From J.43g | RT = 2.29 min (Cond.-D2); LC/MS: Anal. Calcd. for [M + H]+ C41H38FN6O6: 729.28; found: 729.36. HRMS: Anal. Calcd. for [M + H]+ C41H38FN6O6: 729.2837; found: 729.2847. |

| | | |
|---|---|---|
| J.51a | 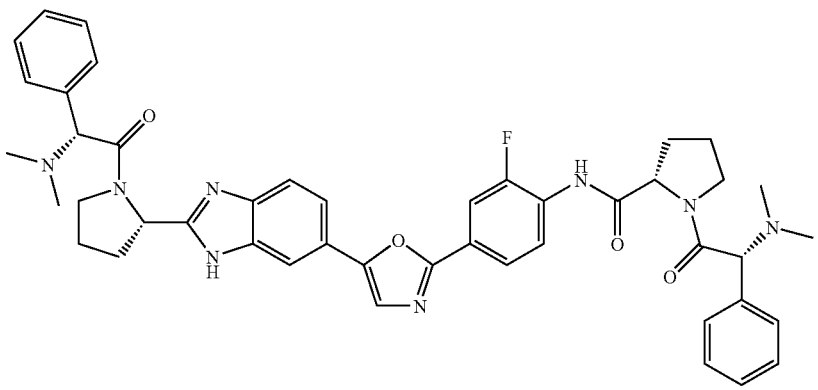<br>From J.43g | RT = 1.93 min (Cond.-D2); LC/MS: Anal. Calcd. for [M + H]+ C45H48FN8O4: 783.38; found: 783.52. HRMS: Anal. Calcd. for [M + H]+ C45H48FN8O4: 783.3783; found: 783.3764. |
| J.51b | 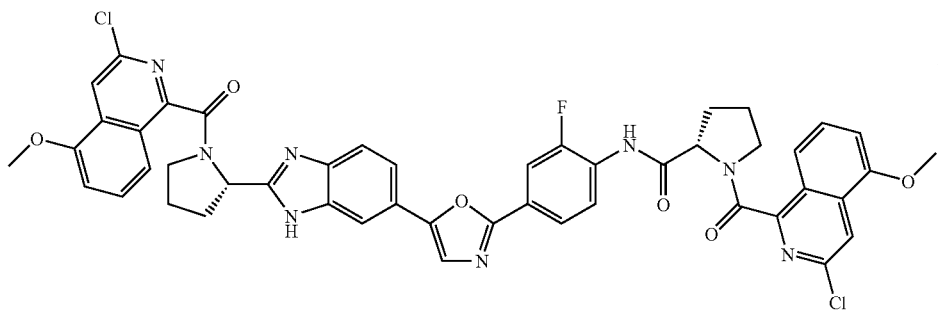<br>From J.43g | RT = 2.89 min (Cond.-D2); LRMS: Anal. Calcd. for [M + H]+ C47H38ClFN8O6: 899.23; found: 897.19. HRMS: Anal. Calcd. for [M + H]+ C47H38ClFN8O6: 899.2275; found: 899.2287. |
| J.52 | 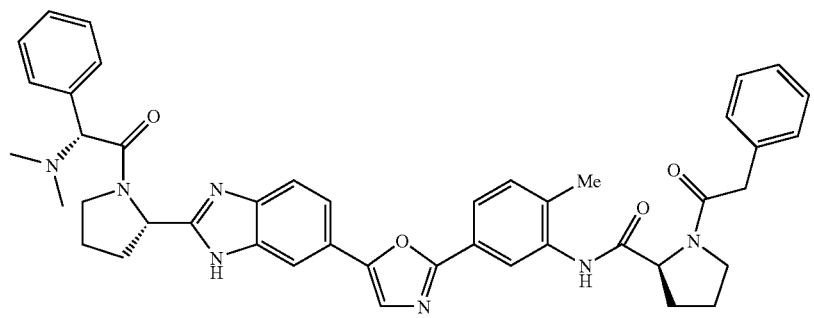<br>From J.43j | RT = 2.23 min (Cond.-D2); LC/MS: Anal. Calcd. for [M + H]+ C44H46N7O4: 736.36; found: 737.00. HRMS: Anal. Calcd. for [M + H]+ C44H46N7O4: 736.3611; found: 736.3622. |
| J.52a | 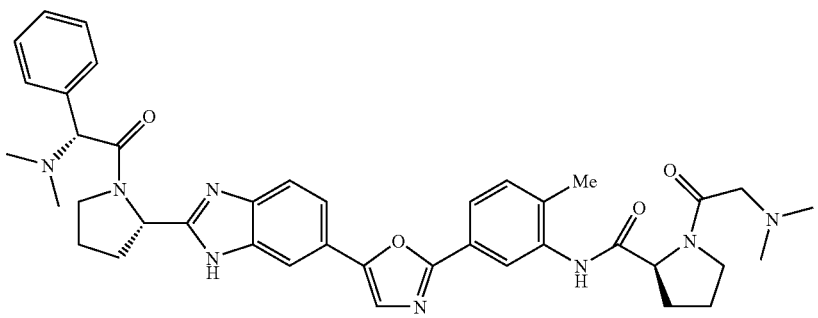<br>From J.43j | RT = 1.75 min (Cond.-D2); LC/MS: Anal. Calcd. for [M + H]+ C40H47N8O4: 703.37; found: 703.81. HRMS: Anal. Calcd. for [M + H]+ C40H47N8O4: 703.3720; found: 703.3748. |

| | | |
|---|---|---|
| J.52b | 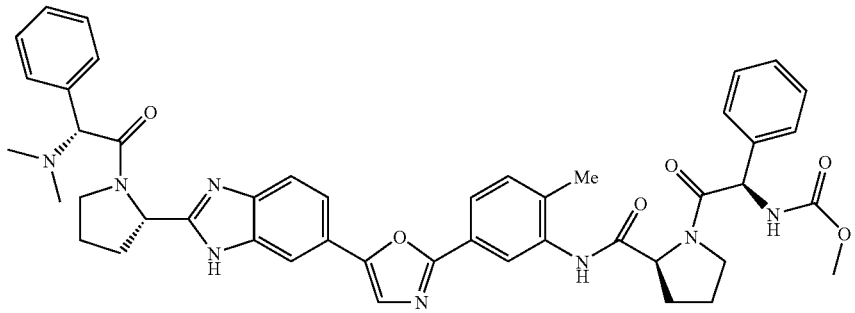<br>From J.43j | RT = 2.22 min (Cond.-D2); LC/MS: Anal. Calcd. for [M + H]$^+$ C46H49N8O6: 809.38; found: 809.57. HRMS: Anal. Calcd. for [M + H]$^+$ C46H49N8O6: 809.3775; found: 809.3803. |
| J.52c | 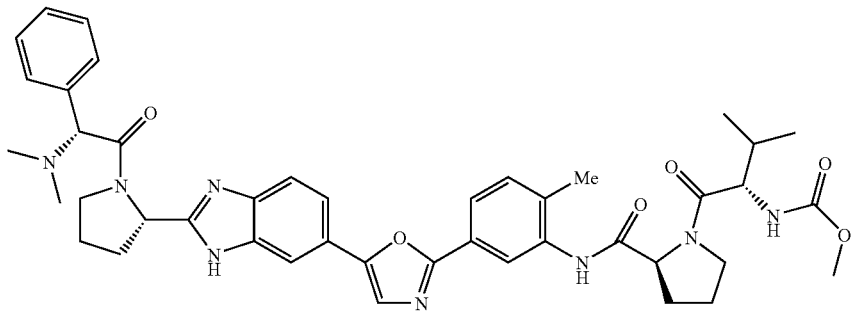<br>From J.43j | RT = 2.27 min (Cond.-D2); LC/MS: Anal. Calcd. for [M + H]$^+$ C43H51N8O6: 775.39; found: 775.39. HRMS: Anal. Calcd. for [M + H]$^+$ C43H51N8O6: 775.3932; found: 775.3921. |
| J.52d | 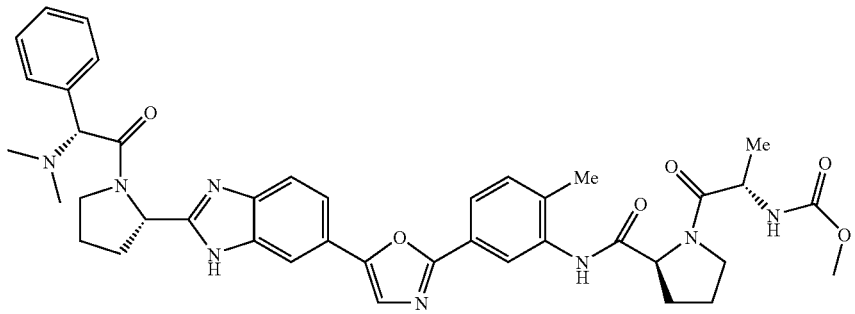<br>From J.43j | RT = 2.09 min (Cond.-D2); LC/MS: Anal. Calcd. for [M + H]$^+$ C41H47N8O6: 747.36; found: 747.34. HRMS: Anal. Calcd. for [M + H]$^+$ C41H47N8O6: 747.3619; found: 747.3610. |
| J.53 | 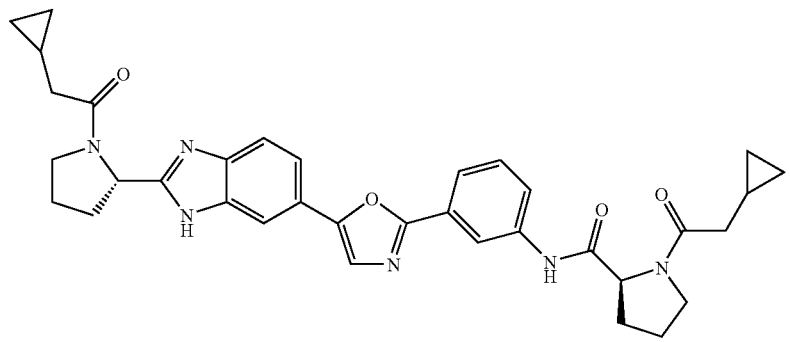<br>From J.43d | RT = 2.22 min (Cond.-D2); LC/MS: Anal. Calcd. for [M + H]$^+$ C$_{35}$H$_{39}$N$_6$O$_4$: 607.30; found: 607.71. HRMS: Anal. Calcd. for [M + H]$^+$ C$_{35}$H$_{39}$N$_6$O$_4$: 607.3033; found: 607.3015. |

-continued

J.53a

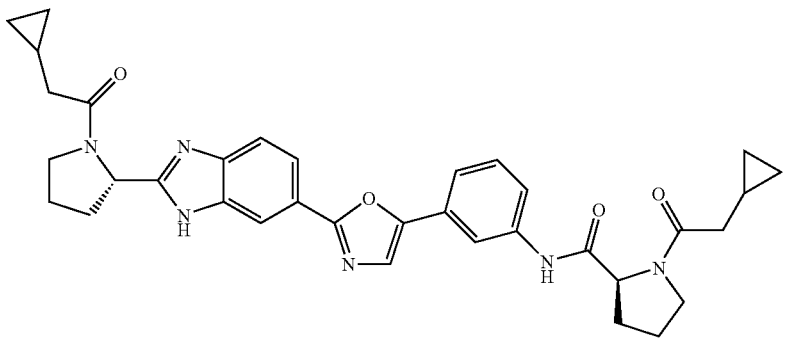

From J.43a

RT = 2.28 min
(Cond.-D2); LC/MS:
Anal. Calcd. for
[M + H]+
$C_{35}H_{39}N_6O_4$: 607.30;
found: 607.34.

BIOLOGICAL ACTIVITY

An HCV Replicon assay was utilized in the present disclosure, and was prepared, conducted and validated as described in commonly owned PCT/US2006/022197 and in O'Boyle et. al. *Antimicrob Agents Chemother.* 2005 April; 49(4):1346-53. Assay methods incorporating luciferase reporters have also been used as described (Apath.com).

HCV-neo replicon cells and replicon cells containing mutations in the NS5A region were used to test the currently described family of compounds. The compounds were determined to have more than 10-fold less inhibitory activity on cells containing mutations than wild-type cells. Thus, the compounds of the present disclosure can be effective in inhibiting the function of the HCV NS5A protein and are understood to be as effective in combinations as previously described in application PCT/US2006/022197 and commonly owned WO/O4014852. Further, the compounds of the present disclosure can be effective against the HCV 1b genotype. It should also be understood that the compounds of the present disclosure can inhibit multiple genotypes of HCV. Table 2 shows the $EC_{50}$ (Effective 50% inhibitory concentration) values of representative compounds of the present disclosure against the HCV 1b genotype. In one embodiment, compounds of the present disclosure are inhibitory versus 1a, 1b, 2a, 2b, 3a, 4a, and 5a genotypes. $EC_{50}$ values against HCV 1b are as follows A (1-10 μM); B (100-999 nM); C (4.57-99 nM); D (2 pM-4.57 nM).

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

TABLE 2

| Example | EC50 Range | Name |
|---|---|---|
| J.21 | D | methyl ((1S)-1-(((2S)-2-(8-(4-(2-((2S)-1-((2S)-2-((methoxycarbonyl)amino)-3-methylbutanoyl)-2-pyrrolidinyl)-1H-imidazol-4-yl)phenyl)-1,4,5,6-tetrahydrobenzo[3,4]cyclohepta[1,2-d]imidazol-2-yl)-1-pyrrolidinyl)carbonyl)-2-methylpropyl)carbamate |
| J.21a | D | (1R)-2-((2S)-2-(8-(2-((2S)-1-((2R)-2-(diethylamino)-2-phenylacetyl)-2-pyrrolidinyl)-1H-benzimidazol-5-yl)-1,4,5,6-tetrahydrobenzo[3,4]cyclohepta[1,2-d]imidazol-2-yl)-1-pyrrolidinyl)-N,N-diethyl-2-oxo-1-phenylethanamine |
| J.22 | D | methyl ((1S)-1-(((2S)-2-(5-(4-(2-((2S)-1-((2S)-2-((methoxycarbonyl)amino)-3-methylbutanoyl)-2-pyrrolidinyl)-1H-imidazol-4-yl)phenyl)-1H-benzimidazol-2-yl)-1-pyrrolidinyl)carbonyl)-2-methylpropyl)carbamate |
| J.22a | D | (1R)-2-((2S)-2-(4-(4-(2-((2S)-1-((2R)-2-(diethylamino)-2-phenylacetyl)-2-pyrrolidinyl)-1H-benzimidazol-5-yl)phenyl)-1H-imidazol-2-yl)-1-pyrrolidinyl)-N,N-diethyl-2-oxo-1-phenylethanamine |
| J.22b | D | methyl ((1R)-2-((2S)-2-(4-(4-(2-((2S)-1-((2R)-2-((methoxycarbonyl)amino)-2-phenylacetyl)-2-pyrrolidinyl)-1H-benzimidazol-5-yl)phenyl)-1H-imidazol-2-yl)-1-pyrrolidinyl)-2-oxo-1-phenylethyl)carbamate |
| J.23 | D | methyl ((1S)-1-(((2S)-2-(5-(3-(2-((2S)-1-((2S)-2-((methoxycarbonyl)amino)-3-methylbutanoyl)-2-pyrrolidinyl)-1H-imidazol-4-yl)phenyl)-1H-benzimidazol-2-yl)-1-pyrrolidinyl)carbonyl)-2-methylpropyl)carbamate |
| J.23a | D | (1R)-2-((2S)-2-(4-(3-(2-((2S)-1-((2R)-2-(diethylamino)-2-phenylacetyl)-2-pyrrolidinyl)-1H-benzimidazol-5-yl)phenyl)-1H-imidazol-2-yl)-1-pyrrolidinyl)-N,N-diethyl-2-oxo-1-phenylethanamine |
| J.23b | D | methyl ((1R)-2-((2S)-2-(4-(3-(2-((2S)-1-((2R)-2-((methoxycarbonyl)amino)-2-phenylacetyl)-2-pyrrolidinyl)-1H-benzimidazol-5-yl)phenyl)-1H-imidazol-2-yl)-1-pyrrolidinyl)-2-oxo-1-phenylethyl)carbamate |

TABLE 2-continued

| Example | EC50 | Range | Name |
|---|---|---|---|
| J.24 | 10 pM | D | methyl ((1S)-1-(((1R,3S,5R)-3-(8-(2-((1R,3S,5R)-2-((2S)-2-((methoxycarbonyl)amino)-3-methylbutanoyl-2-azabicyclo[3.1.0]hex-3-yl)-1H-benzimidazol-5-yl)-1,4,5,6-tetrahydrobenzo[3,4]cyclohepta[1,2-d]imidazol-2-yl)-2-azabicyclo[3.1.0]hex-2-yl)carbonyl)-2-methylpropyl)carbamate |
| J.25 | | D | methyl ((1S)-1-(((2S)-2-(5-(2-((2S)-1-((2S)-2-((methoxycarbonyl)amino)-3-methylbutanoyl)-2-pyrrolidinyl)-4,5-dihydro-3H-naphtho[1,2-d]imidazol-7-yl)-1H-benzimidazol-2-yl)-1-pyrrolidinyl)carbonyl)-2-methylpropyl)carbamate |
| J.26 | 5 pM | D | methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-4-yl)-4-biphenylyl)-1H-benzimidazol-2-yl)-1-pyrrolidinyl)carbonyl)-2-methylpropyl)carbamate |
| J.27 | | D | methyl ((1S)-1-(((2S)-2-(5-(2-((2S)-1-((2S)-2-((methoxycarbonyl)amino)-3-methylbutanoyl)-2-pyrrolidinyl)-3H-naphtho[1,2-d]imidazol-7-yl)-1H-benzimidazol-2-yl)-1-pyrrolidinyl)carbonyl)-2-methylpropyl)carbamate |
| J.27a | | D | (1R)-2-((2R)-2-(7-(2-((2S)-1-((2R)-2-(diethylamino)-2-phenylacetyl)-2-pyrrolidinyl)-1H-benzimidazol-5-yl)-1H-naphtho[1,2-d]imidazol-2-yl)-1-pyrrolidinyl)-N,N-diethyl-2-oxo-1-phenylethanamine |
| J.27b | | D | methyl ((1S)-1-(((2S)-2-(5-(4-(2-((2S)-1-((2S)-2-((methoxycarbonyl)amino)-3-methylbutanoyl)-2-pyrrolidinyl)-1H-naphtho[1,2-d]imidazol-7-yl)phenyl)-1H-benzimidazol-2-yl)-1-pyrrolidinyl)carbonyl)-2-methylpropyl)carbamate |
| J.27c | 3.0 pM | D | methyl ((1R)-2-((2S)-2-(7-(4-(2-((2S)-1-((2R)-2-((methoxycarbonyl)amino)-2-phenylacetyl)-2-pyrrolidinyl)-1H-benzimidazol-5-yl)phenyl)-1H-naphtho[1,2-d]imidazol-2-yl)-1-pyrrolidinyl)-2-oxo-1-phenylethyl)carbamate |
| J.28 | | D | methyl ((1S)-1-(((2S)-2-(5-((4-(2-((2S)-1-((2S)-2-((methoxycarbonyl)amino)-3-methylbutanoyl)-2-pyrrolidinyl)-1H-imidazol-4-yl)phenyl)ethynyl)-1H-benzimidazol-2-yl)-1-pyrrolidinyl)carbonyl)-2-methylpropyl)carbamate |
| J.28a | | D | (1R)-2-((2S)-2-(4-(4-((2-((2S)-1-((2R)-2-(diethylamino)-2-phenylacetyl)-2-pyrrolidinyl)-1H-benzimidazol-5-yl)ethynyl)phenyl)-1H-imidazol-2-yl)-1-pyrrolidinyl)-N,N-diethyl-2-oxo-1-phenylethanamine |
| J.28a.1 | | D | methyl ((1S)-1-(((2S)-2-(5-((4-(4-ethyl-2-((2S)-1-((2S)-2-((methoxycarbonyl)amino)-3-methylbutanoyl)-2-pyrrolidinyl)-1H-imidazol-5-yl)phenyl)ethynyl)-1H-benzimidazol-2-yl)-1-pyrrolidinyl)carbonyl)-2-methylpropyl)carbamate |
| J.28a.2 | | D | methyl ((1S)-1-(((2S)-2-(4-(cyanomethyl)-5-(4-((2-((2S)-1-((2S)-2-((methoxycarbonyl)amino)-3-methylbutanoyl)-2-pyrrolidinyl)-1H-benzimidazol-5-yl)ethynyl)phenyl)-1H-imidazol-2-yl)-1-pyrrolidinyl)carbonyl)-2-methylpropyl)carbamate |
| J.28b | | D | methyl ((1S)-1-(((1R,3S,5R)-3-(5-((4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)ethynyl)-1H-benzimidazol-2-yl)-2-azabicyclo[3.1.0]hex-2-yl)carbonyl)-2-methylpropyl)carbamate |
| J.28c | | D | methyl ((1S)-1-(((1R,3S,5R)-3-(4-(4-((4-fluoro-2-((1R,3S,5R)-2-((2S)-2-((methoxycarbonyl)amino)-3-methylbutanoyl)-2-azabicyclo[3.1.0]hex-3-yl)-1H-benzimidazol-6-yl)ethynyl)phenyl)-1H-imidazol-2-yl)-2-azabicyclo[3.1.0]hex-2-yl)carbonyl)-2-methylpropyl)carbamate |
| J.28d | | D | methyl ((1S)-1-(((1R,3S,5R)-3-(4-(2-fluoro-4-((2-((1R,3S,5R)-2-((2S)-2-((methoxycarbonyl)amino)-3-methylbutanoyl)-2-azabicyclo[3.1.0]hex-3-yl)-1H-benzimidazol-5-yl)ethynyl)phenyl)-1H-imidazol-2-yl)-2-azabicyclo[3.1.0]hex-2-yl)carbonyl)-2-methylpropyl)carbamate |
| J.28e | | D | methyl ((1S)-1-(((2S)-2-(5-((2-((2S)-1-((2S)-2-((methoxycarbonyl)amino)-3-methylbutanoyl)-2-pyrrolidinyl)-4,5-dihydro-3H-naphtho[1,2-d]imidazol-7-yl)ethynyl)-1H-benzimidazol-2-yl)-1-pyrrolidinyl)carbonyl)-2-methylpropyl)carbamate |
| J.28e.1 | | D | methyl ((1R)-2-((2S)-2-(7-((2-((2S)-1-((2R)-2-((methoxycarbonyl)amino)-2-phenylacetyl)-2-pyrrolidinyl)-1H-benzimidazol-5-yl)ethynyl)-4,5-dihydro-1H-naphtho[1,2-d]imidazol-2-yl)-1-pyrrolidinyl)-2-oxo-1-phenylethyl)carbamate |
| J.28f | | D | methyl ((1S)-1-(((2S)-2-(5-((2-((2S)-1-((2S)-2-((methoxycarbonyl)amino)-3-methylbutanoyl)-2-pyrrolidinyl)-3H-naphtho[1,2-d]imidazol-7-yl)ethynyl)-1H-benzimidazol-2-yl)-1-pyrrolidinyl)carbonyl)-2-methylpropyl)carbamate |
| J.28f.1 | | D | methyl ((1R)-2-((2S)-2-(7-((2-((2S)-1-((2R)-2-((methoxycarbonyl)amino)-2-phenylacetyl)-2-pyrrolidinyl)-1H-benzimidazol-5-yl)ethynyl)-1H-naphtho[1,2-d]imidazol-2-yl)-1-pyrrolidinyl)-2-oxo-1-phenylethyl)carbamate |

TABLE 2-continued

| Example | EC50 | Range | Name |
|---|---|---|---|
| J.28g | | D | methyl ((1S)-1-(((2S)-2-(4-fluoro-6-((2-((2S)-1-((2S)-2-((methoxycarbonyl)amino)-3-methylbutanoyl)-2-pyrrolidinyl)-4,5-dihydro-1H-naphtho[1,2-d]imidazol-7-yl)ethynyl)-1H-benzimidazol-2-yl)-1-pyrrolidinyl)carbonyl)-2-methylpropyl)carbamate |
| J.28h | 120 pM | D | methyl ((1S)-1-(((2S)-2-(4-fluoro-6-((2-((2S)-1-((2S)-2-((methoxycarbonyl)amino)-3-methylbutanoyl)-2-pyrrolidinyl)-1H-naphtho[1,2-d]imidazol-7-yl)ethynyl)-1H-benzimidazol-2-yl)-1-pyrrolidinyl)carbonyl)-2-methylpropyl)carbamate |
| J.28h.1 | | D | methyl ((1S)-1-(((1R,3S,5R)-3-(5-((2-((1R,3S,5R)-2-((2S)-2-((methoxycarbonyl)amino)-3-methylbutanoyl)-2-azabicyclo[3.1.0]hex-3-yl)-4,5-dihydro-1H-naphtho[1,2-d]imidazol-7-yl)ethynyl)-1H-benzimidazol-2-yl)-2-azabicyclo[3.1.0]hex-2-yl)carbonyl)-2-methylpropyl)carbamate |
| J.28h.2 | | D | methyl ((1R)-2-((1R,3S,5R)-3-(7-((2-((1R,3S,5R)-2-((2R)-2-((methoxycarbonyl)amino)-2-phenylacetyl)-2-azabicyclo[3.1.0]hex-3-yl)-1H-benzimidazol-5-yl)ethynyl)-4,5-dihydro-1H-naphtho[1,2-d]imidazol-2-yl)-2-azabicyclo[3.1.0]hex-2-yl)-2-oxo-1-phenylethyl)carbamate |
| J.28i | | D | methyl ((1S)-1-(((1R,3S,5R)-3-(5-((2-(((1R,3S,5R)-2-((2S)-2-((methoxycarbonyl)amino)-3-methylbutanoyl)-2-azabicyclo[3.1.0]hex-3-yl)-1H-naphtho[1,2-d]imidazol-7-yl)ethynyl)-1H-benzimidazol-2-yl)-2-azabicyclo[3.1.0]hex-2-yl)carbonyl)-2-methylpropyl)carbamate |
| J.28i.1 | | D | methyl ((1R)-2-((1R,3S,5R)-3-(7-((2-((1R,3S,5R)-2-((2R)-2-((methoxycarbonyl)amino)-2-phenylacetyl)-2-azabicyclo[3.1.0]hex-3-yl)-1H-benzimidazol-5-yl)ethynyl)-1H-naphtho[1,2-d]imidazol-2-yl)-2-azabicyclo[3.1.0]hex-2-yl)-2-oxo-1-phenylethyl)carbamate |
| J.28i.2 | 0.51 pM | D | methyl ((1S)-1-(4,4-difluorocyclohexyl)-2-((1R,3S,5R)-3-(7-((2-((1R,3S,5R)-2-((2S)-2-(4,4-difluorocyclohexyl)-2-((methoxycarbonyl)amino)acetyl)-2-azabicyclo[3.1.0]hex-3-yl)-1H-benzimidazol-5-yl)ethynyl)-1H-naphtho[1,2-d]imidazol-2-yl)-2-azabicyclo[3.1.0]hex-2-yl)-2-oxoethyl)carbamate |
| J.28i.3 | | D | methyl ((1S)-2-((1R,3S,5R)-3-(7-((2-((1R,3S,5R)-2-((2S)-2-((methoxycarbonyl)amino)-2-(tetrahydro-2H-pyran-4-yl)acetyl)-2-azabicyclo[3.1.0]hex-3-yl)-1H-benzimidazol-5-yl)ethynyl)-1H-naphtho[1,2-d]imidazol-2-yl)-2-azabicyclo[3.1.0]hex-2-yl)-2-oxo-1-(tetrahydro-2H-pyran-4-yl)ethyl)carbamate |
| J.28i.4 | | D | methyl ((1S)-2-((1R,3S,5R)-3-(7-((2-((1R,3S,5R)-2-((2S)-2-((methoxycarbonyl)amino)-3-methylbutanoyl)-2-azabicyclo[3.1.0]hex-3-yl)-1H-benzimidazol-5-yl)ethynyl)-1H-naphtho[1,2-d]imidazol-2-yl)-2-azabicyclo[3.1.0]hex-2-yl)-2-oxo-1-(tetrahydro-2H-pyran-4-yl)ethyl)carbamate |
| J.28j | | D | methyl ((1S)-1-(((1R,3S,5R)-3-(4-fluoro-6-((2-(((1R,3S,5R)-2-((2S)-2-((methoxycarbonyl)amino)-3-methylbutanoyl)-2-azabicyclo[3.1.0]hex-3-yl)-4,5-dihydro-1H-naphtho[1,2-d]imidazol-7-yl)ethynyl)-1H-benzimidazol-2-yl)-2-azabicyclo[3.1.0]hex-2-yl)carbonyl)-2-methylpropyl)carbamate |
| J.28k | | D | methyl ((1S)-1-(((1R,3S,5R)-3-(4-fluoro-6-((2-(((1R,3S,5R)-2-((2S)-2-((methoxycarbonyl)amino)-3-methylbutanoyl)-2-azabicyclo[3.1.0]hex-3-yl)-1H-naphtho[1,2-d]imidazol-7-yl)ethynyl)-1H-benzimidazol-2-yl)-2-azabicyclo[3.1.0]hex-2-yl)carbonyl)-2-methylpropyl)carbamate |
| J.28k.1 | | D | benzyl (1R,3S,5R)-3-(7-((2-(((1R,3S,5R)-2-(N-(methoxycarbonyl)-L-valyl)-2-azabicyclo[3.1.0]hex-3-yl)-1H-benzimidazol-5-yl)ethynyl)-1H-naphtho[1,2-d]imidazol-2-yl)-2-azabicyclo[3.1.0]hexane-2-carboxylate |
| J.28l | 7 nM | C | methyl ((1S)-1-(((2S)-2-(5-(3-((2-((2S)-1-((2R)-2-((methoxycarbonyl)amino)-3-methylbutanoyl)-2-pyrrolidinyl)-1H-benzimidazol-5-yl)ethynyl)phenyl)-1H-imidazol-4-yl)-1-pyrrolidinyl)carbonyl)-2-methylpropyl)carbamate |
| J.28m | 55.7 nM | C | (1R)-2-((2S)-2-(5-(3-((2-((2S)-1-((2R)-2-(diethylamino)-2-phenylacetyl)-2-pyrrolidinyl)-1H-benzimidazol-5-yl)ethynyl)phenyl)-1H-imidazol-4-yl)-1-pyrrolidinyl)-N,N-diethyl-2-oxo-1-phenylethanamine |
| J.28n | | D | methyl ((1S)-1-(((2S)-2-(5-((4-(4-((2S)-1-((2S)-2-((methoxycarbonyl)amino)-3-methylbutanoyl)-2-pyrrolidinyl)-1H-imidazol-5-yl)phenyl)ethynyl)-1H-benzimidazol-2-yl)-1-pyrrolidinyl)carbonyl)-2-methylpropyl)carbamate |
| J.28o | | D | methyl ((1S)-1-(((2S,5S)-2-(5-((2-((2S,5S)-1-((2S)-2-((methoxycarbonyl)amino)-3-methylbutanoyl)-5-methyl-2-pyrrolidinyl)-1H-naphtho[1,2-d]imidazol-7-yl)ethynyl)-1H-benzimidazol-2-yl)-5-methyl-1-pyrrolidinyl)carbonyl)-2-methylpropyl)carbamate |
| J.28p | | D | methyl ((1S)-2-((2S,5S)-2-(7-((2-((2S,5S)-1-((2S)-2-((methoxycarbonyl)amino)-2-(tetrahydro-2H-pyran-4-yl)acetyl)-5-methyl-2-pyrrolidinyl)-1H-benzimidazol-5-yl)ethynyl)-1H- |

TABLE 2-continued

| Example | EC50 | Range | Name |
|---|---|---|---|
| JB.8 | | D | naphtho[1,2-d]imidazol-2-yl)-5-methyl-1-pyrrolidinyl)-2-oxo-1-(tetrahydro-2H-pyran-4-yl)ethyl)carbamate<br>methyl ((1S)-1-(((2S)-2-(4-((4-(2-((2S)-1-((2S)-2-((methoxycarbonyl)amino)-3-methylbutanoyl)-2-pyrrolidinyl)-1H-benzimidazol-5-yl)phenyl)ethynyl)-1H-imidazol-2-yl)-1-pyrrolidinyl)carbonyl)-2-methylpropyl)carbamate |
| JB.8.1 | | B | methyl ((1R)-1-(((2S)-2-(4-((4-(2-((2S)-1-((2R)-2-((methoxycarbonyl)amino)-3-methylbutanoyl)-2-pyrrolidinyl)-1H-benzimidazol-5-yl)phenyl)ethynyl)-1H-imidazol-2-yl)-1-pyrrolidinyl)carbonyl)-2-methylpropyl)carbamate |
| JB.9 | | D | methyl ((1S)-2-((2S)-2-(5-(4-((2-((2S)-1-(N-(methoxycarbonyl)-L-alanyl)-2-pyrrolidinyl)-1H-imidazol-4-yl)ethynyl)phenyl)-1H-benzimidazol-2-yl)-1-pyrrolidinyl)-1-methyl-2-oxoethyl)carbamate |
| JB.10 | | D | methyl ((1S,2R)-2-methoxy-1-(((2S)-2-(5-(4-((2-((2S)-1-(N-(methoxycarbonyl)-O-methyl-L-threonyl)-2-pyrrolidinyl)-1H-imidazol-4-yl)ethynyl)phenyl)-1H-benzimidazol-2-yl)-1-pyrrolidinyl)carbonyl)propyl)carbamate |
| JB.11 | | D | methyl ((1R)-2-((2S)-2-(4-((4-(2-((2S)-1-((2R)-2-((methoxycarbonyl)amino)-2-phenylacetyl)-2-pyrrolidinyl)-1H-benzimidazol-5-yl)phenyl)ethynyl)-1H-imidazol-2-yl)-1-pyrrolidinyl)-2-oxo-1-phenylethyl)carbamate |
| JB.12 | 65.2 pM | D | 2-((2S)-1-((2R)-2-phenyl-2-(1-piperidinyl)acetyl)-2-pyrrolidinyl)-5-(4-((2-((2S)-1-((2R)-2-phenyl-2-(1-piperidinyl)acetyl)-2-pyrrolidinyl)-1H-imidazol-4-yl)ethynyl)phenyl)-1H-benzimidazole |
| J.28r | 15.5 pM | D | methyl ((1S)-1-(((1R,3S,5R)-3-(7-(2-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)ethyl)-1H-naphtho[1,2-d]imidazol-2-yl)-2-azabicyclo[3.1.0]hex-2-yl)carbonyl)-2-methylpropyl)carbamate |
| J.28s | | D | methyl ((1S)-2-((1R,3S,5R)-3-(7-(2-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)ethyl)-1H-naphtho[1,2-d]imidazol-2-yl)-2-azabicyclo[3.1.0]hex-2-yl)-2-oxo-1-(tetrahydro-2H-pyran-4-yl)ethyl)carbamate |
| JB.15 | | D | methyl ((1S)-1-(((2S)-2-(4-(2-(4-(2-((2S)-1-((2S)-2-((methoxycarbonyl)amino)-3-methylbutanoyl)-2-pyrrolidinyl)-1H-benzimidazol-5-yl)phenyl)ethyl)-1H-imidazol-2-yl)-1-pyrrolidinyl)carbonyl)-2-methylpropyl)carbamate |
| M.8 | 46.4 nM | C | (S)-1-acetyl-N-(4-((2-((S)-1-(2-phenylacetyl)pyrrolidin-2-yl)-1H-benzo[d]imidazol-6-yl)ethynyl)phenyl)pyrrolidine-2-carboxamide |
| M.9 | | C | (S)-1-(2-phenylacetyl)-N-(4-((2-((S)-1-(2-phenylacetyl)pyrrolidin-2-yl)-1H-benzo[d]imidazol-6-yl)ethynyl)phenyl)pyrrolidine-2-carboxamide |
| M.10 | 202 nM | B | (S)-1-acetyl-N-(4-(2-(2-((S)-1-(2-phenylacetyl)pyrrolidin-2-yl)-1H-benzo[d]imidazol-6-yl)ethyl)phenyl)pyrrolidine-2-carboxamide |
| M.11 | | C | (S)-1-(2-phenylacetyl)-N-(4-(2-(2-((S)-1-(2-phenylacetyl)pyrrolidin-2-yl)-1H-benzo[d]imidazol-6-yl)ethyl)phenyl)pyrrolidine-2-carboxamide |
| J.44 | | D | methyl ((1R)-2-((2S)-2-((5-(2-(2-((2S)-1-((2R)-2-((methoxycarbonyl)amino)-2-phenylacetyl)-2-pyrrolidinyl)-1H-benzimidazol-5-yl)-1,3-oxazol-5-yl)-2-methylphenyl)carbamoyl)-1-pyrrolidinyl)-2-oxo-1-phenylethyl)carbamate |
| J.44a | | D | methyl (R)-2-((S)-2-(5-(2-(2-((S)-1-((R)-2-(dimethylamino)-2-phenylacetyl)pyrrolidin-2-yl)-1H-benzo[d]imidazol-5-yl)oxazol-5-yl)-2-methylphenylcarbamoyl)pyrrolidin-1-yl)-2-oxo-1-phenylethylcarbamate |
| J.45 | | D | methyl ((1R)-2-((2S)-2-((3-(2-(2-((2S)-1-((2R)-2-((methoxycarbonyl)amino)-2-phenylacetyl)-2-pyrrolidinyl)-1H-benzimidazol-5-yl)-1,3-oxazol-5-yl)phenyl)carbamoyl)-1-pyrrolidinyl)-2-oxo-1-phenylethyl)carbamate |
| J.45a | | D | 1-((2R)-2-(dimethylamino)-2-phenylacetyl)-N-(3-(2-(2-((2S)-1-((2R)-2-(dimethylamino)-2-phenylacetyl)-2-pyrrolidinyl)-1H-benzimidazol-5-yl)-1,3-oxazol-5-yl)phenyl)-L-prolinamide |
| J.45b | | D | (S)-1-(2-phenylacetyl)-N-(3-(2-(2-((S)-1-(2-phenylacetyl)pyrrolidin-2-yl)-1H-benzo[d]imidazol-5-yl)oxazol-5-yl)phenyl)pyrrolidine-2-carboxamide |
| J.46 | | D | (S)-1-((R)-2-(dimethylamino)-2-phenylacetyl)-N-(3-(2-((S)-1-((R)-2-(dimethylamino)-2-phenylacetyl)pyrrolidin-2-yl)-1H-benzo[d]imidazol-4-yl)oxazol-5-yl)phenyl)pyrrolidine-2-carboxamide |
| J.47 | | D | 1-((2R)-2-(dimethylamino)-2-phenylacetyl)-N-(3-(5-(2-((2S)-1-((2R)-2-(dimethylamino)-2-phenylacetyl)-2-pyrrolidinyl)-1H- |

TABLE 2-continued

| Example | EC50 | Range | Name |
|---|---|---|---|
| | | | benzimidazol-5-yl)-1,3-oxazol-2-yl)-2-methylphenyl)-L-prolinamide |
| J.47a | | D | methyl ((1R)-2-((2S)-2-((3-(5-(2-((2S)-1-((2R)-2-((methoxycarbonyl)amino)-2-phenylacetyl)-2-pyrrolidinyl)-1H-benzimidazol-5-yl)-1,3-oxazol-2-yl)-2-methylphenyl)carbamoyl)-1-pyrrolidinyl)-2-oxo-1-phenylethyl)carbamate |
| J.48 | | D | 1-((2R)-2-hydroxy-2-phenylacetyl)-N-(3-(5-(2-((2S)-1-((2R)-2-hydroxy-2-phenylacetyl)-2-pyrrolidinyl)-1H-benzimidazol-5-yl)-1,3-oxazol-2-yl)phenyl)-L-prolinamide |
| J.48a | | D | methyl ((1S)-1-(((2S)-2-(5-(2-(3-((((2S)-2-((2S)-2-((methoxycarbonyl)amino)-3-methylbutanoyl)-1-pyrrolidinyl)carbonyl)amino)phenyl)-1,3-oxazol-5-yl)-1H-benzimidazol-2-yl)-1-pyrrolidinyl)carbonyl)-2-methylpropyl)carbamate |
| J.48b | | C | (2R)-2-(dimethylamino)-N-(3-(5-(2-((2S)-1-((2R)-2-(dimethylamino)-2-phenylacetyl)-2-pyrrolidinyl)-1H-benzimidazol-5-yl)-1,3-oxazol-2-yl)phenyl)-2-phenylacetamide |
| J.48c | | D | 1-((2R)-2-acetamido-2-phenylacetyl)-N-(3-(5-(2-((2S)-1-((2R)-2-acetamido-2-phenylacetyl)-2-pyrrolidinyl)-1H-benzimidazol-5-yl)-1,3-oxazol-2-yl)phenyl)-L-prolinamide |
| J.48d | 147 nM | B | 1-((3-chloro-5-methoxy-1-isoquinolinyl)carbonyl)-N-(3-(5-(2-((2S)-1-((3-chloro-5-methoxy-1-isoquinolinyl)carbonyl)-2-pyrrolidinyl)-1H-benzimidazol-5-yl)-1,3-oxazol-2-yl)phenyl)-L-prolinamide |
| J.49 | | D | methyl ((1R)-2-((2S)-2-((5-(5-(2-(1-((2R)-2-((methoxycarbonyl)amino)-2-phenylacetyl)-2-pyrrolidinyl)-1H-benzimidazol-5-yl)-1,3-oxazol-2-yl)-2-methylphenyl)carbamoyl)-1-pyrrolidinyl)-2-oxo-1-phenylethyl)carbamate |
| J.49a | | D | (S)-1-((R)-2-(dimethylamino)-2-phenylacetyl)-N-(5-(5-(2-((S)-1-((R)-2-(dimethylamino)-2-phenylacetyl)pyrrolidin-2-yl)-1H-benzo[d]imidazol-6-yl)oxazol-2-yl)-2-methylphenyl)pyrrolidine-2-carboxamide |
| J.50 | | C | 1-((2R)-2-hydroxy-2-phenylacetyl)-N-(4-(5-(2-((2S)-1-((2R)-2-hydroxy-2-phenylacetyl)-2-pyrrolidinyl)-1H-benzimidazol-5-yl)-1,3-oxazol-2-yl)phenyl)-L-prolinamide |
| J.50a | | D | 1-((2R)-2-(dimethylamino)-2-phenylacetyl)-N-(4-(5-(2-((2S)-1-((2R)-2-(dimethylamino)-2-phenylacetyl)-2-pyrrolidinyl)-1H-benzimidazol-5-yl)-1,3-oxazol-2-yl)phenyl)-L-prolinamide |
| J.50b | | D | 1-((2R)-2-acetamido-2-phenylacetyl)-N-(4-(5-(2-((2S)-1-((2R)-2-acetamido-2-phenylacetyl)-2-pyrrolidinyl)-1H-benzimidazol-5-yl)-1,3-oxazol-2-yl)phenyl)-L-prolinamide |
| J.50c | >10 μM | A | 1-((3-chloro-5-methoxy-1-isoquinolinyl)carbonyl)-N-(4-(5-(2-((2S)-1-((3-chloro-5-methoxy-1-isoquinolinyl)carbonyl)-2-pyrrolidinyl)-1H-benzimidazol-5-yl)-1,3-oxazol-2-yl)phenyl)-L-prolinamide |
| J.51 | | C | N-(2-fluoro-4-(5-(2-((2S)-1-((2R)-2-hydroxy-2-phenylacetyl)-2-pyrrolidinyl)-1H-benzimidazol-5-yl)-1,3-oxazol-2-yl)phenyl)-1-((2R)-2-hydroxy-2-phenylacetyl)-L-prolinamide |
| J.51a | | D | 1-((2R)-2-(dimethylamino)-2-phenylacetyl)-N-(4-(5-(2-((2S)-1-((2R)-2-(dimethylamino)-2-phenylacetyl)-2-pyrrolidinyl)-1H-benzimidazol-5-yl)-1,3-oxazol-2-yl)-2-fluorophenyl)-L-prolinamide |
| J.51b | | B | 1-((3-chloro-5-methoxy-1-isoquinolinyl)carbonyl)-N-(4-(5-(2-((2S)-1-((3-chloro-5-methoxy-1-isoquinolinyl)carbonyl)-2-pyrrolidinyl)-1H-benzimidazol-5-yl)-1,3-oxazol-2-yl)-2-fluorophenyl)-L-prolinamide |
| J.52 | | D | N-(5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-1-(phenylacetyl)-L-prolinamide |
| J.52a | | C | N,N-dimethylglycyl-N-(5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-L-prolinamide |
| J.52b | | D | methyl ((1R)-2-((2S)-2-((5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)carbamoyl)-1-pyrrolidinyl)-2-oxo-1-phenylethyl)carbamate |
| J.52c | | D | N-(methoxycarbonyl)-L-valyl-N-(5-5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-L-prolinamide |
| J.52d | | D | N-(methoxycarbonyl)-L-alanyl-N-(5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-L-prolinamide |

TABLE 2-continued

| Example | EC50 | Range | Name |
|---|---|---|---|
| J.53 | | B | 1-(cyclopropylacetyl)-N-(3-(5-(2-((2S)-1-(cyclopropylacetyl)-2-pyrrolidinyl)-1H-benzimidazol-5-yl)-1,3-oxazol-2-yl)phenyl)-L-prolinamide |
| J.53a | | A | 1-(cyclopropylacetyl)-N-(3-(2-(2-((2S)-1-(cyclopropylacetyl)-2-pyrrolidinyl)-1H-benzimidazol-5-yl)-1,3-oxazol-5-yl)phenyl)-L-prolinamide |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. Compounds of the present disclosure may inhibit multiple genotypes of HCV.

What is claimed is:

1. A compound of Formula (I)

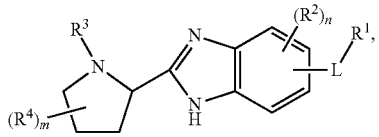

(I)

or a pharmaceutically acceptable salt thereof, wherein
each m is independently 0 or 1;
each n is independently 0 or 1;
L is a bond or is selected from

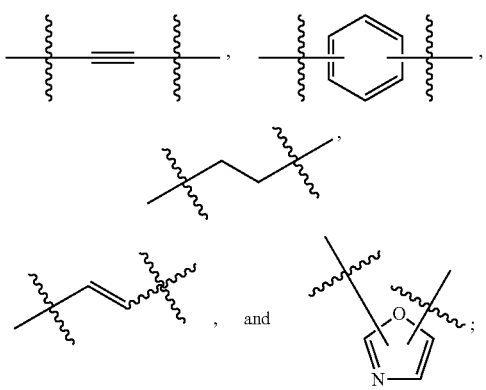

$R^1$ is selected from

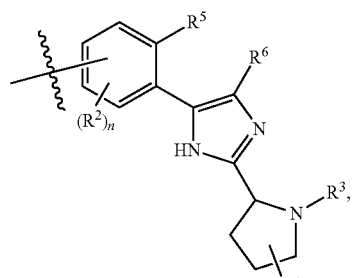

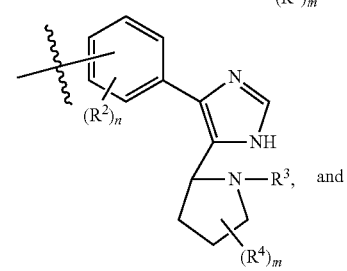

and

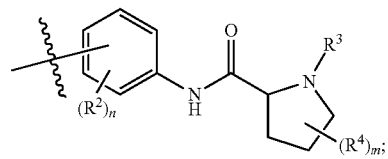

each $R^2$ is independently selected from alkyl and halo;
each $R^3$ is independently selected from hydrogen and —C(O)$R^7$;
$R^4$ is alkyl;
$R^5$ and $R^6$ are independently selected from hydrogen and halo, or
$R^5$ and $R^6$, together with the carbon atoms to which they are attached, form a six- or seven-membered ring optionally containing one heteroatom selected from nitrogen and oxygen and optionally containing an additional double bond;
each $R^7$ is independently selected from alkoxy, alkyl, arylalkyl, cycloalkyl, heterocyclyl, heterocyclylalkyl, (NR$^c$R$^d$)alkenyl, and (NR$^c$R$^d$)alkyl;
$R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkyloxycarbonyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)

OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^x$R$^y$)alkyl, and (NR$^x$R$^y$)carbonyl; and R$^x$ and R$^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{x'}$R$^{y'}$)carbonyl, wherein R$^{x'}$ and R$^{y'}$ are independently selected from hydrogen and alkyl.

2. A compound of claim 1, or a pharmaceutically acceptable salt thereof, wherein L is a bond.

3. A compound of claim 2, or a pharmaceutically acceptable salt thereof, wherein R$^1$ is

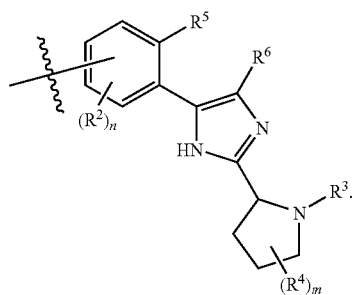

4. A compound of claim 1, or a pharmaceutically acceptable salt thereof, wherein L is

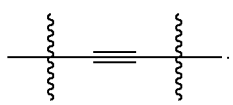 [SMILES: *C#C*]

5. A compound of claim 1, or a pharmaceutically acceptable salt thereof, wherein L is

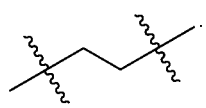 [SMILES: *CC*]

6. A compound of claim 5, or a pharmaceutically acceptable salt thereof, wherein R$^1$ is

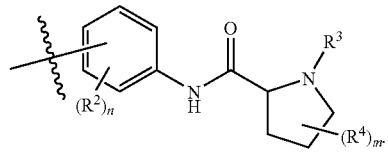

7. A compound of claim 1, or a pharmaceutically acceptable salt thereof, wherein L is

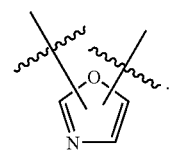

8. A compound of claim 7, or a pharmaceutically acceptable salt thereof, wherein L is selected from

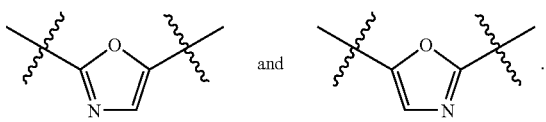

9. A compound of claim 8, or a pharmaceutically acceptable salt thereof, wherein R$^1$ is

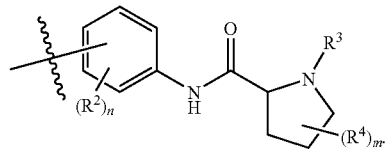

10. A compound selected from (1R)-2-((2S)-2-(8-(2-((2S)-1-((2R)-2-(diethylamino)-2-phenylacetyl)-2-pyrrolidinyl)-1H-benzimidazol-5-yl)-1,4,5,6-tetrahydrobenzo[3,4]cyclohepta[1,2-d]imidazol-2-yl)-1-pyrrolidinyl)-N,N-diethyl-2-oxo-1-phenylethanamine;

methyl ((1S)-1-(((2S)-2-(5-(4-(2-((2S)-1-((2S)-2-((methoxycarbonyl)amino)-3-methylbutanoyl)-2-pyrrolidinyl)-1H-imidazol-4-yl)phenyl)-1H-benzimidazol-2-yl)-1-pyrrolidinyl)carbonyl)-2-methylpropyl) carbamate;

(1R)-2-((2S)-2-(4-(4-(2-((2S)-1-((2R)-2-(diethylamino)-2-phenylacetyl)-2-pyrrolidinyl)-1H-benzimidazol-5-yl)phenyl)-1H-imidazol-2-yl)-1-pyrrolidinyl)-N,N-diethyl-2-oxo-1-phenylethanamine;

methyl ((1R)-2-((2S)-2-(4-(4-(2-((2S)-1-((2R)-2-((methoxycarbonyl)amino)-2-phenylacetyl)-2-pyrrolidinyl)-1H-benzimidazol-5-yl)phenyl)-1H-imidazol-2-yl)-1-pyrrolidinyl)-2-oxo-1-phenylethyl)carbamate;

methyl ((1S)-1-(((2S)-2-(5-(3-(2-((2S)-1-((2S)-2-((methoxycarbonyl)amino)-3-methylbutanoyl)-2-pyrrolidinyl)-1H-imidazol-4-yl)phenyl)-1H-benzimidazol-2-yl)-1-pyrrolidinyl)carbonyl)-2-methylpropyl) carbamate;

(1R)-2-((2S)-2-(4-(3-(2-((2S)-1-((2R)-2-(diethylamino)-2-phenylacetyl)-2-pyrrolidinyl)-1H-benzimidazol-5-yl)phenyl)-1H-imidazol-2-yl)-1-pyrrolidinyl)-N,N-diethyl-2-oxo-1-phenylethanamine;

methyl ((1R)-2-((2S)-2-(4-(3-(2-((2S)-1-((2R)-2-((methoxycarbonyl)amino)-2-phenylacetyl)-2-pyrrolidinyl)-1H-benzimidazol-5-yl)phenyl)-1H-imidazol-2-yl)-1-pyrrolidinyl)-2-oxo-1-phenylethyl)carbamate;

methyl ((1S)-1-(((1R,3S,5R)-3-(8-(2-((1R,3S,5R)-2-((2S)-2-((methoxycarbonyl)amino)-3-methylbutanoyl)-2-azabicyclo[3.1.0]hex-3-yl)-1H-benzimidazol-5-yl)-1,4,5,6-tetrahydrobenzo[3,4]cyclohepta[1,2-d]imidazol-2-yl)-2-azabicyclo[3.1.0]hex-2-yl)carbonyl)-2-methylpropyl)carbamate;

methyl ((1S)-1-(((2S)-2-(5-(2-((2S)-1-((2S)-2-((methoxycarbonyl)amino)-3-methylbutanoyl)-2-pyrrolidinyl)-4,5-dihydro-3H-naphtho[1,2-d]imidazol-7-yl)-1H-benzimidazol-2-yl)-1-pyrrolidinyl)carbonyl)-2-methylpropyl)carbamate;

methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-4-yl)-4-biphenylyl)-1H-benzimidazol-2-yl)-1-pyrrolidinyl)carbonyl)-2-methylpropyl)carbamate;

methyl ((1S)-1-(((2S)-2-(5-(2-((2S)-1-((2S)-2-((methoxycarbonyl)amino)-3-methylbutanoyl)-2-pyrrolidinyl)-3H-naphtho[1,2-d]imidazol-7-yl)-1H-benzimidazol-2-yl)-1-pyrrolidinyl)carbonyl)-2-methylpropyl)carbamate;

methyl ((1S)-1-(((2S)-2-(5-((4-(2-((2S)-1-((2S)-2-((methoxycarbonyl)amino)-3-methylbutanoyl)-2-pyrrolidinyl)-1H-imidazol-4-yl)phenyl)ethynyl)-1H-benzimidazol-2-yl)-1-pyrrolidinyl)carbonyl)-2-methylpropyl)carbamate;

(1R)-2-((2S)-2-(4-(4-(2-((2S)-1-((2R)-2-(diethylamino)-2-phenylacetyl)-2-pyrrolidinyl)-1H-benzimidazol-5-yl)ethynyl)phenyl)-1H-imidazol-2-yl)-1-pyrrolidinyl)-N,N-diethyl-2-oxo-1-phenylethanamine;

methyl ((1S)-1-(((1R,3S,5R)-3-(5-((4-(2-((1R,3S,5R)-2-((2S)-2-((methoxycarbonyl)amino)-3-methylbutanoyl)-2-azabicyclo[3.1.0]hex-3-yl)-1H-imidazol-4-yl)phenyl)ethynyl)-1H-benzimidazol-2-yl)-2-azabicyclo[3.1.0]hex-2-yl)carbonyl)-2-methylpropyl)carbamate;

methyl ((1S)-1-(((1R,3S,5R)-3-(4-(4-((4-fluoro-2-((1R,3S,5R)-2-((2S)-2-((methoxycarbonyl)amino)-3-methylbutanoyl)-2-azabicyclo[3.1.0]hex-3-yl)-1H-benzimidazol-6-yl)ethynyl)phenyl)-1H-imidazol-2-yl)-2-azabicyclo[3.1.0]hex-2-yl)carbonyl)-2-methylpropyl)carbamate;

methyl ((1S)-1-(((1R,3S,5R)-3-(4-(2-fluoro-4-((2-((1R,3S,5R)-2-((2S)-2-((methoxycarbonyl)amino)-3-methylbutanoyl)-2-azabicyclo[3.1.0]hex-3-yl)-1H-benzimidazol-5-yl)ethynyl)phenyl)-1H-imidazol-2-yl)-2-azabicyclo[3.1.0]hex-2-yl)carbonyl)-2-methylpropyl)carbamate;

methyl ((1S)-1-(((2S)-2-(5-((2-((2S)-1-((2S)-2-((methoxycarbonyl)amino)-3-methylbutanoyl)-2-pyrrolidinyl)-4,5-dihydro-3H-naphtho[1,2-d]imidazol-7-yl)ethynyl)-1H-benzimidazol-2-yl)-1-pyrrolidinyl)carbonyl)-2-methylpropyl)carbamate;

methyl ((1S)-1-(((2S)-2-(5-((2-((2S)-1-((2S)-2-((methoxycarbonyl)amino)-3-methylbutanoyl)-2-pyrrolidinyl)-3H-naphtho[1,2-d]imidazol-7-yl)ethynyl)-1H-benzimidazol-2-yl)-1-pyrrolidinyl)carbonyl)-2-methylpropyl)carbamate;

methyl ((1S)-1-(((2S)-2-(4-fluoro-6-((2-((2S)-1-((2S)-2-((methoxycarbonyl)amino)-3-methylbutanoyl)-2-pyrrolidinyl)-4,5-dihydro-1H-naphtho[1,2-d]imidazol-7-yl)ethynyl)-1H-benzimidazol-2-yl)-1-pyrrolidinyl)carbonyl)-2-methylpropyl)carbamate;

methyl ((1S)-1-(((2S)-2-(4-fluoro-6-((2-((2S)-1-((2S)-2-((methoxycarbonyl)amino)-3-methylbutanoyl)-2-pyrrolidinyl)-1H-naphtho[1,2-d]imidazol-7-yl)ethynyl)-1H-benzimidazol-2-yl)-1-pyrrolidinyl)carbonyl)-2-methylpropyl)carbamate;

methyl ((1S)-1-(((1R,3S,5R)-3-(5-((2-((1R,3S,5R)-2-((2S)-2-((methoxycarbonyl)amino)-3-methylbutanoyl)-2-azabicyclo[3.1.0]hex-3-yl)-1H-naphtho[1,2-d]imidazol-7-yl)ethynyl)-1H-benzimidazol-2-yl)-2-azabicyclo[3.1.0]hex-2-yl)carbonyl)-2-methylpropyl)carbamate;

methyl ((1S)-1-(((1R,3S,5R)-3-(4-fluoro-6-((2-((1R,3S,5R)-2-((2S)-2-((methoxycarbonyl)amino)-3-methylbutanoyl)-2-azabicyclo[3.1.0]hex-3-yl)-4,5-dihydro-1H-naphtho[1,2-d]imidazol-7-yl)ethynyl)-1H-benzimidazol-2-yl)-2-azabicyclo[3.1.0]hex-2-yl)carbonyl)-2-methylpropyl)carbamate;

methyl ((1S)-1-(((2S)-2-(5-(3-((2S)-1-((2R)-2-((methoxycarbonyl)amino)-3-methylbutanoyl)-2-pyrrolidinyl)-1H-benzimidazol-5-yl)ethynyl)phenyl)-1H-imidazol-4-yl)-1-pyrrolidinyl)carbonyl)-2-methylpropyl)carbamate;

(1R)-2-((2S)-2-(5-(3-((2-((2S)-1-((2R)-2-(diethylamino)-2-phenylacetyl)-2-pyrrolidinyl)-1H-benzimidazol-5-yl)ethynyl)phenyl)-1H-imidazol-4-yl)-1-pyrrolidinyl)-N,N-diethyl-2-oxo-1-phenylethanamine;

methyl ((1S)-1-(((2S)-2-(5-((4-(4-((2S)-1-((2S)-2-((methoxycarbonyl)amino)-3-methylbutanoyl)-2-pyrrolidinyl)-1H-imidazol-5-yl)phenyl)ethynyl)-1H-benzimidazol-2-yl)-1-pyrrolidinyl)carbonyl)-2-methylpropyl)carbamate;

(S)-1-acetyl-N-(4-((2-((S)-1-(2-phenylacetyl)pyrrolidin-2-yl)-1H-benzo[d]imidazol-6-yl)ethynyl)phenyl)pyrrolidine-2-carboxamide;

(S)-1-(2-phenylacetyl)-N-(4-((2-((S)-1-(2-phenylacetyl)pyrrolidin-2-yl)-1H-benzo[d]imidazol-6-yl)ethynyl)phenyl)pyrrolidine-2-carboxamide;

(S)-1-acetyl-N-(4-(2-(2-((S)-1-(2-phenylacetyl)pyrrolidin-2-yl)-1H-benzo[d]imidazol-6-yl)ethyl)phenyl)pyrrolidine-2-carboxamide;

(S)-1-(2-phenylacetyl)-N-(4-(2-((S)-1-(2-phenylacetyl)pyrrolidin-2-yl)-1H-benzo[d]imidazol-6-yl)ethyl)phenyl)pyrrolidine-2-carboxamide;

methyl ((1R)-2-((2S)-2-((5-(2-(2-((2S)-1-((2R)-2-((methoxycarbonyl)amino)-2-phenylacetyl)-2-pyrrolidinyl)-1H-benzimidazol-5-yl)-1,3-oxazol-5-yl)-2-methylphenyl)carbamoyl)-1-pyrrolidinyl)-2-oxo-1-phenylethyl)carbamate;

methyl (R)-2-((S)-2-(5-(2-(2-((S)-1-((R)-2-(dimethylamino)-2-phenylacetyl)pyrrolidin-2-yl)-1H-benzo[d]imidazol-5-yl)oxazol-5-yl)-2-methylphenylcarbamoyl)pyrrolidin-1-yl)-2-oxo-1-phenylethylcarbamate;

methyl ((1R)-2-((2S)-2-((3-(2-(2-((2S)-1-((2R)-2-((methoxycarbonyl)amino)-2-phenylacetyl)-2-pyrrolidinyl)-1H-benzimidazol-5-yl)-1,3-oxazol-5-yl)phenyl)carbamoyl)-1-pyrrolidinyl)-2-oxo-1-phenylethyl)carbamate;

1-((2R)-2-(dimethylamino)-2-phenylacetyl)-N-(3-(2-(2-((2S)-1-((2R)-2-(dimethylamino)-2-phenylacetyl)-2-pyrrolidinyl)-1H-benzimidazol-5-yl)-1,3-oxazol-5-yl)phenyl)-L-prolinamide;

(S)-1-(2-phenylacetyl)-N-(3-(2-(2-((S)-1-(2-phenylacetyl)pyrrolidin-2-yl)-1H-benzo[d]imidazol-5-yl)oxazol-5-yl)phenyl)pyrrolidine-2-carboxamide;

(S)-1-((R)-2-(dimethylamino)-2-phenylacetyl)-N-(3-(2-(2-((S)-1-((R)-2-(dimethylamino)-2-phenylacetyl)pyrrolidin-2-yl)-1H-benzo[d]imidazol-4-yl)oxazol-5-yl)phenyl)pyrrolidine-2-carboxamide;

1-((2R)-2-(dimethylamino)-2-phenylacetyl)-N-(3-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-L-prolinamide;

methyl ((1R)-2-((2S)-2-((3-(5-(2-((2S)-1-((2R)-2-((methoxycarbonyl)amino)-2-phenylacetyl)-2-pyrrolidinyl)-1H-benzimidazol-5-yl)-1,3-oxazol-2-yl)-2-methylphenyl)carbamoyl)-1-pyrrolidinyl)-2-oxo-1-phenylethyl)carbamate;

1-((2R)-2-hydroxy-2-phenylacetyl)-N-(3-(5-(2-((2S)-1-((2R)-2-hydroxy-2-phenylacetyl)-2-pyrrolidinyl)-1H-benzimidazol-5-yl)-1,3-oxazol-2-yl)phenyl)-L-prolinamide;

methyl ((1S)-1-(((2S)-2-(5-(2-(3-((((2S)-2-((2S)-2-((methoxycarbonyl)amino)-3-methylbutanoyl)-1-pyrrolidinyl)carbonyl)amino)phenyl)-1,3-oxazol-5-yl)-1H-benzimidazol-2-yl)-1-pyrrolidinyl)carbonyl)-2-methylpropyl)carbamate;

(2R)-2-(dimethylamino)-N-(3-(5-(2-((2S)-1-((2R)-2-(dimethylamino)-2-phenylacetyl)-2-pyrrolidinyl)-1H-benzimidazol-5-yl)-1,3-oxazol-2-yl)phenyl)-2-phenylacetamide;

1-((2R)-2-acetamido-2-phenylacetyl)-N-(3-(5-(2-((2S)-1-((2R)-2-acetamido-2-phenylacetyl)-2-pyrrolidinyl)-1H-benzimidazol-5-yl)-1,3-oxazol-2-yl)phenyl)-L-prolinamide;

1-((3-chloro-5-methoxy-1-isoquinolinyl)carbonyl)-N-(3-(5-(2-((2S)-1-((3-chloro-5-methoxy-1-isoquinolinyl)carbonyl)-2-pyrrolidinyl)-1H-benzimidazol-5-yl)-1,3-oxazol-2-yl)phenyl)-L-prolinamide;

methyl ((1R)-2-((2S)-2-((5-(5-(2-(1-((2R)-2-((methoxycarbonyl)amino)-2-phenylacetyl)-2-pyrrolidinyl)-1H-benzimidazol-5-yl)-1,3-oxazol-2-yl)-2-methylphenyl)carbamoyl)-1-pyrrolidinyl)-2-oxo-1-phenylethyl)carbamate;

(S)-1-((R)-2-(dimethylamino)-2-phenylacetyl)-N-(5-(5-(2-((S)-1-((R)-2-(dimethylamino)-2-phenylacetyl)pyrrolidin-2-yl)-1H-benzo[d]imidazol-6-yl)oxazol-2-yl)-2-methylphenyl)pyrrolidine-2-carboxamide;

1-((2R)-2-hydroxy-2-phenylacetyl)-N-(4-(5-(2-((2S)-1-((2R)-2-hydroxy-2-phenylacetyl)-2-pyrrolidinyl)-1H-benzimidazol-5-yl)-1,3-oxazol-2-yl)phenyl)-L-prolinamide;

1-((2R)-2-(dimethylamino)-2-phenylacetyl)-N-(4-(5-(2-((2S)-1-((2R)-2-(dimethylamino)-2-phenylacetyl)-2-pyrrolidinyl)-1H-benzimidazol-5-yl)-1,3-oxazol-2-yl)phenyl)-L-prolinamide;

1-((2R)-2-acetamido-2-phenylacetyl)-N-(4-(5-(2-((2S)-1-((2R)-2-acetamido-2-phenylacetyl)-2-pyrrolidinyl)-1H-benzimidazol-5-yl)-1,3-oxazol-2-yl)phenyl)-L-prolinamide;

1-((3-chloro-5-methoxy-1-isoquinolinyl)carbonyl)-N-(4-(5-(2-((2S)-1-((3-chloro-5-methoxy-1-isoquinolinyl)carbonyl)-2-pyrrolidinyl)-1H-benzimidazol-5-yl)-1,3-oxazol-2-yl)phenyl)-L-prolinamide;

N-(2-fluoro-4-(5-(2-((2S)-1-((2R)-2-hydroxy-2-phenylacetyl)-2-pyrrolidinyl)-1H-benzimidazol-5-yl)-1,3-oxazol-2-yl)phenyl)-1-((2R)-2-hydroxy-2-phenylacetyl)-L-prolinamide;

1-((2R)-2-(dimethylamino)-2-phenylacetyl)-N-(4-(5-(2-((2S)-1-((2R)-2-(dimethylamino)-2-phenylacetyl)-2-pyrrolidinyl)-1H-benzimidazol-5-yl)-1,3-oxazol-2-yl)-2-fluorophenyl)-L-prolinamide;

1-((3-chloro-5-methoxy-1-isoquinolinyl)carbonyl)-N-(4-(5-(2-((2S)-1-((3-chloro-5-methoxy-1-isoquinolinyl)carbonyl)-2-pyrrolidinyl)-1H-benzimidazol-5-yl)-1,3-oxazol-2-yl)-2-fluorophenyl)-L-prolinamide;

N-(5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-1-(phenylacetyl)-L-prolinamide;

N,N-dimethylglycyl-N-(5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-L-prolinamide;

methyl ((1R)-2-((2S)-2-((5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)carbamoyl)-1-pyrrolidinyl)-2-oxo-1-phenylethyl)carbamate;

N-(methoxycarbonyl)-L-valyl-N-(5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-L-prolinamide; and N-(methoxycarbonyl)-L-alanyl-N-(5-(5-(2-((2S)-1-((2R)-2-(dimethylamino)-2-phenylacetyl)-2-pyrrolidinyl)-1H-benzimidazol-5-yl)-1,3-oxazol-2-yl)-2-methylphenyl)-L-prolinamide;

or a pharmaceutically acceptable salt thereof.

11. A composition comprising a compound of claim 1, or a pharmaceutically acceptable salt thereof, and a pharmaceutically acceptable carrier.

12. The composition of claim 11 further comprising one or two additional compounds having anti-HCV activity.

13. The composition of claim 12 wherein at least one of the additional compounds is an interferon or a ribavirin.

14. The composition of claim 13 wherein the interferon is selected from interferon alpha 2B, pegylated interferon alpha, consensus interferon, interferon alpha 2A, and lymphoblastiod interferon tau.

15. The composition of claim 12 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5′-monophospate dehydrogenase inhibitor, amantadine, and rimantadine.

16. The composition of claim 12 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

17. A method of relieving or causing regression of an HCV infection in a patient, comprising administering to the patient a therapeutically effective amount of a compound of claim 1, or a pharmaceutically acceptable salt thereof.

18. The method of claim 17 further comprising administering one or two additional compounds having anti-HCV activity prior to, after or simultaneously with the compound of claim 1, or a pharmaceutically acceptable salt thereof.

19. The method of claim 18 wherein at least one of the additional compounds is an interferon or a ribavirin.

20. The method of claim 19 wherein the interferon is selected from interferon alpha 2B, pegylated interferon alpha, consensus interferon, interferon alpha 2A, and lymphoblastiod interferon tau.

21. The method of claim 18 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

22. The method of claim 18 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *